US011673876B2

(12) United States Patent
Whitehead et al.

(10) Patent No.: US 11,673,876 B2
(45) Date of Patent: Jun. 13, 2023

(54) SUBSTITUTED AMINOBENZYL HETEROARYL COMPOUNDS AS EGFR AND/OR PI3K INHIBITORS

(71) Applicant: Mekanistic Therapeutics LLC, Ann Arbor, MI (US)

(72) Inventors: Christopher E. Whitehead, Ann Arbor, MI (US); Judith S. Leopold, Ann Arbor, MI (US)

(73) Assignee: Mekanistic Therapeutics LLC, Ann Arbor, MI (US)

( * ) Notice: Subject to any disclaimer, the term of this patent is extended or adjusted under 35 U.S.C. 154(b) by 0 days.

(21) Appl. No.: 17/558,399

(22) Filed: Dec. 21, 2021

(65) Prior Publication Data

US 2022/0213054 A1 Jul. 7, 2022

Related U.S. Application Data

(60) Provisional application No. 63/129,368, filed on Dec. 22, 2020.

(51) Int. Cl.
| | | |
|---|---|---|
| *C07D 401/04* | (2006.01) | |
| *A61P 35/00* | (2006.01) | |
| *C07D 401/10* | (2006.01) | |
| *C07D 401/14* | (2006.01) | |
| *C07D 403/04* | (2006.01) | |
| *C07D 413/04* | (2006.01) | |
| *C07D 413/10* | (2006.01) | |

(52) U.S. Cl.
CPC .......... *C07D 401/04* (2013.01); *A61P 35/00* (2018.01); *C07D 401/10* (2013.01); *C07D 401/14* (2013.01); *C07D 403/04* (2013.01); *C07D 413/04* (2013.01); *C07D 413/10* (2013.01)

(58) Field of Classification Search
CPC ............................ C07D 401/04; A61P 35/00
See application file for complete search history.

(56) References Cited

U.S. PATENT DOCUMENTS

| | | | |
|---|---|---|---|
| 3,989,816 | A | 11/1976 | Rajadhyaksha |
| 4,369,174 | A | 1/1983 | Nagai et al. |
| 4,444,762 | A | 4/1984 | Rajadhyaksha |
| 4,842,866 | A | 6/1989 | Horder et al. |
| 5,217,720 | A | 6/1993 | Sekigawa et al. |
| 5,770,581 | A | 6/1998 | Weichselbaum et al. |
| 5,866,572 | A | 2/1999 | Barker et al. |
| 6,002,008 | A | 12/1999 | Wissner et al. |
| 6,225,318 | B1 | 5/2001 | Sobolov-Jaynes et al. |
| 6,569,457 | B2 | 5/2003 | Ullah et al. |
| 6,638,534 | B1 | 10/2003 | Ishibashi et al. |
| 6,689,772 | B1 | 2/2004 | Boschelli et al. |
| 6,897,214 | B2 | 5/2005 | Barker et al. |
| 10,206,924 | B2 | 2/2019 | Whitehead et al. |
| 10,842,791 | B2 | 11/2020 | Whitehead et al. |

| | | | |
|---|---|---|---|
| 2002/0026052 | A1 | 2/2002 | Boschelli et al. |
| 2009/0069320 | A1* | 3/2009 | Reich ............... A61P 25/06 514/266.4 |
| 2009/0258882 | A1 | 10/2009 | Stauffer et al. |
| 2010/0035919 | A1 | 2/2010 | Vasudevan et al. |
| 2010/0179144 | A1 | 7/2010 | Adams et al. |
| 2012/0238587 | A1 | 9/2012 | Lee et al. |
| 2012/0245350 | A1 | 9/2012 | Fontana |
| 2013/0053341 | A1 | 2/2013 | Suzuki et al. |

(Continued)

FOREIGN PATENT DOCUMENTS

| | | |
|---|---|---|
| EP | 1029853 A1 | 8/2000 |
| EP | 1990337 A1 | 11/2008 |

(Continued)

OTHER PUBLICATIONS

Ding et al. JACS, 2002, vol. 124, No. 8, pp. 1594-1596.*
Apsel, B. et al. "Targeted polypharmacology: discovery of dual inhibitors of tyrosine and phosphoinositide kinases," Nat Chem Biol. 2008;4: 691-699.
Apsel, B., "Dual-specificity inhibitors of lipid and protein kinases" University of California, San Francisco, ProQuest Dissertations Publishing, 2008. 3311357.
Atreya, C.E. et al. "PTEN expression is consistent in colorectal cancer primaries and metastases and associates with patient survival." Cancer Med 2013;2: 496-506.
Barrios Sosa, Ana C. et al. "Further studies on ethenyl and ethynyl-4-phenylamino-3-quinolinecarbonitriles: Identification of a subnanomolar Src kinase inhibitor" Bioorg Med. Chem. Letter. 2005, v. 15, pp. 1743-1747.

(Continued)

*Primary Examiner* — Samira J Jean-Louis
(74) *Attorney, Agent, or Firm* — Honigman LLP; Jonathan P. O'Brien; Fernando Alberdi

(57) ABSTRACT

This disclosure is in the field of medicinal chemistry, and relates to a new class of small-molecules having the Formula I,

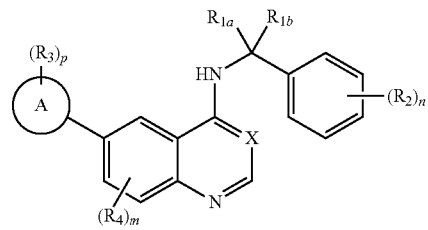

Formula I or a pharmaceutically acceptable salt or solvate thereof, or an enantiomer, a mixture of enantiomers, a mixture of two or more diastereomers, or an isotopic variant thereof, wherein the variables Ring A, X, $R_{1a}$, $R_{1b}$, $R_2$, $R_3$, $R_4$, m, n, and p are described herein, which function as dual inhibitors of EGFR proteins and PI3K proteins. The disclosure further relates to the use of the compounds described herein as therapeutics for the treatment of diseases and conditions mediated by EGFR proteins and/or PI3K proteins, such as cancer and other diseases.

7 Claims, 3 Drawing Sheets

(56) References Cited

U.S. PATENT DOCUMENTS

| | | |
|---|---|---|
| 2013/0165458 A1 | 6/2013 | Huang et al. |
| 2013/0210819 A1 | 8/2013 | Klein |
| 2013/0217671 A1 | 8/2013 | Matsuo et al. |
| 2013/0331405 A1 | 12/2013 | Korkola et al. |
| 2014/0315886 A1 | 10/2014 | Suzuki et al. |
| 2019/0002460 A1 | 1/2019 | Whitehead et al. |
| 2021/0023085 A1 | 1/2021 | Whitehead et al. |

FOREIGN PATENT DOCUMENTS

| | | | |
|---|---|---|---|
| EP | 2060565 | A1 | 5/2009 |
| EP | 2551270 | A2 | 1/2013 |
| EP | 2740729 | A1 | 6/2014 |
| JP | 2000-504713 | A | 4/2000 |
| JP | 2003-528857 | A | 9/2003 |
| WO | 1997030034 | A1 | 8/1997 |
| WO | 1998002434 | A1 | 1/1998 |
| WO | 1999009016 | A1 | 2/1999 |
| WO | 1999035146 | A1 | 7/1999 |
| WO | 2001072711 | A1 | 10/2001 |
| WO | 2003082867 | A1 | 10/2003 |
| WO | 2006071017 | A1 | 7/2006 |
| WO | 2007013950 | A2 | 2/2007 |
| WO | 2007059257 | A2 | 5/2007 |
| WO | 2008012326 | A1 | 1/2008 |
| WO | 2008157191 | A2 | 12/2008 |
| WO | 2009012647 | A1 | 1/2009 |
| WO | 2009155527 | A2 | 12/2009 |
| WO | 2013141586 | A1 | 9/2013 |
| WO | 2016100347 | A2 | 6/2016 |
| WO | 2017023905 | A1 | 2/2017 |
| WO | 2020215037 | A1 | 10/2020 |
| WO | 2020239951 | A1 | 12/2020 |

OTHER PUBLICATIONS

Bethune, G. et al., "Epidermal growth factor receptor (EGFR) in lung cancer: an overview and update" J Thorac Dis. 2010;2(1): 48-51.

Boschelli, D. et al. "Optimization of 7-alkene-3-quinolinecarbonitriles as Src kinase inhibitors" Bioorg. Med. Chem. Lett. 2010, v. 20, pp. 2924-2927.

Buck, E. et al., "Rapamycin synergizes with the epidermal growth factor receptor inhibitor erlotinib in non-small-cell lung, pancreatic, colon, and breast tumors." Mal Cancer Ther. 2006,5: 2676-2684.

Cecil Text book of Medicine, 20th Edition vol. 1 W.B. Saunders Company, 1997, pp. 1004-1010.

Cheng, et al. "Discovery of the Highly Potent PI3KmTOR Dual Inhibitor PF-04979064 through Structure-Based Drug Design." ACS Med Chem Lett. 2013;4: 91-97.

Ciapetti, P. et al, "Chapter 15—Molecular Variations Based on Isosteric Replacements", The Practice of Medicinal Chemistry (Third Edition), Elsevier, NL, Jan. 1, 2008, pp. 290-342.

Cramer, J.D. et al., "The changing therapeutic landscape of head and neck cancer," Nat Rev Clin Oncol, 2019. 16(11): p. 669-683.

Degorce, S. L. et al, "Discovery of Novel Quinoline-6-Carboxamides as Potent, Selective and Orally Bioavailable Inhibitors of Ataxia Telangiectasia Mutated (ATM) Kinase", Journal of Medicinal Chemistry, Jul. 1, 2016, vol. 59, No. 13, pp. 6281-6292.

Eichhorn, P.J. et al., "Phosphatidylinositol 3-kinase hyperactivation results in lapatinib resistance that is reversed by the mTORphosphatidylinositol 3-kinase inhibitor NVP-BEZ235." Cancer Res. 2008;68: 9221-9230.

Elkabets, M. et al., "AXL mediates resistance to PI3Ka inhibition by activating the EGFRPKCmTOR axis in head and neck and esophageal squamous cell carcinomas," Cancer Cell, 2015. 27(4): p. 533-546.

European Search Report, EP Patent Application No. 15870877.6, dated May 3, 2018, 6 pages.

Fan, O.W., et al., "A dual phosphoinositide-3-kinase alphamTOR inhibitor cooperates with blockade of epidermal growth factor receptor in PTEN-mutant glioma." Cancer Res. 2007;67: 7960-7965.

Gadgeel SM, et al., "Preclinical Rationale for PI3KAktmTOR Pathway Inhibitors as Therapy for Epidermal Growth Factor Receptor Inhibitor-Resistant Non-Small-Cell Lung Cancer" Clin Lung Cancer. 2013;14: 322-332.

Grandis, J.R. et al., "Elevated levels of transforming growth factor alpha and epidermal growth factor receptor messenger RNA are early markers of carcinogenesis in head and neck cancer," and D.J. Tweardy, Cancer Research, 1993. 53(15): p. 3579-3584.

Hamada, K., et al., "The PTENPI3K pathway governs normal vascular development and tumor angiogenesis" 2005 Genes Dev 19 (17): 2054-65.

Hieimberger, A.B., et al., "The natural history of EGFR and EGFRvIII in glioblastoma patients" J Trans! Med. 2005;3: 38.

International Search Report and Written Opinion, International Application No. PCTUS2015065827, dated May 2, 2016.

Janku, F. et al., "Targeting the PI3K pathway in cancer: are we making headway?," Nature Reviews Clinical Oncology, 2018. 15: p. 273-291.

Jin, G., et al.,"PTEN mutations and relationship to EGFR, ERBB2, KRAS, and TP53 mutations in non-small cell lung ancers" Lung Cancer. 2010;69: 279-283.

Knight, et al. Discovery of GSK2126458, a Highly Potent Inhibitor of PI3K and the Mammalian Target of Rapamycin. ACS Med Chem Lett. 2010;1: 39-43.

Liu, P. et al., "Targeting the phosphoinositide 3-kinase pathway in cancer," Nature Reviews Drug Discovery, 2009. 8: p. 627-644.

Lui, V.W., et al., "Frequent mutation of the PI3K pathway in head and neck cancer defines predictive biomarkers." Cancer Discov. 2013;3: 761-769.

Morita, M., et al., "Inhibitory effect of the phosphoinositide 3-kinase inhibitor LY294002 on muscarinic acetylcholine receptor-induced calcium entry in PC12h cells", Journ. Pharmacol. Sci. (2007), 105: pp. 258-263.

Nishimura, et al. "Phospshoinositide 3-kinase (PI3K)mammalian target of rapamycin (mTOR) dual inhibitors: iscovery and structure-activity relationships of a series of quinoline and quinoxaline derivatives." J Med Chem. 2011;54: 4735-4751.

Psyrri, A. et al., "Molecular pathways in head and neck cancer: EGFR, PI3K, and more.," American Society of Clinical Oncology educational book. American Society of Clinical Oncology. Annual Meeting, 2013: p. 246-255.

Psyrri, A., et al., "Molecular Pathways in Head and Neck Cancer: EGFR, PI3K, and More" Am Soc Clin Oncol Educ Book 2013: 246-255.

Ptcl.chem.ox.ac.ukMSDS structure activity relationship; Jaworska, 1-8, 2004.

Ratushny, V., et al., "Targeting EGFR resistance networks in Head and Neck Cancer" Cell Signal. 2009;21: 1255-1268.

Sawai, H., et al., "Loss of PTEN expression is associated with colorectal cancer liver metastasis and poor patient survival" BMC Gastroenterol, 2008;8:56.

Simpson, D.R. et al., "Targeting the PI3KAKTmTOR pathway in squamous cell carcinoma of the head and neck," Oral Oncology, 2015. 51(4): p. 291-298.

Spano, J.P., et al., "Epidermal growth factor receptor signaling in colorectal cancer: preclinical data and therapeutic perspectives" Ann Oncol. 2005; 16: 189-194.

Stamos, et al. "Structure of the epidermal growth factor receptor kinase domain alone and in complex with a 4-anilinoquinazoline inhibitor." J Biol Chem. 2002;277(48): 46265-46272.

Tao, J.J. et al., "Antagonism of EGFR and HER3 enhances the response to inhibitors of the PI3K-Akt pathway in triple-negative breast cancer," Science Signaling, 2014. 7(318): p. ra29-ra29.

Xiao, H. et al., "Biologic-like In Vivo Efficacy with Small Molecule Inhibitors of TNF[alpha] Identified Using Scaffold Hopping and Structure-Based Drug Design Approaches", Journal of Medicinal Chemistry, Dec. 10, 2020, vol. 63, No. 23, pp. 15050-15071.

(56) References Cited

OTHER PUBLICATIONS

Yap, T.A. et al., "Drugging PI3K in cancer: refining targets and therapeutic strategies," Current Opinion in Pharmacology, 2015. 23: p. 98-107.
Young, N.R. et al., "Molecular phenotype predicts sensitivity of squamous cell carcinoma of the head and neck to epidermal growth factor receptor inhibition," Molecular Oncology, 2013. 7(3): p. 359-368.
Yun, C.H. et al. "The T790M mutation in EGFR kinase causes drug resistance by increasing the affinity for ATP." Proc Natl Acad Sci U S A. 2008;105: 2070-2075.

\* cited by examiner

SUBSTITUTED AMINOBENZYL HETEROARYL COMPOUNDS AS EGFR AND/OR PI3K INHIBITORS

CROSS REFERENCE TO RELATED APPLICATION

This PCT application claims the benefit of U.S. provisional application No. 63/129,368, filed on Dec. 22, 2020. The entire contents of the aforementioned application is hereby incorporated by reference in its entirety.

STATEMENT REGARDING FEDERALLY SPONSORED RESEARCH OR DEVELOPMENT

This disclosure was made with government support under Grant Nos. R44 CA213715 awarded by the National Institutes of Health. The government has certain rights in the disclosure.

TECHNICAL FIELD OF THE DISCLOSURE

This disclosure is in the field of medicinal chemistry. In particular, the disclosure relates to a new class of small-molecules having a substituted aminobenzyl quinazoline structure or a substituted aminobenzyl quinoline structure, which function as dual inhibitors of EGFR proteins and PI3K proteins. The disclosure further relates to the use of the compounds described herein as therapeutics for the treatment of diseases and conditions mediated by EGFR proteins and/or PI3K proteins, such as cancer and other diseases.

BACKGROUND

Every year more than 830,000 patients are diagnosed with head and neck cancer worldwide and at least 430,000 patients die from this disease (see e.g., Cramer, J. D., et al., Nat Rev Clin Oncol, 2019. 16(11): p. 669-683). Ninety percent of all head and neck cancers are squamous cell carcinomas (HNSCCs) and are characterized by significant heterogeneity at both the clinical and molecular level (see e.g., Psyrri, A., T. Y. Seiwert, and A. Jimeno, American Society of Clinical Oncology educational book. American Society of Clinical Oncology. Annual Meeting, 2013: p. 246-255). EGFR overexpression is an early and frequent molecular change in HNSCC, a change that has been shown to be associated with reduced survival (see e.g., Grandis, J. R. and D. J. Tweardy, Cancer Research, 1993. 53(15): p. 3579-3584). Cetuximab remains the only U.S. FDA-approved EGFR-targeted therapy available for HNSCC. A fundamental problem in EGFR-targeted therapy in HNSCC is patient selection, since a consistent mechanism for resistance has not been identified. PI3K mutations, which are particularly common in HPV+ head and neck cancers, confer increased resistance to EGFR inhibition (see e.g., Simpson, D. R., L. K. Mell, and E. E. W. Cohen, Oral Oncology, 2015. 51(4): p. 291-298; Young, N. R., et al., Molecular Oncology, 2013. 7(3): p. 359-368). PIK3CA has therefore emerged as a candidate biomarker of EGFR resistance. The PI3K/AKT/mTOR pathway, which supports tumor cell survival and progression, is aberrantly activated in a large percentage of human tumors (see e.g., Yap, T. A., et al., Current Opinion in Pharmacology, 2015. 23: p. 98-107; Liu, P., et al., Nature Reviews Drug Discovery, 2009. 8: p. 627-644; Janku, F., T. A. Yap, and F. Meric-Bernstam, Nature Reviews Clinical Oncology, 2018. 15: p. 273-291). Squamous cancers show a particularly high incidence of genomic alterations in this pathway, encompassing PIK3CA mutations and other alterations, for instance in PIK3R1, PTEN, and AKT, that result in activation of this pathway. Despite intensive efforts, the only PI3K inhibitors that have received regulatory approval are idelalisib (PI3Kδ-selective), copanlisib (panPI3K), and alpelisib (PI3Kα-selective). Lack of progress can largely be attributed to unacceptable toxicities, which are in part driven by the need for high exposures to elicit monotherapy activity. The rationale for a dual EGFR/PI3K inhibitor program is driven by the central premise that 1) a panPI3K/mTOR inhibitor approach is superior to isoform-selective approaches, since molecular alterations of downstream players in the PI3K pathway, e.g. PTEN, can obviate the need for PI3K activity (see e.g., Tao, J. J., et al., Science Signaling, 2014. 7(318): p. ra29-ra29), and 2) EGFR and PI3K play reciprocal roles in tumor adaptation when the other kinase is targeted. Anti-EGFR treatment has been shown to reverse acquired and intrinsic resistance to PI3Kα inhibition in HNSCC (see e.g., Elkabets, M., et al., Cancer Cell, 2015. 27(4): p. 533-546). AXL was shown to interact with EGFR to activate PLCγ and PKC, leading to activation of mTOR in a PI3K-independent manner.

Accordingly, the present disclosure provides compounds of Formula I that are small molecule inhibitors of EGFR and/or PI3K enzymes suitable for treating cancer.

SUMMARY

The compounds of Formula I are substituted benzylamino compounds and may have advantages over the analogous unsubstituted benzylamino compounds or analogous phenylamino compounds. For example, the compounds of Formula I may possess properties selected from one or more of increased solubility in pH 7.4 aqueous buffer solution, increased solubility in simulated intestinal fluid (SIF), and increased solubility in simulated gastric fluid (SGF), as compared to the analogous unsubstituted benzylamino compounds or analogous phenylamino compounds. Increased solubility in the above described mediums can be indicative of increased bioavailability in a biological system, such as a human subject. Further, an increase in bioavailability may allow for equivalent biological activity of smaller doses, compared to the required dose of a less soluble active pharmaceutical ingredient (API).

In one aspect, the disclosure includes a compound of Formula I

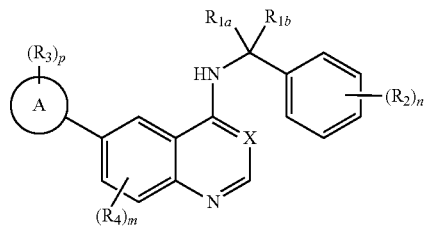

Formula I or a pharmaceutically acceptable salt or solvate thereof, or an enantiomer, a mixture of enantiomers, a mixture of two or more diastereomers, or an isotopic variant thereof, wherein Ring A is selected from phenyl or a 5 or 6 membered heteroaryl;

X is N or C—$R_5$;

$R_{1a}$ is selected from the group consisting of H or $C_{1-6}$ alkyl;

$R_{1b}$ is selected from the group consisting of $C_{1-6}$ alkyl, cycloalkyl, hetercycloalkyl, aryl, heteroaryl, OR', $N(R')_2$, C(O)R', C(O)OR', C(O)N(R')$_2$, halo, CN, and $NO_2$, wherein each $C_{1-6}$ alkyl, cycloalkyl, hetercycloalkyl, aryl, or heteroaryl is optionally and independently substituted with one or more R" substituents;

or, $R_{1a}$ and $R_{1b}$, together with the methylene moiety to which they are attached, form a spirocyclic ring selected from a $C_{3-7}$ cycloalkyl or 3-7 membered heterocycloalkyl, each of which is optionally and independently substituted with one or more R" substituents;

each $R_2$ is independently selected from halo, OH, $C_{1-6}$ alkyl, haloalkyl, $OC_{1-6}$ alkyl, CN, $NH_2$, $NHC_{1-6}$ alkyl, $N(C_{1-6}$ alkyl)$_2$, C(O)$C_{1-6}$ alkyl, C(O)O$C_{1-6}$ alkyl, C(O)$NH_2$, C(O)NH$C_{1-6}$ alkyl, and C(O)N($C_{1-6}$ alkyl)$_2$;

or one $R_2$ substituent and $R_{1b}$, together with the phenyl group to which $R_2$ is attached and the carbon atom to which $R_{1b}$ is attached, form a bicyclic group having the general structure

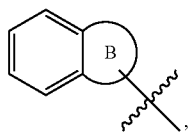

wherein Ring B is a $C_{3-7}$ cycloalkyl or 4-7 membered heterocycloalkyl, each of which is optionally substituted with one or more substituents independently selected from halo, OH, $C_{1-6}$ alkyl, haloalkyl, $OC_{1-6}$ alkyl, CN, $NH_2$, $NHC_{1-6}$ alkyl, $N(C_{1-6}$ alkyl)$_2$, C(O)$C_{1-6}$ alkyl, C(O)O$C_{1-6}$ alkyl, C(O)$NH_2$, C(O)NH$C_{1-6}$ alkyl, and C(O)N($C_{1-6}$ alkyl)$_2$;

each $R_3$ is independently selected from $C_{1-6}$ alkyl, a 5-6 membered heteroaryl, a 5-6 membered heterocycloalkyl, halo, CN, $NO_2$, OR', $N(R')_2$, C(O)R', C(O)OR', C(O)N(R')$_2$, OC(O)OR', OC(O)N(R')$_2$, NR'C(O)N(R')$_2$, SOR', SON(R')$_2$, $SO_2$R', $SO_2$N(R')$_2$, NR'SOR', NR'SON(R')$_2$, NR'$SO_2$R', and NR'$SO_2$N(R')$_2$, wherein the $C_{1-6}$ alkyl, hetercycloalkyl, and heteroaryl are each optionally and independently substituted with one or more R" substituents;

or two $R_3$ substituents, together with Ring A, to which they are attached, form a fused bicyclic heterocycloalkyl, a fused bicyclic cycloalkyl, a fused bicyclic aryl, or a fused bicyclic heteroaryl, each of which is optionally and independently substituted with one or more R" substituents;

each $R_4$ is selected from halo, OH, $NH_2$, CN, $C_{1-6}$ alkyl, and $OC_{1-6}$ alkyl;

each $R_5$ is selected from hydrogen, halo, OH, $NH_2$, CN, and $C_{1-6}$ alkyl;

each R' is independently selected from hydrogen, OH, CN, $C_{1-6}$ alkyl, cycloalkyl, hetercycloalkyl, aryl, and heteroaryl, each of which is optionally and independently substituted with one or more R" substituents;

each R" is independently selected from the group consisting of $C_{1-6}$ alkyl, cycloalkyl, hetercycloalkyl, aryl, heteroaryl, $OC_{1-6}$ alkyl, oxo, OH, halo, CN, $NH_2$, $NHC_{1-6}$ alkyl, $N(C_{1-6}$ alkyl)$_2$, C(O)$C_{1-6}$ alkyl, C(O)O$C_{1-6}$ alkyl, C(O)$NH_2$, C(O)NH$C_{1-6}$ alkyl, and C(O)N($C_{1-6}$ alkyl)$_2$, wherein each $C_{1-6}$ alkyl, cycloalkyl, hetercycloalkyl, aryl, and heteroaryl is optionally and independently substituted with one or more substituents selected from halo, oxo, alkoxy, CN, $NH_2$, C(O)$C_{1-6}$ alkyl, C(O)O$C_{1-6}$ alkyl, and C(O)NH$C_{1-6}$ alkyl; and m, n, and p are each an integer selected from 0-4.

In another aspect, the disclosure includes a pharmaceutical composition comprising a compound or salt according to Formula (I) described herein and a pharmaceutically acceptable excipient.

In another aspect, the disclosure includes a method of modulating the activity of an EGFR and/or PI3K enzyme in a biological sample, said method comprising contacting the biological sample with a compound, salt or a composition described herein.

In another aspect, the disclosure includes a method of preventing or treating an EGFR and/or PI3K mediated disease in a subject, said method comprising administering to the subject a compound, salt or a composition described herein.

In one embodiment of this aspect, the EGFR and/or PI3K mediated disease is a cancer.

DETAILED DESCRIPTION OF THE DISCLOSURE

Figure 1:
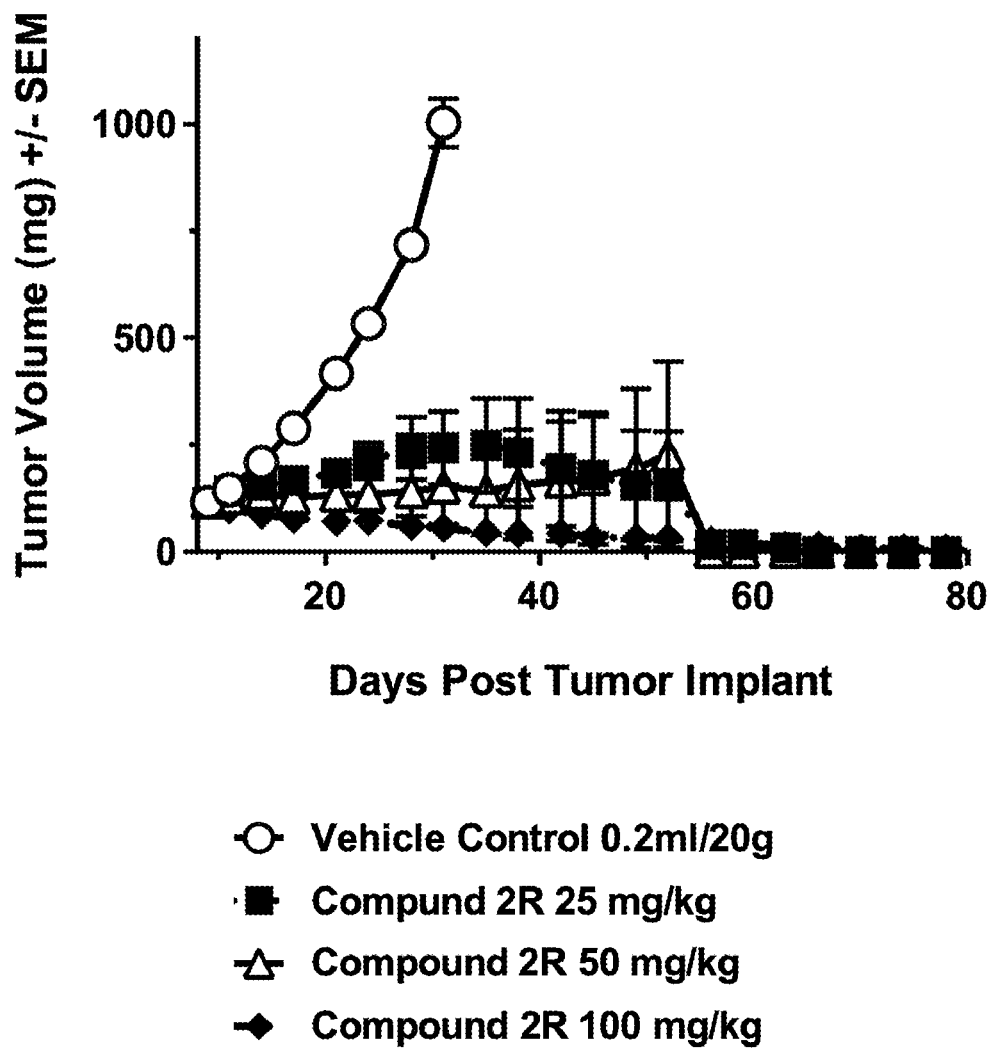
FIG. 1 is a line graph showing a Therapeutic Index Study of Compound 2R against the human squamous head and neck cancer model CAL-33 at 25 mg/Kg, 50 mg/Kg, and 100 mg/Kg vs. control on the mean tumor burden of a test group.

The present disclosure provides a method for preventing, treating, reducing, inhibiting or controlling a neoplasia, tumor or cancer and/or the establishment of metastases in a subject involving administering a compound of Formula I or a pharmaceutically acceptable salt thereof.

For purposes of this disclosure, the chemical elements are identified in accordance with the Periodic Table of the Elements, CAS version, Handbook of Chemistry and Physics, 98th Ed. Additionally, general principles of organic chemistry are described in "Organic Chemistry", Second Ed., Thomas Sorrell, University Science Books, Sausolito: 2006, and "March's Advanced Organic Chemistry", 7th Ed., Ed.: Smith, M. B. and March, J., John Wiley & Sons, New York: 2015, the entire contents of which are hereby incorporated by reference.

Definitions

As used herein, "about" means within acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" can mea range of up to 20%. When particular values are provided in the application and claims, unless otherwise stated, the meaning of "about" should be assumed to be within acceptable error range for that particular value.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

The term "pharmaceutically acceptable salt" as used herein, refers to any salt (e.g., obtained by reaction with an acid or a base) of a compound of the present disclosure that is physiologically tolerated in the target patient (e.g., a mammal). Salts of the compounds of the present disclosure may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the disclosure and their pharmaceutically acceptable acid addition salts.

As used herein, "pharmaceutically acceptable carrier" includes any and all solvents, dispersion media, coatings, surfactants, antioxidants, preservatives {e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329).

As used herein, "pharmaceutically acceptable carrier" or "pharmaceutical acceptable excipient" includes any material which, when combined with an active ingredient, allows the ingredient to retain biological activity and is non-reactive with the subject's immune system, and can include any and all solvents, diluents, carriers, dispersion media, coatings, antibacterial and antifungal agents, isotonic and absorption delaying agents, and the like that are physiologically compatible, non-toxic, and does not interfere with the mechanism of action of the compound of Formula I or a pharmaceutically acceptable salt thereof. Preferably, the pharmaceutical acceptable excipient is suitable for intravenous, intramuscular, subcutaneous, parenteral, spinal or epidermal administration (e.g., by injection or infusion). Depending on the route of administration, a compound of Formula I or a pharmaceutically acceptable salt thereof, may be coated in a material to protect the compound from the action of acids and other natural conditions that may inactivate the compound. Pharmaceutically acceptable excipients include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The methods of treatment of the disclosure comprise administering a safe and effective amount of a compound described herein or a pharmaceutically-acceptable salt thereof to a patient in need thereof.

As used herein, the term "subject" is intended to include human and non-human animals. Preferred subjects include human patients in need of enhancement of an immune response that may be beneficial in the patient's treatment and/or prevention of cancer and/or cancer metastasis. The methods are particularly suitable for treating human patients having a disorder that can be treated by augmenting the T-cell mediated immune response. In a particular embodiment, the methods are particularly suitable for treatment of cancer cells in vivo.

"Such as" has the same meaning as "such as but not limited to." Similarly, "include" has the same meaning as "include but not limited to," while "including" has the same meaning as "including but not limited to."

The terms "tumor," "cancer" and "neoplasia" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumor, cancer or neoplasia to other sites, locations or regions within the subject, in which the sites, locations or regions are distinct from the primary tumor or cancer.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl.

As used herein, an "alkylene" group refers to a bivalent alkyl group that connects to two attachment points simultaneously, wherein the alkylene unit can be bivalent on the same carbon or two different carbons of the alkyl moiety. Examples of alkylene groups are, without limitation, methylene, ethylene, propylene, and butylene, as well as branched structures, such as —$CH_2(CH_2)$-(1,1-ethylene) and —$CH_2CH_2(CH_2)$-(1,2-propylene).

As used herein an "aryl" group refers to a mono-, bi-, or tri-cyclic ring system wherein all rings in the system are aromatic and contain no heteroatoms in the ring. Examples of aryl groups include, but are not limited to phenyl, naphthyl, anthracenyl, and tetracenyl.

As used herein, a "carbocycle" or "carbocyclyl" group refers to a mono-, bi-, or tricyclic (fused or bridged) hydrocarbon ring system that contains no heteroatoms in the ring structures, wherein at least one of the rings in the system is non-aromatic, and can be completely saturated or partially unsaturated. The terms "carbocycle" or "carbocyclyl" encompass a "cycloalkyl" group and a "cycloalkenyl" group, each of which is set forth below.

As used herein, a "cycloalkyl" group refers to a saturated carbocyclic mono-, bi-, or tricyclic (fused or bridged) ring system of 3-20 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic mono-, bi, or tricyclic (fused or bridged) ring system of 3-20 (e.g., 4-8) carbon atoms, wherein at least one ring in the system has one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

As used herein, the terms "heterocycle" and "heterocyclyl" are used interchangeably and refer to a mono-, bi-, or tricyclic (fused or bridged) non-aromatic hydrocarbon ring system that contains at least one heteroatom in the ring structure and can be completely saturated or partially unsaturated. The terms "heterocycle" and "heterocyclyl" encompass a "heterocycloalkyl" group and a "heterocycloalkenyl" group, each of which is set forth below.

As used herein, a "heterocycloalkyl" group refers to a 3-20 membered mono-, di-, or tricylic (fused or bridged) (e.g., 5- to 10-membered) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thipheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0.3.7]nonyl.

A "heterocycloalkenyl" group, as used herein, refers to a 3-20 membered mono-, di-, or tricylic (fused or bridged) (e.g., 5- to 10-membered) non-aromatic ring structure, in which one or more of the ring atoms is a heteroatom (e.g., N, O, S, or combinations thereof), and wherein at least one of the ring structures has one or more double bonds.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzothiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizinyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicaliphatic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0.3.7]nonyl.

As used herein, an "alkoxy" group refers to an alkyl-O— group where "alkyl" has been defined previously.

As used herein, a "carbonyl" refers to —C(O)—.

As used herein, an "oxo" refers to =O.

As used herein a "carboxy" refers to —C(O)OH.

As used herein an "ester" refers to —C(O)O—W, in which W is, for example, alkyl, carbocyclyl, or heterocyclyl.

As described herein, compounds of the disclosure may optionally be substituted with one or more substituents, such as are illustrated generally herein, or as exemplified by particular classes, subclasses, and species of the disclosure.

The phrase "optionally substituted" is used interchangeably with the phrase "substituted or unsubstituted." As described herein, compounds of the disclosure can optionally be substituted with one or more substituents, as exemplified by particular classes, subclasses, and species of the disclosure.

In general, the term "substituted," whether preceded by the term "optionally" or not, refers to the replacement of hydrogen radicals in a given structure with the radical of a specified substituent. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this disclosure are those combinations that result in the formation of stable or chemically feasible compounds.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

Additionally, unless otherwise stated, structures depicted herein are also meant to include compounds that differ only in the presence of one or more isotopically enriched atoms. Examples of isotopes that can be incorporated into compounds of the disclosure and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present disclosure and pharmaceutically acceptable salts of said compounds that contain the aforementioned isotopes and/or other isotopes of other atoms are within the scope of the present disclosure. Isotopically-labelled compounds of the present disclosure, for example those into which radioactive isotopes, such as $^3H$ and $^{14}C$, are incorporated, are useful in drug and/or substrate tissue distribution assays. Tritiated hydrogen ($^3H$) and carbon-14 ($^{14}C$) isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium ($^2H$) can afford certain therapeutic advantages resulting from greater metabolic stability, for example increased in vivo half-life or reduced dosage requirements and may be preferred in some circumstances. Isotopically labeled compounds of the disclosure can generally be prepared by carrying out the procedures disclosed in the schemes and/or in the examples below, and substituting a readily available isotopically labeled reagent for a non-isotopically labeled reagent.

Unless otherwise stated, structures depicted herein are also meant to include all isomeric (e.g., enantiomeric, diastereomeric, and geometric (or conformational)) forms of the structure. "Isomer" refers to compounds that have the same composition and molecular weight but differ in physical and/or chemical properties; for example (Z) and (E) double bond isomers, and (Z) and (E) conformational isomers. The structural difference may be in constitution (geometric isomers) or in the ability to rotate the plane of polarized light (stereoisomers); for example, the R and S configurations for each asymmetric center. The compounds of the disclosure may contain one or more asymmetric centers, also referred to as chiral centers, and may, therefore, exist as individual enantiomers, diastereomers, or other stereoisomeric forms, or as mixtures thereof. All such isomeric forms are included within the present disclosure, including mixtures thereof. Chiral centers may also be present in a substituent such as an alkyl group.

Where the stereochemistry of a chiral center present in a compound of the disclosure, or in any chemical structure illustrated herein, is not specified the structure is intended to encompass any stereoisomer and all mixtures thereof. Thus, compounds of the disclosure containing one or more chiral centers may be used as racemic mixtures, enantiomerically enriched mixtures, or as enantiomerically pure individual stereoisomers.

Individual stereoisomers of a compound of the disclosure which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

Unless otherwise stated, all tautomeric forms of the compounds of the disclosure are within the scope of the disclosure.

Any numerical range disclosed herein encompasses the and lower limits and each intervening value, unless otherwise specified. Other than in the working examples, or where otherwise indicated, numerical values (such as numbers expressing quantities of ingredients, reaction conditions) as used in the specification and claims are modified by the term "about". Accordingly, unless indicated to the contrary, such numbers are approximations that may vary depending upon the desired properties sought to be obtained. At the very least, and not as an attempt to limit the application of the doctrine of equivalents to the scope of the claims, each numerical parameter should be construed in light of the number of significant digits and ordinary rounding techniques.

While the numerical parameters setting forth the scope of the disclosed subject matter are approximations, the numerical values set forth in the working examples are reported as precisely as possible. Any numerical value, however, inherently contains certain errors necessarily resulting from the standard deviation found in its respective testing measurements.

Unless defined otherwise, the meanings of technical and scientific terms as used herein are those commonly understood by one of ordinary skill in the art to which the disclosed subject matter belongs.

Embodiments

In one aspect, the disclosure includes a compound of Formula I

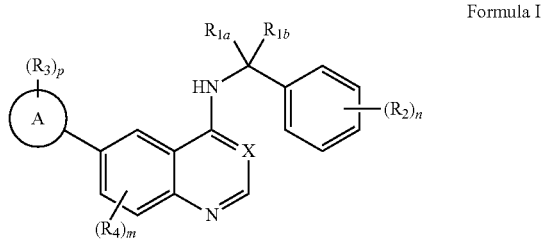

Formula I or a pharmaceutically acceptable salt or solvate thereof, or an enantiomer, a mixture of enantiomers, a mixture of two or more diastereomers, or an isotopic variant thereof, wherein Ring A is selected from phenyl or a 5 or 6 membered heteroaryl;

X is N or C—$R^5$;

$R_{1a}$ is selected from the group consisting of H or $C_{1-6}$ alkyl;

$R_{1b}$ is selected from the group consisting of $C_{1-6}$ alkyl, cycloalkyl, hetercycloalkyl, aryl, heteroaryl, OR', N(R')$_2$, C(O)R', C(O)OR', C(O)N(R')$_2$, halo, CN, and NO$_2$, wherein each $C_{1-6}$ alkyl, cycloalkyl, hetercycloalkyl, aryl, or heteroaryl is optionally and independently substituted with one or more R" substituents;

or, $R_{1a}$ and $R_{1b}$, together with the methylene moiety to which they are attached, form a spirocyclic ring selected from a $C_{3-7}$ cycloalkyl or 3-7 membered heterocycloalkyl, each of which is optionally and independently substituted with one or more R" substituents;

each $R_2$ is independently selected from halo, OH, $C_{1-6}$ alkyl, haloalkyl, OC$_{1-6}$ alkyl, CN, NH$_2$, NHC$_{1-6}$ alkyl, N(C$_{1-6}$ alkyl)$_2$, C(O)C$_{1-6}$ alkyl, C(O)OC$_{1-6}$ alkyl, C(O)NH$_2$, C(O)NHC$_{1-6}$ alkyl, and C(O)N(C$_{1-6}$ alkyl)$_2$;

or one $R_2$ substituent and $R_{1b}$, together with the phenyl group to which $R_2$ is attached and the carbon atom to which $R_{1b}$ is attached, form a bicyclic group having the general structure

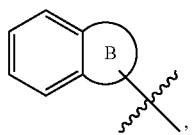

wherein Ring B is a $C_{3-7}$ cycloalkyl or 4-7 membered heterocycloalkyl, each of which is optionally substituted with one or more substituents independently selected from halo, OH, $C_{1-6}$ alkyl, haloalkyl, OC$_{1-6}$ alkyl, CN, NH$_2$, NHC$_{1-6}$ alkyl, N(C$_{1-6}$ alkyl)$_2$, C(O)C$_{1-6}$ alkyl, C(O)OC$_{1-6}$ alkyl, C(O)NH$_2$, C(O)NHC$_{1-6}$ alkyl, and C(O)N(C$_{1-6}$ alkyl)$_2$;

each $R_3$ is independently selected from $C_{1-6}$ alkyl, a 5-6 membered heteroaryl, a 5-6 membered heterocycloalkyl, halo, CN, NO$_2$, OR', N(R')$_2$, C(O)R', C(O)OR', C(O)N(R')$_2$, OC(O)OR', OC(O)N(R')$_2$, NR'C(O)N(R')$_2$, SOR', SON(R')$_2$, SO$_2$R', SO$_2$N(R')$_2$, NR'SOR', NR'SON(R')$_2$, NR'SO$_2$R', and NR'SO$_2$N(R')$_2$, wherein the $C_{1-6}$ alkyl, hetercycloalky, and heteroaryl are each optionally and independently substituted with one or more R" substituents;

or two $R_3$ substituents, together with Ring A, to which they are attached, form a fused bicyclic heterocycloalkyl, a fused bicyclic cycloalkyl, a fused bicyclic aryl, or a fused bicyclic heteroaryl, each of which is optionally and independently substituted with one or more R" substituents;

each $R_4$ is selected from halo, OH, NH$_2$, CN, $C_{1-6}$ alkyl, and OC$_{1-6}$ alkyl;

each $R_5$ is selected from hydrogen, halo, OH, NH$_2$, CN, and $C_{1-6}$ alkyl;

each R' is independently selected from hydrogen, OH, CN, $C_{1-6}$ alkyl, cycloalkyl, hetercycloalkyl, aryl, and heteroaryl, each of which is optionally and independently substituted with one or more R" substituents;

each R" is independently selected from the group consisting of $C_{1-6}$ alkyl, cycloalkyl, hetercycloalkyl, aryl, heteroaryl, OC$_{1-6}$ alkyl, oxo, OH, halo, CN, NH$_2$, NHC$_{1-6}$ alkyl, N(C$_{1-6}$ alkyl)$_2$, C(O)C$_{1-6}$ alkyl, C(O)OC$_{1-6}$ alkyl, C(O)NH$_2$, C(O)NHC$_{1-6}$ alkyl, and C(O)N(C$_{1-6}$ alkyl)$_2$, wherein each $C_{1-6}$ alkyl, cycloalkyl, hetercycloalkyl, aryl, and heteroaryl is optionally and independently substituted with one or substituents selected from halo, oxo, alkoxy, CN, NH$_2$, C(O)C$_{1-6}$ alkyl, C(O)OC$_{1-6}$ alkyl, and C(O)NHC$_{1-6}$ alkyl; and m, n, and p are each an integer selected from 0-4.

In one embodiment, $R_{1a}$ is H.

In another embodiment, $R_{1b}$ is $C_{1-6}$ alkyl, cycloalkyl, hetercycloalkyl, aryl, heteroaryl, OC$_{1-6}$ alkyl, OH, NH$_2$, NHC$_{1-6}$ alkyl, N(C$_{1-6}$ alkyl)$_2$, C(O)C$_{1-6}$ alkyl, C(O)OC$_{1-6}$ alkyl, C(O)NH$_2$, C(O)NHC$_{1-6}$ alkyl, C(O)N(C$_{1-6}$ alkyl)$_2$, halo, CN, or NO$_2$, wherein each $C_{1-6}$ alkyl, cycloalkyl, hetercycloalkyl, aryl, or heteroaryl is optionally and independently substituted with OC$_{1-6}$ alkyl, oxo, OH, halo, CN, NH$_2$, NHC$_{1-6}$ alkyl, N(C$_{1-6}$ alkyl)$_2$, C(O)C$_{1-6}$ alkyl, C(O)OC$_{1-6}$ alkyl, C(O)NH$_2$, C(O)NHC$_{1-6}$ alkyl, C(O)N(C$_{1-6}$ alkyl)$_2$.

In another embodiment, $R_{1b}$ is $C_{1-6}$ alkyl, OC$_{1-6}$ alkyl, OH, NH$_2$, NHC$_{1-6}$ alkyl, N(C$_{1-6}$ alkyl)$_2$, C(O)C$_{1-6}$ alkyl, C(O)NH$_2$, C(O)NHC$_{1-6}$ alkyl, C(O)N(C$_{1-6}$ alkyl)$_2$, halo, or CN, wherein each $C_{1-6}$ alkyl is optionally and independently substituted with OC$_{1-6}$ alkyl, OH, halo, or CN.

In a further embodiment, $R_{1b}$ is $C_{1-6}$ alkyl, OC$_{1-6}$ alkyl, OH, halo, or CN, wherein each $C_{1-6}$ alkyl is optionally and independently substituted with OH, CN, or halo.

In still a further embodiment, $R_{1b}$ is $C_{1-6}$ alkyl, $C_{1-6}$ alkyl-OH, or CN.

In still a further embodiment, $R_{1b}$ is methyl, CN, or CH$_2$OH.

In another embodiment, $R_{1a}$ and $R_{1b}$, together with the methylene moiety to which they are attached, form a spirocyclic ring selected from a $C_{3-7}$ cycloalkyl or 3-7 membered heterocycloalkyl, each of which is optionally and independently substituted with $C_{1-6}$ alkyl, OC$_{1-6}$ alkyl, oxo, OH, halo, CN, C(O)C$_{1-6}$ alkyl, C(O)OC$_{1-6}$ alkyl, C(O)NH$_2$, C(O)NHC$_{1-6}$ alkyl, or C(O)N(C$_{1-6}$ alkyl)$_2$, wherein each $C_{1-6}$ alkyl is optionally and independently substituted with one or substituents selected from halo, alkoxy, CN, or NH$_2$.

In another embodiment, $R_{1a}$ and $R_{1b}$, together with the methylene moiety to which they are attached, form a spirocyclic ring selected from a $C_{3-7}$ cycloalkyl or 3-7 membered heterocycloalkyl, each of which is optionally and independently substituted with oxo, OH, halo, or CN.

In a further embodiment, $R_{1a}$ and $R_{1b}$, together with the methylene moiety to which they are attached, form an unsubstituted spirocyclic ring selected from a $C_{3-7}$ cycloalkyl or 3-7 membered heterocycloalkyl.

In still a further embodiment, $R_{1a}$ and $R_{1b}$, together with the methylene moiety to which they are attached, form a

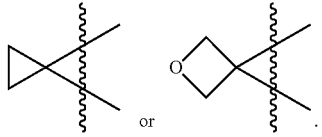

or

In another embodiment, each $R_2$ substituent is independently selected from halo, OH, $C_{1-6}$ alkyl, haloalkyl, $OC_{1-6}$ alkyl, CN, $NH_2$, $C(O)C_{1-6}$ alkyl, and $C(O)NH_2$.

In a further embodiment, each $R_2$ substituent is independently selected from halo and OH.

In one embodiment, n is 0 or 1.

In a further embodiment, n is 0.

In one embodiment, one $R_2$ substituent and $R_{1b}$, together with the phenyl group to which $R_2$ is attached and the carbon atom to which $R_{1b}$ is attached, form a bicyclic group having the general structure

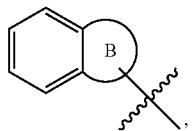

wherein Ring B is a $C_{3-7}$ cycloalkyl or 4-7 membered heterocycloalkyl, each of which is optionally substituted with one or more substituents independently selected from halo, OH, $C_{1-6}$ alkyl, haloalkyl, $OC_{1-6}$ alkyl, CN, $NH_2$, $C(O)C_{1-6}$ alkyl, $C(O)OC_{1-6}$ alkyl, or $C(O)NH_2$.

In one embodiment, Ring B is a $C_{4-6}$ cycloalkyl or 4-6 membered heterocycloalkyl, each of which is optionally substituted with one or more substituents independently selected from halo, OH, $OC_{1-6}$ alkyl, CN, or $NH_2$, $C(O)C_{1-6}$ alkyl.

In a further embodiment, Ring B is a $C_{4-5}$ cycloalkyl or 5 membered heterocycloalkyl, each of which is optionally substituted with OH.

In another embodiment, the general structure

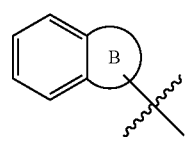

is selected from

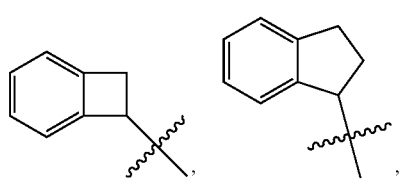

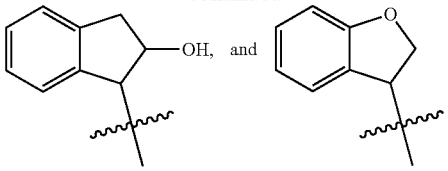

In one embodiment, each $R_3$ is independently selected from $C_{1-6}$ alkyl, a 5-6 membered heteroaryl, a 5-6 membered heterocycloalkyl, halo, CN, $NO_2$, OH, $OC_{1-6}$ alkyl, $N(C_{1-6}$ alkyl$)_2$, $NH(C_{1-6}$ alkyl), $NH_2$, $C(O)H$, $C(O)C_{1-6}$ alkyl, COOH, $C(O)OC_{1-6}$ alkyl, $C(O)NH_2$, $C(O)NH(C_{1-6}$ alkyl), $C(O)NH(C_{3-6}$ cycloalkyl), $C(O)NH(CN)$, $C(O)NH(OH)$, $C(O)N(C_{1-6}$ alkyl)(OH), $C(O)N(C_{1-6}$ alkyl$)_2$, $OC(O)OC_{1-6}$ alkyl, $OC(O)NH_2$, $OC(O)NH(C_{1-6}$ alkyl), $OC(O)N(C_{1-6}$ alkyl$)_2$, $NHC(O)NH_2$, $NHC(O)NH(C_{1-6}$ alkyl), $NHC(O)N(C_{1-6}$ alkyl$)_2$, $N(C_{1-6}$ alkyl$)C(O)NH_2$, $N(C_{1-6}$ alkyl$)C(O)NH(C_{1-6}$ alkyl), $N(C_{1-6}$ alkyl$)C(O)N(C_{1-6}$ alkyl$)_2$, $SO(C_{1-6}$ alkyl), $SONH_2$, $SONH(C_{1-6}$ alkyl), $SON(C_{1-6}$ alkyl$)_2$, $SO_2(C_{1-6}$ alkyl), $SO_2NH_2$, $SO_2NH(C_{1-6}$ alkyl), $SO_2N(C_{1-6}$ alkyl$)_2$, $N(C_{1-6}$ alkyl$)SO(C_{1-6}$ alkyl), $NHSO(C_{1-6}$ alkyl), $N(C_{1-6}$ alkyl$)SO_2(C_{1-6}$ alkyl), $NHSO_2(C_{1-6}$ alkyl), $NHSO_2NH_2$, $NHSO_2NH(C_{1-6}$ alkyl), $NHSO_2N(C_{1-6}$ alkyl$)_2$, $N(C_{1-6}$ alkyl$)SO_2NH_2$, $N(C_{1-6}$ alkyl$)SO_2NH(C_{1-6}$ alkyl), and $N(C_{1-6}$ alkyl$)SO_2N(C_{1-6}$ alkyl$)_2$, wherein each $C_{1-6}$ alkyl, heteroaryl, and heterocycloalkyl are each optionally and independently substituted with one or more R" substituents.

In another embodiment, each $R_3$ is independently selected from $C_{1-6}$ alkyl, a 5-6 membered heteroaryl, a 5-6 membered heterocycloalkyl, halo, CN, $NO_2$, OH, $OC_{1-6}$ alkyl, $N(C_{1-6}$ alkyl$)_2$, $NH(C_{1-6}$ alkyl), $NH_2$, $C(O)H$, $C(O)C_{1-6}$ alkyl, COOH, $C(O)OC_{1-6}$ alkyl, $C(O)NH_2$, $C(O)NH(C_{1-6}$ alkyl), $C(O)NH(C_{3-6}$ cycloalkyl), $C(O)NH(CN)$, $C(O)NH(OH)$, $C(O)N(C_{1-6}$ alkyl)(OH), $C(O)N(C_{1-6}$ alkyl$)_2$, $OC(O)OC_{1-6}$ alkyl, $OC(O)NH_2$, $OC(O)NH(C_{1-6}$ alkyl), $OC(O)N(C_{1-6}$ alkyl$)_2$, $NHC(O)NH_2$, $NHC(O)NH(C_{1-6}$ alkyl), $NHC(O)N(C_{1-6}$ alkyl$)_2$, $N(C_{1-6}$ alkyl$)C(O)NH_2$, $N(C_{1-6}$ alkyl$)C(O)NH(C_{1-6}$ alkyl), $N(C_{1-6}$ alkyl$)C(O)N(C_{1-6}$ alkyl$)_2$, $SO_2(C_{1-6}$ alkyl), $SO_2NH_2$, $SO_2NH(C_{1-6}$ alkyl), $SO_2N(C_{1-6}$ alkyl$)_2$, $NHSO_2(C_{1-6}$ alkyl), $N(C_{1-6}$ alkyl$)SO_2(C_{1-6}$ alkyl), $NHSO_2NH_2$, $NHSO_2NH(C_{1-6}$ alkyl), $NHSO_2N(C_{1-6}$ alkyl$)_2$, $N(C_{1-6}$ alkyl$)SO_2NH_2$, $N(C_{1-6}$ alkyl$)SO_2NH(C_{1-6}$ alkyl), and $N(C_{1-6}$ alkyl$)SO_2N(C_{1-6}$ alkyl$)_2$, wherein each $C_{1-6}$ alkyl, heteroaryl, and heterocycloalkyl are each optionally and independently substituted with one or more R" substituents.

In one embodiment, each $R_3$ is independently selected from $C_{1-6}$ alkyl, a 5-6 membered heteroaryl, a 5-6 membered heterocycloalkyl, halo, CN, OH, $OC_{1-6}$ alkyl, $NH_2$, $C(O)H$, $C(O)NH_2$, $C(O)NH(C_{1-6}$ alkyl), $C(O)NH(C_{3-6}$ cycloalkyl), $C(O)NH(CN)$, $C(O)NH(OH)$, $C(O)N(C_{1-6}$ alkyl)(OH), $C(O)N(C_{1-6}$ alkyl$)_2$, $NHC(O)NH_2$, $NHC(O)NH(C_{1-6}$ alkyl), $NHC(O)N(C_{1-6}$ alkyl$)_2$, $N(C_{1-6}$ alkyl$)C(O)NH_2$, $N(C_{1-6}$ alkyl$)C(O)NH(C_{1-6}$ alkyl), $N(C_{1-6}$ alkyl$)C(O)N(C_{1-6}$ alkyl$)_2$, $SO_2(C_{1-6}$ alkyl), $SO_2NH_2$, $SO_2NH(C_{1-6}$ alkyl), $SO_2N(C_{1-6}$ alkyl$)_2$, $N(C_{1-6}$ alkyl$)SO_2(C_{1-6}$ alkyl), $NHSO_2(C_{1-6}$ alkyl), $NHSO_2NH_2$, $NHSO_2NH(C_{1-6}$ alkyl), $NHSO_2N(C_{1-6}$ alkyl$)_2$, wherein each $C_{1-6}$ alkyl, heteroaryl, and heterocycloalkyl are each optionally and independently substituted with one or more R" substituents.

In another embodiment, each $R_3$ is independently selected from $C_{1-6}$ alkyl, a 5-6 membered heteroaryl, a 5-6 membered heterocycloalkyl, halo, CN, OH, $OC_{1-6}$ alkyl, $NH_2$, $C(O)H$, $C(O)NH_2$, $C(O)NH(C_{1-6}$ alkyl), $C(O)NH(C_{3-6}$ cycloalkyl), $C(O)NH(CN)$, $C(O)NH(OH)$, $C(O)N(C_{1-6}$ alkyl)(OH), $C(O)N(C_{1-6}$ alkyl$)_2$, $NHC(O)NH(C_{1-6}$ alkyl), $SO_2(C_{1-6}$ alkyl), NHSO$_2$(C$_{1-6}$ alkyl), wherein each C$_{1-6}$ alkyl, heteroaryl, and heterocycloalkyl are each optionally and independently substituted with one or more R" substituents.

In a further embodiment, each R$_3$ is independently selected from C$_{1-6}$ alkyl, triazolyl, oxadiazolyl, halo, CN, OH, OC$_{1-6}$ alkyl, NH$_2$, C(O)H, C(O)NH$_2$, C(O)NH(C$_{1-6}$ alkyl), C(O)NH(C$_{3-6}$ cycloalkyl), C(O)NH(CN), C(O)NH(OH), C(O)N(C$_{1-6}$ alkyl)(OH), C(O)N(C$_{1-6}$ alkyl)$_2$, NHC(O)NH(C$_{1-6}$ alkyl), SO$_2$(C$_{1-6}$ alkyl), NHSO$_2$(C$_{1-6}$ alkyl), wherein each C$_{1-6}$ alkyl, triazolyl and oxadiazolyl, are each optionally and independently substituted with one or more substituents independently selected from oxo, OH, halo, C$_{1-6}$ alkyl, NH$_2$, NHC$_{1-6}$ alkyl, and N(C$_{1-6}$ alkyl)$_2$.

In still a further embodiment, each R$_3$ substituent is independently selected from halo, CN, NH$_2$, OH, C(O)H, C(O)N(CH$_3$)$_2$, C(O)NH(CH$_3$), C(O)NH(Et), C(O)NH(isopropyl), C(O)NH(tert-butyl), C(O)NH(cyclopropyl), C(O)NCH$_3$(CN), C(O)NH(OH), C(O)NCH$_3$(OH), C(O)NH$_2$, NHC(O)NHCH$_3$, NHS(O)$_2$CH$_3$, S(O)$_2$CH$_3$, methyl, methoxy, NHS(O)$_2$CH$_2$CH$_2$N(CH$_3$)$_2$, CF$_3$, CH$_2$OH, C(CH$_3$)$_2$OH,

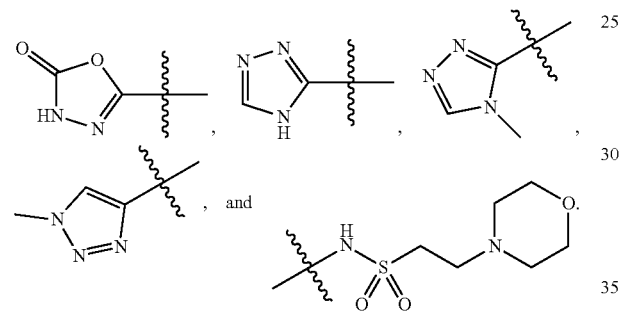

, and

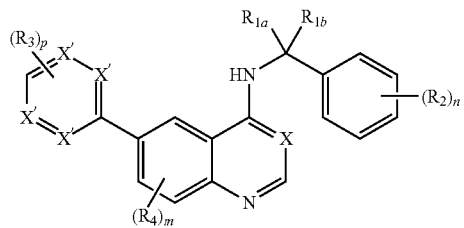

In one embodiment, the compound of Formula I is a compound of Formula Ia

Formula Ia

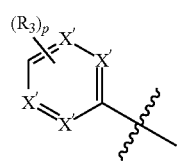

or a pharmaceutically acceptable salt or solvate thereof, or an enantiomer, a mixture of enantiomers, a mixture of two or more diastereomers, or an isotopic variant thereof,
wherein each X' is independently CH, C—R$_3$, or N.

In one embodiment, the ring

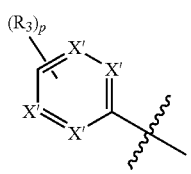

is a phenyl, pyridyl, pyrimidyl, pyrazyl, or triazyl, which is optionally substituted by R$_3$.

In a further embodiment, the ring

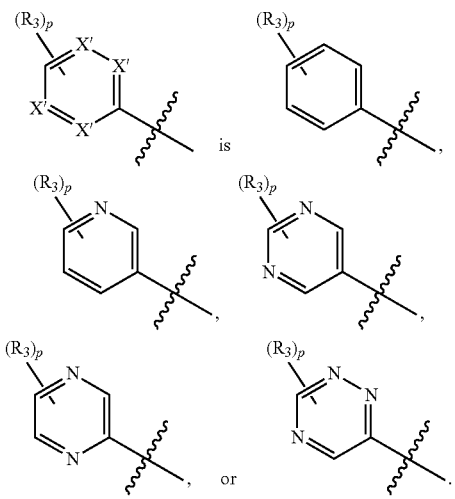

is

, or

.

In one embodiment, p is 0, 1, or 2.
In a further embodiment, p is 1 or 2.
In another further embodiment, the ring

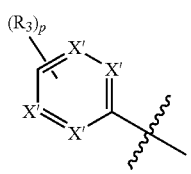

is selected from

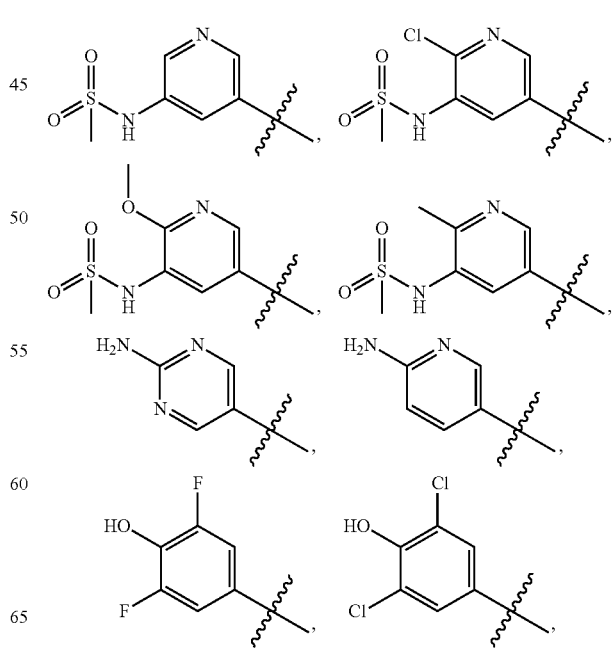

-continued
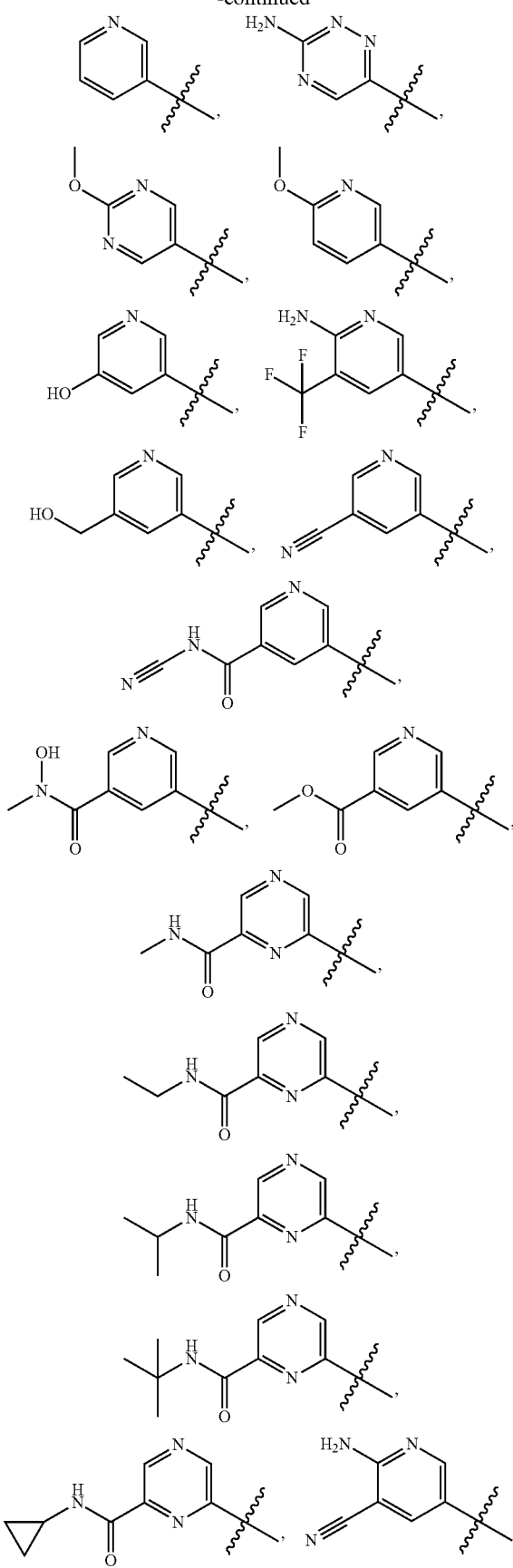
-continued
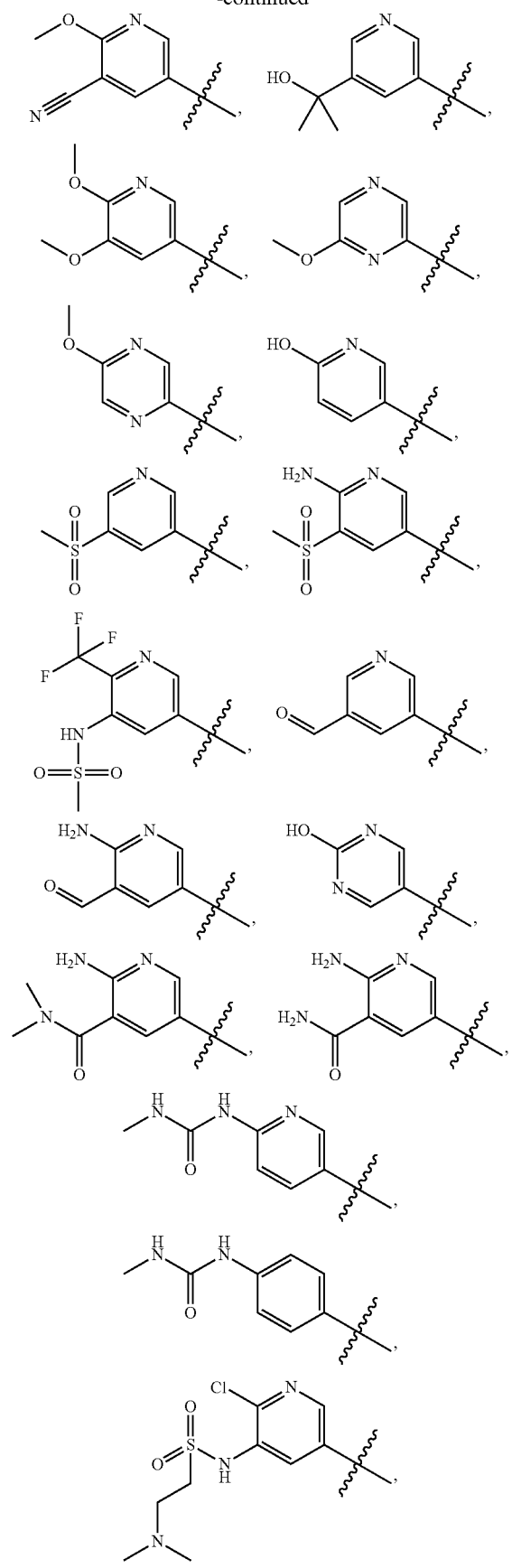

-continued

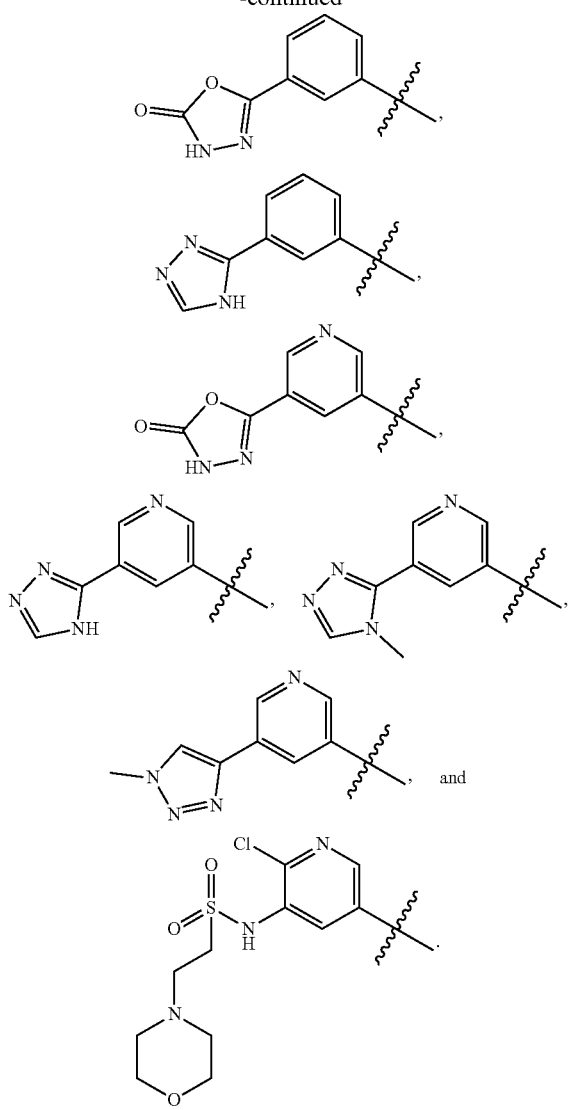

In one embodiment, two $R_3$ substituents, together with Ring A, to which they are attached, form a fused bicyclic heteroaryl, which is optionally and independently substituted with one or more R" substituents.

In a further embodiment, two $R_3$ substituents, together with Ring A, to which they are attached, form a fused bicyclic heteroaryl, which is optionally and independently substituted with one or more substituents independently selected from $C_{1-6}$ alkyl, halo, OH, $OC_{1-6}$ alkyl, oxo, CN, $NH_2$, $NH(C_{1-6}$ alkyl), and $N(C_{1-6}$ alkyl$)_2$.

In still a further embodiment, two $R_3$ substituents, together with Ring A, to which they are attached, form a fused bicyclic heteroaryl, which is optionally and independently substituted with one or more substituents independently selected from $C_{1-6}$ alkyl, oxo, and $NH_2$.

In one embodiment, the compound of Formula I is a compound of Formula Ib

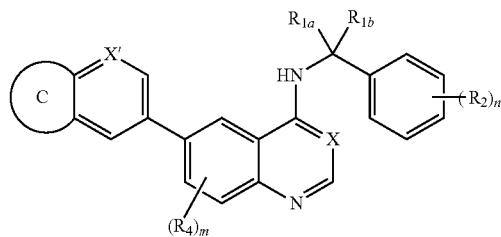

Formula Ib or a pharmaceutically acceptable salt or solvate thereof, or an enantiomer, a mixture of enantiomers, a mixture of two or more diastereomers, or an isotopic variant thereof, wherein Ring C is a phenyl, a 5-6 membered heteroaryl, or a 5-6 membered heterocyclic ring; and X' is CH, C—R", or N.

In one embodiment, Ring C of Formula Ib is a phenyl ring.

In one embodiment, Ring C of Formula Ib is a 5 membered heteroaryl or a 5 membered heterocyclic ring.

In a further embodiment, Ring C of Formula Ib is pyrrole, pyrazole, imidazole, triazole, oxazole, hydrofuran, dihydrofuran, hydropyrrole, dihydropyrrole, hydroimidazole, dihydroimidazole, hydrooxazole, dihydrooxazole, or

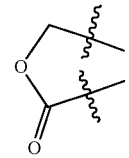

In one embodiment, the compound of Formula I is a compound of Formula Ic-1, Formula Ic-2, or Formula Ic-3:

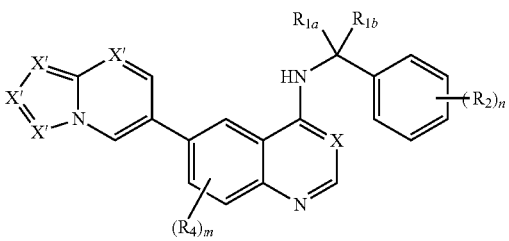

Formula Ic-1

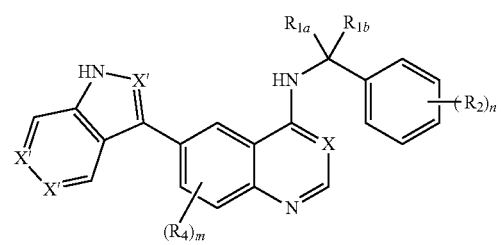

Formula Ic-2

Formula Ic-3

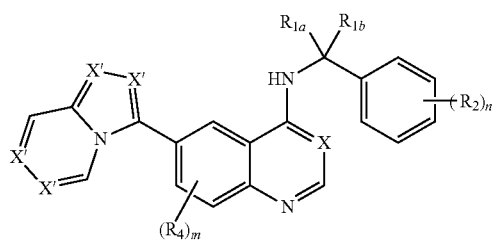

or a pharmaceutically acceptable salt or solvate thereof, or an enantiomer, a mixture of enantiomers, a mixture of two or more diastereomers, or an isotopic variant thereof,
wherein each X' is independently CH or N.

In another embodiment, the ring

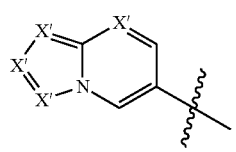

of Formula Ic-1 is

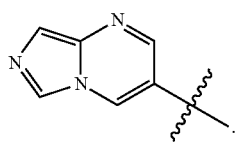

In another embodiment, the ring

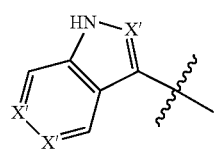

of Formula Ic-2 is

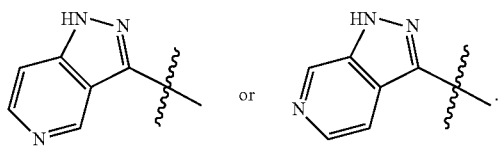 [SMILES: *c1n[nH]c2ccncc12 ; *c1n[nH]c2cnccc12]

In another embodiment, the ring

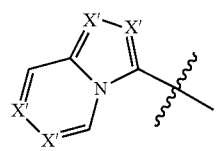

of Formula Ic-3 is

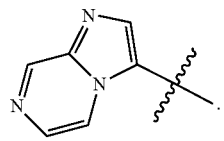 [SMILES: *c1cnc2cnccn12]

In a further embodiment, Ring A is a bicyclic group selected from

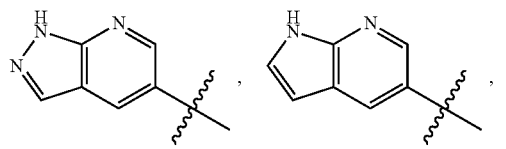
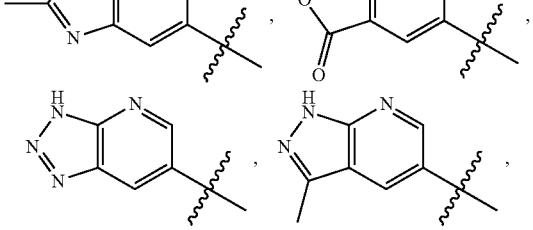
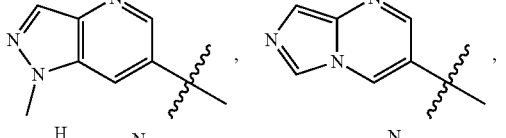
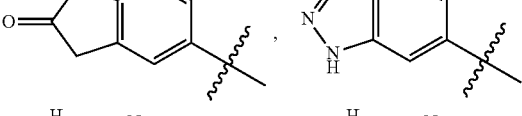
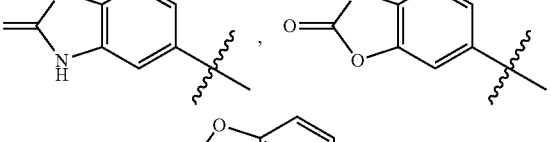
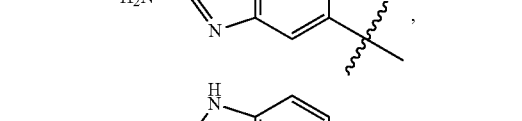
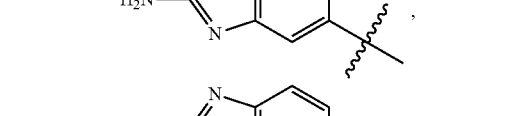
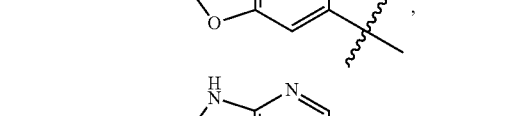
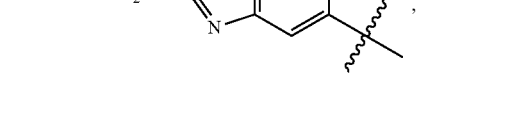

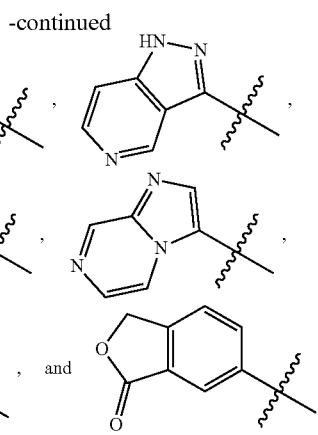

In one embodiment, m is 0.
In another embodiment, X is N.
In another embodiment, X is C—H or C—CN.
In a further embodiment, X is C—CN.

In another aspect, the disclosure includes a pharmaceutical composition comprising a compound of Formula I, Ia, Ib, Ic-1, Ic-2, or Ic-3, or a pharmaceutically acceptable salt or solvate thereof, or an enantiomer, a mixture of enantiomers, a mixture of two or more diastereomers, or an isotopic variant thereof described herein and a pharmaceutically acceptable excipient.

In another aspect, the disclosure includes a method of modulating the activity of an EGFR and/or PI3K enzyme in a biological sample, said method comprising contacting the biological sample with a compound, salt or a composition described herein.

In another aspect, the disclosure includes a method of preventing or treating an EGFR and/or PI3K mediated disease in a subject, said method comprising administering to the subject a compound, salt or a composition described herein.

In one embodiment, the EGFR and/or PI3K mediated disease is a cancer.

In a further embodiment, the cancer is selected from neoplasm, giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma, gastrinoma, cholangiocarcinoma, hepatocellular carcinoma; combined hepatocellular carcinoma and cholangiocarcinoma, trabecular adenocarcinoma, adenoid cystic carcinoma; adenocarcinoma in adenomatous polyp; adenocarcinoma, familial polyposis coli, solid carcinoma; carcinoid tumor, bronchiolo-alveolar adenocarcinoma, papillary adenocarcinoma, chromophobe carcinoma; acidophil carcinoma; oxyphilic adenocarcinoma, basophil carcinoma; clear cell adenocarcinoma, granular cell carcinoma; follicular adenocarcinoma, papillary and follicular adenocarcinoma, nonencapsulating sclerosing carcinoma; adrenal cortical carcinoma; endometroid carcinoma; skin appendage carcinoma; apocrine adenocarcinoma, sebaceous adenocarcinoma, ceruminous adenocarcinoma, mucoepidermoid carcinoma; cystadenocarcinoma, papillary cystadenocarcinoma, papillary serous cystadenocarcinoma, mucinous cystadenocarcinoma, mucinous adenocarcinoma, signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma with squamous metaplasia, thymoma, malignant; ovarian stromal tumor, thecoma, granulosa cell tumor, androblastoma, Sertoli cell carcinoma; Leydig cell tumor, lipid cell tumor, paraganglioma, extra-mammary paraganglioma, pheochromocytoma, glomangiosarcoma, amelanotic melanoma; superficial spreading melanoma; melanoma in giant pigmented nevus; epithelioid cell melanoma; blue nevus, sarcoma; fibrosarcoma, fibrous histiocytoma, myxosarcoma, liposarcoma, leiomyosarcoma, rhabdomyosarcoma, embryonal rhabdomyosarcoma, alveolar rhabdomyosarcoma, stromal sarcoma; mixed tumor; Mullerian mixed tumor; nephroblastoma, hepatoblastoma, carcinosarcoma, mesenchymoma, Brenner tumor, phyllodes tumor, synovial sarcoma; mesothelioma, dysgerminoma, embryonal carcinoma; teratoma, struma ovarii, choriocarcinoma, mesonephroma, hemangiosarcoma, hemangioendothelioma, Kaposi's sarcoma; hemangiopericytoma, lymphangiosarcoma, osteosarcoma, juxtacortical osteosarcoma, chondrosarcoma, chondroblastoma, mesenchymal chondrosarcoma, giant cell tumor of bone; Ewing's sarcoma; odontogenic tumor, ameloblastic odontosarcoma, ameloblastoma, ameloblastic fibrosarcoma, pinealoma, chordoma, glioma, ependymoma, astrocytoma, protoplasmic astrocytoma, fibrillary astrocytoma, astroblastoma, glioblastoma, oligodendroglioma, oligodendroblastoma, primitive neuroectodermal, cerebellar sarcoma; ganglioneuroblastoma, neuroblastoma, retinoblastoma, olfactory neurogenic tumor; meningioma, neurofibrosarcoma, neurilemmoma, granular cell tumor, lymphoma; Hodgkin's disease; Hodgkin's; paragranuloma, lymphoma—small lymphocytic, lymphoma—large cell, diffuse; lymphoma, follicular; mycosis fungoides, other specified non-Hodgkin's lymphomas; histiocytosis, multiple myeloma, mast cell sarcoma; immunoproliferative small intestinal disease; leukemia; lymphoid leukemia; plasma cell leukemia; erythroleukemia, lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In still a further embodiment, the cancer is selected from prostate cancer, liver cancer, renal cancer, lung cancer, breast cancer, colorectal cancer, pancreatic cancer, brain cancer, hepatocellular cancer, lymphoma, leukemia, gastric cancer, cervical cancer, ovarian cancer, thyroid cancer, melanoma, carcinomas of the head and neck, head and neck cancer, breast cancer, skin cancer and soft tissue sarcoma and/or other forms of carcinoma.

In yet a further embodiment, the cancer is selected from breast cancer, carcinomas of the head and neck, head and neck cancer, and skin cancer.

In one embodiment, the head and neck cancer is squamous head and neck cancer. In another embodiment, the breast cancer is triple negative breast cancer.

In another embodiment, the cancer is a metastatic or a malignant cancer.

In some embodiments, the compound of Formula I is a compound selected from the compounds listed in Table 1, or a pharmaceutically acceptable salt or solvate thereof, or an enantiomer, a mixture of enantiomers, a mixture of two or more diastereomers, or an isotopic variant thereof.

In one embodiment, a compound or salt described herein has a solubility that is at least 0.5 times more soluble that a compound of Formula X or X'.

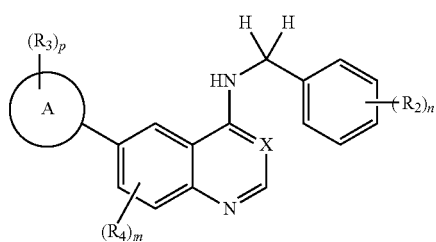

Formula X

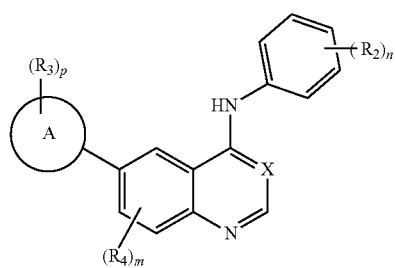

Formula X' wherein $R_2$, $R_3$, $R_4$, X, m, n, p, and Ring A are defined as for Formula I, as measured in simulated intestinal fluid pH of 6.8.

In a further embodiment, the compound or salt is at least 2 times more soluble that a compound of Formula X or X'.

In another further embodiment, the compound or salt is at least 5 times more soluble that a compound of Formula X or X'.

In still a further embodiment, the compound or salt is at least 10 times more soluble that a compound of Formula X or X'.

In one embodiment, the compound of Formula X is Comparative Compound 2, and the compound of Formula X' is Comparative Compound 1 or Comparative Compound 2:

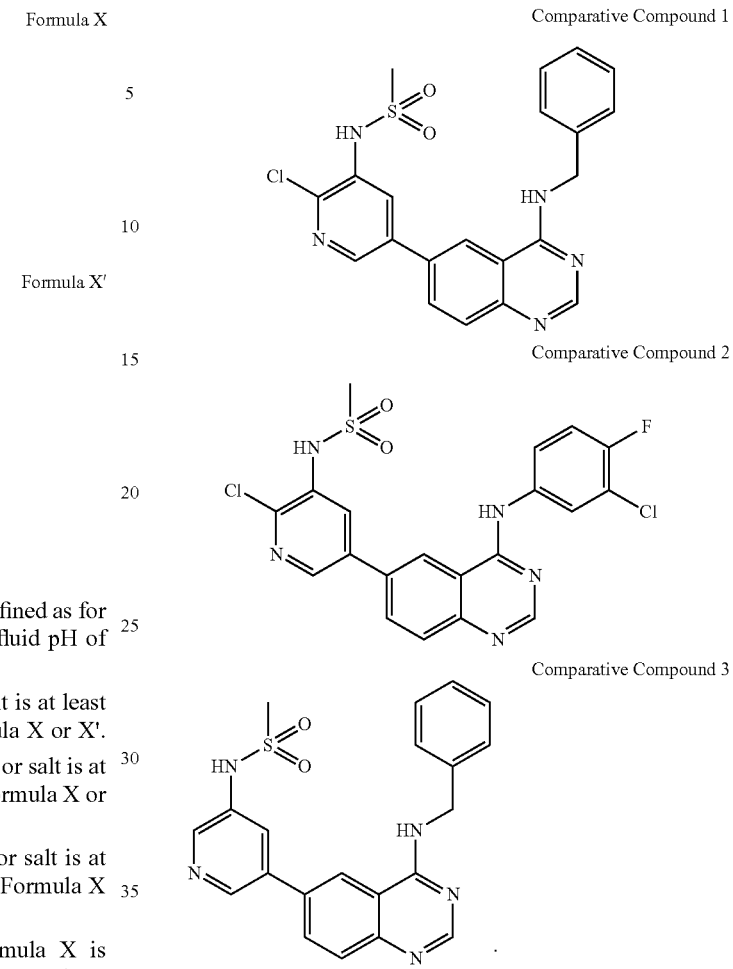

TABLE 1

Compounds of the disclosure listed by name and structure

| Cmp # | IUPAC Name | Structure |
|---|---|---|
| 1 | N-(5-(4-((1-phenylethyl)amino)quinazolin-6-yl)pyridin-3-yl)methanesulfonamide | 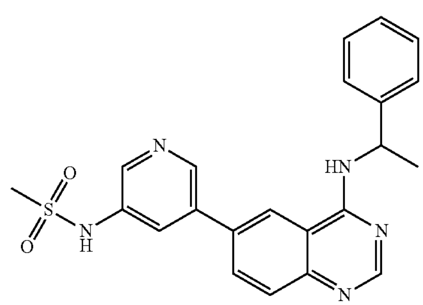 [SMILES: CC(Nc1ncnc2ccc(-c3cncc(NS(C)(=O)=O)c3)cc12)c1ccccc1] |

TABLE 1-continued

Compounds of the disclosure listed by name and structure

| Cmp # | IUPAC Name | Structure |
|---|---|---|
| 2 | N-(2-chloro-5-(4-((1-phenylethyl)amino)quinazolin-6-yl)pyridin-3-yl)methanesulfonamide | 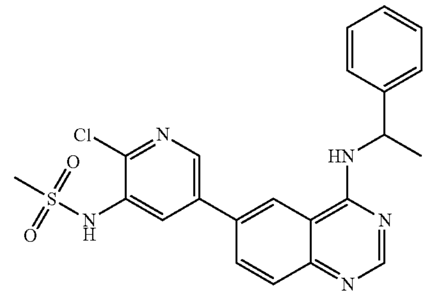 [SMILES: CC(Nc1ncnc2ccc(-c3cnc(Cl)c(NS(C)(=O)=O)c3)cc12)c1ccccc1] |
| 2R | N-(2-chloro-5-(4-((1R-phenylethyl)amino)quinazolin-6-yl)pyridin-3-yl)methanesulfonamide | 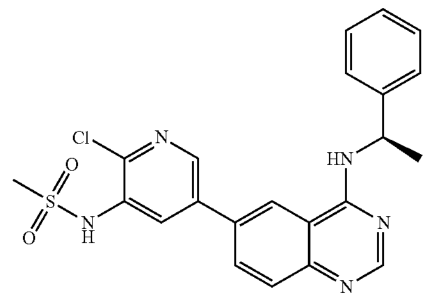 [SMILES: C[C@@H](Nc1ncnc2ccc(-c3cnc(Cl)c(NS(C)(=O)=O)c3)cc12)c1ccccc1] |
| 2S | N-(2-chloro-5-(4-((1S-phenylethyl)amino)quinazolin-6-yl)pyridin-3-yl)methanesulfonamide | 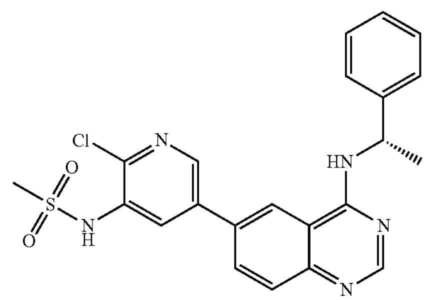 [SMILES: C[C@H](Nc1ncnc2ccc(-c3cnc(Cl)c(NS(C)(=O)=O)c3)cc12)c1ccccc1] |
| 3 | N-(2-methoxy-5-(4-((1-phenylethyl)amino)quinazolin-6-yl)pyridin-3-yl)methanesulfonamide | 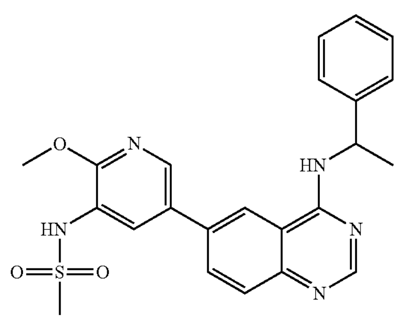 [SMILES: COc1ncc(-c2ccc3ncnc(NC(C)c4ccccc4)c3c2)cc1NS(C)(=O)=O] |
| 4 | N-(2-methyl-5-(4-((1-phenylethyl)amino)quinazolin-6-yl)pyridin-3-yl)methanesulfonamide | 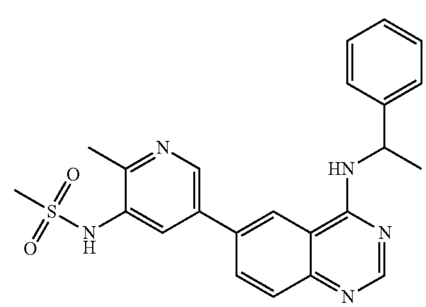 [SMILES: Cc1ncc(-c2ccc3ncnc(NC(C)c4ccccc4)c3c2)cc1NS(C)(=O)=O] |

TABLE 1-continued

Compounds of the disclosure listed by name and structure

| Cmp # | IUPAC Name | Structure |
|---|---|---|
| 5 | N-(2-chloro-5-(4-((1-phenylethyl)amino)quinazolin-6-yl)pyridin-3-yl)-2-(dimethylamino)ethane-1-sulfonamide | 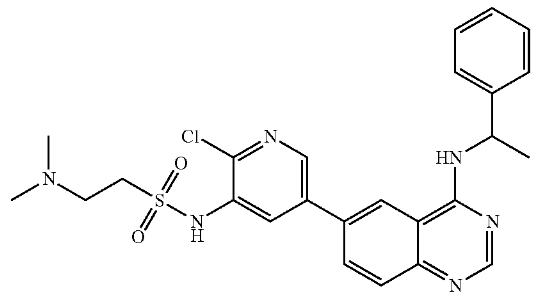 [SMILES: CC(Nc1ncnc2ccc(-c3cnc(Cl)c(NS(=O)(=O)CCN(C)C)c3)cc12)c1ccccc1] |
| 6 | N-(2-chloro-5-(4-((1-phenylethyl)amino)quinazolin-6-yl)pyridin-3-yl)-2-morpholinoethane-1-sulfonamide | 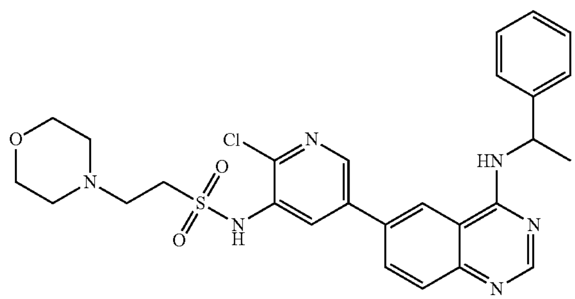 [SMILES: CC(Nc1ncnc2ccc(-c3cnc(Cl)c(NS(=O)(=O)CCN4CCOCC4)c3)cc12)c1ccccc1] |
| 7 | 6-(2-aminopyrimidin-5-yl)-N-(1-phenylethyl)quinazolin-4-amine | 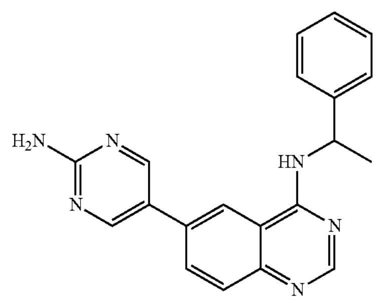 [SMILES: CC(Nc1ncnc2ccc(-c3cnc(N)nc3)cc12)c1ccccc1] |
| 8 | N-(1-phenylethyl)-6-(1H-pyrazolo[3,4-b]pyridin-5-yl)quinazolin-4-amine | 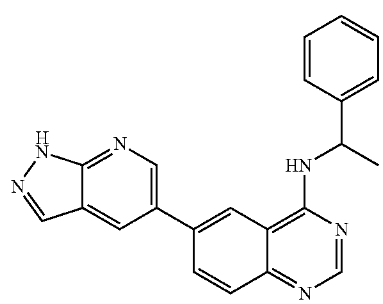 [SMILES: CC(Nc1ncnc2ccc(-c3cnc4[nH]ncc4c3)cc12)c1ccccc1] |
| 9 | N-(1-phenylethyl)-6-(1H-pyrrolo[2,3-b]pyridin-5-yl)quinazolin-4-amine | 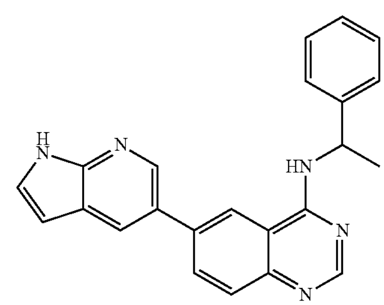 [SMILES: CC(Nc1ncnc2ccc(-c3cnc4[nH]ccc4c3)cc12)c1ccccc1] |

TABLE 1-continued

Compounds of the disclosure listed by name and structure

| Cmp # | IUPAC Name | Structure |
|---|---|---|
| 10 | 6-(2-methyl-3H-imidazo[4,5-b]pyridin-6-yl)-N-(1-phenylethyl)quinazolin-4-amine | 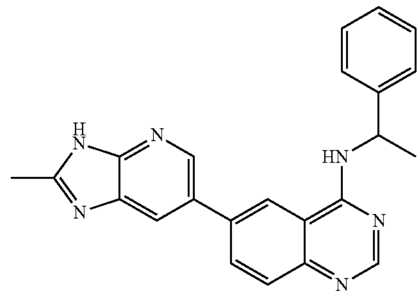 [SMILES: Cc1nc2cc(-c3ccc4ncnc(NC(C)c5ccccc5)c4c3)cnc2[nH]1] |
| 11 | 6-(6-aminopyridin-3-yl)-N-(1-phenylethyl)quinazolin-4-amine | 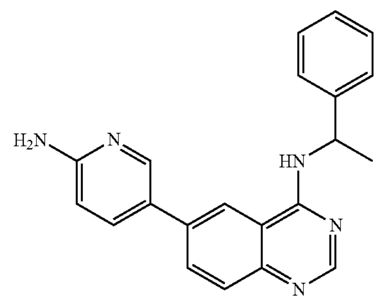 |
| 12 | 6-(3-amino-1,2,4-triazin-6-yl)-N-(1-phenylethyl)quinazolin-4-amine | 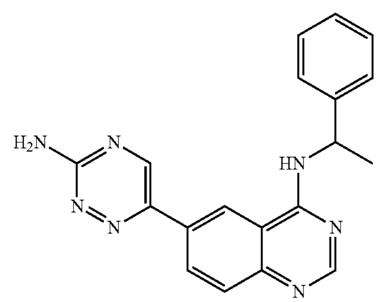 [SMILES: CC(Nc1ncnc2ccc(-c3cnc(N)nn3)cc12)c1ccccc1] |
| 13 | 6-(2-methoxypyrimidin-5-yl)-N-(1-phenylethyl)quinazolin-4-amine | 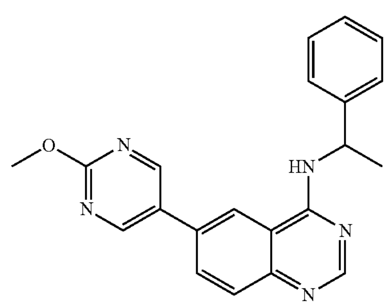 [SMILES: COc1ncc(-c2ccc3ncnc(NC(C)c4ccccc4)c3c2)cn1] |
| 14 | 6-(6-methoxypyridin-3-yl)-N-(1-phenylethyl)quinazolin-4-amine | 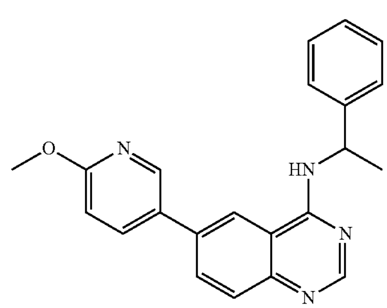 [SMILES: COc1ccc(-c2ccc3ncnc(NC(C)c4ccccc4)c3c2)cn1] |

TABLE 1-continued

Compounds of the disclosure listed by name and structure

| Cmp # | IUPAC Name |
|---|---|
| 15 | 5-(4-((1-phenylethyl)amino)quinazolin-6-yl)pyridin-3-ol |
| 16 | 6-(6-amino-5-(trifluoromethyl)pyridin-3-yl)-N-(1-phenylethyl)quinazolin-4-amine |
| 17 | (5-(4-((1-phenylethyl)amino)quinazolin-6-yl)pyridin-3-yl)methanol |
| 18 | 5-(4-((1-phenylethyl)amino)quinazolin-6-yl)nicotinonitrile |
| 19 | 2-amino-5-(4-((1-phenylethyl)amino)quinazolin-6-yl)nicotinonitrile |

TABLE 1-continued

Compounds of the disclosure listed by name and structure

| Cmp # | IUPAC Name | Structure |
|---|---|---|
| 20 | 3-(4-((1-phenylethyl)amino)quinazolin-6-yl)furo[3,4-b]pyridin-5(7H)-one | 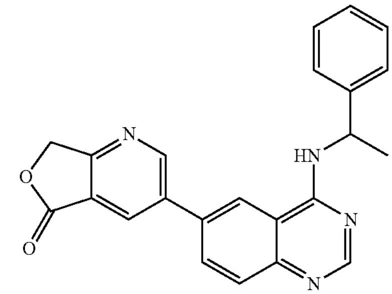 [SMILES: CC(Nc1ncnc2ccc(-c3cnc4c(c3)C(=O)OC4)cc12)c1ccccc1] |
| 21 | 2-(5-(4-((1-phenylethyl)amino)quinazolin-6-yl)pyridin-3-yl)propan-2-ol | 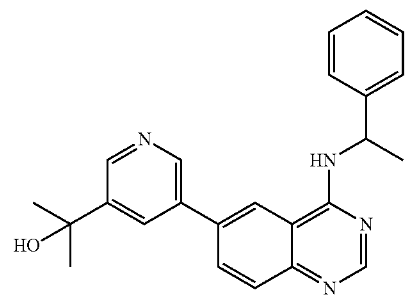 [SMILES: CC(Nc1ncnc2ccc(-c3cncc(C(C)(C)O)c3)cc12)c1ccccc1] |
| 22 | 6-(5,6-dimethoxypyridin-3-yl)-N-(1-phenylethyl)quinazolin-4-amine | 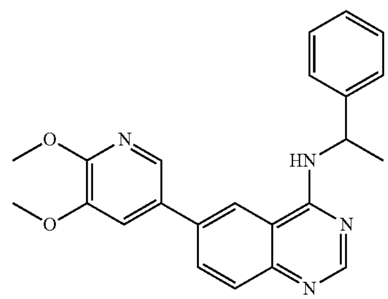 [SMILES: COc1cc(-c2ccc3ncnc(NC(C)c4ccccc4)c3c2)cnc1OC] |
| 23 | 6-(6-methoxypyrazin-2-yl)-N-(1-phenylethyl)quinazolin-4-amine | 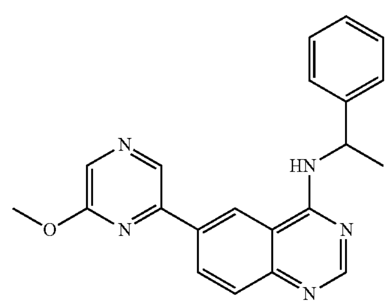 [SMILES: COc1cncc(-c2ccc3ncnc(NC(C)c4ccccc4)c3c2)n1] |
| 24 | 6-(3H-[1,2,3]triazolo[4,5-b]pyridin-6-yl)-N-(1-phenylethyl)quinazolin-4-amine | 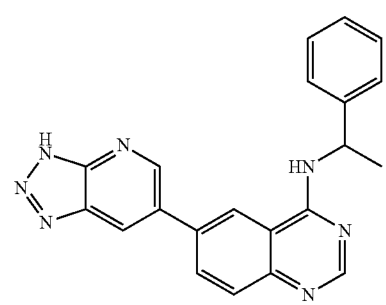 [SMILES: CC(Nc1ncnc2ccc(-c3cnc4[nH]nnc4c3)cc12)c1ccccc1] |

TABLE 1-continued

Compounds of the disclosure listed by name and structure

| Cmp # | IUPAC Name | Structure |
|---|---|---|
| 25 | 6-(3-methyl-1H-pyrazolo[3,4-b]pyridin-5-yl)-N-(1-phenylethyl)quinazolin-4-amine | 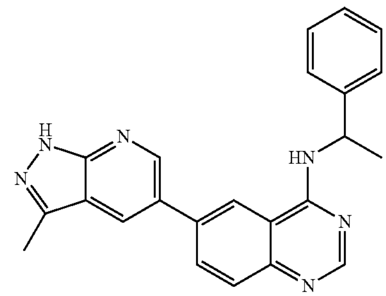 [SMILES: Cc1n[nH]c2ncc(-c3ccc4ncnc(NC(C)c5ccccc5)c4c3)cc12] |
| 26 | 6-(5-methoxypyrazin-2-yl)-N-(1-phenylethyl)quinazolin-4-amine | 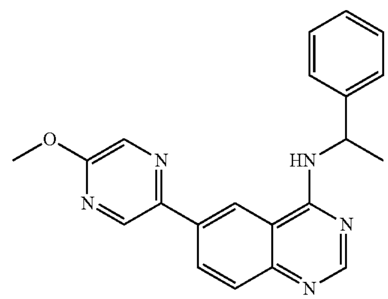 [SMILES: COc1cnc(-c2ccc3ncnc(NC(C)c4ccccc4)c3c2)cn1] |
| 27 | 6-(1-methyl-1H-pyrazolo[4,3-b]pyridin-6-yl)-N-(1-phenylethyl)quinazolin-4-amine | 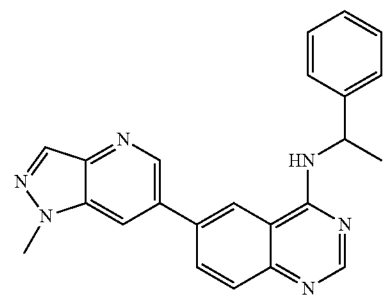 [SMILES: CC(Nc1ncnc2ccc(-c3cnc4cnn(C)c4c3)cc12)c1ccccc1] |
| 28 | N-(1-phenylethyl)-6-(1H-pyrazolo[4,3-b]pyridin-6-yl)quinazolin-4-amine | 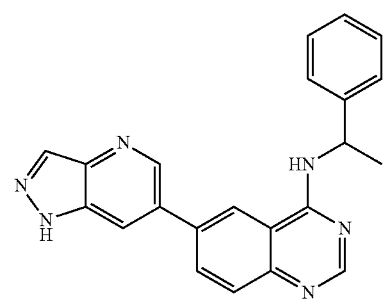 [SMILES: CC(Nc1ncnc2ccc(-c3cnc4cn[nH]c4c3)cc12)c1ccccc1] |
| 29 | 5-(4-((1-phenylethyl)amino)quinazolin-6-yl)pyridin-2-ol | 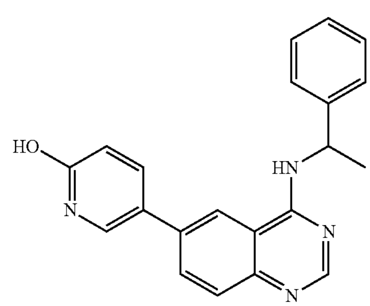 [SMILES: CC(Nc1ncnc2ccc(-c3ccc(O)nc3)cc12)c1ccccc1] |

TABLE 1-continued

Compounds of the disclosure listed by name and structure

| Cmp # | IUPAC Name | Structure |
|---|---|---|
| 30 | 6-(5-(methylsulfonyl)pyridin-3-yl)-N-(1-phenylethyl) quinazolin-4-amine | 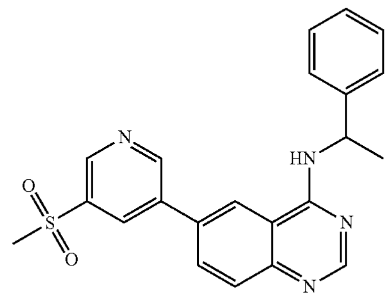 [SMILES: CC(Nc1ncnc2ccc(-c3cncc(S(C)(=O)=O)c3)cc12)c1ccccc1] |
| 31 | 6-(6-amino-5-(methylsulfonyl)pyridin-3-yl)-N-(1-phenylethyl)quinazolin-4-amine | 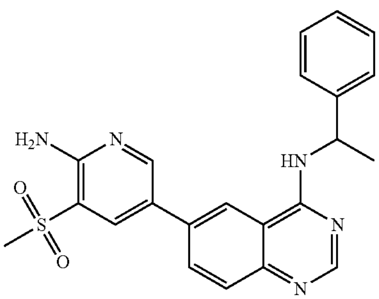 [SMILES: CC(Nc1ncnc2ccc(-c3cnc(N)c(S(C)(=O)=O)c3)cc12)c1ccccc1] |
| 32 | 5-(4-((1-phenylethyl)amino)quinazolin-6-yl)nicotinaldehyde | 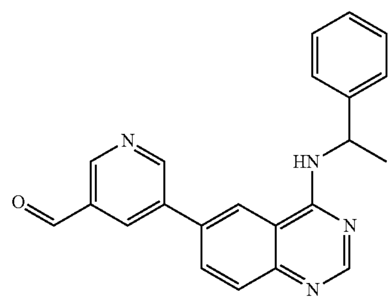 [SMILES: CC(Nc1ncnc2ccc(-c3cncc(C=O)c3)cc12)c1ccccc1] |
| 33 | 2-amino-5-(4-((1-phenylethyl)amino)quinazolin-6-yl)nicotinaldehyde | 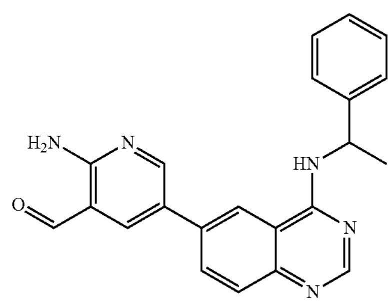 [SMILES: CC(Nc1ncnc2ccc(-c3cnc(N)c(C=O)c3)cc12)c1ccccc1] |
| 34 | 6-(imidazo[1,5-a]pyrimidin-3-yl)-N-(1-phenylethyl)quinazolin-4-amine | 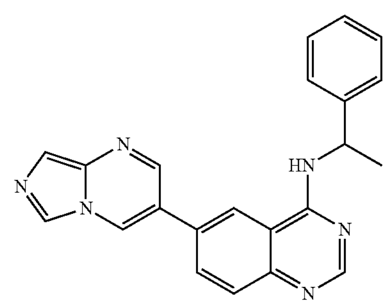 [SMILES: CC(Nc1ncnc2ccc(-c3cnc4cncn4c3)cc12)c1ccccc1] |

TABLE 1-continued

Compounds of the disclosure listed by name and structure

| Cmp # | IUPAC Name |
|---|---|
| 35 | 5-(4-((1-phenylethyl)amino)quinazolin-6-yl)pyrimidin-2-ol |
| 36 | 2-amino-N,N-dimethyl-5-(4-((1-phenylethyl)amino)quinazolin-6-yl)nicotinamide |
| 37 | 2-amino-5-(4-((1-phenylethyl)amino)quinazolin-6-yl)nicotinamide |
| 38 | 5-(4-((1-phenylethyl)amino)quinazolin-6-yl)-1,3-dihydro-2H-pyrrolo[2,3-b]pyridin-2-one |
| 39 | 6-(4-((1-phenylethyl)amino)quinazolin-6-yl)-1,3-dihydro-2H-imidazo[4,5-b]pyridin-2-one |

TABLE 1-continued

Compounds of the disclosure listed by name and structure

| Cmp # | IUPAC Name | Structure |
|---|---|---|
| 40 | 6-(4-((1-phenylethyl)amino)quinazolin-6-yl)oxazolo[4,5-b]pyridin-2(3H)-one | 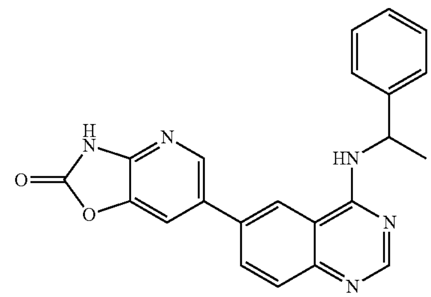 [SMILES: CC(Nc1ncnc2ccc(-c3cnc4[nH]c(=O)oc4c3)cc12)c1ccccc1] |
| 41 | 5-(4-((1-phenylethyl)amino)quinazolin-6-yl)benzo[d]oxazol-2-amine | 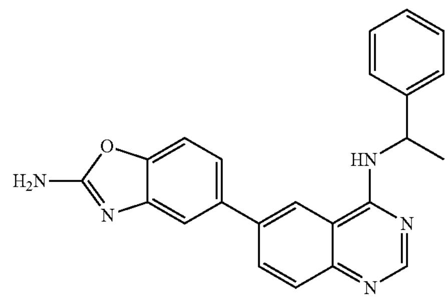 [SMILES: CC(Nc1ncnc2ccc(-c3ccc4oc(N)nc4c3)cc12)c1ccccc1] |
| 42 | 6-(2-amino-1H-benzo[d]imidazol-5-yl)-N-(1-phenylethyl)quinazolin-4-amine | 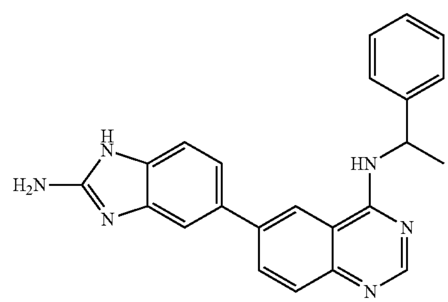 [SMILES: CC(Nc1ncnc2ccc(-c3ccc4[nH]c(N)nc4c3)cc12)c1ccccc1] |
| 43 | 6-(4-((1-phenylethyl)amino)quinazolin-6-yl)benzo[d]oxazol-2-amine | 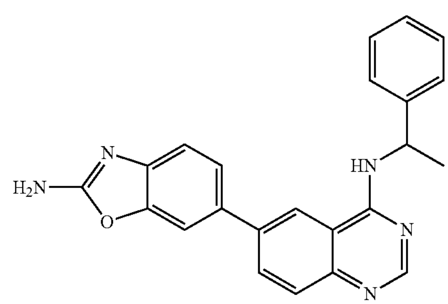 [SMILES: CC(Nc1ncnc2ccc(-c3ccc4nc(N)oc4c3)cc12)c1ccccc1] |
| 44 | 6-(2-amino-3H-imidazo[4,5-b]pyridin-6-yl)-N-(1-phenylethyl)quinazolin-4-amine | 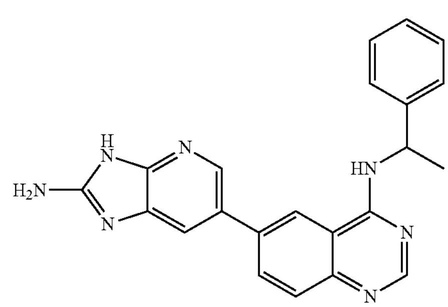 [SMILES: CC(Nc1ncnc2ccc(-c3cnc4[nH]c(N)nc4c3)cc12)c1ccccc1] |

TABLE 1-continued

Compounds of the disclosure listed by name and structure

| Cmp # | IUPAC Name | Structure |
|---|---|---|
| 45 | 1-methyl-3-(5-(4-((1-phenylethyl)amino)quinazolin-6-yl)pyridin-2-yl)urea | 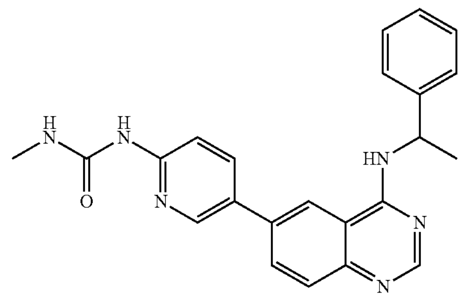 |
| 46 | 1-methyl-3-(4-(4-((1-phenylethyl)amino)quinazolin-6-yl)phenyl)urea | 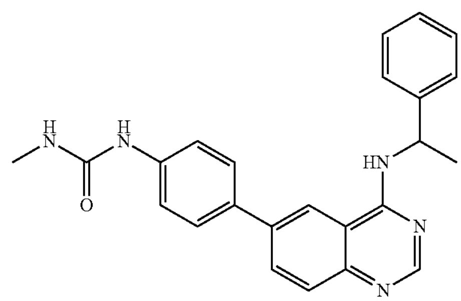 [SMILES: CNC(=O)Nc1ccc(-c2ccc3ncnc(NC(C)c4ccccc4)c3c2)cc1] |
| 47 | N-(5-(3-cyano-4-((1-phenylethyl)amino)quinolin-6-yl)pyridin-3-yl)methanesulfonamide | 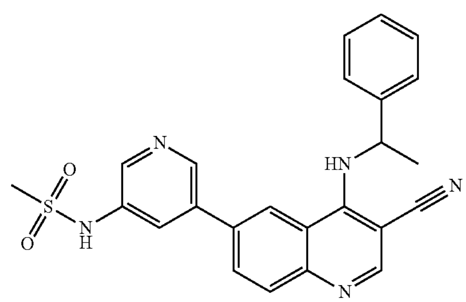 [SMILES: CC(Nc1c(C#N)cnc2ccc(-c3cncc(NS(C)(=O)=O)c3)cc12)c1ccccc1] |
| 48 | N-(2-chloro-5-(3-cyano-4-((1-phenylethyl)amino)quinolin-6-yl)pyridin-3-yl)methanesulfonamide | 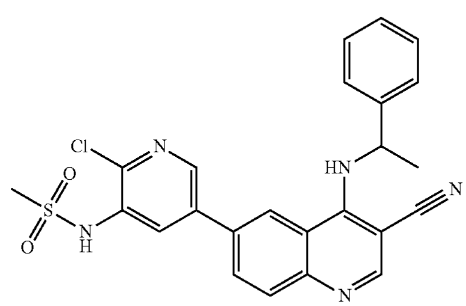 [SMILES: CC(Nc1c(C#N)cnc2ccc(-c3cnc(Cl)c(NS(C)(=O)=O)c3)cc12)c1ccccc1] |
| 48R | N-(2-chloro-5-(3-cyano-4-((1R-phenylethyl)amino)quinolin-6-yl)pyridin-3-yl)methanesulfonamide | 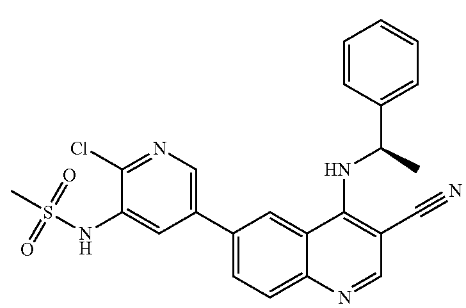 [SMILES: C[C@@H](Nc1c(C#N)cnc2ccc(-c3cnc(Cl)c(NS(C)(=O)=O)c3)cc12)c1ccccc1] |

TABLE 1-continued

Compounds of the disclosure listed by name and structure

| Cmp # | IUPAC Name | Structure |
|---|---|---|
| 48S | N-(2-chloro-5-(3-cyano-4-((1S-phenylethyl)amino)quinolin-6-yl)pyridin-3-yl)methanesulfonamide | 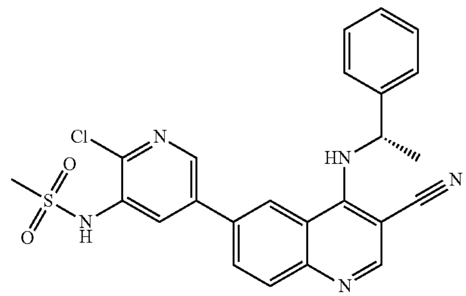 [SMILES: C[C@H](Nc1c(C#N)cnc2ccc(-c3cnc(Cl)c(NS(C)(=O)=O)c3)cc12)c1ccccc1] |
| 49 | N-(5-(3-cyano-4-((1-phenylethyl)amino)quinolin-6-yl)-2-methoxypyridin-3-yl)methanesulfonamide | 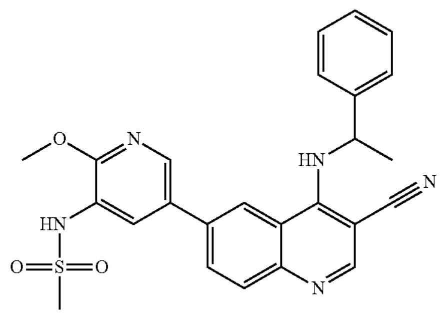 [SMILES: COc1ncc(-c2ccc3ncc(C#N)c(NC(C)c4ccccc4)c3c2)cc1NS(C)(=O)=O] |
| 50 | N-(5-(3-cyano-4-((1-phenylethyl)amino)quinolin-6-yl)-2-methylpyridin-3-yl)methanesulfonamide | 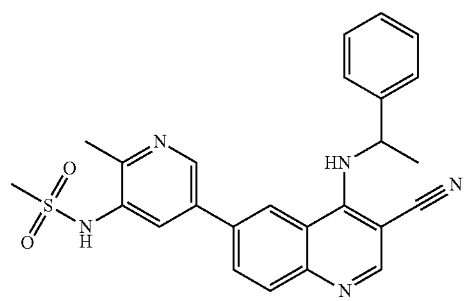 [SMILES: Cc1ncc(-c2ccc3ncc(C#N)c(NC(C)c4ccccc4)c3c2)cc1NS(C)(=O)=O] |
| 51 | N-(2-chloro-5-(3-cyano-4-((1-phenylethyl)amino)quinolin-6-yl)pyridin-3-yl)-2-(dimethylamino)ethane-1-sulfonamide | 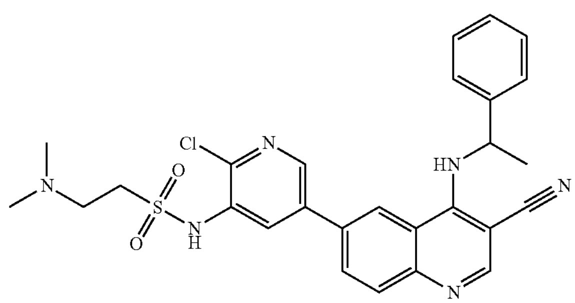 [SMILES: CC(Nc1c(C#N)cnc2ccc(-c3cnc(Cl)c(NS(=O)(=O)CCN(C)C)c3)cc12)c1ccccc1] |
| 52 | N-(2-chloro-5-(3-cyano-4-((1-phenylethyl)amino)quinolin-6-yl)pyridin-3-yl)-2-morpholinoethane-1-sulfonamide | 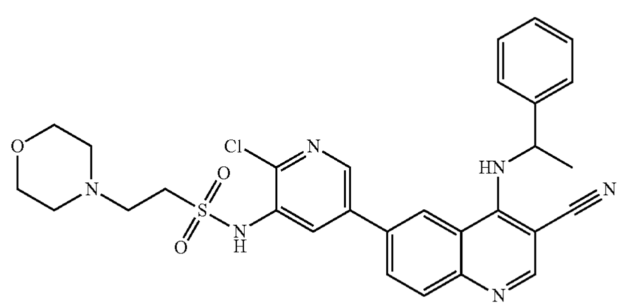 [SMILES: CC(Nc1c(C#N)cnc2ccc(-c3cnc(Cl)c(NS(=O)(=O)CCN4CCOCC4)c3)cc12)c1ccccc1] |

TABLE 1-continued

Compounds of the disclosure listed by name and structure

| Cmp # | IUPAC Name | Structure |
|---|---|---|
| 53 | 6-(2-aminopyrimidin-5-yl)-4-((1-phenylethyl)amino)quinoline-3-carbonitrile | 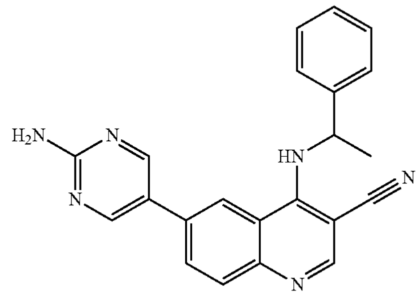 |
| 53R | (R)-6-(2-aminopyrimidin-5-yl)-4-((1-phenylethyl)amino)quinoline-3-carbonitrile | 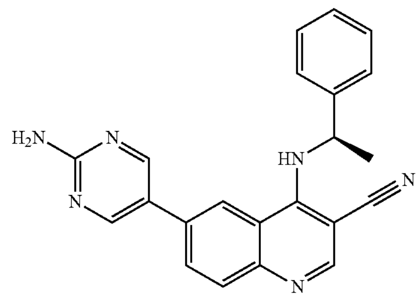 [SMILES: C[C@@H](Nc1c(C#N)cnc2ccc(-c3cnc(N)nc3)cc12)c1ccccc1] |
| 54 | 4-((1-phenylethyl)amino)-6-(1H-pyrazolo[3,4-b]pyridin-5-yl)quinoline-3-carbonitrile | 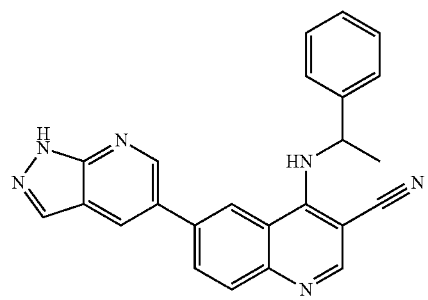 [SMILES: CC(Nc1c(C#N)cnc2ccc(-c3cnc4[nH]ncc4c3)cc12)c1ccccc1] |
| 54R | (R)-4-((1-phenylethyl)amino)-6-(1H-pyrazolo[3,4-b]pyridin-5-yl)quinoline-3-carbonitrile | 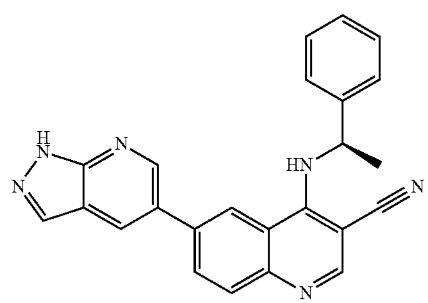 [SMILES: C[C@@H](Nc1c(C#N)cnc2ccc(-c3cnc4[nH]ncc4c3)cc12)c1ccccc1] |
| 55 | 4-((1-phenylethyl)amino)-6-(1H-pyrrolo[2,3-b]pyridin-5-yl)quinoline-3-carbonitrile | 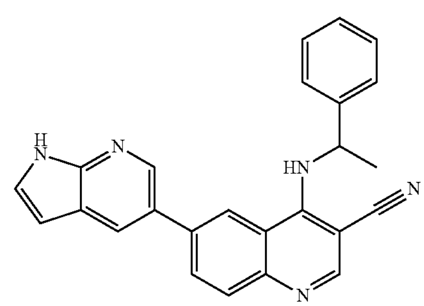 [SMILES: CC(Nc1c(C#N)cnc2ccc(-c3cnc4[nH]ccc4c3)cc12)c1ccccc1] |

TABLE 1-continued

Compounds of the disclosure listed by name and structure

| Cmp # | IUPAC Name |
|---|---|
| 56 | 6-(2-methyl-3H-imidazo[4,5-b]pyridin-6-yl)-4-((1-phenylethyl)amino)quinoline-3-carbonitrile |
| 57 | 6-(6-aminopyridin-3-yl)-4-((1-phenylethyl)amino)quinoline-3-carbonitrile |
| 58 | 6-(3-amino-1,2,4-triazin-6-yl)-4-((1-phenylethyl)amino)quinoline-3-carbonitrile |
| 59 | 6-(2-methoxypyrimidin-5-yl)-4-((1-phenylethyl)amino)quinoline-3-carbonitrile |
| 60 | 6-(6-methoxypyridin-3-yl)-4-((1-phenylethyl)amino)quinoline-3-carbonitrile |

TABLE 1-continued

Compounds of the disclosure listed by name and structure

| Cmp # | IUPAC Name | Structure |
|---|---|---|
| 61 | 6-(5-hydroxypyridin-3-yl)-4-(((1-phenylethyl)amino)quinoline-3-carbonitrile | 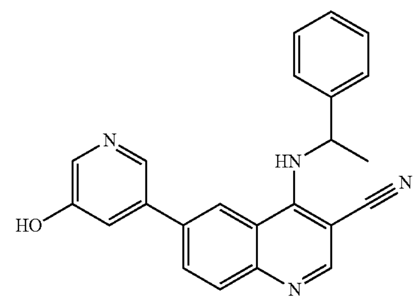 [SMILES: CC(Nc1c(C#N)cnc2ccc(-c3cncc(O)c3)cc12)c1ccccc1] |
| 62 | 6-(6-amino-5-(trifluoromethyl)pyridin-3-yl)-4-((1-phenylethyl)amino)quinoline-3-carbonitrile | 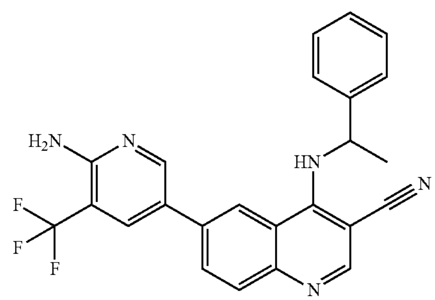 [SMILES: CC(Nc1c(C#N)cnc2ccc(-c3cnc(N)c(C(F)(F)F)c3)cc12)c1ccccc1] |
| 63 | 6-(5-(hydroxymethyl)pyridin-3-yl)-4-((1-phenylethyl)amino)quinoline-3-carbonitrile | 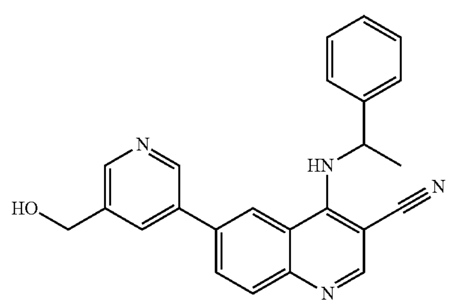 [SMILES: CC(Nc1c(C#N)cnc2ccc(-c3cncc(CO)c3)cc12)c1ccccc1] |
| 64 | 6-(5-cyanopyridin-3-yl)-4-((1-phenylethyl)amino)quinoline-3-carbonitrile | 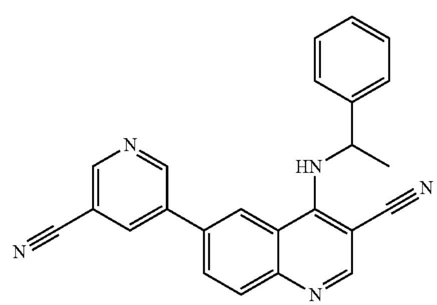 [SMILES: CC(Nc1c(C#N)cnc2ccc(-c3cncc(C#N)c3)cc12)c1ccccc1] |
| 65 | 6-(6-amino-5-cyanopyridin-3-yl)-4-((1-phenylethyl)amino)quinoline-3-carbonitrile | 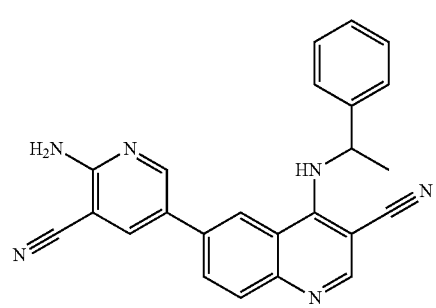 [SMILES: CC(Nc1c(C#N)cnc2ccc(-c3cnc(N)c(C#N)c3)cc12)c1ccccc1] |

TABLE 1-continued

Compounds of the disclosure listed by name and structure

| Cmp # | IUPAC Name | Structure |
|---|---|---|
| 66 | 6-(5-oxo-5,7-dihydrofuro[3,4-b]pyridin-3-yl)-4-((1-phenylethyl)amino)quinoline-3-carbonitrile | 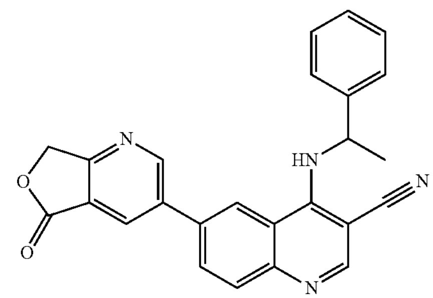 [SMILES: CC(Nc1c(C#N)cnc2ccc(-c3cnc4c(c3)C(=O)OC4)cc12)c1ccccc1] |
| 67 | 6-(5-(2-hydroxypropan-2-yl)pyridin-3-yl)-4-((l-phenylethyl)amino)quinoline-3-carbonitrile | 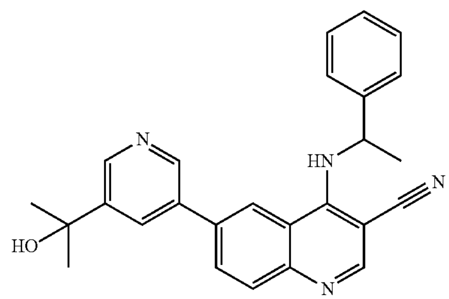 [SMILES: CC(Nc1c(C#N)cnc2ccc(-c3cncc(C(C)(C)O)c3)cc12)c1ccccc1] |
| 68 | 6-(5,6-dimethoxypyridin-3-yl)-4-((1-phenylethyl)amino)quinoline-3-carbonitrile | 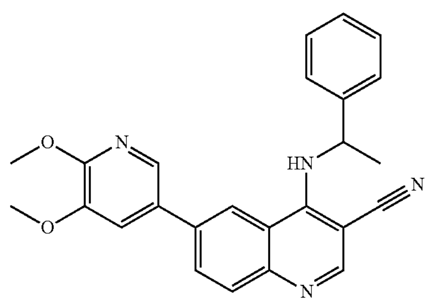 [SMILES: COc1cc(-c2ccc3ncc(C#N)c(NC(C)c4ccccc4)c3c2)cnc1OC] |
| 69 | 6-(6-methoxypyrazin-2-yl)-4-((1-phenylethyl)amino)quinoline-3-carbonitrile | 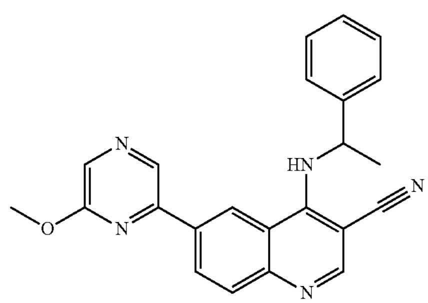 [SMILES: COc1cncc(-c2ccc3ncc(C#N)c(NC(C)c4ccccc4)c3c2)n1] |
| 70 | 6-(3H-[1,2,3]triazolo[4,5-b]pyridin-6-yl)-4-((1-phenylethyl)amino)quinoline-3-carbonitrile | 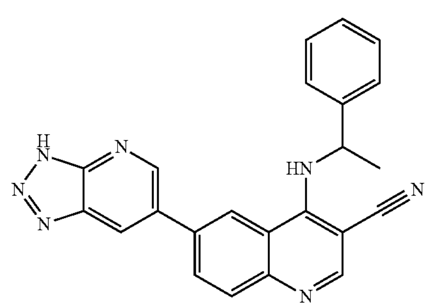 [SMILES: CC(Nc1c(C#N)cnc2ccc(-c3cnc4[nH]nnc4c3)cc12)c1ccccc1] |

TABLE 1-continued

Compounds of the disclosure listed by name and structure

| Cmp # | IUPAC Name | Structure |
|---|---|---|
| 71 | 6-(3-methyl-1H-pyrazolo[3,4-b]pyridin-5-yl)-4-((1-phenylethyl)amino)quinoline-3-carbonitrile | 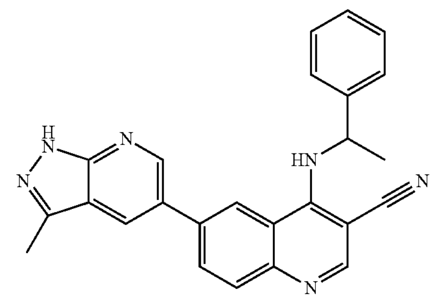 [SMILES: Cc1n[nH]c2ncc(-c3ccc4ncc(C#N)c(NC(C)c5ccccc5)c4c3)cc12] |
| 72 | 6-(5-methoxypyrazin-2-yl)-4-((1-phenylethyl)amino)quinoline-3-carbonitrile | 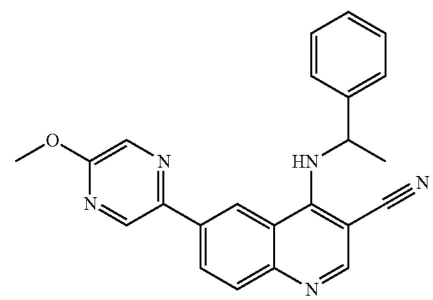 [SMILES: COc1cnc(-c2ccc3ncc(C#N)c(NC(C)c4ccccc4)c3c2)cn1] |
| 73 | 6-(1-methyl-1H-pyrazolo[4,3-b]pyridin-6-yl)-4-((1-phenylethyl)amino)quinoline-3-carbonitrile | 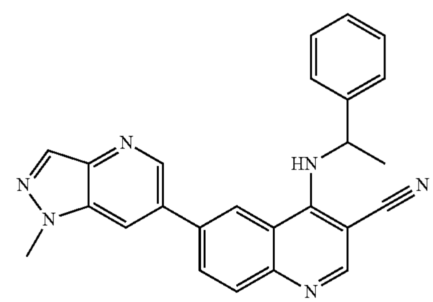 [SMILES: CC(Nc1c(C#N)cnc2ccc(-c3cnc4cnn(C)c4c3)cc12)c1ccccc1] |
| 74 | 4-((1-phenylethyl)amino)-6-(1H-pyrazolo[4,3-b]pyridin-6-yl)quinoline-3-carbonitrile | 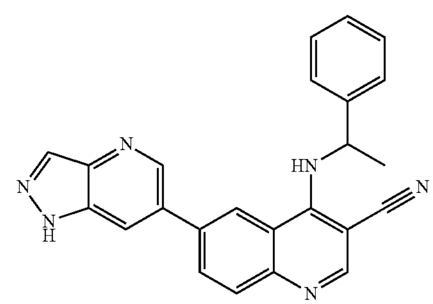 [SMILES: CC(Nc1c(C#N)cnc2ccc(-c3cnc4cn[nH]c4c3)cc12)c1ccccc1] |
| 75 | 6-(6-hydroxypyridin-3-yl)-4-((1-phenylethyl)amino)quinoline-3-carbonitrile | 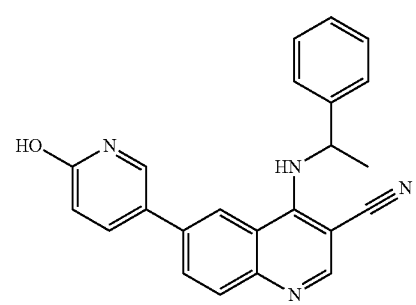 |

TABLE 1-continued

Compounds of the disclosure listed by name and structure

| Cmp # | IUPAC Name | Structure |
|---|---|---|
| 76 | 6-(5-(methylsulfonyl)pyridin-3-yl)-4-((1-phenylethyl)amino)quinoline-3-carbonitrile | 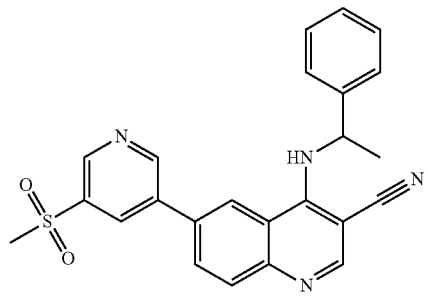 [SMILES: CC(Nc1c(C#N)cnc2ccc(-c3cncc(S(C)(=O)=O)c3)cc12)c1ccccc1] |
| 77 | 6-(6-amino-5-(methylsulfonyl)pyridin-3-yl)-4-((1-phenylethyl)amino)quinoline-3-carbonitrile | 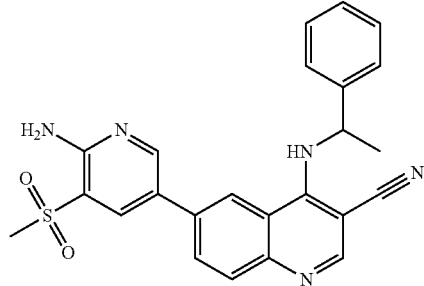 [SMILES: CC(Nc1c(C#N)cnc2ccc(-c3cnc(N)c(S(C)(=O)=O)c3)cc12)c1ccccc1] |
| 78 | 6-(5-formylpyridin-3-yl)-4-((1-phenylethyl)amino)quinoline-3-carbonitrile | 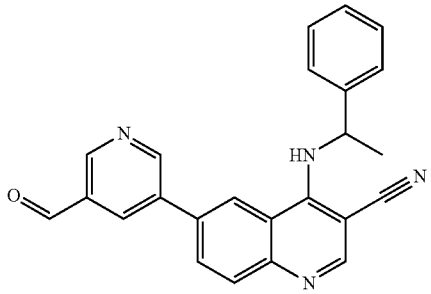 [SMILES: CC(Nc1c(C#N)cnc2ccc(-c3cncc(C=O)c3)cc12)c1ccccc1] |
| 79 | 6-(6-amino-5-formylpyridin-3-yl)-4-((1-phenylethyl)amino)quinoline-3-carbonitrile | 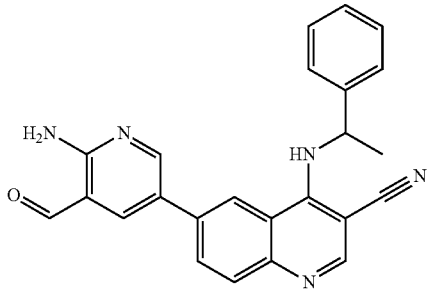 [SMILES: CC(Nc1c(C#N)cnc2ccc(-c3cnc(N)c(C=O)c3)cc12)c1ccccc1] |
| 80 | 6-(imidazo[1,5-a]pyrimidin-3-yl)-4-((1-phenylethyl)amino)quinoline-3-carbonitrile | 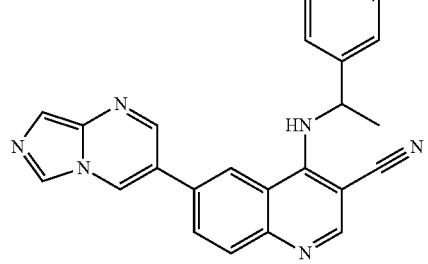 |

TABLE 1-continued

Compounds of the disclosure listed by name and structure

| Cmp # | IUPAC Name | Structure |
|---|---|---|
| 81 | 6-(2-hydroxypyrimidin-5-yl)-4-((1-phenylethyl)amino)quinoline-3-carbonitrile | 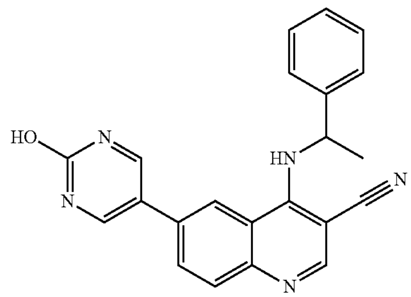 [SMILES: CC(Nc1c(C#N)cnc2ccc(-c3cnc(O)nc3)cc12)c1ccccc1] |
| 82 | 2-amino-5-(3-cyano-4-((1-phenylethyl)amino)quinolin-6-yl)-N,N-dimethylnicotinamide | 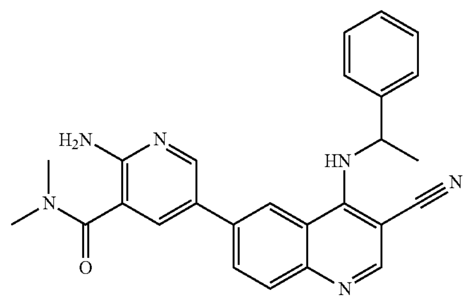 [SMILES: CC(Nc1c(C#N)cnc2ccc(-c3cnc(N)c(C(=O)N(C)C)c3)cc12)c1ccccc1] |
| 83 | 2-amino-5-(3-cyano-4-((1-phenylethyl)amino)quinolin-6-yl)nicotinamide | 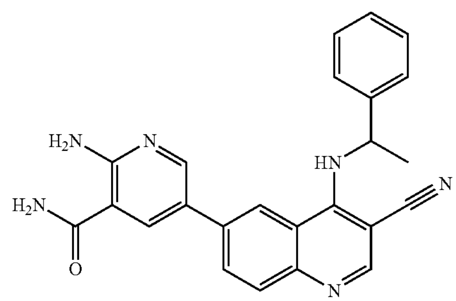 [SMILES: CC(Nc1c(C#N)cnc2ccc(-c3cnc(N)c(C(N)=O)c3)cc12)c1ccccc1] |
| 84 | 6-(2-oxo-2,3-dihydro-1H-pyrrolo[2,3-b]pyridin-5-yl)-4-((1-phenylethyl)amino)quinoline-3-carbonitrile | 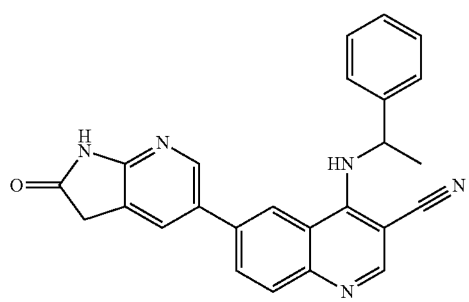 [SMILES: CC(Nc1c(C#N)cnc2ccc(-c3cnc4c(c3)CC(=O)N4)cc12)c1ccccc1] |
| 85 | 6-(2-oxo-2,3-dihydro-1H-imidazo[4,5-b]pyridin-6-yl)-4-((1-phenylethyl)amino)quinoline-3-carbonitrile | 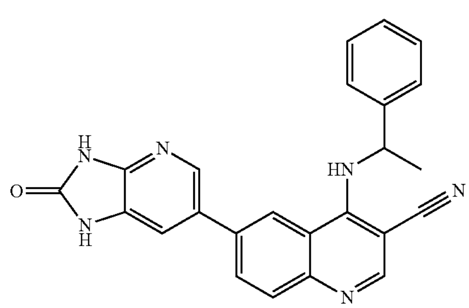 [SMILES: CC(Nc1c(C#N)cnc2ccc(-c3cnc4[nH]c(=O)[nH]c4c3)cc12)c1ccccc1] |

TABLE 1-continued

Compounds of the disclosure listed by name and structure

| Cmp # | IUPAC Name | Structure |
|---|---|---|
| 86 | 6-(2-oxo-2,3-dihydrooxazolo[4,5-b]pyridin-6-yl)-4-((1-phenylethyl)amino)quinoline-3-carbonitrile | 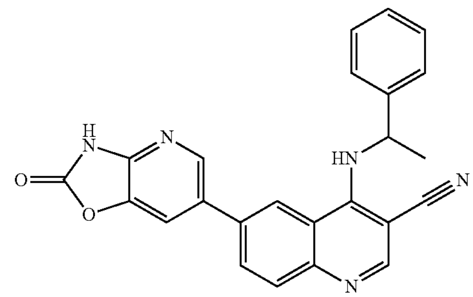 [SMILES: CC(Nc1c(C#N)cnc2ccc(-c3cnc4[nH]c(=O)oc4c3)cc12)c1ccccc1] |
| 87 | 6-(2-aminobenzo[d]oxazol-5-yl)-4-((1-phenylethyl)amino)quinoline-3-carbonitrile | 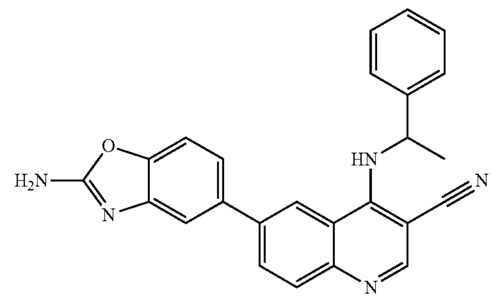 [SMILES: CC(Nc1c(C#N)cnc2ccc(-c3ccc4oc(N)nc4c3)cc12)c1ccccc1] |
| 88 | 6-(2-amino-1H-benzo[d]imidazol-5-yl)-4-((1-phenylethyl)amino)quinoline-3-carbonitrile | 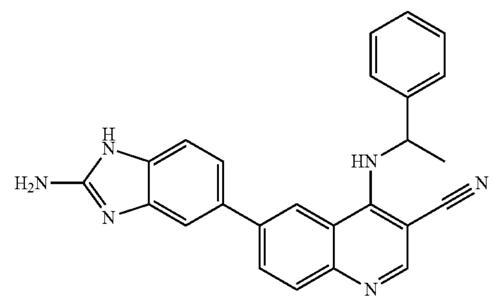 [SMILES: CC(Nc1c(C#N)cnc2ccc(-c3ccc4[nH]c(N)nc4c3)cc12)c1ccccc1] |
| 89 | 6-(2-aminobenzo[d]oxazol-6-yl)-4-((1-phenylethyl)amino)quinoline-3-carbonitrile | 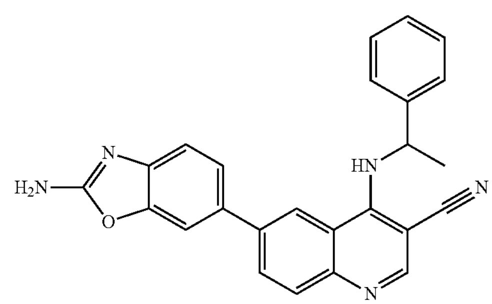 [SMILES: CC(Nc1c(C#N)cnc2ccc(-c3ccc4nc(N)oc4c3)cc12)c1ccccc1] |
| 90 | 6-(2-amino-3H-imidazo[4,5-b]pyridin-6-yl)-4-(1-phenylethyl)amino)quinoline-3-carbonitrile | 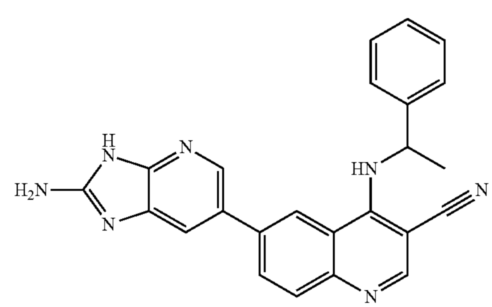 [SMILES: CC(Nc1c(C#N)cnc2ccc(-c3cnc4[nH]c(N)nc4c3)cc12)c1ccccc1] |

TABLE 1-continued

Compounds of the disclosure listed by name and structure

| Cmp # | IUPAC Name | Structure |
|---|---|---|
| 91 | 1-(5-(3-cyano-4-((1-phenylethyl)amino)quinolin-6-yl)pyridin-2-yl)-3-methylurea | 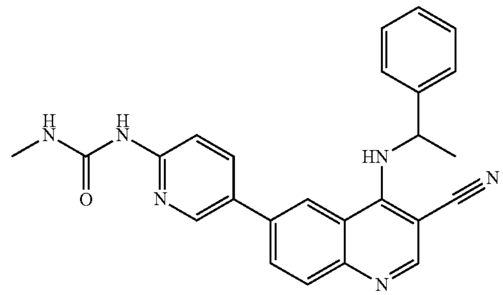 [SMILES: CNC(=O)Nc1ccc(-c2ccc3ncc(C#N)c(NC(C)c4ccccc4)c3c2)cn1] |
| 92 | 1-(4-(3-cyano-4-((1-phenylethyl)amino)quinolin-6-yl)phenyl)-3-methylurea | 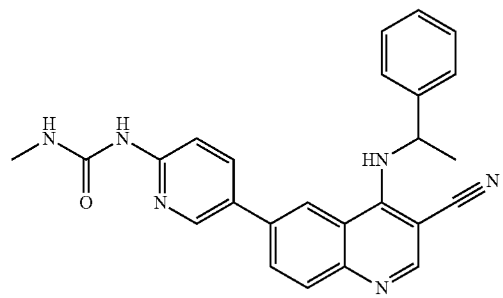 [SMILES: CNC(=O)Nc1ccc(-c2ccc3ncc(C#N)c(NC(C)c4ccccc4)c3c2)cn1] |
| 93 | N-(2-chloro-5-(3-cyano-4-((1-(2-fluorophenyl)ethyl)amino)quinolin-6-yl)pyridin-3-yl)methanesulfonamide | 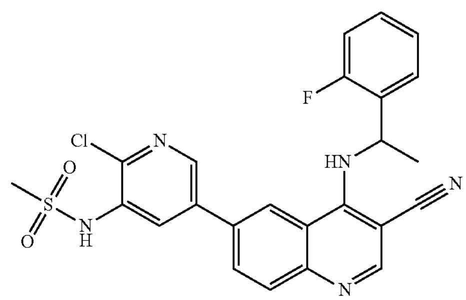 [SMILES: CC(Nc1c(C#N)cnc2ccc(-c3cnc(Cl)c(NS(C)(=O)=O)c3)cc12)c1ccccc1F] |
| 94 | N-(2-chloro-5-(3-cyano-4-((1-(2-hydroxyphenyl)ethyl)amino)quinolin-6-yl)pyridin-3-yl)methanesulfonamide | 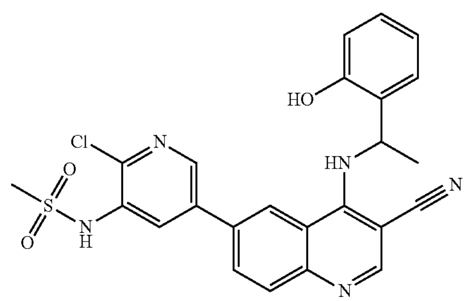 [SMILES: CC(Nc1c(C#N)cnc2ccc(-c3cnc(Cl)c(NS(C)(=O)=O)c3)cc12)c1ccccc1O] |
| 95 | N-(2-chloro-5-(3-cyano-4-((1-(3-fluorophenyl)ethyl)amino)quinolin-6-yl)pyridin-3-yl)methanesulfonamide | 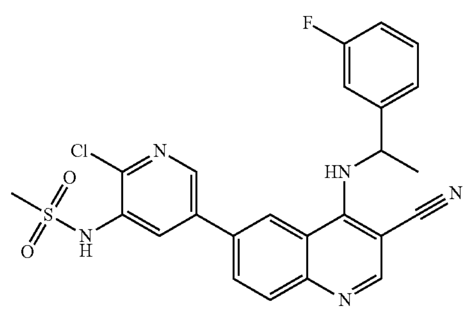 [SMILES: CC(Nc1c(C#N)cnc2ccc(-c3cnc(Cl)c(NS(C)(=O)=O)c3)cc12)c1cccc(F)c1] |

TABLE 1-continued

Compounds of the disclosure listed by name and structure

| Cmp # | IUPAC Name | Structure |
|---|---|---|
| 96 | N-(2-chloro-5-(3-cyano-4-((1-(3-hydroxyphenyl)ethyl)amino)quinolin-6-yl)pyridin-3-yl)methanesulfonamide | 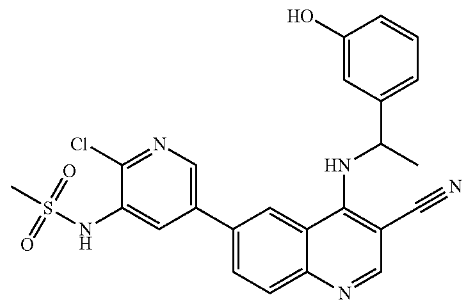 [SMILES: CC(Nc1c(C#N)cnc2ccc(-c3cnc(Cl)c(NS(C)(=O)=O)c3)cc12)c1cccc(O)c1] |
| 97 | N-(2-chloro-5-(3-cyano-4-((1-(4-fluorophenyl)ethyl)amino)quinolin-6-yl)pyridin-3-yl)methanesulfonamide | 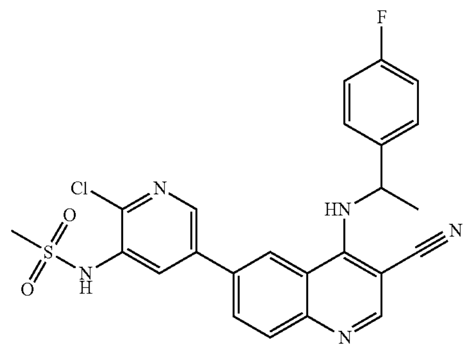 |
| 97R | N-(2-chloro-5-(3-cyano-4-((1R-(4-fluorophenyl)ethyl)amino)quinolin-6-yl)pyridin-3-yl)methanesulfonamide | 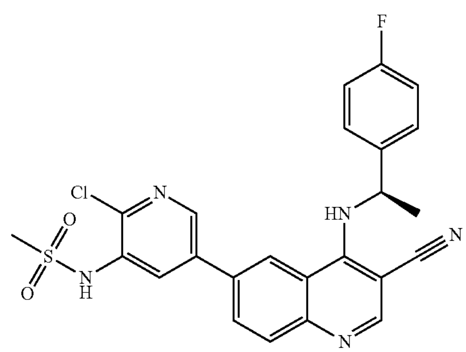 |
| 97S | N-(2-chloro-5-(3-cyano-4-((1S-(4-fluorophenyl)ethyl)amino)quinolin-6-yl)pyridin-3-yl)methanesulfonamide | 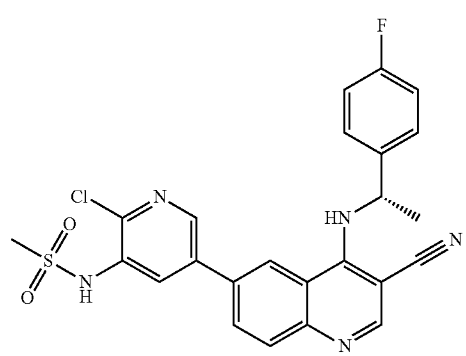 [SMILES: CC(Nc1c(C#N)cnc2ccc(-c3cnc(Cl)c(NS(C)(=O)=O)c3)cc12)c1ccc(F)cc1] |

TABLE 1-continued

Compounds of the disclosure listed by name and structure

| Cmp # | IUPAC Name |
|---|---|
| 98 | N-(2-chloro-5-(3-cyano-4-((1-(4-hydroxyphenyl)ethyl)amino)quinolin-6-yl)pyridin-3-yl)methanesulfonamide |
| 99 | N-(2-chloro-5-(3-cyano-4-((cyano(phenyl)methyl)amino)quinolin-6-yl)pyridin-3-yl)methanesulfonamide |
| 100 | N-(5-(4-(bicyclo[4.2.0]octa-1(6),2,4-trien-7-ylamino)-3-cyanoquinolin-6-yl)-2-chloropyridin-3-yl)methanesulfonamide |
| 101 | N-(2-chloro-5-(3-cyano-4-((2,3-dihydro-1H-inden-1-yl)amino)quinolin-6-yl)pyridin-3-yl)methanesulfonamide |
| 102 | N-(2-chloro-5-(3-cyano-4-((2,3-dihydrobenzofuran-3-yl)amino)quinolin-6-yl)pyridin-3-yl)methanesulfonamide |

TABLE 1-continued

Compounds of the disclosure listed by name and structure

| Cmp # | IUPAC Name | Structure |
|---|---|---|
| 103 | N-(2-chloro-5-(3-cyano-4-((2-hydroxy-2,3-dihydro-1H-inden-1-yl)amino)quinolin-6-yl)pyridin-3-yl)methanesulfonamide | 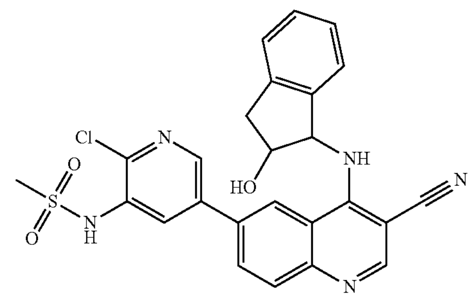 [SMILES: CS(=O)(=O)Nc1cc(-c2ccc3ncc(C#N)c(NC4c5ccccc5CC4O)c3c2)cnc1Cl] |
| 104 | N-(2-chloro-5-(3-cyano-4-((2-hydroxy-1-phenylethyl)amino)quinolin-6-yl)pyridin-3-yl)methanesulfonamide | 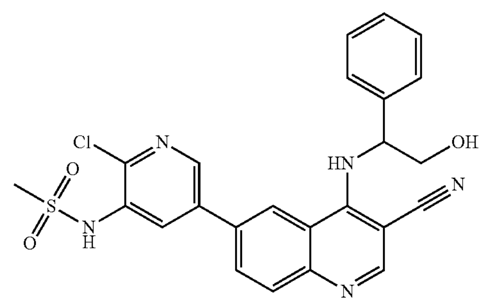 [SMILES: CS(=O)(=O)Nc1cc(-c2ccc3ncc(C#N)c(NC(CO)c4ccccc4)c3c2)cnc1Cl] |
| 104S | (S)-N-(2-chloro-5-(3-cyano-4-((2-hydroxy-1-phenylethyl)amino)quinolin-6-yl)pyridin-3-yl)methanesulfonamide | 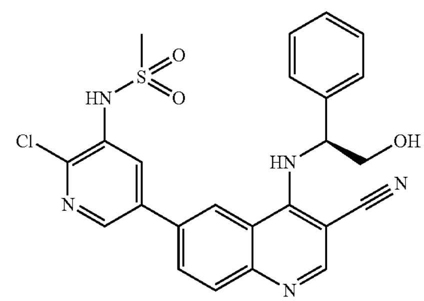 [SMILES: CS(=O)(=O)Nc1cc(-c2ccc3ncc(C#N)c(N[C@H](CO)c4ccccc4)c3c2)cnc1Cl] |
| 104R | (R)-N-(2-chloro-5-(3-cyano-4-((2-hydroxy-1-phenylethyl)amino)quinolin-6-yl)pyridin-3-yl)methanesulfonamide | 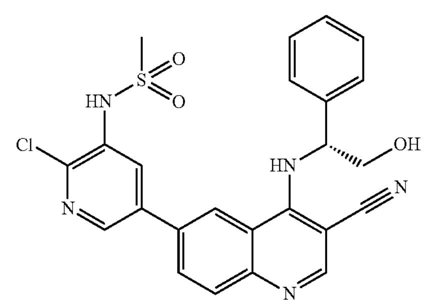 [SMILES: CS(=O)(=O)Nc1cc(-c2ccc3ncc(C#N)c(N[C@@H](CO)c4ccccc4)c3c2)cnc1Cl] |
| 105 | N-(2-chloro-5-(3-cyano-4-((3-phenyloxetan-3-yl)amino)quinolin-6-yl)pyridin-3-yl)methanesulfonamide | 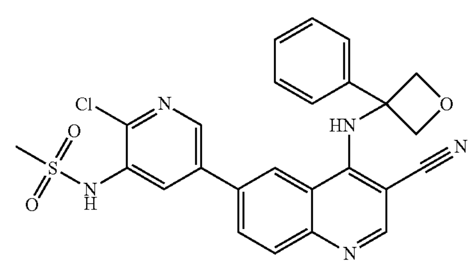 [SMILES: CS(=O)(=O)Nc1cc(-c2ccc3ncc(C#N)c(NC4(c5ccccc5)COC4)c3c2)cnc1Cl] |

TABLE 1-continued

Compounds of the disclosure listed by name and structure

| Cmp # | IUPAC Name |
|---|---|
| 106 | N-(2-chloro-5-(3-cyano-4-((1-phenylcyclopropyl)amino)quinolin-6-yl)pyridin-3-yl)methanesulfonamide |
| 107 | N-(2-chloro-5-(4-((1-(2-fluorophenyl)ethyl)amino)quinazolin-6-yl)pyridin-3-yl)methanesulfonamide |
| 108 | N-(2-chloro-5-(4-((1-(2-hydroxyphenyl)ethyl)amino)quinazolin-6-yl)pyridin-3-yl)methanesulfonamide |
| 109 | N-(2-chloro-5-(4-((1-(3-fluorophenyl)ethyl)amino)quinazolin-6-yl)pyridin-3-yl)methanesulfonamide |
| 110 | N-(2-chloro-5-(4-((1-(3-hydroxyphenyl)ethyl)amino)quinazolin-6-yl)pyridin-3-yl)methanesulfonamide |

TABLE 1-continued

Compounds of the disclosure listed by name and structure

| Cmp # | IUPAC Name | Structure |
|---|---|---|
| 111 | N-(2-chloro-5-(4-((1-(4-fluorophenyl)ethyl)amino)quinazolin-6-yl)pyridin-3-yl)methanesulfonamide | 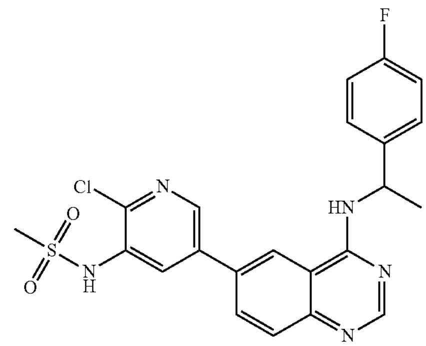 [SMILES: CC(Nc1ncnc2ccc(-c3cnc(Cl)c(NS(C)(=O)=O)c3)cc12)c1ccc(F)cc1] |
| 111R | N-(2-chloro-5-(4-((1R-(4-fluorophenyl)ethyl)amino)quinazolin-6-yl)pyridin-3-yl)methanesulfonamide | 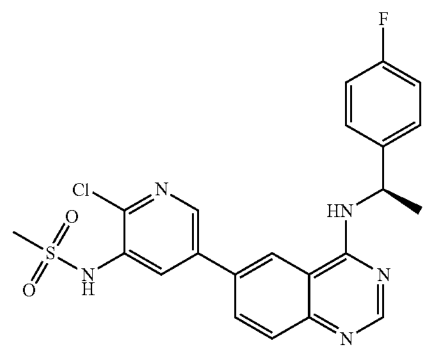 [SMILES: C[C@@H](Nc1ncnc2ccc(-c3cnc(Cl)c(NS(C)(=O)=O)c3)cc12)c1ccc(F)cc1] |
| 111S | N-(2-chloro-5-(4-((1S-(4-fluorophenyl)ethyl)amino)quinazolin-6-yl)pyridin-3-yl)methanesulfonamide | 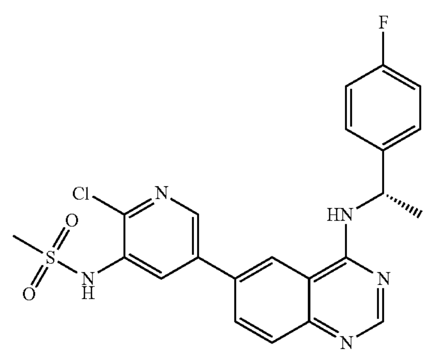 [SMILES: C[C@H](Nc1ncnc2ccc(-c3cnc(Cl)c(NS(C)(=O)=O)c3)cc12)c1ccc(F)cc1] |
| 112 | N-(2-chloro-5-(4-((1-(4-hydroxyphenyl)ethyl)amino)quinazolin-6-yl)pyridin-3-yl)methanesulfonamide | 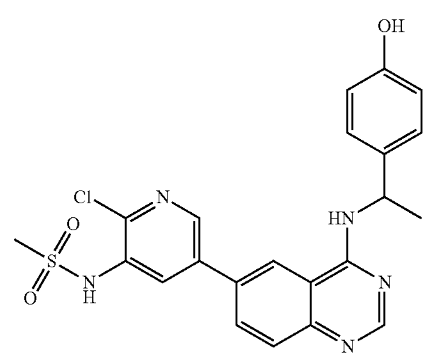 [SMILES: CC(Nc1ncnc2ccc(-c3cnc(Cl)c(NS(C)(=O)=O)c3)cc12)c1ccc(O)cc1] |

TABLE 1-continued

Compounds of the disclosure listed by name and structure

| Cmp # | IUPAC Name | Structure |
|---|---|---|
| 113 | N-(2-chloro-5-(4-((cyano(phenyl)methyl)amino)quinazolin-6-yl)pyridin-3-yl)methanesulfonamide | 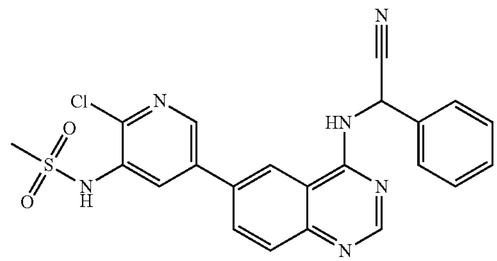 [SMILES: CS(=O)(=O)Nc1cc(-c2ccc3ncnc(NC(C#N)c4ccccc4)c3c2)cnc1Cl] |
| 114 | N-(5-(4-(bicyclo[4.2.0]octa-1(6),2,4-trien-7-ylamino)quinazolin-6-yl)-2-chloropyridin-3-yl)methanesulfonamide | 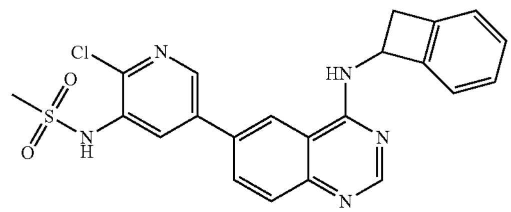 [SMILES: CS(=O)(=O)Nc1cc(-c2ccc3ncnc(NC4Cc5ccccc54)c3c2)cnc1Cl] |
| 115 | N-(2-chloro-5-(4-((2,3-dihydro-1H-inden-1-yl)amino)quinazolin-6-yl)pyridin-3-yl)methanesulfonamide | 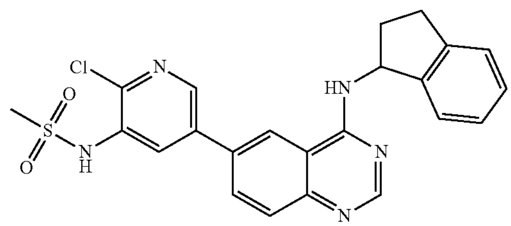 [SMILES: CS(=O)(=O)Nc1cc(-c2ccc3ncnc(NC4CCc5ccccc54)c3c2)cnc1Cl] |
| 116 | N-(2-chloro-5-(4-((2,3-dihydrobenzofuran-3-yl)amino)quinazolin-6-yl)pyridin-3-yl)methanesulfonamide | 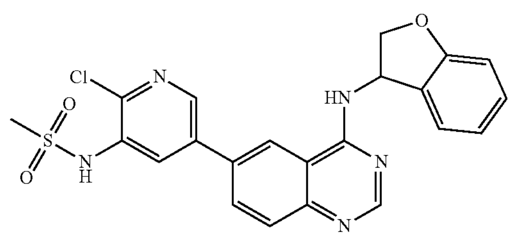 [SMILES: CS(=O)(=O)Nc1cc(-c2ccc3ncnc(NC4COc5ccccc54)c3c2)cnc1Cl] |
| 117 | N-(2-chloro-5-(4-((2-hydroxy-2,3-dihydro-1H-inden-1-yl)amino)quinazolin-6-yl)pyridin-3-yl)methanesulfonamide | 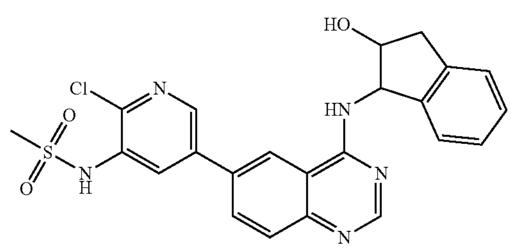 [SMILES: CS(=O)(=O)Nc1cc(-c2ccc3ncnc(NC4c5ccccc5CC4O)c3c2)cnc1Cl] |
| 118 | N-(2-chloro-5-(4-((2-hydroxy-1-phenylethyl)amino)quinazolin-6-yl)pyridin-3-yl)methanesulfonamide | 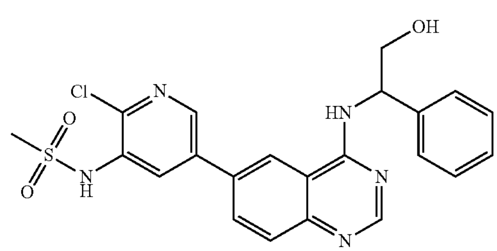 [SMILES: CS(=O)(=O)Nc1cc(-c2ccc3ncnc(NC(CO)c4ccccc4)c3c2)cnc1Cl] |

TABLE 1-continued

Compounds of the disclosure listed by name and structure

| Cmp # | IUPAC Name | Structure |
|---|---|---|
| 119 | N-(2-chloro-5-(4-((3-phenyloxetan-3-yl)amino)quinazolin-6-yl)pyridin-3-yl)methanesulfonamide | 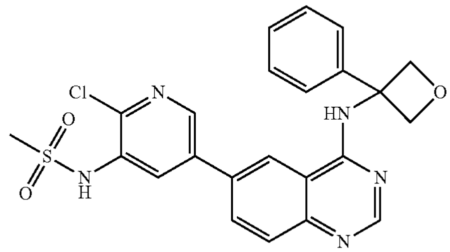 [SMILES: CS(=O)(=O)Nc1cc(-c2ccc3ncnc(NC4(c5ccccc5)COC4)c3c2)cnc1Cl] |
| 120 | N-(2-chloro-5-(4-((1-phenylcyclopropyl)amino)quinazolin-6-yl)pyridin-3-yl)methanesulfonamide | 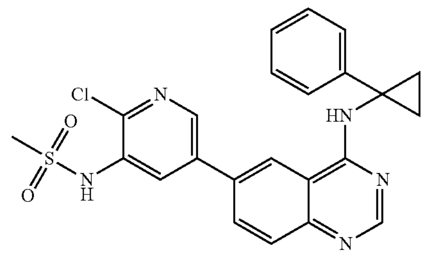 [SMILES: CS(=O)(=O)Nc1cc(-c2ccc3ncnc(NC4(c5ccccc5)CC4)c3c2)cnc1Cl] |
| 121 | 6-(2-aminopyrimidin-5-yl)-N-(1-(4-fluorophenyl)ethyl)quinazolin-4-amine | 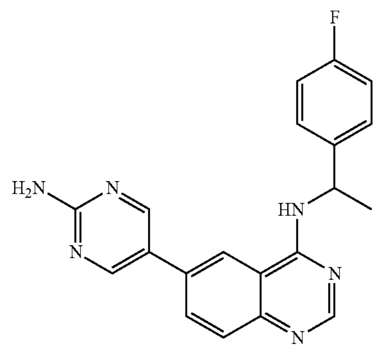 [SMILES: CC(Nc1ncnc2ccc(-c3cnc(N)nc3)cc12)c1ccc(F)cc1] |
| 121R | 6-(2-aminopyrimidin-5-yl)-N-(1R-(4-fluorophenyl)ethyl)quinazolin-4-amine | 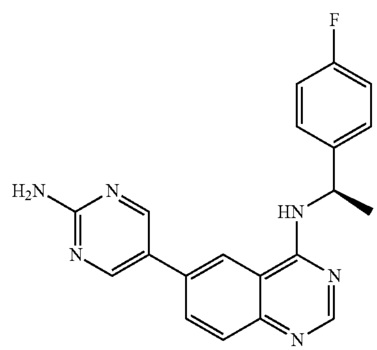 [SMILES: C[C@@H](Nc1ncnc2ccc(-c3cnc(N)nc3)cc12)c1ccc(F)cc1] |
| 122 | 4'-(1-phenylethyl)amino)-[3,6'-biquinoline]-3'-carbonitrile | 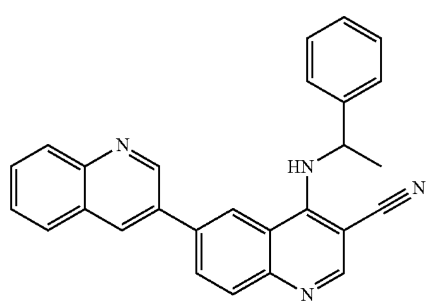 [SMILES: CC(Nc1c(C#N)cnc2ccc(-c3cnc4ccccc4c3)cc12)c1ccccc1] |

TABLE 1-continued

Compounds of the disclosure listed by name and structure

| Cmp # | IUPAC Name | Structure |
|-------|------------|-----------|
| 123 | 4-((1-phenylethyl)amino)-6-(pyridin-3-yl)quinoline-3-carbonitrile | 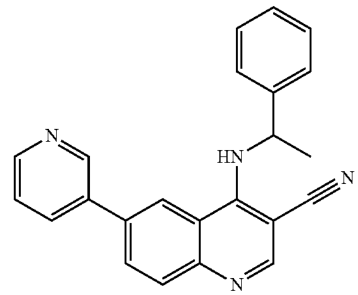 [SMILES: CC(Nc1c(C#N)cnc2ccc(-c3cccnc3)cc12)c1ccccc1] |
| 124 | 4-((1-phenylethyl)amino)-6-(1H-pyrazolo[4,3-c]pyridin-3-yl)quinoline-3-carbonitrile | 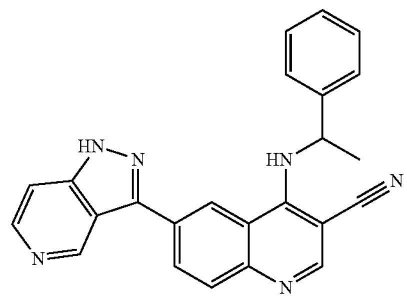 [SMILES: CC(Nc1c(C#N)cnc2ccc(-c3n[nH]c4ccncc34)cc12)c1ccccc1] |
| 125 | 4-((1-phenylethyl)amino)-6-(1H-pyrazolo[3,4-c]pyridin-3-yl)quinoline-3-carbonitrile | 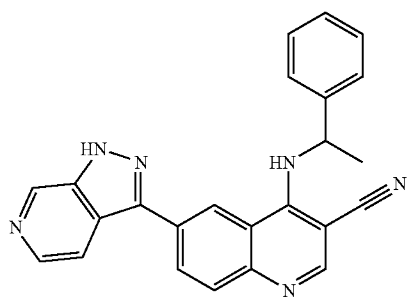 [SMILES: CC(Nc1c(C#N)cnc2ccc(-c3n[nH]c4cnccc34)cc12)c1ccccc1] |
| 126 | 6-(5-cyano-6-methoxypyridin-3-yl)-4-((1-phenylethyl)amino)quinoline-3-carbonitrile | 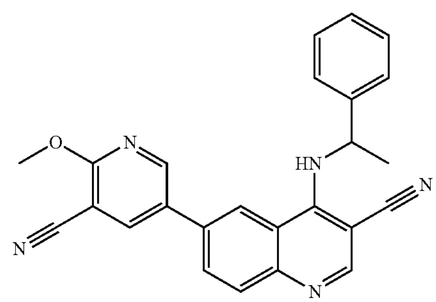 [SMILES: COc1ncc(-c2ccc3ncc(C#N)c(NC(C)c4ccccc4)c3c2)cc1C#N] |
| 127 | 6-(3-(5-oxo-4,5-dihydro-1,3,4-oxadiazol-2-yl)phenyl)-4-((1-phenylethyl)amino)quinoline-3-carbonitrile | 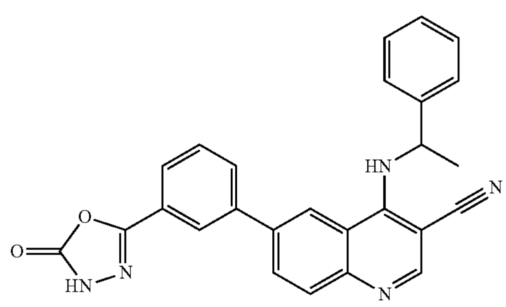 [SMILES: CC(Nc1c(C#N)cnc2ccc(-c3cccc(-c4n[nH]c(=O)o4)c3)cc12)c1ccccc1] |

TABLE 1-continued

Compounds of the disclosure listed by name and structure

| Cmp # | IUPAC Name | Structure |
|---|---|---|
| 128 | 6-(3-(4H-1,2,4-triazol-3-yl)phenyl)-4-((1-phenylethyl)amino)quinoline-3-carbonitrile | 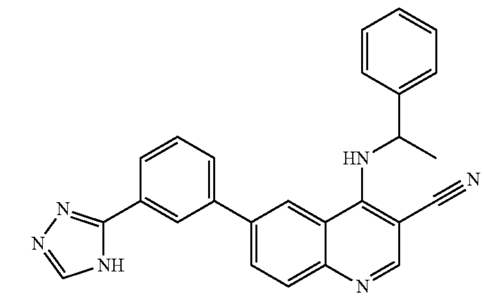 [SMILES: CC(Nc1c(C#N)cnc2ccc(-c3cccc(-c4nnc[nH]4)c3)cc12)c1ccccc1] |
| 129 | 6-(5-(5-oxo-4,5-dihydro-1,3,4-oxadiazol-2-yl)pyridin-3-yl)-4-((1-phenylethyl)amino)quinoline-3-carbonitrile | 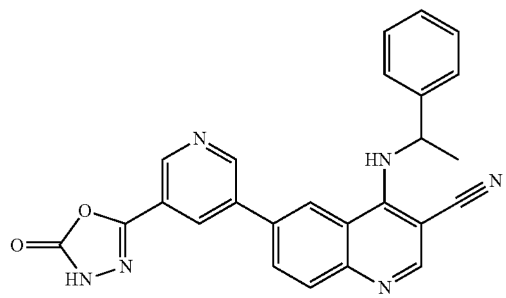 [SMILES: CC(Nc1c(C#N)cnc2ccc(-c3cncc(-c4n[nH]c(=O)o4)c3)cc12)c1ccccc1] |
| 130 | 6-(3,5-difluoro-4-hydroxyphenyl)-4-((1-phenylethyl)amino)quinoline-3-carbonitrile | 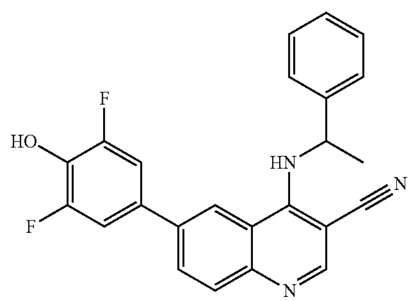 [SMILES: CC(Nc1c(C#N)cnc2ccc(-c3cc(F)c(O)c(F)c3)cc12)c1ccccc1] |
| 131 | 6-(3,5-dichloro-4-hydroxyphenyl)-4-((1-phenylethyl)amino)quinoline-3-carbonitrile | 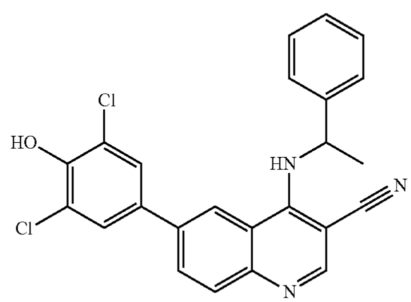 [SMILES: CC(Nc1c(C#N)cnc2ccc(-c3cc(Cl)c(O)c(Cl)c3)cc12)c1ccccc1] |
| 132 | (R)-2-methoxy-5-(4-((1-phenylethyl)amino)quinazolin-6-yl)nicotinonitrile | 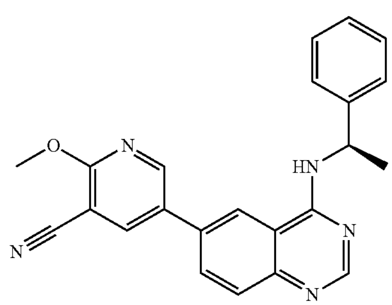 [SMILES: COc1ncc(-c2ccc3ncnc(N[C@H](C)c4ccccc4)c3c2)cc1C#N] |

TABLE 1-continued

Compounds of the disclosure listed by name and structure

| Cmp # | IUPAC Name | Structure |
|---|---|---|
| 133 | (R)-N-cyano-5-(4-((1-phenylethyl)amino)quinazolin-6-yl)nicotinamide | 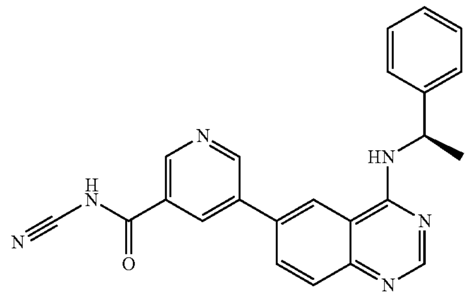 [SMILES: C[C@@H](Nc1ncnc2ccc(-c3cncc(C(=O)NC#N)c3)cc12)c1ccccc1] |
| 134 | (R)-N-hydroxy-N-methyl-5-(4-((1-phenylethyl)amino)quinazolin-6-yl)nicotinamide | 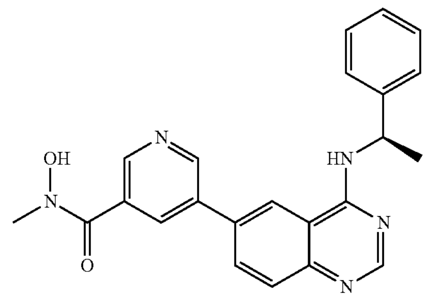 [SMILES: C[C@@H](Nc1ncnc2ccc(-c3cncc(C(=O)N(C)O)c3)cc12)c1ccccc1] |
| 135 | methyl (R)-5-(4-((1-phenylethyl)amino)quinazolin-6-yl)nicotinate | 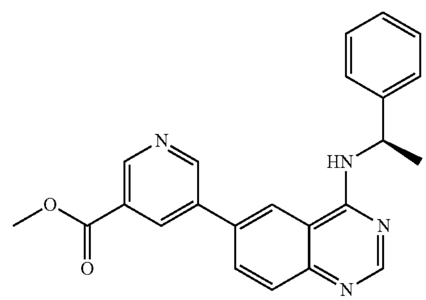 [SMILES: COC(=O)c1cncc(-c2ccc3ncnc(N[C@H](C)c4ccccc4)c3c2)c1] |
| 136 | (R)-6-(4-((1-phenylethyl)amino)quinazolin-6-yl)isobenzofuran-1(3H)-one | 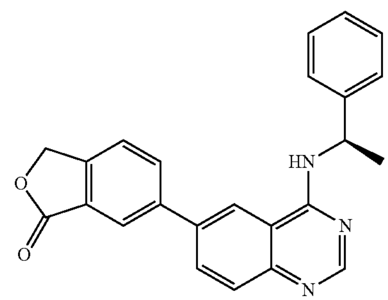 [SMILES: C[C@@H](Nc1ncnc2ccc(-c3ccc4c(c3)C(=O)OC4)cc12)c1ccccc1] |
| 137 | (R)-6-(3-(4H-1,2,4-triazol-3-yl)phenyl)-N-(1-phenylethyl)quinazolin-4-amine | 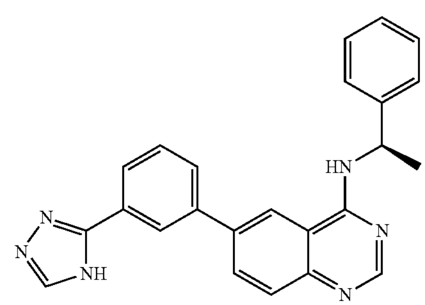 [SMILES: C[C@@H](Nc1ncnc2ccc(-c3cccc(-c4nnc[nH]4)c3)cc12)c1ccccc1] |

TABLE 1-continued

Compounds of the disclosure listed by name and structure

| Cmp # | IUPAC Name | Structure |
|---|---|---|
| 138 | (R)-6-(5-(4H-1,2,4-triazol-3-yl)pyridin-3-yl)-N-(1-phenylethyl)quinazolin-4-amine | 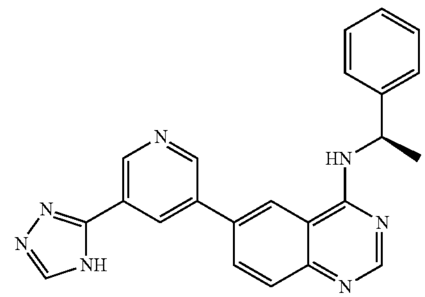 [SMILES: C[C@@H](Nc1ncnc2ccc(-c3cncc(-c4nnc[nH]4)c3)cc12)c1ccccc1] |
| 139 | 6-(imidazo[1,2-a]pyrazin-3-yl)-N-(1-phenylethyl)quinazolin-4-amine | 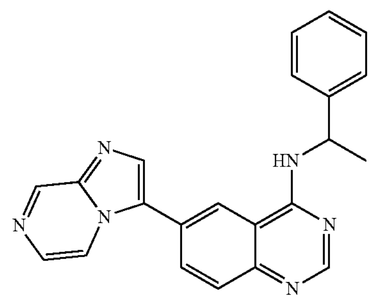 [SMILES: CC(Nc1ncnc2ccc(-c3cnc4cnccn34)cc12)c1ccccc1] |
| 140 | 2((6-(imidazo[1,2-a]pyrazin-3-yl)quinazolin-4-yl)amino)-2-phenylethan-1-ol | 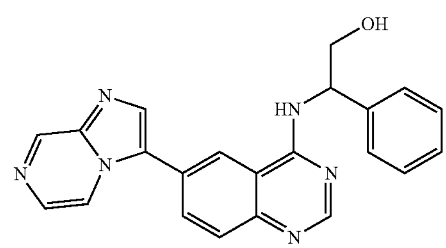 [SMILES: OCC(Nc1ncnc2ccc(-c3cnc4cnccn34)cc12)c1ccccc1] |
| 141 | (R)-6-(5-(4-methyl-4H-1,2,4-triazol-3-yl)pyridin-3-yl)-N-(1-phenylethyl)quinazolin-4-amine | 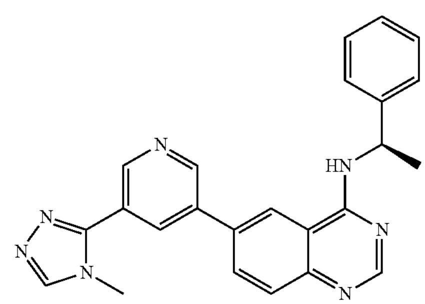 [SMILES: C[C@@H](Nc1ncnc2ccc(-c3cncc(-c4nncn4C)c3)cc12)c1ccccc1] |
| 142 | (R)-6-(5-(1-methyl-1H-1,2,3-triazol-4-yl)pyridin-3-yl)-N-(1-phenylethyl)quinazolin-4-amine | 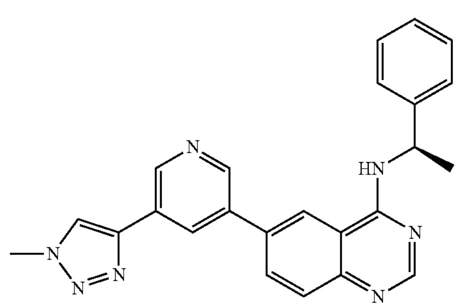 [SMILES: C[C@@H](Nc1ncnc2ccc(-c3cncc(-c4cn(C)nn4)c3)cc12)c1ccccc1] |

TABLE 1-continued

Compounds of the disclosure listed by name and structure

| Cmp # | IUPAC Name | Structure |
|---|---|---|
| 143 | (R)-N-methyl-6-(4-((1-phenylethyl)amino)quinazolin-6-yl)pyrazine-2-carboxamide | 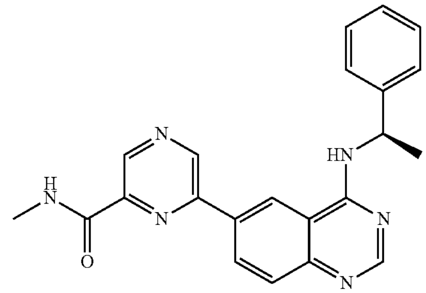 [SMILES: CNC(=O)c1cncc(-c2ccc3ncnc(N[C@H](C)c4ccccc4)c3c2)n1] |
| 144 | (R)-N-ethyl-6-(4-((1-phenylethyl)amino)quinazolin-6-yl)pyrazine-2-carboxamide | 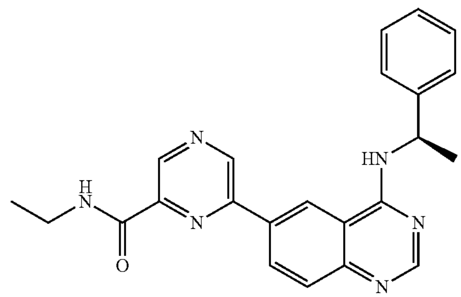 [SMILES: CCNC(=O)c1cncc(-c2ccc3ncnc(N[C@H](C)c4ccccc4)c3c2)n1] |
| 145 | (R)-N-isopropyl-6-(4-((1-phenylethyl)amino)quinazolin-6-yl)pyrazine-2-carboxamide | 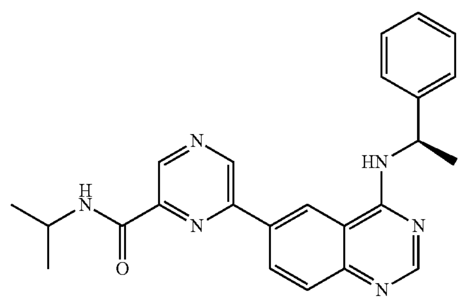 [SMILES: CC(C)NC(=O)c1cncc(-c2ccc3ncnc(N[C@H](C)c4ccccc4)c3c2)n1] |
| 146 | (R)-N-(tert-butyl)-6-(4-((1-phenylethyl)amino)quinazolin-6-yl)pyrazine-2-carboxamide | 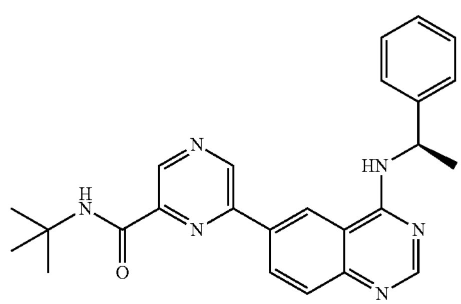 [SMILES: C[C@@H](Nc1ncnc2ccc(-c3cncc(C(=O)NC(C)(C)C)n3)cc12)c1ccccc1] |
| 147 | (R)-N-cyclopropyl-6-(4-((1-phenylethyl)amino)quinazolin-6-yl)pyrazine-2-carboxamide | 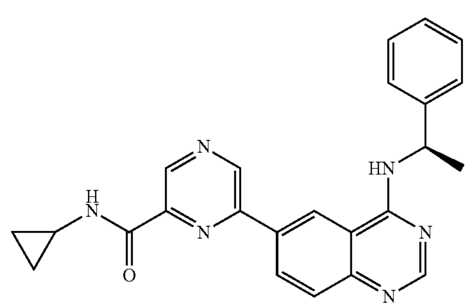 [SMILES: C[C@@H](Nc1ncnc2ccc(-c3cncc(C(=O)NC4CC4)n3)cc12)c1ccccc1] |

TABLE 1-continued

Compounds of the disclosure listed by name and structure

| Cmp # | IUPAC Name | Structure |
|---|---|---|
| 148 | N-(5-(4-((1-phenylethyl)amino)quinazolin-6-yl)-2-(trifluoromethyl)pyridin-3-yl)methanesulfonamide | 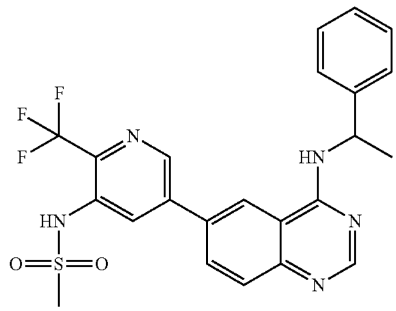 [SMILES: CC(Nc1ncnc2ccc(-c3cnc(C(F)(F)F)c(NS(C)(=O)=O)c3)cc12)c1ccccc1] |

In another aspect, the disclosure provides a compound of Formula Ia-1

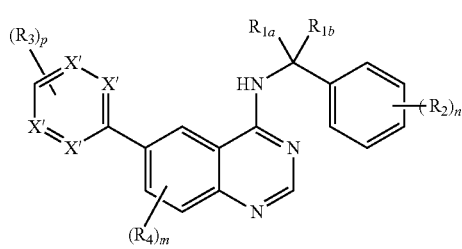

Formula Ia-1 or a pharmaceutically acceptable salt or solvate thereof, or an enantiomer, a mixture of enantiomers, a mixture of two or more diastereomers, or an isotopic variant thereof,
wherein,
each X' is N, C—$R_3$, or CH;
$R_{1a}$ is selected from the group consisting of H or $C_{1-6}$ alkyl;
$R_{1b}$ is selected from the group consisting of $C_{1-6}$ alkyl, cycloalkyl, hetercycloalkyl, aryl, heteroaryl, OR', N(R')$_2$, C(O)R', C(O)OR', C(O)N(R')$_2$, halo, CN, and NO$_2$, wherein each $C_{1-6}$ alkyl, cycloalkyl, hetercycloalkyl, aryl, or heteroaryl is optionally and independently substituted with one or more R" substituents;
each $R_2$ is independently selected from halo, OH, $C_{1-6}$ alkyl, haloalkyl, OC$_{1-6}$ alkyl, CN, NH$_2$, NHC$_{1-6}$ alkyl, N(C$_{1-6}$ alkyl)$_2$, C(O)C$_{1-6}$ alkyl, C(O)OC$_{1-6}$ alkyl, C(O)NH$_2$, C(O)NHC$_{1-6}$ alkyl, and C(O)N(C$_{1-6}$ alkyl)$_2$;
each $R_3$ is independently selected from $C_{1-6}$ alkyl, a 5-6 membered heteroaryl, a 5-6 membered heterocycloalkyl, halo, CN, NO$_2$, OR', N(R')$_2$, C(O)R', C(O)OR', C(O)N(R')$_2$, OC(O)OR', OC(O)N(R')$_2$, NR'C(O)N(R')$_2$, SOR', SON(R')$_2$, SO$_2$R', SO$_2$N(R')$_2$, NR'SOR', NR'SON(R')$_2$, NR'SO$_2$R', and NR'SO$_2$N(R')$_2$, wherein the $C_{1-6}$ alkyl, hetercycloalky, and heteroaryl are each optionally and independently substituted with one or more R" substituents;
each $R_4$ is selected from halo, OH, NH$_2$, CN, $C_{1-6}$ alkyl, and OC$_{1-6}$ alkyl;
each R' is independently selected from hydrogen, OH, CN, $C_{1-6}$ alkyl, cycloalkyl, hetercycloalkyl, aryl, and heteroaryl, each of which is optionally and independently substituted with one or more R" substituents;

each R" is independently selected from the group consisting of $C_{1-6}$ alkyl, cycloalkyl, hetercycloalkyl, aryl, heteroaryl, OC$_{1-6}$ alkyl, oxo, OH, halo, CN, NH$_2$, NHC$_{1-6}$ alkyl, N(C$_{1-6}$ alkyl)$_2$, C(O)C$_{1-6}$ alkyl, C(O)OC$_{1-6}$ alkyl, C(O)NH$_2$, C(O)NHC$_{1-6}$ alkyl, and C(O)N(C$_{1-6}$ alkyl)$_2$, wherein each $C_{1-6}$ alkyl, cycloalkyl, hetercycloalkyl, aryl, and heteroaryl is optionally and independently substituted with one or substituents selected from halo, oxo, alkoxy, CN, NH$_2$, C(O)C$_{1-6}$ alkyl, C(O)OC$_{1-6}$ alkyl, and C(O)NHC$_{1-6}$ alkyl; and m, n, and p are each an integer selected from 0-4.

In one embodiment, $R_{1a}$ is H.

In another embodiment, $R_{1b}$ is $C_{1-6}$ alkyl, $C_{1-6}$ alkyl-OH, or CN.

In a further embodiment, $R_{1b}$ is methyl, CN, or CH$_2$OH.

In one embodiment, each $R_2$ substituent is independently selected from halo and OH.

In another embodiment, n is 0.

In one embodiment, each $R_3$ substituent is independently selected from halo, CN, NH$_2$, OH, C(O)H, C(O)N(CH$_3$)$_2$, C(O)NH(CH$_3$), C(O)NH(Et), C(O)NH(isopropyl), C(O)NH(tert-butyl), C(O)NH(cyclopropyl), C(O)NCH$_3$(CN), C(O)NH(OH), C(O)NCH$_3$(OH), C(O)NH$_2$, NHC(O)NHCH$_3$, NHS(O)$_2$CH$_3$, S(O)$_2$CH$_3$, methyl, methoxy, NHS(O)$_2$CH$_2$CH$_2$N(CH$_3$)$_2$, CF$_3$, CH$_2$OH, C(CH$_3$)$_2$OH,

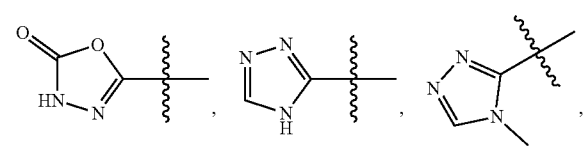

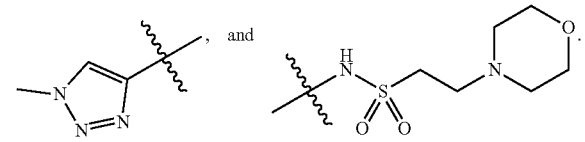

In one embodiment, the ring
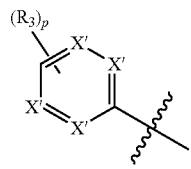
is a phenyl, pyridyl, pyrimidyl, pyrazyl, or triazyl, which is optionally substituted by $R_3$.
In a further embodiment, the ring
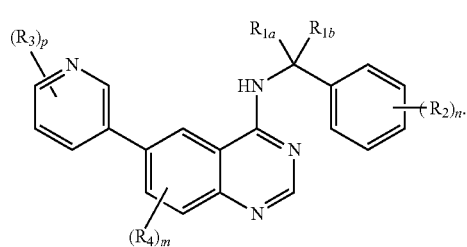 is 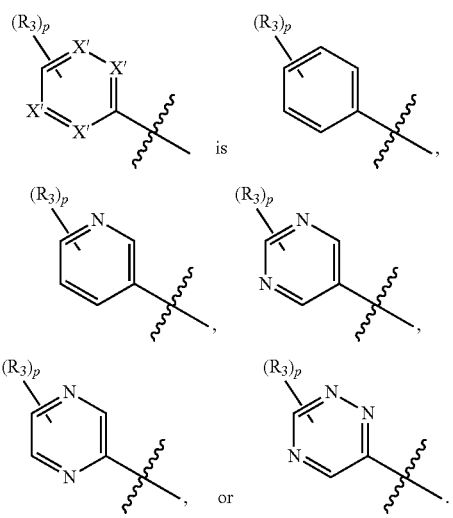
or
In one embodiment, p is 1 or 2.
In one embodiment, the compound of Formula Ia-1 is a compound of Formula Ia-2
Formula Ia-2
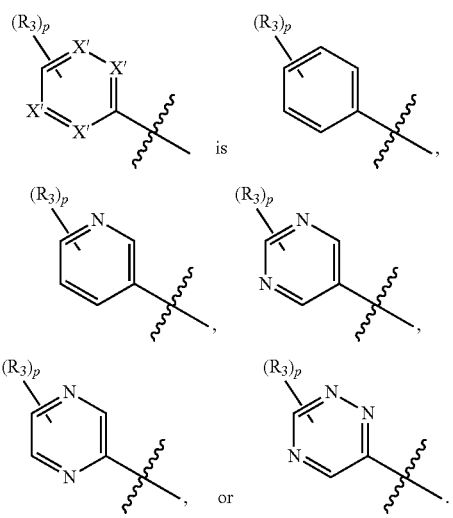
In another embodiment, the ring
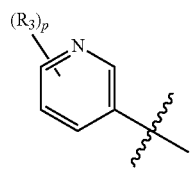
of Formula Ia-2 is selected from
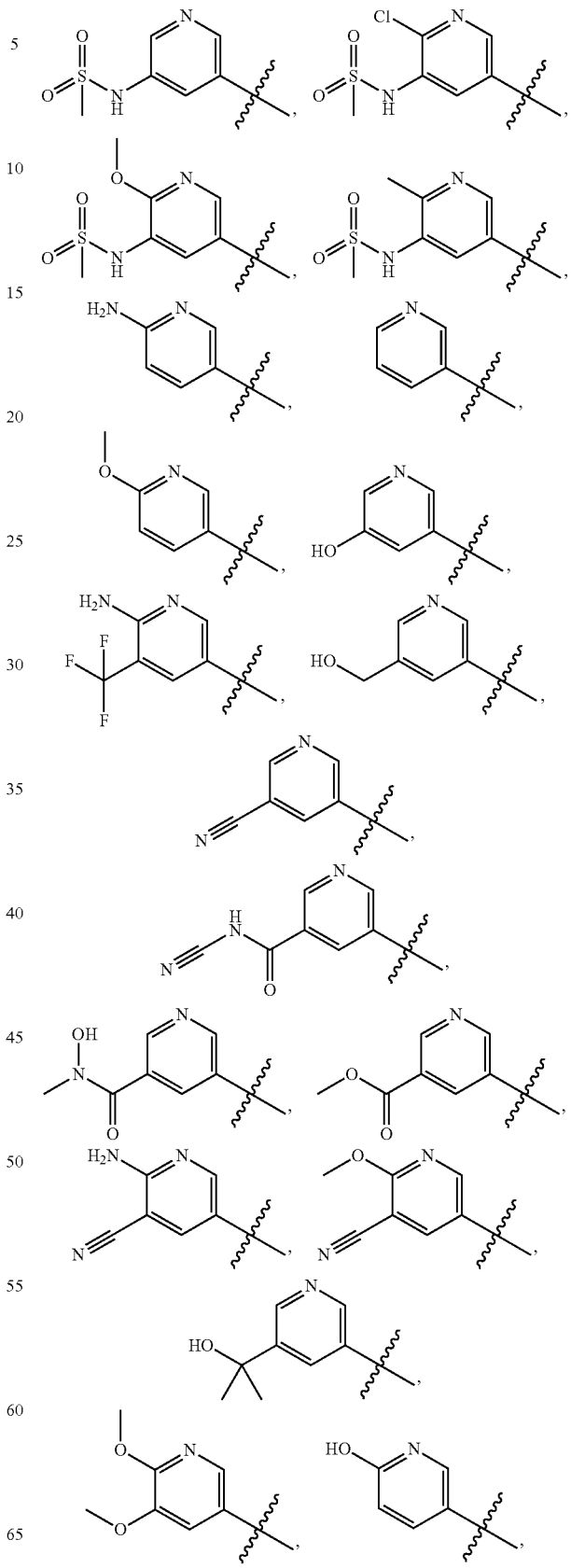

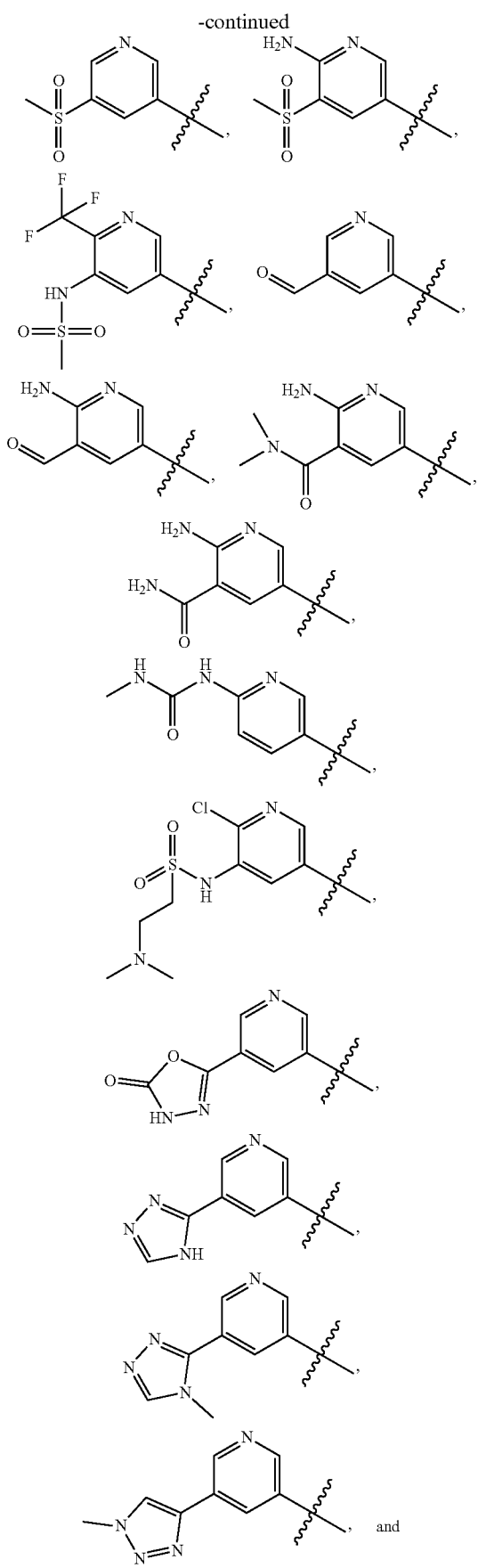

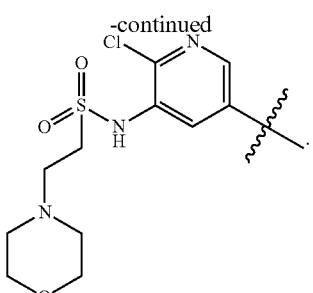

In one embodiment, m is 0.

In another embodiment, the compound of Formula Ia-1 is a compound selected from Compounds 1, 2, 2R, 2S, 3-6, 11, 14-16, 21, 22, 29-33, 36, 37, 45, 107-111, 111R, 111S, 112, 113, 118, 132-135, 138, 141, 142, and 148.

In one aspect, the disclosure includes a pharmaceutical composition comprising a compound or salt described herein, and a pharmaceutically acceptable excipient.

In another aspect, the disclosure includes a method of modulating an EGFR and/or PI3K enzyme in a biological sample, said method comprising contacting the biological sample with a compound or salt described herein.

In still another aspect, the disclosure includes a method of preventing or treating an EGFR and/or PI3K mediated disease in a subject, said method comprising administering to the subject a compound or salt described herein.

In one embodiment of this aspect, the EGFR and/or PI3K mediated disease is a cancer.

In another embodiment, the cancer is selected from prostate cancer, liver cancer, renal cancer, lung cancer, breast cancer, colorectal cancer, pancreatic cancer, brain cancer, hepatocellular cancer, lymphoma, leukemia, gastric cancer, cervical cancer, ovarian cancer, thyroid cancer, melanoma, carcinomas of the head and neck, head and neck cancer, skin cancer and soft tissue sarcoma and/or other forms of carcinoma.

In a further embodiment, the cancer is a metastatic or a malignant cancer.

In another embodiment, the cancer is selected from breast cancer, carcinomas of the head and neck, head and neck cancer, and skin cancer.

In a further embodiment, the head and neck cancer is squamous head and neck cancer.

In another further embodiment, the breast cancer is triple negative breast cancer.

In another aspect, the disclosure provides a compound of Formula I,

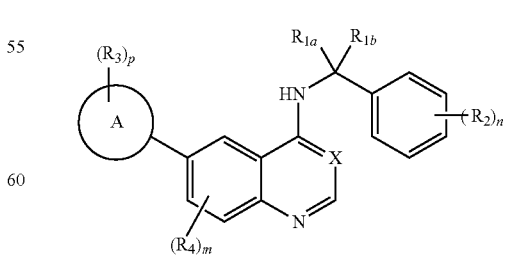

Formula I wherein the compound of Formula I has an increased solubility compared to a compound of Formula X or a compound of Formula X'

Formula X

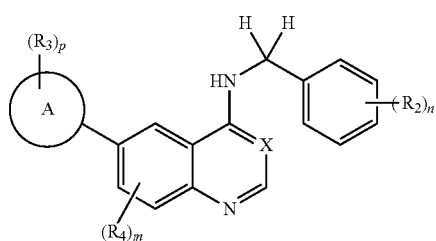

Formula X'

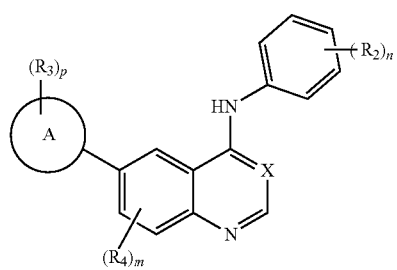

Wherein $R^{1a}$, $R^{1b}$, $R_2$, $R_3$, $R_4$, X, m, n, p, and Ring A are all defined herein.

One embodiment of this aspect, $R_{1a}$ is hydrogen and $R_{1b}$ is $C_{1-6}$ alkyl. In a further embodiment, $R_{1a}$ is hydrogen and $R_{1b}$ is methyl, ethyl, propyl, isopropyl, n-butyl, isobutyl, t-butyl, pentyl, or hexyl. In still a further embodiment, $R_{1a}$ is hydrogen and $R_{1b}$ is methyl.

In one embodiment of this aspect, the compound of Formula I is selected from a compound listed in Table 1. In a further embodiment of this aspect, the compound of Formula I is selected from Compound 2, 2R, 2S, 8, 10, 22, 48, 48R, 48S, 111, 111R, and 111S. In a further embodiment of this aspect, the compound of Formula I is selected from Compound 2R, 48R, and 111R.

In one embodiment of this aspect, the compound of Formula X' is Comparative Compound 1 or Comparative Compound 3, which have the structures below.

Comparative Compound 1

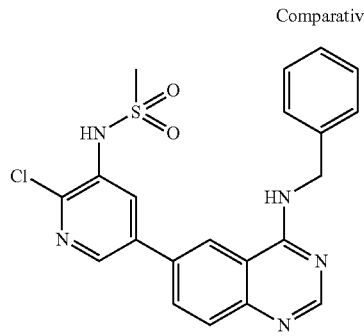

Comparative Compound 3

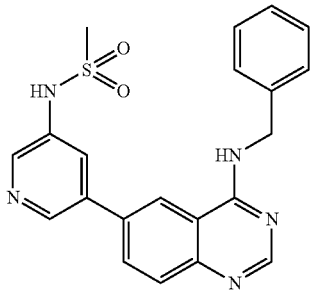

In another embodiment of this aspect, the compound of Formula X is Comparative Compound 2, which has the structure Comparative Compound 2

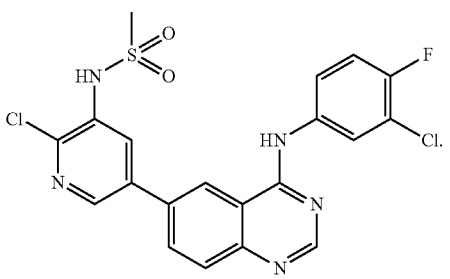

In one embodiment, the compound of Formula I is at least 0.5 times more soluble than a compound of Formula X or a compound of Formula X'. In another embodiment, the compound of Formula I is at least twice as soluble as a compound of Formula X or a compound of Formula X'. In another embodiment, the compound of Formula I is at least 5.0 times more soluble than a compound of Formula X or a compound of Formula X'. In another embodiment, the compound of Formula I is at least 10 times more soluble than a compound of Formula X or a compound of Formula X'. In another embodiment, the compound of Formula I is at least 50 times more soluble than a compound of Formula X or a compound of Formula X'. In another embodiment, the compound of Formula I is at least 100 times more soluble than a compound of Formula X or a compound of Formula X'.

In one embodiment, the compound of Formula I has increased solubility over a compound of Formula X or a compound of Formula X' in phosphate buffered saline (PBS) at about pH 7.4.

In another embodiment, the compound of Formula I has increased solubility over a compound of Formula X or a compound of Formula X' in simulated intestinal fluid (SIF).

In another embodiment, the compound of Formula I has increased solubility over a compound of Formula X or a compound of Formula X' in simulated gastric fluid (SGF).

Pharmaceutically Acceptable Salts, Compositions, and Formulations

It also will be appreciated that certain of the compounds of the present disclosure can exist in free form for treatment, or where appropriate, as a pharmaceutically acceptable derivative (e.g., a salt) thereof. According to the present disclosure, a pharmaceutically acceptable derivative includes, but is not limited to, pharmaceutically acceptable prodrugs, salts, esters, salts of such esters, or any other adduct or derivative that upon administration to a patient in need is capable of providing, directly or indirectly, a compound as otherwise described herein, or a metabolite or residue thereof.

As used herein, the term "pharmaceutically acceptable salt" refers to those salts that are, within the scope of sound medical judgement, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+($C_{1-4}$ alkyl)$_4$ salts. This disclosure also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

A compound of Formula I, or a pharmaceutically acceptable salt thereof, can be formulated as pharmaceutical compositions comprising a therapeutically or prophylactically effective amount of the compound or salt, and one or more pharmaceutically compatible (acceptable) ingredients. In some aspects, pharmaceutical compositions of a compound of Formula I, or a pharmaceutically acceptable salt thereof, and pharmaceutical excipients are provided in which an effective amount of the compound or salt, is in admixture with the excipients, suitable for administration to a mammal. In preferred aspects, a compound of Formula I, or a pharmaceutically acceptable salt thereof, is formulated for administration to a human. The present disclosure provides a pharmaceutical composition comprising a compound of Formula I, or a pharmaceutically acceptable salt thereof, formulated for administration to a human subject in need thereof. The formulated composition comprising a compound of Formula I, or a pharmaceutically acceptable salt thereof, will generally comprise one or more pharmaceutically compatible (acceptable) ingredients.

Exemplary pharmaceutical or non-pharmaceutical compositions typically include one or more carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable excipients include, for example, amino acids, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will typically contain a therapeutically effective amount of a compound of Formula I, or a pharmaceutically acceptable salt thereof, in purified form, together with a suitable amount of carrier so as to provide the form for proper administration to the subject. The formulations correspond to the mode of administration.

The pharmaceutically acceptable carrier or vehicle can be particulate, so that the compositions are, for example, in tablet or powder form. The carrier(s) can be liquid, with the compositions being, for example, an oral syrup, flavored water, or injectable liquid.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant, and flavor enhancer. In some aspects, the composition is formulated into a powder and the end user mixes the power in aqueous solution for oral administration. In a composition for administration by injection (as described above), one or more of a surfactant, preservative, wetting agent, dispersing agent, suspending agent, buffer, stabilizer and isotonic agent can also be included.

The composition and preparation of capsules are well known in the art. For example, capsules may be prepared from gelatin (e.g., Type A, Type B), carrageenan (e.g., kappa, iota, lambda) and/or modified cellulose (e.g., hydroxypropyl methyl cellulose, methyl cellulose, hydroxypropyl methyl cellulose acetate succinate, hydroxypropyl methyl cellulose phthalate, cellulose acetate phthalate), and optionally one or more excipients such as oils (e.g., fish oil, olive oil, corn oil, soybean oil, coconut oil, tri-, di- and monoglycerides), plasticizers (e.g., glycerol, glycerin, sorbitol, polyethylene glycol, citric acid, citric acid esters such as triethylcitrate, polyalcohols), co-solvents (e.g., triacetin, propylene carbonate, ethyl lactate, propylene glycol, oleic acid, dimethylisosorbide, stearyl alcohol, cetyl alcohol, cetostearyl alcohol, glyceryl behenate, glyceryl palmitostearate), surfactants, buffering agents, lubricating agents, humectants, preservatives, colorants and flavorants. Capsules may be hard or soft. Examples of hard capsules include ConiSnap®, DRcaps®, OceanCaps®, Pearlcaps®, Plantcaps®, DUOCAP®, Vcaps®, and Vcaps®. Plus capsules available from Capsugel®. Hard capsules may be prepared, for example, by forming two telescoping capsule halves, filling one of the halves with a fill comprising a compound of Formula I, or a pharmaceutically acceptable salt thereof, and sealing the capsule halves together. The fill may be in any suitable form, such as dry powder, granulation, suspension or liquid. Examples of soft capsules include soft gelatin (also called softgel or soft elastic) capsules, such as SGcaps®. Soft capsules may be prepared, for example, by rotary die, plate, reciprocating die or Accogel® machine method. In embodiments, the capsule may be a liquid-filled hard capsule or a soft-gelatin capsule.

Tablets can be made by compression or molding, optionally with one or more accessory ingredients. Compressed tablets can be prepared by compressing in a suitable machine a compound of formula (I) or pharmaceutically acceptable salt thereof in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide sustained, extended, delayed or controlled release. Methods of formulating such sustained, extended, delayed or controlled release compositions are known in the art and disclosed in issued U.S. patents, including but not limited to U.S. Pat. Nos. 4,369,174, 4,842,866, and the references cited therein. Coatings, for example enteric coatings, can be used for delivery of compounds to the intestine (see, e.g., U.S. Pat. Nos. 6,638,534, 5,217,720, 6,569,457, and the references cited therein). In addition to tablets, other dosage forms, such as capsules, granulations and gel-caps, can be formulated to provide sustained, extended, delayed or controlled release.

In one embodiment, the pharmaceutical composition is formulated for parenteral administration. Examples of a pharmaceutical composition suitable for parenteral administration include aqueous sterile injection solutions and non-aqueous sterile injection solutions, each containing, for example, anti-oxidants, buffers, bacteriostatic agents and/or solutes that render the formulation isotonic with the blood of the intended recipient; and aqueous sterile suspensions and non-aqueous sterile suspensions, each containing, for example, suspending agents and/or thickening agents. The formulations can be presented in unit-dose or multi-dose containers, for example, sealed ampules or vials, and can be stored in a freeze dried (lyophilized) condition requiting only the addition of a sterile liquid carrier, such as water, immediately prior to use. In one embodiment, the pharmaceutical composition is formulated for intravenous administration.

In some embodiments, the pharmaceutical composition further includes a pharmaceutically acceptable excipient. A pharmaceutically acceptable excipient may be any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Remington: The Science and Practice of Pharmacy, 21.sup.st Ed. (Lippincott Williams & Wilkins, Baltimore, Md., 2005). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropyl methylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of a compound of Formula I, or a pharmaceutically acceptable salt thereof, the manner of administration, the composition employed, and the severity of the disease or condition being treated.

In addition to administering the compound as a raw chemical, the compounds of the disclosure may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the disclosure may be administered to any patient which may experience the beneficial effects of the compounds of the disclosure. Foremost among such patients are mammals, e.g., humans, although the disclosure is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present disclosure are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this disclosure are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present disclosure. Various modifications and alterations of the compositions and methods described above can readily be achieved using expertise available in the art and are within the scope of the disclosure.

Methods of Treatment

In some embodiments of the present disclosure, the compound of Formula I, or a pharmaceutically acceptable salt thereof, can be employed under a variety of conditions and therapeutic uses to treat a variety of diseases or conditions related to the aberrant expression of PI3K and/or EGFR activity, including cancer.

The exact amount required will vary from subject to subject, depending on the species, age, and general condition of the subject, the severity of the infection, the particular agent, its mode of administration, and the like. The compounds of the disclosure are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this disclosure can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the disclosure may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the present disclosure contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The present disclosure may be used to treat a neoplastic disease, such as solid or non-solid cancers. As used herein, "treatment" encompasses the prevention, reduction, control and/or inhibition of a neoplastic disease. Such diseases include a sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or hematopoietic neoplastic disorders (e.g., myeloma, lymphoma or leukemia). In particular aspects, a neoplasm, tumor or cancer includes a lung adenocarcinoma, lung carcinoma, diffuse or interstitial gastric carcinoma, colon adenocarcinoma, prostate adenocarcinoma, esophagus carcinoma, breast carcinoma, pancreas adenocarcinoma, ovarian adenocarcinoma, adenocarcinoma of the adrenal gland, adenocarcinoma of the endometrium or uterine adenocarcinoma and carcinomas of the head and neck.

Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. Cancers that may be treated according to the disclosure include but are not limited to cells or neoplasms of the bladder, blood, bone, bone marrow, brain, breast, colon, esophagus, gastrointestinal system, gum, head, kidney, liver, lung, nasopharynx, neck, ovary, prostate, skin, stomach, testis, tongue, or uterus. In addition, the cancer may specifically be of the following histological type, though it is not limited to the following: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma, gastrinoma, malignant; cholangiocarcinoma, hepatocellular carcinoma; combined hepatocellular carcinoma and cholangiocarcinoma, trabecular adenocarcinoma, adenoid cystic carcinoma; adenocarcinoma in adenomatous polyp; adenocarcinoma, familial polyposis coli, solid carcinoma; carcinoid tumor, malignant; bronchiolo-alveolar adenocarcinoma, papillary adenocarcinoma, chromophobe carcinoma; acidophil carcinoma; oxyphilic adenocarcinoma, basophil carcinoma; clear cell adenocarcinoma, granular cell carcinoma; follicular adenocarcinoma, papillary and follicular adenocarcinoma, nonencapsulating sclerosing carcinoma; adrenal cortical carcinoma; endometroid carcinoma; skin appendage carcinoma; apocrine adenocarcinoma, sebaceous adenocarcinoma, ceruminous adenocarcinoma, mucoepidermoid carcinoma; cystadenocarcinoma, papillary cystadenocarcinoma, papillary serous cystadenocarcinoma, mucinous cystadenocarcinoma, mucinous adenocarcinoma, signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma with squamous metaplasia, thymoma, malignant; ovarian stromal tumor, malignant; thecoma, malignant; granulosa cell tumor, malignant; androblastoma, malignant; Sertoli cell carcinoma; Leydig cell tumor, malignant; lipid cell tumor, malignant; paraganglioma, malignant; extra-mammary paraganglioma, malignant; pheochromocytoma, glomangiosarcoma, malignant melanoma; amelanotic melanoma; superficial spreading melanoma; malignant melanoma in giant pigmented nevus; epithelioid cell melanoma; blue nevus, malignant; sarcoma; fibrosarcoma, fibrous histiocytoma, malignant; myxosarcoma, liposarcoma, leiomyosarcoma, rhabdomyosarcoma, embryonal rhabdomyosarcoma, alveolar rhabdomyosarcoma, stromal sarcoma; mixed tumor; Mullerian mixed tumor; nephroblastoma, hepatoblastoma, carcinosarcoma, mesenchymoma, malignant; Brenner tumor, malignant; phyllodes tumor, malignant; synovial sarcoma; mesothelioma, malignant; dysgerminoma, embryonal carcinoma; teratoma, malignant; struma ovarii, malignant; choriocarcinoma, mesonephroma, malignant; hemangiosarcoma, hemangioendothelioma, malignant; Kaposi's sarcoma; hemangiopericytoma, malignant; lymphangiosarcoma, osteosarcoma, juxtacortical osteosarcoma, chondrosarcoma, chondroblastoma, malignant; mesenchymal chondrosarcoma, giant cell tumor of bone; Ewing's sarcoma; odontogenic tumor, malignant; ameloblastic odontosarcoma, ameloblastoma, malignant; ameloblastic fibrosarcoma, pinealoma, malignant; chordoma, glioma, malignant; ependymoma, astrocytoma, protoplasmic astrocytoma, fibrillary astrocytoma, astroblastoma, glioblastoma, oligodendroglioma, oligodendroblastoma, primitive neuroectodermal, cerebellar sarcoma; ganglioneuroblastoma, neuroblastoma, retinoblastoma, olfactory neurogenic tumor; meningioma, malignant; neurofibrosarcoma, neurilemmoma, malignant; granular cell tumor, malignant; malignant lymphoma; Hodgkin's disease; Hodgkin's; paragranuloma, malignant lymphoma, small lymphocytic, malignant lymphoma, large cell, diffuse; malignant lymphoma, follicular; mycosis fungoides, other specified non-Hodgkin's lymphomas; malignant histiocytosis, multiple myeloma, mast cell sarcoma; immunoproliferative small intestinal disease; leukemia; lymphoid leukemia; plasma cell leukemia; erythroleukemia, lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Preferably, the neoplastic disease may be tumors associated with a cancer selected from prostate cancer, liver cancer, renal cancer, lung cancer, breast cancer, colorectal cancer, pancreatic cancer, brain cancer, hepatocellular cancer, lymphoma, leukemia, gastric cancer, cervical cancer, ovarian cancer, thyroid cancer, melanoma, carcinomas of the head and neck, head and neck cancer, skin cancer and soft tissue sarcoma and/or other forms of carcinoma. The tumor may be metastatic or a malignant tumor.

In some embodiments, the neoplastic disease to be treated is pancreatic cancer, breast cancer, lung cancer, prostate cancer and skin cancer. Most preferably, the neoplastic disease to be treated is pancreatic cancer, colorectal cancer and/or carcinomas of the head and neck.

Combination Therapies

Some embodiments of the present disclosure provide methods for administering an effective amount of a compound of the disclosure and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present disclosure. Indeed, the present disclosure contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present disclosure provide a compound of the disclosure and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present disclosure include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracene-diones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present disclosure. For example, the U.S. Food and Drug Administration maintains a formulary of oncolytic agents approved for use in the United States. International counterpart agencies to the U.S.F.D.A. maintain similar formularies. Table 2 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 2

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile,a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], sub strain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl)ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |

TABLE 2-continued

| | | |
|---|---|---|
| Cytarabine (1-b-D-Arabinofuranosyl cytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5 (10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |

TABLE 2-continued

| | | |
|---|---|---|
| etoposide, VP-16<br>(4'-demethylepipodophyllotoxin 9-[4,6-<br>O-(R)-ethylidene-(beta)-D-<br>glucopyranosidel) | Vepesid | Bristol-Myers Squibb |
| Exemestane<br>(6-methylenandrosta-1,4-diene-3,17-<br>dione) | Aromasin | Pharmacia & Upjohn<br>Company |
| Filgrastim<br>(r-metHuG-CSF) | Neupogen | Amgen, Inc |
| floxuridine (intraarterial)<br>(2'-deoxy-5-fluorouridine) | FUDR | Roche |
| Fludarabine<br>(fluorinated nucleotide analog of the<br>antiviral agent vidarabine, 9-b-D-<br>arabinofuranosyladenine (ara-A)) | Fludara | Berlex Laboratories,<br>Inc., Cedar Knolls, NJ |
| Fluorouracil, 5-FU<br>(5-fluoro-2,4(1H,3H)-pyrimidinedione) | Adrucil | ICN Pharmaceuticals,<br>Inc., Humacao, Puerto<br>Rico |
| Fulvestrant<br>(7-alpha-[9-(4,4,5,5,5-<br>pentafluoropentylsulphinyl)nonyl]estra-<br>1,3,5-(10)-triene-3,17-beta-diol) | Faslodex | IPR Pharmaceuticals,<br>Guayama, Puerto Rico |
| Gemcitabine<br>(2'-deoxy-2',2'-difluorocytidine<br>monohydrochloride (b-isomer)) | Gemzar | Eli Lilly |
| Gemtuzumab Ozogamicin<br>(anti-CD33 hP67.6) | Mylotarg | Wyeth Ayerst |
| Goserelin acetate | Zoladex<br>Implant | AstraZeneca<br>Pharmaceuticals |
| Hydroxyurea | Hydrea | Bristol-Myers Squibb |
| Ibritumomab Tiuxetan<br>(immunoconjugate resulting from a<br>thiourea covalent bond between the<br>monoclonal antibody Ibritumomab and<br>the linker-chelator tiuxetan [N-[2-<br>bis(carboxymethyl)amino]-3-(p-<br>isothiocyanatophenyl)-propyl]-[N-[2-<br>bis(carboxymethyl)amino]-2-(methyl)-<br>ethyl]glycine) | Zevalin | Biogen IDEC, Inc.,<br>Cambridge MA |
| Idarubicin<br>(5,12-Naphthacenedione, 9-acetyl-7-<br>[(3-amino-2,3,6-trideoxy-(alpha)-L-<br>lyxo-hexopyranosyl)oxy]-7,8,9,10-<br>tetrahydro-6,9,11-<br>trihydroxyhydrochloride, (7S-cis)) | Idamycin | Pharmacia & Upjohn<br>Company |
| Ifosfamide<br>(3-(2-chloroethyl)-2-[(2-<br>chloroethyl)amino]tetrahydro-2H-<br>1,3,2-oxazaphosphorine 2-oxide) | IFEX | Bristol-Myers Squibb |
| Imatinib Mesilate<br>(4-[(4-Methyl-1-piperazinyl)methyl]-<br>N-[4-methyl-3-[[4-(3-pyridinyl)-2-<br>pyrimidinyl]amino]-phenyl]benzamide<br>methanesulfonate) | Gleevec | Novartis AG, Basel,<br>Switzerland |
| Interferon alfa-2a<br>(recombinant peptide) | Roferon-A | Hoffmann-La Roche,<br>Inc., Nutley, NJ |
| Interferon alfa-2b<br>(recombinant peptide) | Intron A<br>(Lyophilized<br>Betaseron) | Schering AG, Berlin,<br>Germany |
| Irinotecan HCl<br>((4S)-4,11-diethyl-4-hydroxy-9-[(4-<br>piperi-dinopiperidino)carbonyloxy]-<br>1H-pyrano[3',4':6,7]indolizino[1,2-b]<br>quinoline-3,14(4H,12H) dione<br>hydrochloride trihydrate) | Camptosar | Pharmacia & Upjohn<br>Company |
| Letrozole<br>(4,4'-(1H-1,2,4-Triazol-1-ylmethylene)<br>dibenzonitrile) | Femara | Novartis |
| Leucovorin<br>(L-Glutamic acid, N[4[[(2amino-5-<br>formyl1,4,5,6,7,8 hexahydro4oxo6-<br>pteridinyl)methyl]amino]benzoyl],<br>calcium salt (1:1)) | Wellcovorin,<br>Leucovorin | Immunex, Corp., Seattle,<br>WA |
| Levamisole HCl<br>((-)-( S)-2,3,5,6-tetrahydro-6-<br>phenylimidazo [2,1-b] thiazole<br>monohydrochloride $C_{11}H_{12}N_2S \bullet HCl$) | Ergamisol | Janssen Research<br>Foundation, Titusville,<br>NJ |
| Lomustine<br>(1-(2-chloro-ethyl)-3-cyclohexyl-1-<br>nitrosourea) | CeeNU | Bristol-Myers Squibb |

TABLE 2-continued

| | | |
|---|---|---|
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl)amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R, 3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |

TABLE 2-continued

| | | |
|---|---|---|
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino)methyl]-4-ethyl-4,9-dihydroxy-1H-pyrano[3',4': 6,7]indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)]-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB—, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The amounts of each of the active agents in the combinations described herein can include amounts of each agent that are found to be clinically relevant amounts that provide therapeutic benefit in the aggregate when dosed in combination. For example, the additional active agent may be dosed or provided in compositions which are dosed with the compounds of the present disclosure in amounts that do cause adverse effects and that may be titrated when studied in a clinical trial of the combination. In each case, the combination may be provided in compositions that may be administered separately or formulated in a single composition and may be dosed in amounts that are either therapeutically effective amounts individually, or when one or both of the active agents of the combination are dosed at sub-optimal or sub-therapeutic levels, if the combination as a whole is therapeutically effective.

The present disclosure provides methods for administering a compound of the disclosure with radiation therapy. The disclosure is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present disclosure.

Antimicrobial therapeutic agents may also be used as therapeutic agents in the present disclosure. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present disclosure, a compound of the disclosure and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

EXAMPLES

General Synthetic Schemes

Compounds of Formula I can be synthesized using the general methods provided in Scheme 1. In accordance with Scheme 1, a bromide compound of formula G1 can be converted to a borane compound of formula G2 by reacting with an agent such as 4,4,5,5-tetramethyl-2-(4,4,5,5-tetramethyl-1,3,2-dioxaborolan-2-yl)-1,3,2-dioxaborolane, or the like. A compound of formula G2 can then be coupled to a compound of formula G5 to provide a compound of Formula I, using coupling chemistry known to those having skill in the art, such as palladium catalyzed coupling conditions. The compound of formula G5 can be synthesized by reacting a compound of formula G3 with a compound of formula G4 under nucleophilic aromatic substitution conditions. It will be also understood that the order of reactions as specified in Scheme 1 can also be reversed, so that a compound of formula G2 reacts with a compound of formula G3 to form an intermediate product, followed by reacting the intermediate product with a compound of formula G4 to provide a compound of Formula I. It will also be understood that the compounds represented by formula G4 can possess a stereocenter, wherein $R_{1a}$ and $R_{1b}$ are different. Further, a compound of G4 can be a single enantiomer or a racemic mixture of enantiomers, which will provide an enantiomeric or racemic compound of Formula I, respectively. It will be generally understood to one having skill in the art that reaction conditions that are successful when using one enantiomer of a compound of formula G4 as starting material will most likely be equally successful for the other enantiomer of the compound of formula G4.

Scheme 1: Synthesis of compounds of Formula I

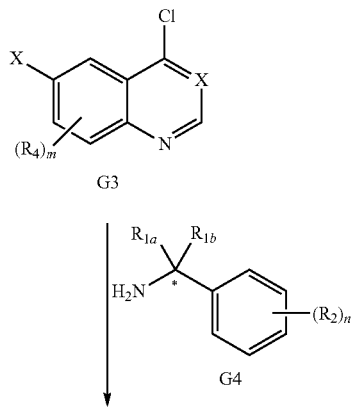

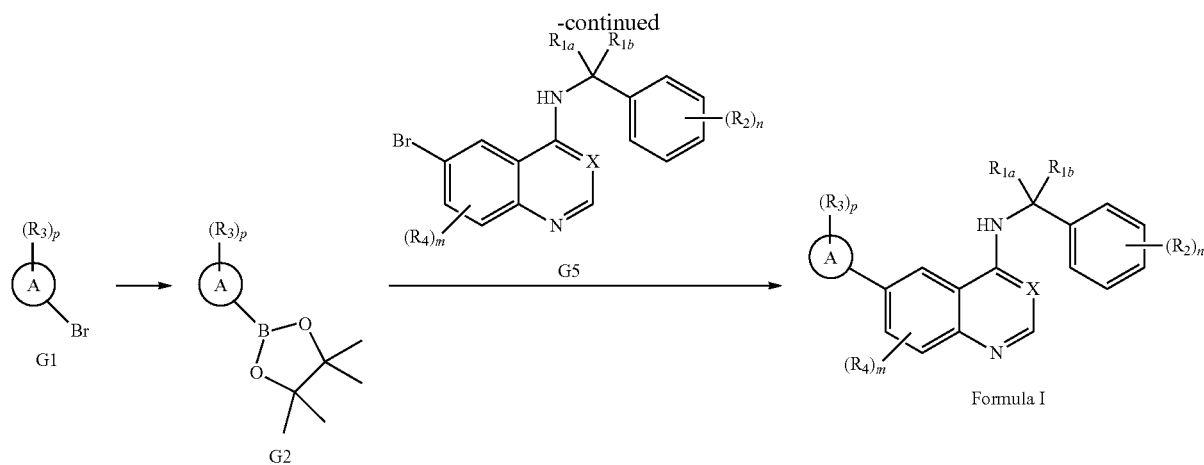

Compounds of Formula I can also be synthesized according to Scheme 2. Following the scheme, a compound of Formula G6 first undergoes nucleophilic substitution with an amine of Formula G7. The resulting compound of Formula G8, where Xa is a group appropriate for functional group interconversion to the tetramethyl-1,3,2-dioxaborolane, is converted to a compound of Formula G9. Exposure of the compound of Formula of G9 to a compound of Formula G10 under coupling conditions, for example palladium catalyzed coupling conditions provides a compound of Formula I.

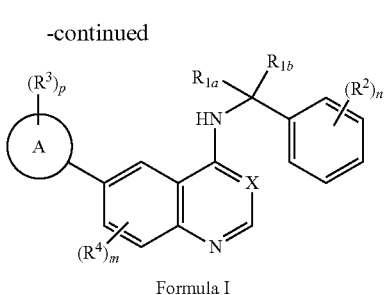

Synthetic Examples

Example 1: N-[5-[4-(1-phenylethylamino)quinazolin-6-yl]-3-pyridyl]methanesulfonamide (Compound 1)

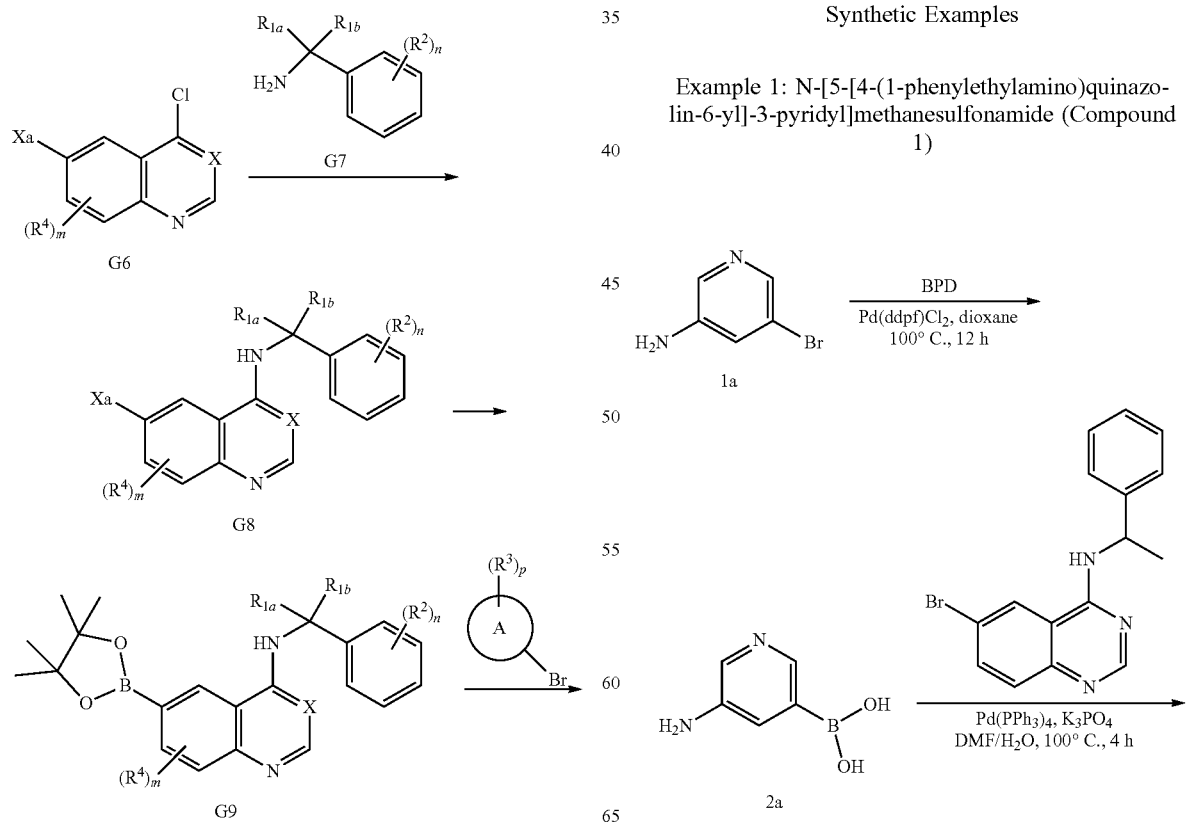

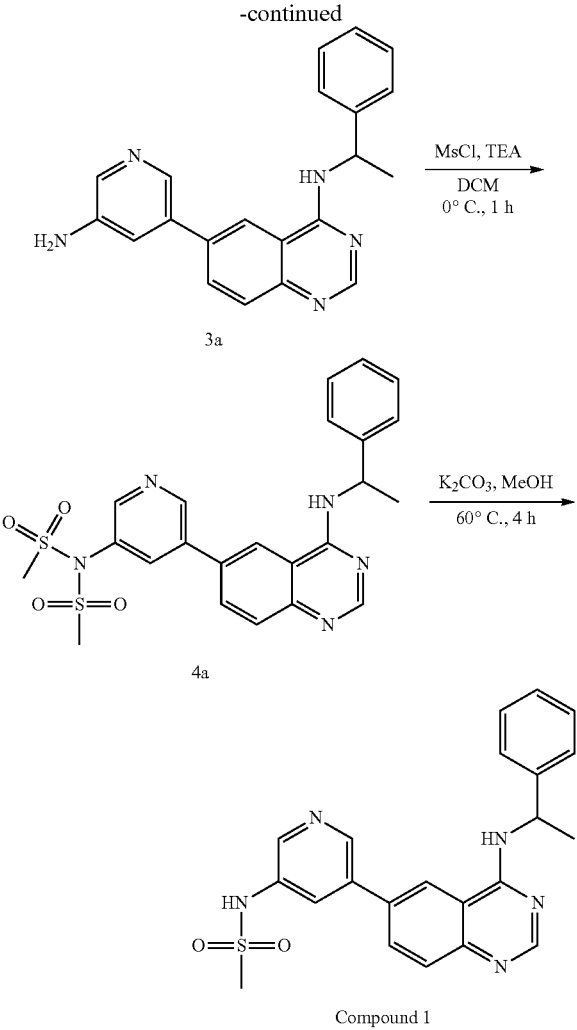

3a

4a

Compound 1

Step 1: Synthesis of (5-amino-3-pyridyl) boronic acid (2a)

To a stirred solution of BPD (1.76 g, 6.94 mmol, 1.2 eq) in dioxane (5 mL) was added 5-bromopyridin-3-amine, 1a, (1 g, 5.78 mmol, 1 eq), AcOK (1.70 g, 17.34 mmol, 3 eq) and Pd(dppf)Cl$_2$.CH$_2$Cl$_2$ (472.02 mg, 578.00 μmol, 0.1 eq), the reaction was purged with Ar 3 times, and stirred at 100° C. for 16 h under Ar. LCMS showed starting material was consumed completely and the MS of desired product was detected. The crude product was triturated with EtOAc (6 mL) at 25° C. for 60 min. Then filtered and filtrate was concentrate in vacuum. Compound 2a (5-amino-3-pyridyl) boronic acid (2 g, crude) was obtained as a black solid.

Step 2: Synthesis of 6-(5-amino-3-pyridyl)-N-(1-phenylethyl)quinazolin-4-amine (3a)

To a stirred solution of (5-amino-3-pyridyl) boronic acid, 2a, (402.32 mg, 1.83 mmol, 2 eq) in DMF (4 mL) and H$_2$O (1.5 mL) was added 6-bromo-N-(1-phenylethyl) quinazolin-4-amine (300 mg, 914.06 μmol, 1 eq), K$_3$PO$_4$ (582.07 mg, 2.74 mmol, 3 eq) and Pd(PPh$_3$)$_4$ (105.63 mg, 91.41 μmol, 0.1 eq), the reaction was stirred at 100° C. for 4 h under N$_2$. LCMS showed starting material was consumed completely and the MS of desired product was detected. The reaction was filtered, and filtrate was purified by prep-HPLC (column: C18-1 150*30 mm*5 um; mobile phase: [water (TFA)-ACN]; B %: 1%-45%, 8 min). Compound 3a, 6-(5-amino-3-pyridyl)-N-(1-phenylethyl)quinazolin-4-amine (80 mg, 175.66 μmol, 19.22% yield, TFA) was obtained as a white solid.

Step 3: Synthesis of N-methylsulfonyl-N-[5-[4-(1-phenylethylamino)quinazolin-6-yl]-3-pyridyl]methanesulfonamide (4a)

To a stirred solution of 6-(5-amino-3-pyridyl)-N-(1-phenylethyl)quinazolin-4-amine, 3a, (40 mg, 117.16 μmol, 1 eq) in dry DCM (2 mL) was added TEA (59.28 mg, 585.81 μmol, 81.54 L, 5 eq), the reaction was degassed with N$_2$ and cooled to 0° C. Then MsCl (50 mg, 436.49 μmol, 33.78 μL, 3.73 eq) was dropwise added to the reaction at 0° C. The reaction was stirred at 0° C. for 1 h under N$_2$. TLC (PE:EtOAc=1:1, R$_f$=0.53) showed the starting material remained and a new spot formed. Then MsCl (50 mg, 436.49 μmol, 33.78 μL, 3.73 eq) was added, and the mixture was stirred at 0° C. for 1 h. LCMS showed starting material was consumed completely and the MS of desired product was detected. The reaction was quenched by adding 5 mL water and extracted with DCM (3*5 mL). The organic layer was washed with brine (5 mL), dried over anhydrous Na$_2$SO$_4$, then filtered and concentrated in vacuum. Compound 4a, N-methylsulfonyl-N-[5-[4-(1-phenylethylamino) quinazolin-6-yl]-3-pyridyl] methanesulfonamide (40 mg, 80.39 μmol, 68.61% yield) was obtained as a yellow oil.

Step 4: Synthesis of N-[5-[4-(1-phenylethylamino) quinazolin-6-yl]-3-pyridyl]methanesulfonamide (Compound 1)

To a stirred solution of N-methylsulfonyl-N-[5-[4-(1-phenylethylamino) quinazolin-6-yl]-3-pyridyl] methanesulfonamide, 4a, (40 mg, 80.39 μmol, 1 eq) in MeOH (2 mL) was added K$_2$CO$_3$ (22.22 mg, 160.78 μmol, 2 eq), the reaction was stirred at 60° C. for 2 h. LCMS showed starting material was consumed completely and the MS of desired product was detected. The reaction was filtered, and filtrate was purified by prep-HPLC (column: Waters Xbridge BEH C18 100*30 mm*10 um; mobile phase: [water (NH$_4$HCO$_3$)-ACN]; B %: 20%-50%, 10 min). Compound 1, N-[5-[4-(1-phenylethylamino) quinazolin-6-yl]-3-pyridyl] methanesulfonamide (5.64 mg, 13.33 mol, 16.58% yield, 99.13% purity) was obtained as a white solid. $^1$H NMR (400 MHz, DMSO-d$_6$) δ ppm 8.82 (s, 2H), 8.66 (br d, J=7.88 Hz, 1H), 8.47 (d, J=2.25 Hz, 1H), 8.44 (s, 1H), 8.07 (dd, J=8.63, 1.63 Hz, 1H), 7.93 (t, J=2.06 Hz, 1H), 7.80 (d, J=8.63 Hz, 1H), 7.45 (d, J=7.50 Hz, 2H), 7.32 (t, J=7.57 Hz, 2H), 7.19-7.25 (m, 1H), 5.65 (t, J=7.25 Hz, 1H), 3.12 (s, 3H), 1.62 (d, J=7.13 Hz, 3H). MS (M+H)$^+$=420.1

Example 2: Synthesis of N-[2-chloro-5-(4,4,5,5-tetramethyl-1,3,2-dioxaborolan-2-yl)-3-pyridyl]-N-methylsulfonyl-methanesulfonamide (3b)

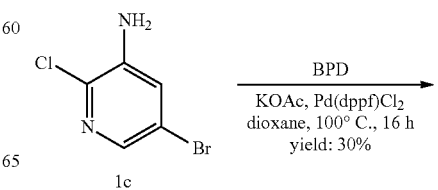

1c

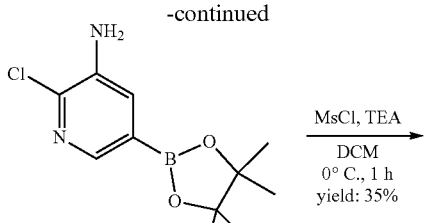

Step 1: Synthesis of 2-chloro-5-(4,4,5,5-tetramethyl-1,3,2-dioxaborolan-2-yl)pyridin-3-amine (2c)

To a stirred solution of 5-bromo-2-chloro-pyridin-3-amine, 1c, (20 g, 96.41 mmol, 1 eq) in dioxane (250 mL) was added 4,4,5,5-tetramethyl-2-(4,4,5,5-tetramethyl-1,3,2-dioxaborolan-2-yl)-1,3,2-dioxaborolane (29.38 g, 115.69 mmol, 1.2 eq), KOAc (23.65 g, 241.01 mmol, 2.5 eq), and Pd(dppf)Cl$_2$ (3.53 g, 4.82 mmol, 0.05 eq), and the mixture was purged with N$_2$ 3 times, and then stirred at 100° C. for 16 h. TLC (Petroleum ether/Ethyl acetate=5:1, R$_f$=0.25) showed a little starting material was remaining and a new spot was formed. The reaction mixture was poured into water (150 mL). The aqueous phase was extracted with ethyl acetate (300 mL*3). The combined organic phase was dried with anhydrous Na$_2$SO$_4$, filtered and concentrated in vacuum. The residue was purified by flash column (ISCO 120 g silica, 10-15% Ethyl acetate in Petroleum ether, gradient over 15 min). Compound 2c, 2-chloro-5-(4,4,5,5-tetramethyl-1,3,2-dioxaborolan-2-yl) pyridin-3-amine (6.75 g, 26.52 mmol, 30% yield) was obtained as a yellow solid.

Step 2: Synthesis of N-[2-chloro-5-(4,4,5,5-tetramethyl-1,3,2-dioxaborolan-2-yl)-3-pyridyl]-N-methylsulfonyl-methanesulfonamide (3b)

To a stirred solution of 2-chloro-5-(4,4,5,5-tetramethyl-1,3,2-dioxaborolan-2-yl)pyridin-3-amine, 2c, (27 g, 106.08 mmol, 1 eq) in DCM (200 mL) was added TEA (42.94 g, 424.33 mmol, 59.06 mL, 4 eq), MsCl (31.170 g, 272.11 mmol, 21.06 mL, 2.57 eq) at 0° C. The mixture was stirred at 0° C. for 1 h. TLC (Petroleum ether/Ethyl acetate=3:1, R$_f$=0.84) showed starting material was consumed completely and new spot was formed. The reaction mixture was concentrate in vacuum. The residue was poured into MeOH (10 mL). The mixture was stirred at 20° C. for 1 h, filtered, and the filter cake was concentrate in vacuum to give the crude product. Compound 3b, N-[2-chloro-5-(4,4,5,5-tetramethyl-1,3,2-dioxaborolan-2-yl)-3-pyridyl]-N-methylsulfonyl-methanesulfonamide (20 g, 48.70 mmol, 46% yield) was obtained as a white solid. $^1$H NMR (400 MHz, CHLOROFORM-d) δ=8.77 (d, J=1.8 Hz, 1H), 8.04 (d, J=1.6 Hz, 1H), 3.53 (s, 6H), 1.45-1.32 (m, 12H)

Example 3: Synthesis of N-[2-chloro-5-[4-(1-phenylethylamino)quinazolin-6-yl]-3-pyridyl]methanesulfonamide (Compound 2)

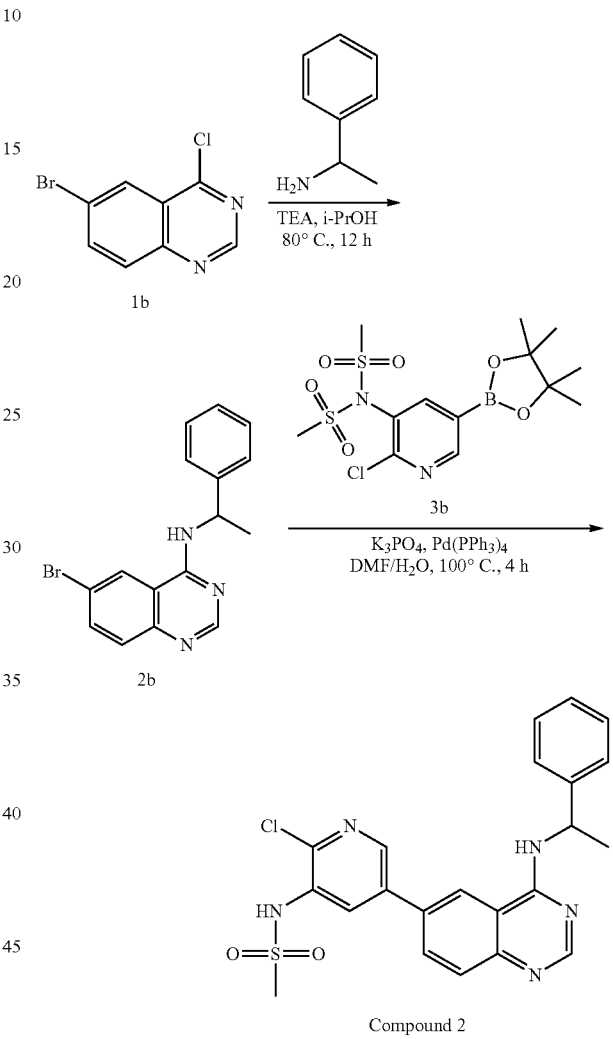

Step 1: Synthesis of 6-bromo-N-(1-phenylethyl)quinazolin-4-amine (2b)

To a stirred solution of 6-bromo-4-chloro-quinazoline, 1b, (3 g, 12.32 mmol, 1 eq) in i-PrOH (30 mL) was added 1-phenylethanamine (1.49 g, 12.32 mmol, 1.57 mL, 1 eq) and TEA (1.99 g, 19.71 mmol, 2.74 mL, 1.6 eq), the reaction was stirred at 80° C. for 16 h under N$_2$. LCMS showed starting material was consumed completely and the MS of desired product was detected. The reaction mixture was cooled to ambient temperature, quenched with water (50 mL) and extracted with ethyl acetate (50 mL). The organic layer was washed with water, brine, dried over anhydrous sodium sulfate, filtered and concentrated in vacuum. Compound 2b, 6-bromo-N-(1-phenylethyl) quinazolin-4-amine (3 g, 9.14 mmol, 74.19% yield) was obtained as white solid.

Step 2: Synthesis of N-[2-chloro-5-[4-(1-phenylethylamino)quinazolin-6-yl]-3-pyridyl]methanesulfonamide (Compound 2)

To a stirred solution of 6-bromo-N-(1-phenylethyl)quinazolin-4-amine, 2b, (50 mg, 152.34 μmol, 1 eq) in DMF (2 mL) and H$_2$O (0.5 mL) was added N-[2-chloro-5-(4,4,5,5-tetramethyl-1,3,2-dioxaborolan-2-yl)-3-pyridyl]-N-methylsulfonyl-methanesulfonamide (62.57 mg, 152.34 μmol, 1 eq), K$_3$PO$_4$ (97.01 mg, 457.03 μmol, 3 eq) and Pd(PPh$_3$)$_4$ (17.60 mg, 15.23 μmol, 0.1 eq), the reaction was stirred at 80° C. for 3 h under N$_2$. LCMS showed starting material was consumed completely and the MS of desired product was detected. The reaction was filtered, and filtrate was evaporated to obtain the product. The crude product was purified by prep-HPLC (column: Phenomenex C18 75*30 mm*3 um; mobile phase: [water (NH$_4$HCO$_3$)-ACN]; B %: 10%-40%, 8 min). Compound 2 N-[2-chloro-5-[4-(1-phenylethylamino) quinazolin-6-yl]-3-pyridyl]methanesulfonamide (8.53 mg, 18.79 μmol, 12.33% yield, 100% purity) was obtained as white solid. $^1$H NMR (400 MHz, DMSO-d$_6$) δ ppm 9.98 (br s, 1H), 8.85 (d, J=1.63 Hz, 1H), 8.79 (d, J=2.25 Hz, 1H), 8.67 (br d, J=7.88 Hz, 1H), 8.44 (s, 1H), 8.24 (d, J=2.38 Hz, 1H), 8.14 (dd, J=8.76, 1.75 Hz, 1H), 7.80 (d, J=8.63 Hz, 1H), 7.45 (d, J=7.38 Hz, 2H), 7.33 (t, J=7.57 Hz, 2H), 7.16-7.27 (m, 1H), 5.65 (t, J=7.25 Hz, 1H), 3.17 (s, 3H), 1.63 (d, J=7.00 Hz, 3H). MS (M+H)$^+$=454.0

Compounds 2R and 2S were synthesized analogously to Compound 2 in Example 3 using the appropriate chiral version of Intermediate 2b.

Compound 2R: $^1$H NMR (400 MHz, DMSO-d6) δ=10.97 (br d, J=7.6 Hz, 1H), 9.97 (br s, 1H), 9.45 (s, 1H), 8.94-8.86 (m, 2H), 8.43 (dd, J=1.6, 8.8 Hz, 1H), 8.36 (d, J=2.4 Hz, 1H), 8.01 (d, J=8.8 Hz, 1H), 7.57 (d, J=7.4 Hz, 2H), 7.40-7.33 (m, 2H), 7.31-7.24 (m, 1H), 5.85 (t, J=7.2 Hz, 1H), 3.25 (s, 3H), 1.75 (d, J=7.0 Hz, 3H). MS (M+H)$^+$=454.0

Compound 2S: $^1$H NMR (400 MHz, DMSO-d6) δ=9.98 (br s, 1H), 8.85 (s, 1H), 8.79 (d, J=2.2 Hz, 1H), 8.67 (br d, J=7.7 Hz, 1H), 8.44 (s, 1H), 8.24 (d, J=2.2 Hz, 1H), 8.14 (dd, J=1.6, 8.7 Hz, 1H), 7.80 (d, J=8.7 Hz, 1H), 7.45 (d, J=7.5 Hz, 2H), 7.33 (t, J=7.6 Hz, 2H), 7.26-7.19 (m, 1H), 5.65 (quin, J=7.1 Hz, 1H), 3.17 (s, 3H), 1.63 (d, J=7.0 Hz, 3H). MS (M+H)$^+$=454.1

Example 4: Synthesis of N-[2-methoxy-5-[4-(1-phenylethylamino)quinazolin-6-yl]-3-pyridyl]methanesulfonamide (Compound 3)

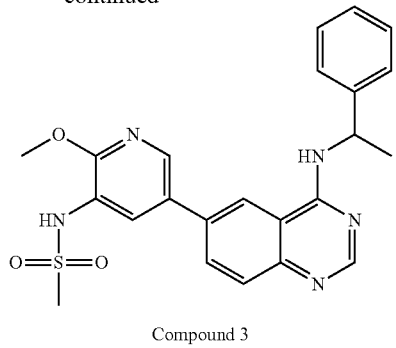

Compound 3

To a stirred solution of 6-bromo-N-(1-phenylethyl)quinazolin-4-amine (50 mg, 152.34 μmol, 1 eq) in DMF (2 mL) and H$_2$O (0.5 mL) was added N-[2-methoxy-5-(4,4,5,5-tetramethyl-1,3,2-dioxaborolan-2-yl)-3-pyridyl]methanesulfonamide (50.00 mg, 152.34 μmol, 1 eq), K$_3$PO$_4$ (97.01 mg, 457.03 μmol, 3 eq) and Pd(PPh$_3$)$_4$ (17.60 mg, 15.23 μmol, 0.1 eq), the reaction was stirred at 80° C. for 3 h under N$_2$. LCMS showed starting material was consumed completely and the MS of desired product was detected. The reaction was filtered, and filtrate was purified by prep-HPLC (column: Phenomenex Luna C18 150*30 mm*5 um; mobile phase: [water (TFA)-ACN]; B %: 10%-40%, 8 min). Compound 3, N-[2-methoxy-5-[4-(1-phenylethylamino) quinazolin-6-yl]-3-pyridyl]methanesulfonamide (47.45 mg, 82.94 μmol, 54.44% yield, 98.50% purity, TFA) was obtained as white solid. $^1$H NMR (400 MHz, DMSO-d$_6$) δ ppm 10.18 (br d, J=7.50 Hz, 1H), 9.52 (s, 1H), 8.94 (d, J=1.38 Hz, 1H), 8.88 (s, 1H), 8.53 (d, J=2.25 Hz, 1H), 8.35 (dd, J=8.76, 1.63 Hz, 1H), 8.07 (d, J=2.25 Hz, 1H), 7.88 (d, J=8.75 Hz, 1H), 7.49 (d, J=7.38 Hz, 2H), 7.38 (t, J=7.57 Hz, 2H), 7.25-7.33 (m, 1H), 5.83 (t, J=7.25 Hz, 1H), 4.00 (s, 3H), 3.09 (s, 3H), 1.70 (d, J=7.00 Hz, 3H). MS (M+H)$^+$=450.1

Example 5

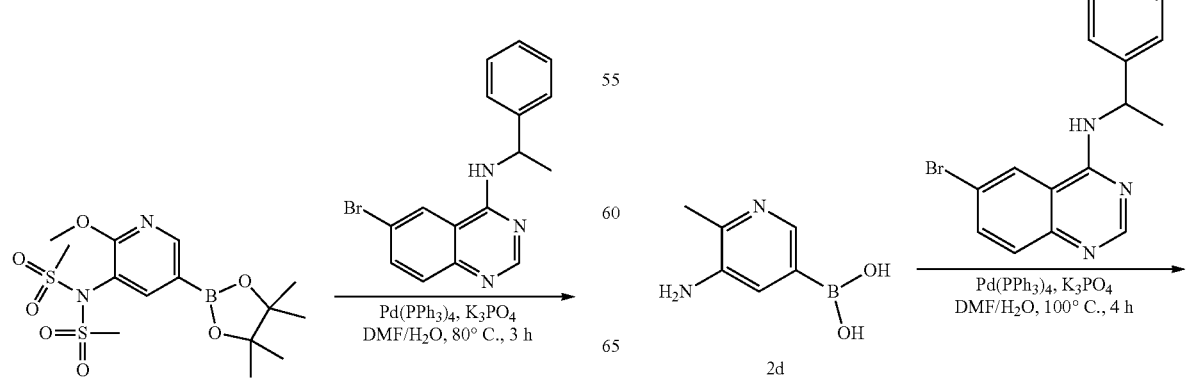

-continued

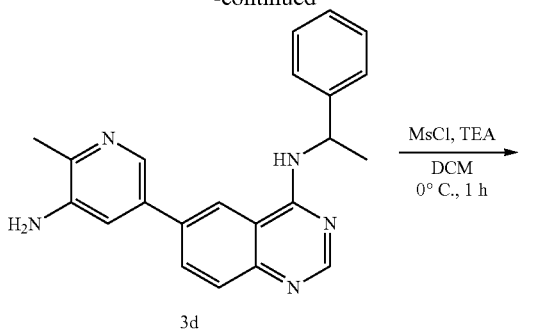

3d

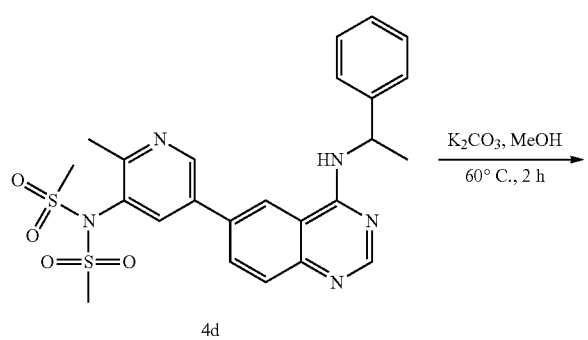

4d

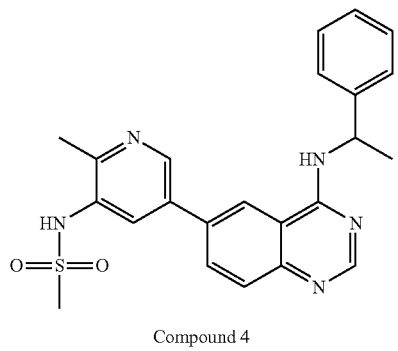

Compound 4

Step 1: Synthesis of (5-amino-6-methyl-3-pyridyl) boronic acid (2)

To a stirred solution of 5-bromo-2-methyl-pyridin-3-amine, 1d, (1 g, 5.35 mmol, 1 eq) in dioxane (5 mL) was added BPD (1.63 g, 6.42 mmol, 1.2 eq), AcOK (1.57 g, 16.04 mmol, 3 eq) and Pd(dppf)Cl$_2$.CH$_2$Cl$_2$ (436.62 mg, 534.65 μmol, 0.1 eq), the reaction was purged with Ar 3 times, and stirred at 100° C. for 16 h under Ar. LCMS showed starting material was consumed completely and the MS of desired product was detected. The reaction mixture was poured into water (50 mL). The aqueous phase was extracted with ethyl acetate (50 mL*2). The combined organic phase was dried with anhydrous Na$_2$SO$_4$, filtered and concentrated in vacuum. Compound 2d, (5-amino-6-methyl-3-pyridyl) boronic acid (2.8 g, crude) was obtained as black oil.

Step 2: Synthesis of 6-(5-amino-6-methyl-3-pyridyl)-N-(1-phenylethyl) quinazolin-4-amine (3d)

To a stirred solution of 6-bromo-N-(1-phenylethyl)quinazolin-4-amine, 2d, (420.59 mg, 1.28 mmol, 1 eq) in DMF (4 mL) and H$_2$O (1.5 mL) was added (5-amino-6-methyl-3-pyridyl)boronic acid (194.51 mg, 1.28 mmol, 1 eq), K$_3$PO$_4$ (815.12 mg, 3.84 mmol, 3 eq) and Pd(PPh$_3$)$_4$ (147.91 mg, 128.00 μmol, 0.1 eq), the reaction was stirred at 100° C. for 4 h under N$_2$. LCMS showed starting material was consumed completely and the MS of desired product was detected. The reaction was filtered, and filtrate was purified by prep-HPLC (column: C18-1 150*30 mm*5 um; mobile phase: [water (TFA)-ACN]; B %: 1%-45%, 8 min). Compound 3d, 6-(5-amino-6-methyl-3-pyridyl)-N-(1-phenylethyl) quinazolin-4-amine (70 mg, 144.70 μmol, 10.78% yield, TFA) was obtained as yellow solid.

Step 3: Synthesis of N-[2-methyl-5-[4-(1-phenylethylamino)quinazolin-6-yl]-3-pyridyl]-N-methylsulfonyl-methanesulfonamide (4d)

To a stirred solution of 6-(5-amino-6-methyl-3-pyridyl)-N-(1-phenylethyl) quinazolin-4-amine (40 mg, 112.54 μmol, 1 eq) in DCM (2 mL) was added TEA (56.94 mg, 562.69 mol, 78.32 μL, 5 eq), the reaction was degassed with N$_2$ and cooled to 0° C. Then MsCl (55 mg, 1.57 mmol, 37.16 μL, 4 eq) was dropwise added to the reaction at 0° C. The reaction was stirred at 0° C. for 1 h under N$_2$. LCMS showed starting material was consumed completely and the MS of desired product was detected. The reaction was quenched by adding 5 mL water and extracted with DCM (3*5 mL). The organic layer was washed with brine (5 mL), dried over anhydrous Na$_2$SO$_4$, then filtered and concentrated in vacuum. Compound 4d, N-[2-methyl-5-[4-(1-phenylethylamino) quinazolin-6-yl]-3-pyridyl]-N-methylsulfonyl-methanesulfonamide (40 mg, 78.18 μmol, 69.47% yield) was obtained as a yellow oil.

Step 4: Synthesis of N-[2-methyl-5-[4-(1-phenylethylamino)quinazolin-6-yl]-3-pyridyl]methanesulfonamide (Compound 4)

To a stirred solution of N-[2-methyl-5-[4-(1-phenylethylamino) quinazolin-6-yl]-3-pyridyl]-N-methylsulfonyl-methanesulfonamide, 4d, (40 mg, 78.18 μmol, 1 eq) in MeOH (2 mL) was added K$_2$CO$_3$ (21.61 mg, 156.37 μmol, 2 eq), the reaction was stirred at 60° C. for 2 h. LCMS showed starting material was consumed completely and the MS of desired product was detected. The reaction was filtered, and filtrate was purified by prep-HPLC (column: Waters Xbridge BEH C18 100*30 mm*10 um; mobile phase: [water (NH$_4$HCO$_3$)-ACN]; B %: 25%-50%, 10 min). Compound 4, N-[2-methyl-5-[4-(1-phenylethylamino) quinazolin-6-yl]-3-pyridyl]methanesulfonamide (3.5 mg, 8.91 μmol, 11.40% yield, 96.59% purity) was obtained as a white solid. $^1$H NMR (400 MHz, DMSO-d$_6$) δ ppm 8.79 (s, 1H), 8.76 (s, 1H), 8.64 (br d, J=7.88 Hz, 1H), 8.42 (s, 1H), 8.08 (dd, J=8.63, 1.63 Hz, 1H), 7.99 (d, J=1.88 Hz, 1H), 7.78 (d, J=8.63 Hz, 1H), 7.45 (d, J=7.50 Hz, 2H), 7.32 (t, J=7.57 Hz, 2H), 7.18-7.25 (m, 1H), 5.65 (br t, J=7.25 Hz, 1H), 3.05 (s, 3H), 2.56 (s, 3H), 1.62 (d, J=7.13 Hz, 3H). MS (M+H)$^+$=434.2

Example 6: Synthesis of 6-(2-aminopyrimidin-5-yl)-N-(1-phenylethyl) quinazolin-4-amine (Compound 7)

Example 7: Synthesis of N-(1-phenylethyl)-6-(1H-pyrazolo[3, 4-b] pyridin-5-Yl) quinazolin-4-amine (Compound 8)

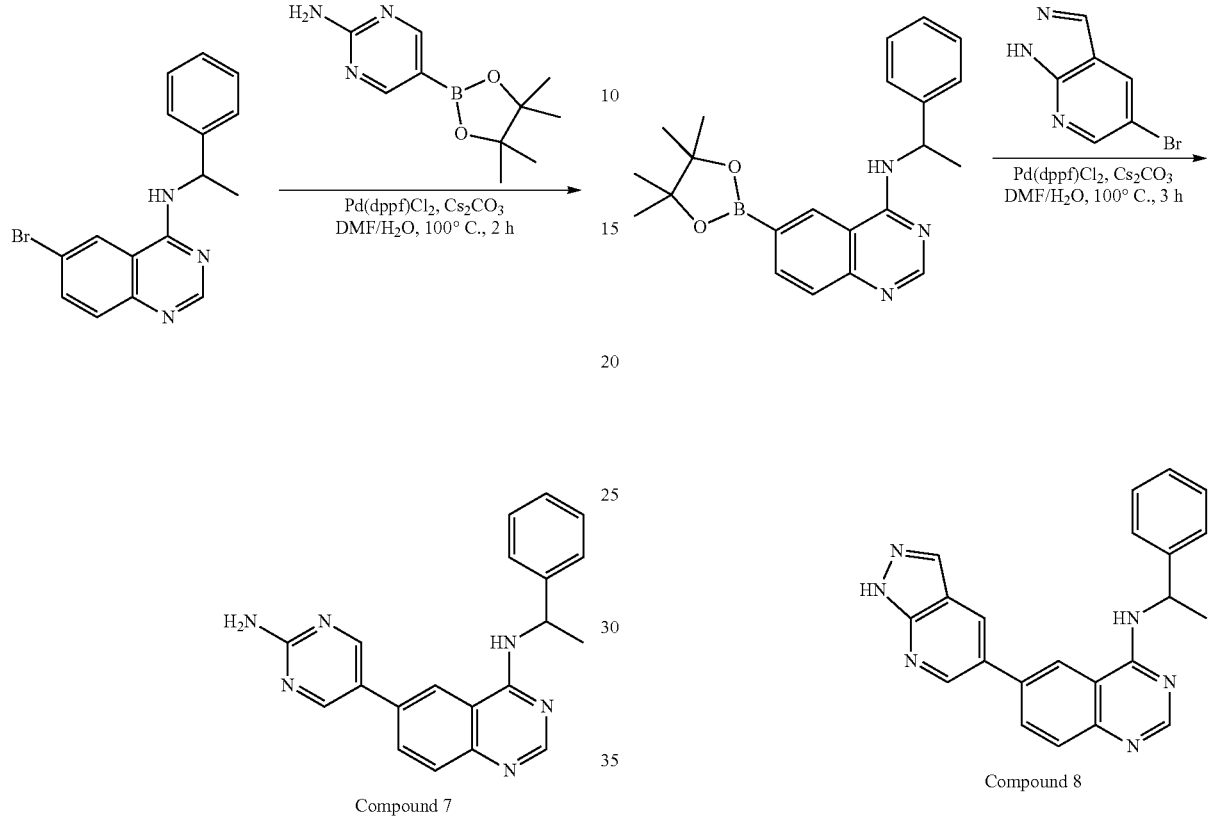

Compound 7

Compound 8

To a solution of 6-bromo-N-(1-phenylethyl)quinazolin-4-amine (100 mg, 304.69 mol, 1 eq) in DMF (0.5 mL) and H$_2$O (0.1 mL) was added Cs$_2$CO$_3$ (297.82 mg, 914.06 µmol, 3 eq), Pd(dppf)Cl$_2$ (22.29 mg, 30.47 µmol, 0.1 eq) and 5-(4,4,5,5-tetramethyl-1,3,2-dioxaborolan-2-yl) pyrimidin-2-amine (67.36 mg, 304.69 µmol, 1 eq), the mixture was bubbled with N$_2$ for 1 minute and stirred at 100° C. for 2 h. LCMS showed starting material was consumed completely and the MS of desired product was detected. The reaction mixture was filtered, and filtrate was concentrated in vacuum. The crude product was purified by prep-HPLC (column: Phenomenex luna C18 80*40 mm*3 um; mobile phase: [water (0.04% HCl)-ACN]; B %: 10%-40%, 7 min) Compound 7, 6-(2-aminopyrimidin-5-yl)-N-(1-phenylethyl) quinazolin-4-amine (13.84 mg, 36.53 µmol, 11.99% yield, 100% purity, HCl) was obtained as a pale yellow solid. $^1$H NMR (400 MHz, DMSO-d$_6$) δ ppm 10.67 (br d, J=5.63 Hz, 1H), 9.20 (s, 1H) 8.98 (s, 2H), 8.90 (s, 1H), 8.40 (dd, J=8.76, 1.75 Hz, 1H), 7.91 (d, J=8.75 Hz, 1H), 7.55 (d, J=7.38 Hz, 2H), 7.35-7.40 (m, 2H), 7.26-7.31 (m, 1H), 5.85 (quin, J=7.29 Hz, 1H), 1.74 (d, J=7.00 Hz, 3H). MS (M+H)$^+$=343.1

To a stirred solution of N-(1-phenylethyl)-6-(4,4,5,5-tetramethyl-1,3,2-dioxaborolan-2-yl)quinazolin-4-amine (100 mg, 266.47 µmol, 1 eq) in DMF (2 mL) and H$_2$O (0.4 mL) was added Cs$_2$CO$_3$ (260.47 mg, 799.41 µmol, 3 eq), Pd(dppf)Cl$_2$ (19.50 mg, 26.65 µmol, 0.1 eq) and 5-bromo-2H-pyrazolo[3,4-b]pyridine (52.77 mg, 266.47 µmol, 1 eq), the mixture was bubbled with N$_2$, and the reaction was stirred at 100° C. for 3 h. LCMS showed starting material was consumed completely and the MS of desired product was detected. The reaction mixture was concentrated in vacuum. The crude product was purified by prep-HPLC (column: Phenomenex luna C18 80*40 mm*3 um; mobile phase: [water (0.04% HCl)-ACN]; B %: 19%-39%, 7 min). Compound N-(1-phenylethyl)-6-(1H-pyrazolo[3,4-b]pyridin-5-yl)quinazolin-4-amine (5.33 mg, 12.39 µmol, 4.65% yield, 93.63% purity, HCl) was obtained as a yellow solid. $^1$H NMR (400 MHz, DMSO-d$_6$) δ ppm 10.50 (br s, 1H), 9.17 (s, 1H), 9.09 (d, J=2.13 Hz, 1H), 8.95 (s, 1H), 8.73 (d, J=2.13 Hz, 1H), 8.52 (dd, J=8.75, 1.75 Hz, 1H), 8.31 (s, 1H), 7.96 (d, J=8.63 Hz, 1H), 7.53 (d, J=7.50 Hz, 2H), 7.39 (t, J=7.50 Hz, 2H), 7.26-7.34 (m, 1H), 5.79-5.99 (m, 1H), 1.74 (d, J=7.00 Hz, 3H). MS (M+H)$^+$=367.1

Example 8: Synthesis of 6-(2-methyl-1H-imidazo[4,5-b]pyridin-6-yl)-N-(1-phenylethyl) quinazolin-4-amine (Compound 10)

Example 9: Synthesis of 2-[5-[4-(1-phenylethylamino)quinazolin-6-yl]-3-pyridyl]propan-2-ol (Compound 21)

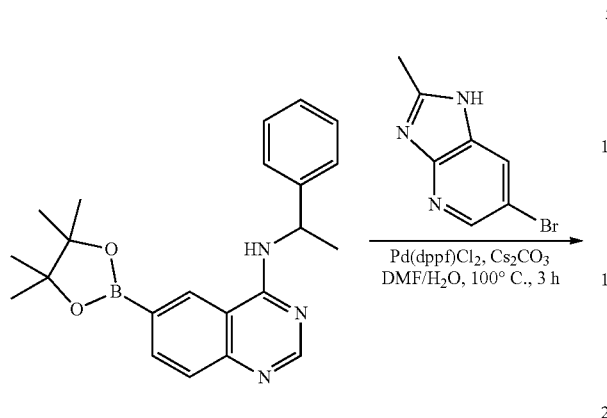

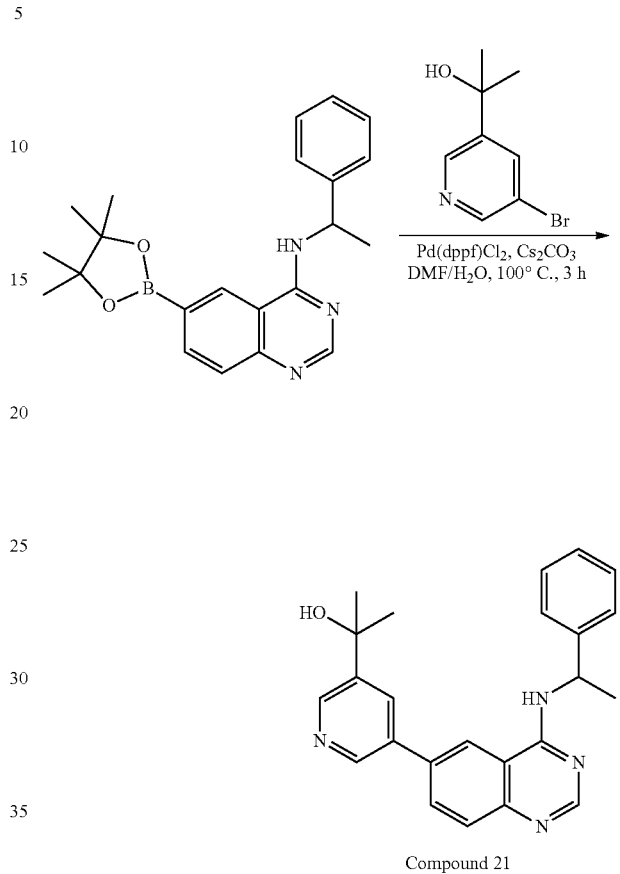

Compound 10

Compound 21

To a solution of N-(1-phenylethyl)-6-(4, 4, 5, 5-tetramethyl-1, 3, 2-dioxaborolan-2-yl) quinazolin-4-amine (100 mg, 266.47 μmol, 1 eq) in DMF (2 mL) and H$_2$O (0.4 mL) was added Cs$_2$CO$_3$ (260.47 mg, 799.42 μmol, 3 eq), Pd(dppf)Cl$_2$ (19.50 mg, 26.65 μmol, 0.1 eq) and 6-bromo-2-methyl-1H-imidazo[4,5-b]pyridine (56.50 mg, 266.47 μmol, 1 eq), the mixture was bubbled with N$_2$, and stirred at 100° C. for 3 h. LCMS showed starting material was consumed completely and the MS of the desired product was detected. The reaction mixture was concentrated in vacuum, and the crude product was purified by prep-HPLC (column: Phenomenex Luna C18 100*30 mm*5 um; mobile phase: [water (0.04% HCl)-ACN]; B %: 1%-35%, 10 min). Compound 10, 6-(2-methyl-1H-imidazo[4,5-b]pyridin-6-yl)-N-(1-phenylethyl)quinazolin-4-amine (7.09 mg, 17.01 μmol, 6.38% yield, 100% purity, HCl) was obtained as a white solid. $^1$H NMR (400 MHz, DMSO-d$_6$) δ ppm 10.98 (br s, 1H), 9.47 (br s, 1H), 9.09 (s, 1H), 8.94 (s, 1H), 8.76 (br s, 1H), 8.56 (dd, J=8.76, 1.63 Hz, 1H), 8.02 (d, J=8.63 Hz, 1H), 7.59 (d, J=7.50 Hz, 2H), 7.34-7.42 (m, 2H), 7.25-7.32 (m, 1H), 5.87 (quin, J=7.10 Hz, 1H), 2.79 (s, 3H), 1.77 (d, J=7.00 Hz, 3H). MS (M+H)$^+$=381.1

To a stirred solution of N-(1-phenylethyl)-6-(4,4,5,5-tetramethyl-1,3,2-dioxaborolan-2-yl)quinazolin-4-amine (100 mg, 266.47 μmol, 1 eq) in DMF (1 mL) and H$_2$O (0.2 mL) was added Cs$_2$CO$_3$ (260.47 mg, 799.42 μmol, 3 eq), Pd(dppf)Cl$_2$ (19.50 mg, 26.65 μmol, 0.1 eq) and 2-(5-bromo-3-pyridyl)propan-2-ol (57.58 mg, 266.47 μmol, 1 eq), the mixture was bubbled with N$_2$, the mixture was stirred at 100° C. for 3 h. LCMS showed starting material was consumed completely and the MS of desired product was detected. The reaction mixture was concentrated in vacuum. The crude product was purified by prep-HPLC (column: Welch Xtimate C18 100*25 mm*3 um; mobile phase: [water (0.04% HCl)-ACN]; B %: 5%-35%, 8 min). Compound 2-[5-[4-(1-phenylethylamino)quinazolin-6-yl]-3-pyridyl]propan-2-ol (61.61 mg, 141.46 μmol, 53.09% yield 96.65% purity, HCl) was obtained as a brown solid. $^1$H NMR (400 MHz, DMSO-d6) δ ppm 11.55 (br d, J=7.75 Hz, 1H) 9.95 (d, J=1.25 Hz, 1H) 9.48 (d, J=1.75 Hz, 1H) 9.26 (s, 1H) 8.90-8.95 (m, 2H) 8.62 (dd, J=8.82, 1.69 Hz, 1H) 8.05 (d, J=8.75 Hz, 1H) 7.63 (d, J=7.38 Hz, 2H) 7.32-7.39 (m, 2H) 7.23-7.29 (m, 1H) 5.86 (quin, J=7.13 Hz, 1H) 1.80 (d, J=7.00 Hz, 3H) 1.65 (s, 6H). MS (M+H)$^+$=385.1

Example 10: Synthesis of 6-(5, 6-dimethoxy-3-pyridyl)-N-(1-phenylethyl) quinazolin-4-amine (Compound 22)

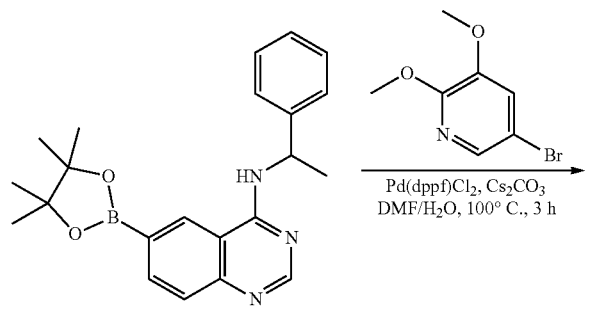

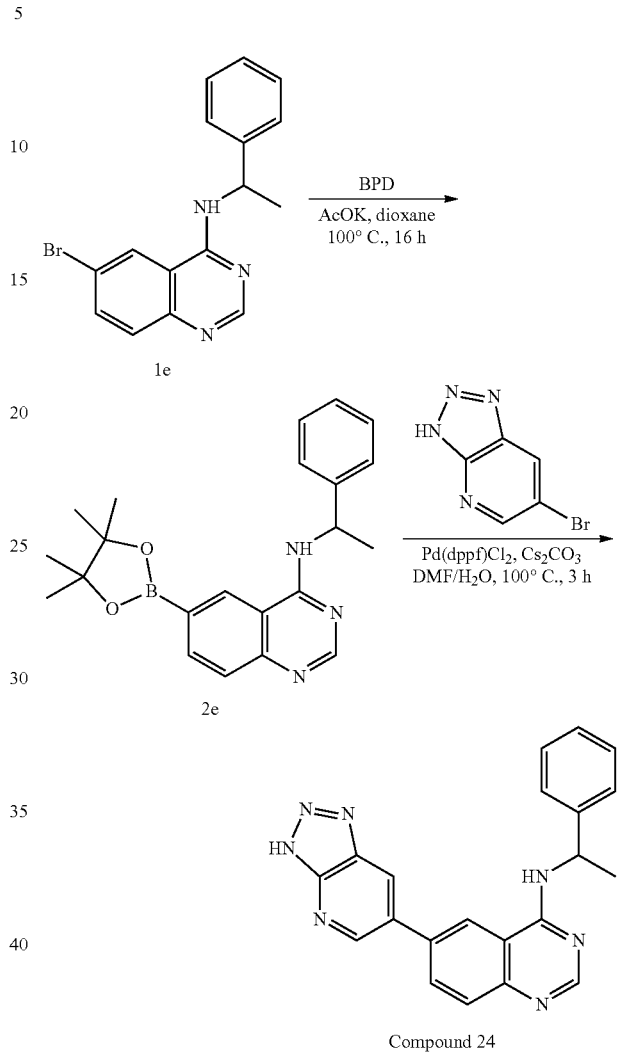

To a solution of N-(1-phenylethyl)-6-(4,4,5,5-tetramethyl-1, 3, 2-dioxaborolan-2-yl) quinazolin-4-amine (200 mg, 532.95 μmol, 1 eq) in DMF (2.5 mL) and H$_2$O (0.5 mL) was added Cs$_2$CO$_3$ (520.93 mg, 1.60 mmol, 3 eq), 5-bromo-2,3-dimethoxy-pyridine (116.21 mg, 532.95 μmol, 1 eq), Pd(dppf)Cl$_2$ (39.00 mg, 53.29 μmol, 0.1 eq), the mixture was bubbled with N$_2$ for 1 minute, and then stirred at 100° C. for 3 h. LCMS showed starting material was consumed completely and the MS of desired product was detected. The reaction mixture was concentrated in vacuum. The crude product was purified by prep-HPLC (column: Welch Xtimate C18 100*25 mm*3 um; mobile phase: [water (0.04% HCl)-ACN]; B %: 25%-45%, 8 min). Compound 22, 6-(5, 6-dimethoxy-3-pyridyl)-N-(1-phenylethyl) quinazolin-4-amine (18.27 mg, 41.49 μmol, 7.79% yield, 96.04% purity, HCl) was obtained as a pale yellow solid. $^1$H NMR (400 MHz, DMSO-d6) δ ppm 10.77 (br d, J=6.97 Hz, 1H), 9.25 (s, 1H), 8.90 (s, 1H), 8.40-8.46 (m, 1H), 8.26 (d, J=1.96 Hz, 1H), 7.84-7.93 (m, 2H), 7.56 (d, J=7.58 Hz, 2H), 7.34-7.39 (m, 2H), 7.29 (d, J=7.34 Hz, 1H), 5.85 (quin, J=7.18 Hz, 1H), 3.95 (d, J=9.05 Hz, 6H), 1.75 (d, J=6.97 Hz, 3H). MS (M+H)$^+$=387.1

Example 11: Synthesis of N-(1-phenylethyl)-6-(3H-triazolo [4,5-b]pyridin-6-yl)quinazolin-4-amine (Compound 24)

Step 1: Synthesis of N-(1-phenylethyl)-6-(4, 4, 5, 5-tetramethyl-1, 3, 2-dioxaborolan-2-yl) quinazolin-4-amine (2e)

To a stirred solution of 6-bromo-N-(1-phenylethyl) quinazolin-4-amine, 1e, (4 g, 12.19 mmol, 1 eq) in dioxane (8 mL) was added AcOK (3.60 g, 36.68 mmol, 3.01 eq), Pd(dppf)Cl$_2$.CH$_2$Cl$_2$ (995.27 mg, 1.22 mmol, 0.1 eq), BPD (3.71 g, 14.62 mmol, 1.2 eq), the mixture was purged with Ar, the mixture was stirred at 110° C. for 4 h under Ar. LCMS showed starting material was consumed completely and the MS of desired product was detected. TLC (PE: EtOAc=1:1, R$_f$=0.35) showed the starting material was consumed completely and new spot was formed. The residue was partitioned between ethyl acetate (100 mL) and H$_2$O (50 mL). The separated organic layer was washed with water, dried over Na$_2$SO$_4$ and evaporated to dryness. The residue was purified by flash column (ISCO 10 g silica, 50-60% Ethyl acetate in Petroleum ether, gradient over 20 min). Compound 2e, N-(1-phenylethyl)-6-(4, 4, 5, 5-tetramethyl- 1, 3, 2-dioxaborolan-2-yl) quinazolin-4-amine (1.5 g, 4.00 mmol, 32.80% yield) was obtained as brown oil. $^1$H NMR (400 MHz, DMSO-d$_6$) δ ppm 8.85 (d, J=7.75 Hz, 1H), 8.80 (s, 1H), 8.42 (s, 1H), 7.98 (dd, J=8.32, 1.06 Hz, 1H), 7.63 (d, J=8.25 Hz, 1H), 7.45 (d, J=7.38 Hz, 2H), 7.31 (t, J=7.63 Hz, 2H), 7.13-7.25 (m, 1H), 5.64 (quin, J=7.19 Hz, 1H), 1.56-1.66 (m, 3H), 1.08 (s, 12H). MS (M+H)+=376.3

Step 2: Synthesis of N-(1-phenylethyl)-6-(3H-triazolo [4,5-b]pyridin-6-yl)quinazolin-4-amine (Compound 24)

To a stirred solution of N-(1-phenylethyl)-6-(4, 4, 5, 5-tetramethyl-1, 3, 2-dioxaborolan-2-yl) quinazolin-4-amine, 2e, (150 mg, 399.71 µmol, 1 eq) in DMF (2.5 mL) and H$_2$O (0.5 mL) was added K$_3$PO$_4$ (254.54 mg, 1.20 mmol, 3 eq), palladium; triphenylphosphane (46.19 mg, 39.97 µmol, 0.1 eq) and 6-bromo-3H-trazolo[4,5-b]pyridine (63.64 mg, 319.77 µmol, 0.8 eq), the mixture was bubbled with N$_2$, and then stirred at 100° C. for 3 h. LCMS showed starting material was consumed completely and the MS of desired product was detected. The reaction mixture was concentrated in vacuum. The crude product was purified by prep-HPLC (column: Waters Xbridge BEH C18 100*30 mm*10 um; mobile phase: [water (10 mM NH$_4$HCO$_3$)-ACN]; B %: 15%-40%, 8 min). Compound 24, N-(1-phenylethyl)-6-(3H-triazolo[4,5-b]pyridin-6-yl)quinazolin-4-amine (3.47 mg, 9.36 µmol, 2.34% yield, 99.14% purity) was obtained as a white solid. $^1$H NMR (400 MHz, DMSO-d$_6$) δ ppm 9.25 (d, J=2.00 Hz, 1H), 8.95 (d, J=1.75 Hz, 1H), 8.83 (s, 1H), 8.66 (br d, J=7.63 Hz, 1H), 8.45 (s, 1H), 8.31 (dd, J=8.63, 1.88 Hz, 1H), 7.82 (d, J=8.63 Hz, 1H), 7.48 (d, J=7.63 Hz, 2H), 7.34 (t, J=7.57 Hz, 2H), 7.19-7.27 (m, 1H), 5.67 (t, J=7.25 Hz, 1H), 1.64 (d, J=7.13 Hz, 3H). MS (M+H)+=368.1

Example 12: Synthesis of 6-(1-methylpyrazolo[4,3-b]pyridin-6-yl)-N-(1-phenylethyl)quinazolin-4-amine (Compound 27)

To a stirred solution of N-(1-phenylethyl)-6-(4,4,5,5-tetramethyl-1,3,2-dioxaborolan-2-yl)quinazolin-4-amine (100 mg, 266.47 µmol, 1 eq) in DMF (2 mL) and H$_2$O (0.4 mL) was added Cs$_2$CO$_3$ (260.47 mg, 799.42 µmol, 3 eq), Pd(dppf)Cl$_2$ (19.50 mg, 26.65 µmol, 0.1 eq) and 6-bromo-1-methyl-pyrazolo[4,3-b]pyridine (56.50 mg, 266.47 µmol, 1 eq), the mixture was bubbled with N$_2$, and then stirred at 100° C. for 3 h. LCMS showed starting material was consumed completely and the MS of desired product was detected. The reaction mixture was concentrated in vacuum. The crude product was purified by prep-HPLC (column: Phenomenex luna C18 80*40 mm*3 um; mobile phase: [water (0.04% HCl)-ACN]; B %: 15%-35%, 7 min) Compound 27, 6-(1-methylpyrazolo[4,3-b]pyridin-6-yl)-N-(1-phenylethyl)quinazolin-4-amine (42.87 mg, 99.21 µmol, 37.23% yield, 96.48% purity, HCl) was obtained as yellow solid. $^1$H NMR (400 MHz, DMSO-d6) δ ppm 10.91 (br d, J=7.46 Hz, 1H), 9.50 (br s, 1H), 9.15 (d, J=1.83 Hz, 1H), 8.86-8.97 (m, 2H), 8.60 (dd, J=8.68, 1.71 Hz, 1H), 8.38 (d, J=0.61 Hz, 1H), 8.01 (d, J=8.80 Hz, 1H), 7.59 (d, J=8.07 Hz, 2H), 7.38 (t, J=7.52 Hz, 2H), 7.24-7.33 (m, 1H), 5.80-5.97 (m, 1H), 4.21 (s, 3H), 1.77 (d, J=6.97 Hz, 3H). MS (M+H)+=381.1

Example 13: Synthesis of 2-amino-N, N-dimethyl-5-[4-(1-phenylethylamino) quinazolin-6-yl] pyridine-3-carboxamide (Compound 36)

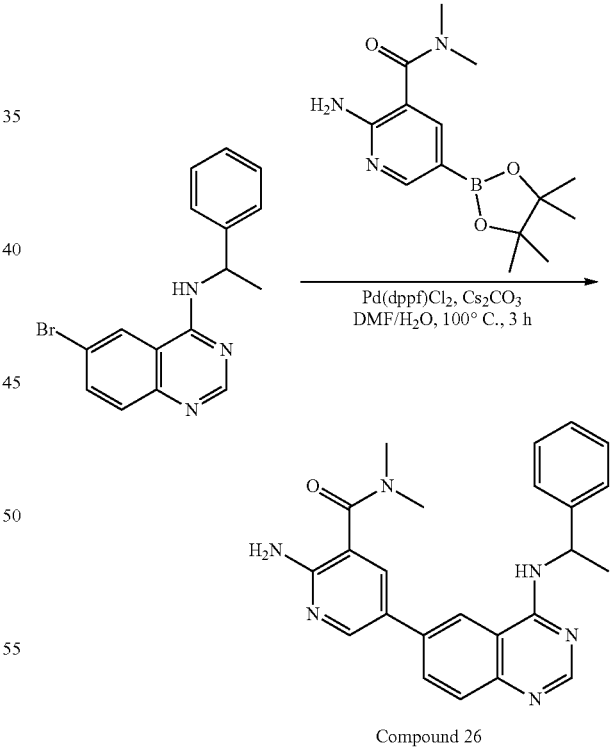

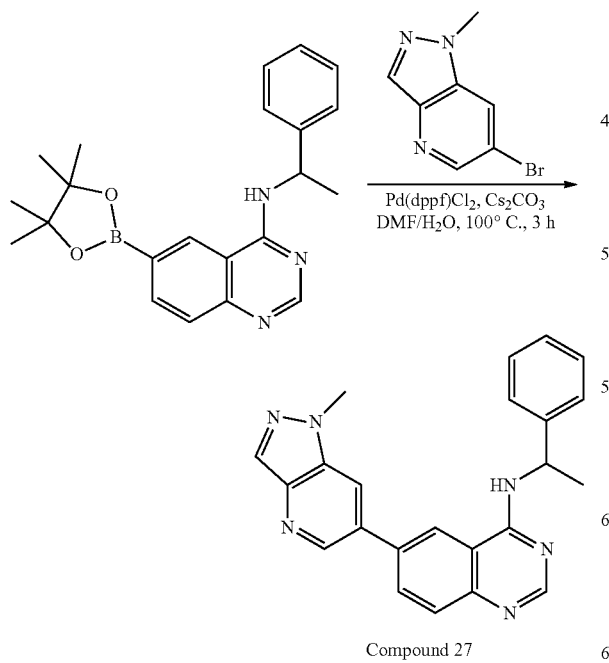

Compound 27

To a stirred solution of 6-bromo-N-(1-phenylethyl)quinazolin-4-amine (150 mg, 457.03 µmol, 1 eq) in DMF (3 mL) and H$_2$O (0.5 mL) was added 2-amino-N, N-dimethyl-5-(4, 4, 5, 5-tetramethyl-1, 3, 2-dioxaborolan-2-yl)pyridine-3-carboxamide (133.07 mg, 457.03 µmol, 1 eq) Cs$_2$CO$_3$ (446.73 mg, 1.37 mmol, 3 eq) and Pd(dppf)Cl$_2$ (33.44 mg, 45.70 µmol, 0.1 eq), the mixture was bubbled with N$_2$ for 1 minute, and stirred at 100° C. for 3 h. LCMS showed starting material was consumed completely and the MS of desired product was detected. The reaction mixture was filtered, and filtrate was purified by prep-HPLC (column: Welch Xtimate C18 100*25 mm*3 um; mobile phase: [water (0.04% HCl)-ACN]; B %: 10%-40%, 8 min). Compound 36 2-amino-N,N-dimethyl-5-[4-(1-phenylethylamino) quinazolin-6-yl] pyridine-3-carboxamide (80.96 mg, 174.17 mol, 38.11% yield, 96.58% purity, HCl) was obtained as a white solid. $^1$H NMR (400 MHz, DMSO-$d_6$) δ ppm 10.87 (br d, J=7.13 Hz, 1H), 9.29 (s, 1H), 8.89 (s, 1H), 8.78 (d, J=2.25 Hz, 1H), 8.40-8.47 (m, 2H), 7.91 (d, J=8.88 Hz, 1H), 7.56 (d, J=7.38 Hz, 2H), 7.33-7.40 (m, 2H), 7.24-7.31 (m, 1H), 5.85 (quin, J=7.13 Hz, 1H), 3.00 (br d, J=11.01 Hz, 6H), 1.75 (d, J=7.00 Hz, 3H). MS (M+H)$^+$=413.1

Example 14: Synthesis of 5-[4-(1-phenylethyl-amino)quinazolin-6-yl]-1,3-benzoxazol-2-amine (Compound 41)

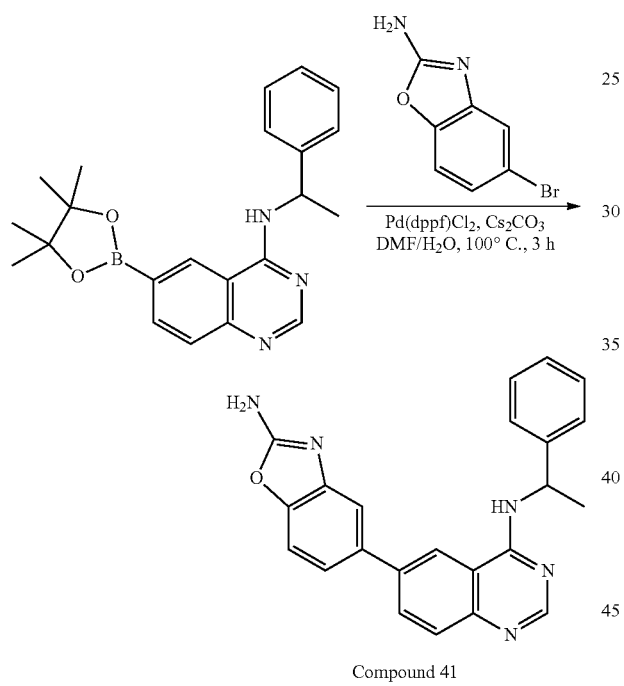

Compound 41

To a solution of N-(1-phenylethyl)-6-(4, 4, 5, 5-tetramethyl-1, 3, 2-dioxaborolan-2-yl)quinazolin-4-amine (100 mg, 266.47 μmol, 1 eq) in DMF (0.5 mL) and H$_2$O (0.1 mL) was added Cs$_2$CO$_3$ (260.47 mg, 799.42 μmol, 3 eq), Pd(dppf)Cl$_2$ (19.50 mg, 26.65 μmol, 0.1 eq) and 5-bromo-1,3-benzoxazol-2-amine (56.77 mg, 266.47 μmol, 1 eq), the mixture was bubbled with N$_2$, and then stirred at 100° C. for 3 h. LCMS showed starting material was consumed completely and the MS of desired product was detected. The reaction mixture was concentrated in vacuum. The crude product was purified by prep-HPLC (column: Phenomenex Luna C18 100*30 mm*5 um; mobile phase: [water (0.04% HCl)-ACN]; B %: 10%-40%, 10 min) Compound 41 5-[4-(1-phenylethylamino)quinazolin-6-yl]-1,3-benzoxazol-2-amine (23.95 mg, 62.28 μmol, 23.37% yield, 99.18% purity) was obtained as a off-white solid. $^1$H NMR (400 MHz, DMSO-$d_6$) δ ppm 10.55 (br d, J=7.38 Hz, 1H), 9.07 (s, 1H), 8.92 (s, 1H), 8.42 (dd, J=8.76, 1.75 Hz, 1H), 7.93 (br d, J=8.63 Hz, 2H), 7.78 (s, 1H), 7.49-7.59 (m, 4H), 7.35-7.42 (m, 2H), 7.25-7.33 (m, 1H), 5.87 (quin, J=7.13 Hz, 1H), 1.74 (d, J=7.13 Hz, 3H). MS (M+H)$^+$=382.1

Example 15

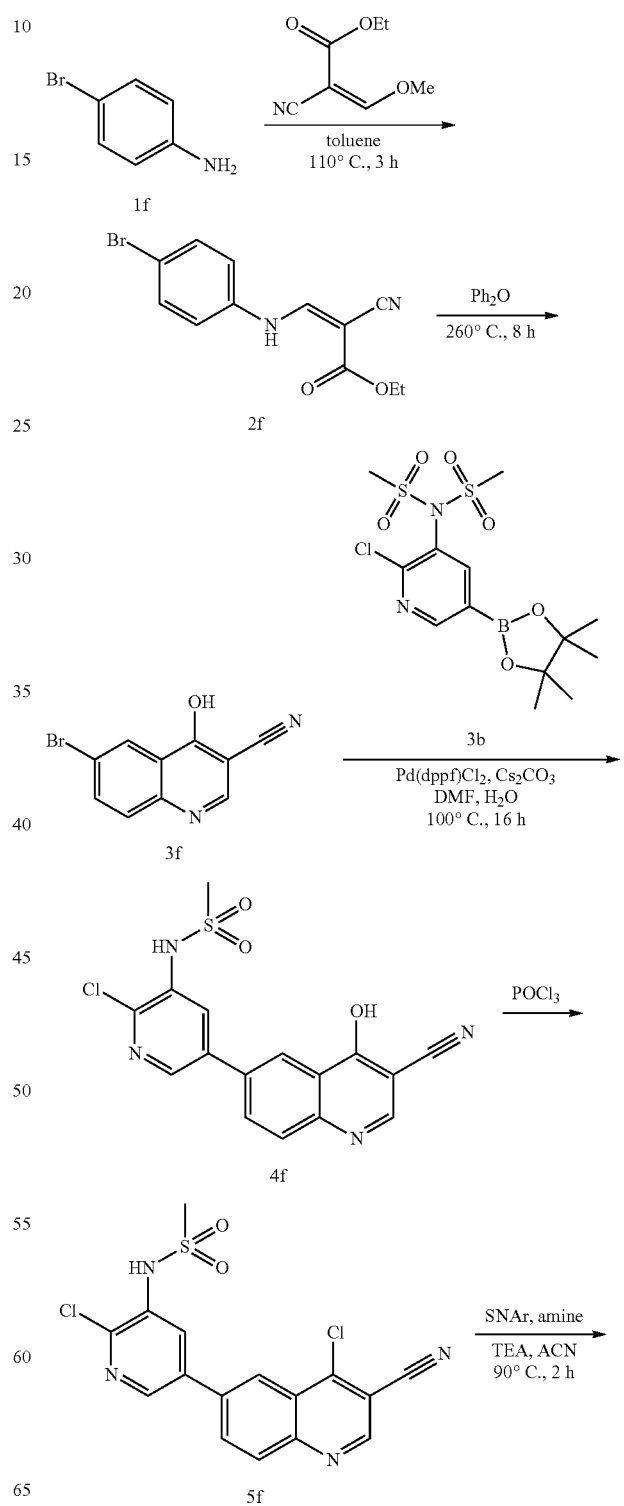

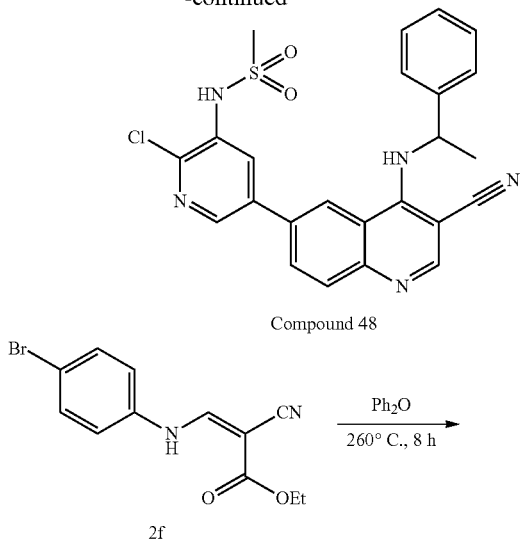

Compound 48

Step 1: Synthesis of ethyl (Z)-3-(4-bromoanilino)-2-cyano-prop-2-enoate (2f)

A solution of 4-bromoaniline (184.88 g, 1.07 mol, 1 eq) in toluene (1.5 L) was added ethyl (E)-2-cyano-3-ethoxy-prop-2-enoate (200 g, 1.18 mol, 1.1 eq), the mixture was stirred at 110° C. for 6 h. TLC (Petroleum ether/Ethyl acetate=3:1, $R_f$=0.88) showed starting material was consumed completely and a new spot was formed. The reaction mixture was filtered, and filter cake was concentrate in vacuum to give a crude product. Compound 2f, ethyl (Z)-3-(4-bromoanilino)-2-cyano-prop-2-enoate (143 g, 484.53 mmol, 45.08% yield) was obtained as a white solid. $^1$H NMR (400 MHz, CHLOROFORM-d) δ=10.74 (br d, J=13.0 Hz, 1H), 8.68-7.78 (m, 1H), 7.54-7.46 (m, 2H), 7.10-6.96 (m, 2H), 4.35-4.21 (m, 2H), 1.35 (td, J=7.1, 9.5 Hz, 3H)

Step 2: Synthesis of 6-bromo-4-hydroxy-quinoline-3-carbonitrile (3f)

A solution of ethyl (Z)-3-(4-bromoanilino)-2-cyano-prop-2-enoate (23 g, 77.93 mmol, 1 eq) in Ph$_2$O (200 mL) was stirred at 270° C. for 8 h. TLC (Petroleum ether/Ethyl acetate=3:1, $R_f$=0.43) showed a little starting material remained and a new spot was formed. The reaction mixture was poured into MTBE (200 mL). The reaction mixture was filtered, and filter cake was concentrate in vacuum to give a crude product. Compound 3f, 6-bromo-4-hydroxy-quinoline-3-carbonitrile (38.16 g, crude) was obtained as a brown solid. $^1$H NMR (400 MHz, DMSO-d$_6$) δ=12.96 (br s, 1H), 8.76 (s, 1H), 8.16 (br s, 1H), 7.99-7.85 (m, 1H), 7.58 (br d, J=8.8 Hz, 1H).

Step 3: Synthesis of N-[2-chloro-5-(3-cyano-4-hydroxy-6-quinolyl)-3-pyridyl]methanesulfonamide (4f)

To a stirred solution of N-[2-chloro-5-(4,4,5,5-tetramethyl-1,3,2-dioxaborolan-2-yl)-3-pyridyl]-N-methylsulfonylmethanesulfonamide, 3b, (4 g, 9.74 mmol, 1 eq) in dioxane (30 mL) and H$_2$O (6 mL) was added 6-bromo-4-hydroxy-quinoline-3-carbonitrile, 3f, (3.15 g, 12.66 mmol, 1.3 eq), Cs$_2$CO$_3$ (9.52 g, 29.22 mmol, 3 eq), Pd(dppf)Cl$_2$ (712.64 mg, 973.94 μmol, 0.1 eq), the mixture was bubbled with N$_2$ 3 times, and stirred at 100° C. for 2 h. LCMS showed the starting material was consumed completely, and desired MS was detected. The reaction mixture was filtered and the filtrate was purified by prep-HPLC (column: Agela DuraShell C18 250*70 mm*10 um; mobile phase: [water (10 mM NH$_4$HCO$_3$)-ACN]; B %: 1%-20%, 20 min). Compound 4f N-[2-chloro-5-(3-cyano-4-hydroxy-6-quinolyl)-3-pyridyl]methanesulfonamide (2.52 g, 6.72 mmol, 69.03% yield) was obtained as a yellow solid. MS (M+H)$^+$=375.0

Step 4: Synthesis of N-[2-chloro-5-(4-chloro-3-cyano-6-quinolyl)-3-pyridyl]methanesulfonamide (5f)

To a solution of POCl$_3$ (18 mL) was added N-[2-chloro-5-(3-cyano-4-hydroxy-6-quinolyl)-3-pyridyl]methanesulfonamide (2.5 g, 6.67 mmol, 1 eq), the mixture was purged with N$_2$ 3 times, and stirred at 130° C. for 16 h. LCMS showed the starting material was consumed completely, and desired MS was detected. The reaction mixture was concentrate in vacuum. The residue was dissolved with ethyl acetate (10 mL). The mixture was poured into water (20 mL), and the aqueous phase was extracted with ethyl acetate (20 mL*2). The combined organic phase was dried with anhydrous Na$_2$SO$_4$, filtered and concentrated in vacuum. The crude product was purified by flash column (ISCO 20 g silica, 70% ethyl acetate in petroleum ether, gradient over 20 min). Based on TLC (Petroleum ether/Ethyl acetate=0:1, $R_f$=0.78). Compound 5f, N-[2-chloro-5-(4-chloro-3-cyano-6-quinolyl)-3-pyridyl] methanesulfonamide (1.2 g, 3.05 mmol, 45.75% yield) was obtained as a yellow solid. $^1$H NMR (400 MHz, DMSO-d$_6$) δ=9.95 (s, 1H), 9.26 (s, 1H), 8.82 (d, J=2.3 Hz, 1H), 8.57 (d, J=1.9 Hz, 1H), 8.45-8.42 (m, 1H), 8.36-8.32 (m, 1H), 8.31 (d, J=2.3 Hz, 1H), 3.21 (s, 3H). MS (M+H)$^+$=393.0

Step 5: Synthesis of N-[2-chloro-5-[3-cyano-4-(1-phenylethylamino)-6-quinolyl]-3-pyridyl]methanesulfonamide (Compound 48)

To a stirred solution of N-[2-chloro-5-(4-chloro-3-cyano-6-quinolyl)-3-pyridyl]methanesulfonamide (80 mg, 203.43 μmol, 1 eq) in MeCN (3 mL) was added 1-phenylethanamine (24.65 mg, 203.43 μmol, 25.95 μL, 1 eq), and TEA (32.94 mg, 325.50 μmol, 45.30 μL, 1.6 eq), and the mixture was stirred at 90° C. for 2 h. LCMS showed the starting material was consumed completely, and desired MS was detected. The reaction mixture was concentrated in vacuum, and the crude product was purified by prep-HPLC (column: Phenomenex luna C18 80*40 mm*3 um; mobile phase: [water (0.04% HCl)-ACN]; B %: 23%-50%, 7 min). Compound 48, N-[2-chloro-5-[3-cyano-4-(1-phenylethylamino)-6-quinolyl]-3-pyridyl] methanesulfonamide (41.7 mg, 81.06 μmol, 39.85% yield, 100% purity, HCl) was obtained as an off-white solid. $^1$H NMR (400 MHz, DMSO-d$_6$) δ=10.00 (s, 1H), 9.38 (br s, 1H), 9.13 (s, 1H), 8.96 (br s, 1H), 8.87 (d, J=2.3 Hz, 1H), 8.37-8.27 (m, 2H), 8.07 (d, J=8.6 Hz, 1H), 7.51-7.45 (m, 2H), 7.39 (t, J=7.6 Hz, 2H), 7.33-7.27 (m, 1H), 6.10-5.95 (m, 1H), 3.20 (s, 3H), 1.81 (d, J=6.6 Hz, 3H). MS (M+H)$^+$=478.0.

Compounds 48R and 48S were synthesized using a procedure analogous to Compound 48 in Example 15, substituting (1R)-1-phenylethanamine or (1S)-1-phenylethanamine for racemic 1-phenylethanamine.

Compound 48R: $^1$H NMR (400 MHz, DMSO-d6) δ=10.00 (s, 1H), 9.03 (s, 1H), 8.98 (br d, J=6.9 Hz, 1H), 8.87-8.80 (m, 2H), 8.31-8.25 (m, 2H), 8.02 (d, J=8.8 Hz, 1H), 7.49-7.44 (m, 2H), 7.38 (t, J=7.6 Hz, 2H), 7.32-7.26 (m, 1H), 5.98 (br t, J=7.2 Hz, 1H), 3.20 (s, 3H), 1.78 (d, J=6.8 Hz, 3H). MS (M+H)$^+$=478.0.

Compound 48S: $^1$H NMR (400 MHz, DMSO-d6) δ=10.00 (br s, 1H), 9.04 (s, 1H), 9.00 (br s, 1H), 8.88-8.80 (m, 2H), 8.32-8.25 (m, 2H), 8.02 (d, J=8.8 Hz, 1H), 7.50-7.43 (m, 2H), 7.38 (t, J=7.5 Hz, 2H), 7.35-7.26 (m, 1H), 5.98 (br t, J=7.2 Hz, 1H), 3.20 (s, 3H), 1.78 (d, J=6.7 Hz, 3H). MS (M+H)$^+$=478.0.

Example 16: Synthesis of 6-(2-aminopyrimidin-5-yl)-4-(1-phenylethylamino) quinoline-3-carbonitrile (Compound 53)

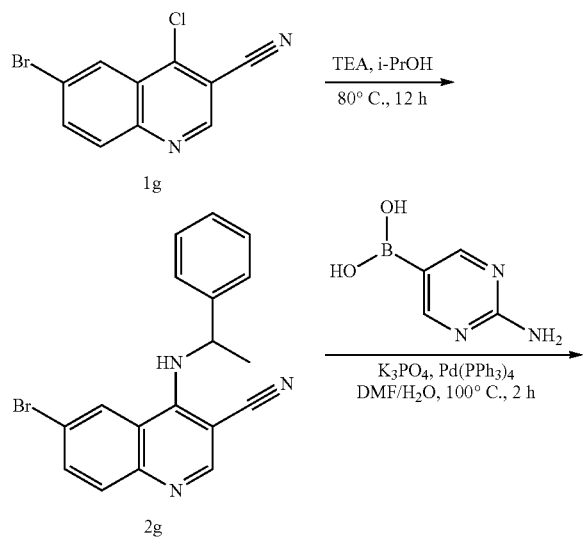

Compound 53

Step 1: Synthesis of 6-bromo-4-(1-phenylethylamino)quinoline-3-carbonitrile (2 g)

To a stirred solution of 6-bromo-4-chloro-quinoline-3-carbonitrile (1 g, 3.74 mmol, 1 eq) in i-PrOH (15 mL) was added TEA (605.22 mg, 5.98 mmol, 832.49 μL, 1.6 eq) 1-phenylethanamine (543.59 mg, 4.49 mmol, 572.20 μL, 1.2 eq), the mixture was stirred at 80° C. for 12 h. LCMS showed the starting material was consumed completely and desired MS was detected. The reaction mixture was concentrate in vacuum. Compound 2g, 6-bromo-4-(1-phenylethylamino)quinoline-3-carbonitrile (1.1 g, 3.12 mmol, 83.54% yield) was obtained as a brown solid. MS (M+H)$^+$=354.1.

Step 2: Synthesis of 6-(2-aminopyrimidin-5-yl)-4-(1-phenylethylamino) quinoline-3-carbonitrile (Compound 53)

To a stirred solution of 6-bromo-4-(1-phenylethylamino) quinoline-3-carbonitrile (500 mg, 1.42 mmol, 1 eq) in DMF (5 mL) and H$_2$O (1 mL) was added (2-aminopyrimidin-5-yl)boronic acid (197.20 mg, 1.42 mmol, 1 eq), Pd(PPh$_3$)$_4$ (1.64 g, 1.42 mmol, 1 eq) and K$_3$PO$_4$ (903.96 mg, 4.26 mmol, 3 eq), the mixture was bubbled with N$_2$ for 1 minute, and stirred at 100° C. for 3 h. LCMS showed the starting material was consumed completely and desired MS was detected. The reaction mixture was filtered, and filtrate was purified by prep-HPLC (column: Phenomenex luna C18 250*50 mm*10 um; mobile phase: [water (0.04% HCl)-ACN]; B %: 10%-40%, 10 min). Compound 53 6-(2-aminopyrimidin-5-yl)-4-(1-phenylethylamino)quinoline-3-carbonitrile (157.87 mg, 379.75 μmol, 26.75% yield, 96.91% purity, HCl) was obtained as a yellow solid. $^1$H NMR (400 MHz, DMSO-d6) δ=10.09 (br d, J=8.3 Hz, 1H), 9.36 (s, 1H), 9.18 (s, 2H), 9.08 (s, 1H), 8.41 (dd, J=1.6, 8.8 Hz, 1H), 8.14 (d, J=8.9 Hz, 1H), 7.55 (d, J=7.4 Hz, 2H), 7.43-7.35 (m, 2H), 7.33-7.28 (m, 1H), 6.14-6.03 (m, 1H), 1.87 (d, J=6.8 Hz, 3H). MS (M+H)$^+$=367.1.

Compound 53R was synthesized using the analogous procedure for Compound 53 in Example 16 with chiral starting material.

Compound 53R: $^1$H NMR (400 MHz, DMSO-d$_6$) δ=10.00 (br s, 1H), 9.30 (br s, 1H), 9.12 (br s, 1H), 9.07 (s, 1H), 8.40 (br d, J=8.8 Hz, 1H), 8.13 (br d, J=8.7 Hz, 1H), 7.54 (br d, J=7.6 Hz, 2H), 7.42-7.37 (m, 2H), 7.34-7.27 (m, 1H), 6.19-5.86 (m, 1H), 1.86 (br d, J=6.6 Hz, 3H). MS (M+H)$^+$=367.1

Example 17

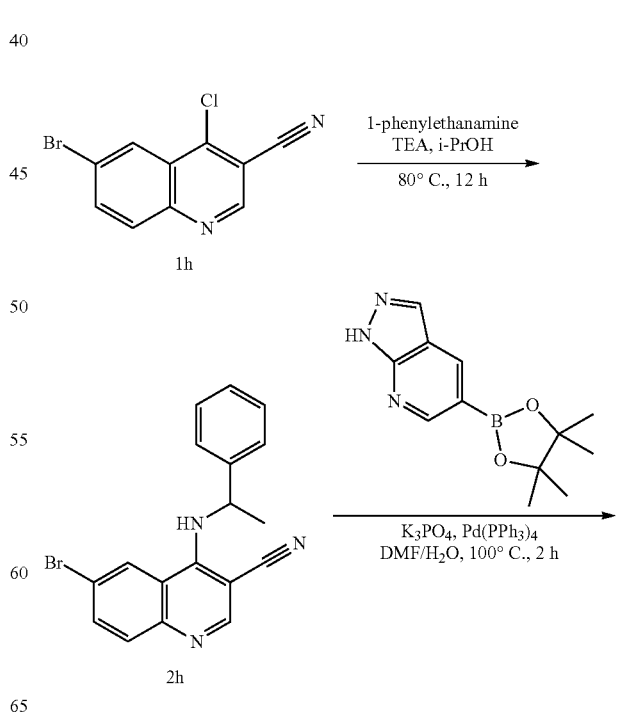

-continued

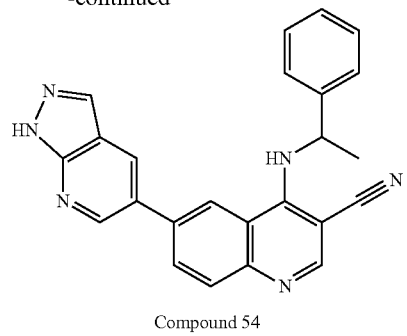

Compound 54

Step 1: Synthesis of 6-bromo-4-(1-phenylethyl-amino)quinoline-3-carbonitrile (2h)

To a stirred solution of 6-bromo-4-chloro-quinoline-3-carbonitrile (1 g, 3.74 mmol, 1 eq) in i-PrOH (15 mL) was added TEA (605.22 mg, 5.98 mmol, 832.49 μL, 1.6 eq), 1-phenylethanamine (543.59 mg, 4.49 mmol, 572.20 μL, 1.2 eq), the mixture was stirred at 80° C. for 12 h. LCMS showed the starting material was consumed completely and desired MS was detected. The reaction mixture was concentrate in vacuum. Compound 2h, 6-bromo-4-(1-phenyl-ethylamino)quinoline-3-carbonitrile (1.1 g, 3.12 mmol, 83.54% yield) was obtained as a brown solid. MS (M+H)$^+$ =354.1.

Step 2: Synthesis of 6-(2-aminopyrimidin-5-yl)-4-(1-phenylethylamino) quinoline-3-carbonitrile (Compound 54)

To a stirred solution of 6-bromo-4-(1-phenylethylamino) quinoline-3-carbonitrile (500 mg, 1.42 mmol, 1 eq) in DMF (5 mL) and H$_2$O (1 mL) was added 5-(4,4,5,5-tetramethyl-1,3,2-dioxaborolan-2-yl)-1H-pyrazolo[3,4-b]pyridine (348.02 mg, 1.42 mmol, 1 eq), Pd(PPh$_3$)$_4$ (164.04 mg, 142.00 μmol, 0.1 eq) and K$_3$PO$_4$ (903.96 mg, 4.26 mmol, 3 eq), the mixture was bubbled with N$_2$ for 1 minute, and stirred at 100° C. for 3 h. LCMS showed the starting material was concentrate in vacuum. The reaction mixture was filtered, and filtrate was concentrated to afford 20 mg crude product. The crude product was purified by prep-HPLC (column: Phenomenex luna C18 80*40 mm*3 um; mobile phase: [water (0.1% TFA)-ACN]; B %: 17%-30%, 7 min). Compound 54, 4-(1-phenylethylamino)-6-(1H-pyrazolo[3,4-b]pyridin-5-yl)quinoline-3-carbonitrile (10.40 mg, 20.62 mol, 1.45% yield, 100% purity, TFA) was obtained as a pale yellow solid. $^1$H NMR (400 MHz, DMSO-d6) δ=9.18-9.00 (m, 2H), 8.97-8.86 (m, 1H), 8.78 (s, 1H), 8.71 (d, J=1.8 Hz, 1H), 8.35 (br d, J=8.8 Hz, 1H), 8.30 (s, 1H), 8.00 (d, J=8.7 Hz, 1H), 7.47 (br d, J=7.6 Hz, 2H), 7.38 (t, J=7.5 Hz, 2H), 7.32-7.23 (m, 1H), 6.08-5.88 (m, 1H), 1.79 (d, J=6.7 Hz, 3H). MS (M+H)$^+$=391.1.

Example 18: Synthesis of 4-[[(1R)-1-phenylethyl] amino]-6-(1H-pyrazolo [3, 4-b] pyridin-5-yl) quinoline-3-carbonitrile (Compound 54R)

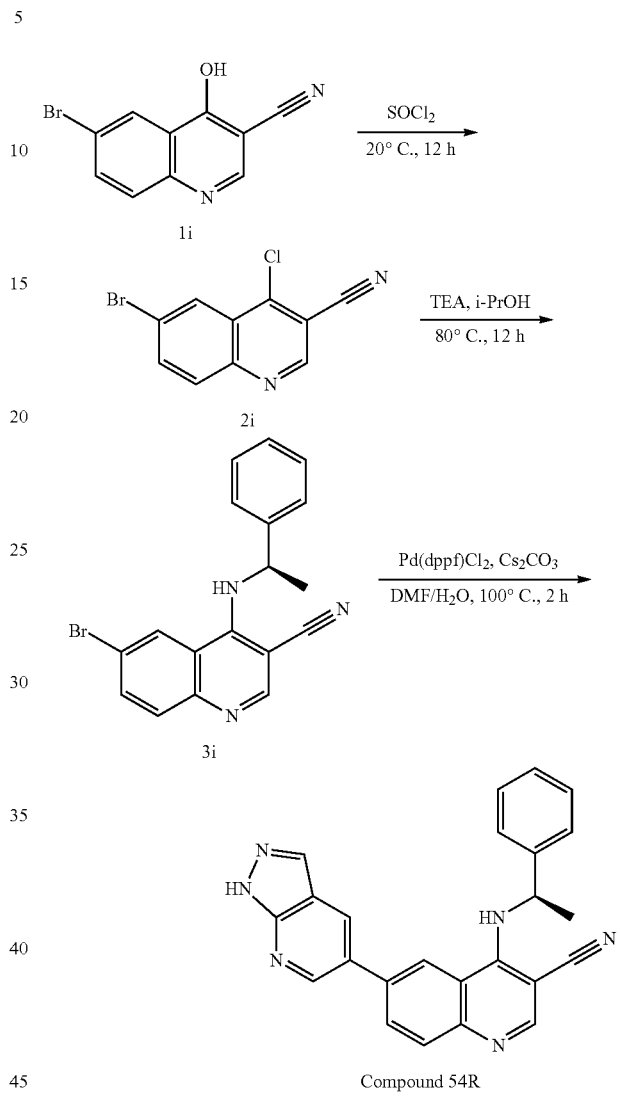

Step 1: Synthesis of 6-bromo-4-chloro-quinoline-3-carbonitrile (2i)

To a solution of 6-bromo-4-hydroxy-quinoline-3-carbonitrile (10 g, 40.15 mmol, 1 eq) in SOCl$_2$ (50 mL) was added DMF (293.47 mg, 4.02 mmol, 308.92 μL, 0.1 eq), the mixture was purged with N$_2$, the reaction was stirred at 20° C. for 12 h. LCMS showed starting material was consumed completely and the MS of desired product was detected. The reaction mixture was concentrated in vacuum. Compound 2i 6-bromo-4-chloro-quinoline-3-carbonitrile (10.3 g, 38.50 mmol, 95.90% yield) was obtained as a black solid. MS (M+H)$^+$=269.1

Step 2: Synthesis of 6-bromo-4-[[(1R)-1-phenyl-ethyl] amino] quinoline-3-carbonitrile (3i)

To a solution of 6-bromo-4-chloro-quinoline-3-carboni-trile, 2i, (2 g, 7.48 mmol, 1 eq) in i-PrOH (15 mL) was added (1R)-1-phenylethanamine (996.58 mg, 8.22 mmol, 1.06 mL, 1.1 eq) and TEA (1.21 g, 11.96 mmol, 1.66 mL, 1.6 eq), the mixture was purged with $N_2$, the reaction was stirred at 80° C. for 12 h. LCMS showed starting material was consumed completely and the MS of desired product was detected. The reaction mixture was filtered and filtrate was concentrated in vacuum. Compound 3i, 6-bromo-4-[[(1R)-1-phenylethyl]amino] quinoline-3-carbonitrile (2.4 g, 6.81 mmol, 91.14% yield) was obtained as black oil. MS $(M+H)^+=352.1$

Step 3: Synthesis of 4-[[(1R)-1-phenylethyl]amino]-6-(1H-pyrazolo [3, 4-b]pyridin-5-yl) quinoline-3-carbonitrile (Compound 54R)

To a solution of 6-bromo-4-[[(1R)-1-phenylethyl] amino] quinoline-3-carbonitrile (1.57 g, 4.46 mmol, 1 eq) in DMF (15 mL) and $H_2O$ (3 mL) was added $Cs_2CO_3$ (4.36 g, 13.37 mmol, 3 eq), Pd(dppf)$Cl_2$ (326.15 mg, 445.73 µmol, 0.1 eq) and 5-(4,4,5,5-tetramethyl-1,3,2-dioxaborolan-2-yl)-1H-pyrazolo [3,4-b]pyridine (1.09 g, 4.46 mmol, 1 eq), the mixture was bubbled with $N_2$, and the reaction was stirred at 100° C. for 3 h. LC-MS showed starting material was consumed completely and the MS of desired product was detected. The reaction was filtered, the filter caked was concentrated in vacuum. The filer cake was purified by prep-HPLC (column: Phenomenex luna C18 250*50 mm*10 um; mobile phase: [water (0.04% HCl)-ACN]; B %: 15%-45%, 10 min). Compound 54R, 4-[[(1R)-1-phenylethyl]amino]-6-(1H-pyrazolo[3, 4-b]pyridin-5-yl) quinoline-3-carbonitrile (70.43 mg, 159.40 µmol, 3.58% yield, 96.62% purity, HCl) was obtained as a yellow solid. $^1$H NMR (400 MHz, DMSO-d6) δ ppm 9.79 (br s, 1H), 9.25 (br s, 1H), 9.13 (br d, J=9.17 Hz, 2H), 8.78 (br d, J=1.59 Hz, 1H), 8.50 (br d, J=8.80 Hz, 1H), 8.32 (s, 1H), 8.10-8.21 (m, 1H), 7.52 (br d, J=7.46 Hz, 2H), 7.41 (t, J=7.64 Hz, 2H), 7.28-7.35 (m, 1H), 6.10 (br t, J=6.97 Hz, 1H), 1.85 (br d, J=6.60 Hz, 3H). MS $(M+H)^+=391.1$

Example 19: Synthesis of 4-(1-phenylethylamino)-6-(1H-pyrrolo [2, 3-b]pyridin-5-yl) quinoline-3-carbonitrile (Compound 55)

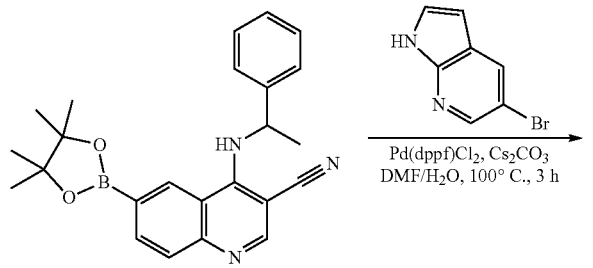

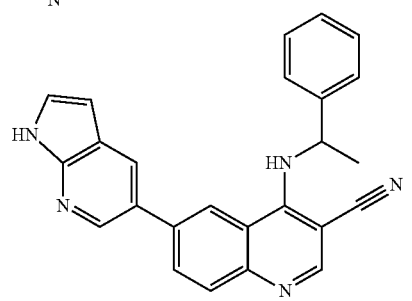

Compound 55

To a solution of 4-(1-phenylethylamino)-6-(4,4,5,5-tetramethyl-1,3,2-dioxaborolan-2-yl)quinoline-3-carbonitrile (80 mg, 200.35 µmol, 1 eq) in DMF (0.5 mL) and $H_2O$ (0.1 mL) was added $Cs_2CO_3$ (195.84 mg, 601.06 µmol, 3 eq), Pd(dppf)$Cl_2$ (14.66 mg, 20.04 µmol, 0.1 eq) and 5-bromo-1H-pyrrolo[2,3-b]pyridine (39.48 mg, 200.35 µmol, 1 eq), the mixture was bubbled with $N_2$, and the reaction was stirred at 100° C. for 3 h. LCMS showed starting material was consumed completely and the MS of desired product was detected. The reaction was purified by prep-HPLC (column: Phenomenex luna C18 80*40 mm*3 um; mobile phase: [water (0.04% HCl)-ACN]; B %: 20%-40%, 7 min). Compound 55, 4-(1-phenylethylamino)-6-(1H-pyrrolo[2,3-b]pyridin-5-yl)quinoline-3-carbonitrile (12.19 mg, 28.28 µmol, 14.11% yield, 98.80% purity, HCl) was obtained as a yellow solid. $^1$H NMR (400 MHz, DMSO-d6) δ ppm 12.00 (br s, 1H) 9.81 (br d, J=7.82 Hz, 1H) 9.20 (s, 1H) 9.13 (s, 1H) 8.84 (d, J=1.96 Hz, 1H) 8.54 (s, 1H) 8.49 (dd, J=8.80, 1.34 Hz, 1H) 8.14 (d, J=8.80 Hz, 1H) 7.59-7.64 (m, 1H) 7.52 (d, J=7.46 Hz, 2H) 7.41 (t, J=7.64 Hz, 2H) 7.28-7.35 (m, 1H) 6.62 (dd, J=3.30, 1.71 Hz, 1H) 6.00-6.18 (m, 1H) 1.85 (d, J=6.60 Hz, 3H). MS $(M+H)^+=390.0$

Example 20: Synthesis of 6-(2-methyl-3H-imidazo[4,5-b]pyridin-6-yl)-4-(1-phenylethylamino) quinoline-3-carbonitrile (Compound 56)

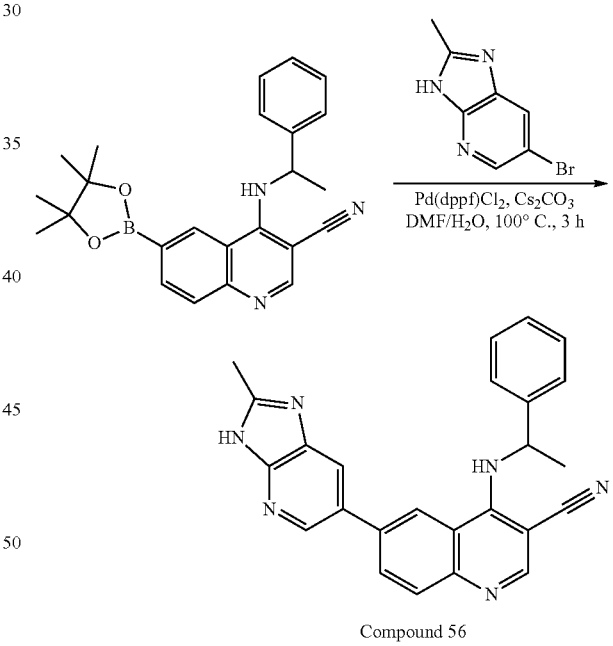

Compound 56

To a stirred solution of 4-(1-phenylethylamino)-6-(4, 4, 5, 5-tetramethyl-1, 3, 2-dioxaborolan-2-yl)quinoline-3-carbonitrile (120 mg, 300.53 µmol, 1 eq) in DMF (0.5 mL) and $H_2O$ (0.1 mL) was added $Cs_2CO_3$ (293.76 mg, 901.60 µmol, 3 eq), Pd(dppf)$Cl_2$ (21.99 mg, 30.05 µmol, 0.1 eq) and 6-bromo-2-methyl-1H-imidazo[4,5-b]pyridine (82.84 mg, 390.69 µmol, 1.3 eq), the mixture was bubbled with $N_2$, and stirred at 100° C. for 3 h. LCMS showed starting material was consumed completely and the MS of desired product was detected. The reaction mixture was filtered, the filtrate was concentrated in vacuum to afford crude product (20 mg), the crude product was purified by prep-HPLC (column:

Phenomenex luna C18 80*40 mm*3 um; mobile phase: [water (0.04% HCl)-ACN]; B %: 12%-28%, 7 min). Compound 56 6-(2-methyl-3H-imidazo[4, 5-b]pyridin-6-yl)-4-(1-phenylethylamino)quinoline-3-carbonitrile (9 mg, 18.76 µmol, 6.24% yield, 91.93% purity, HCl) was obtained as a brown solid. $^1$H NMR (400 MHz, DMSO-d6) δ ppm 10.26 (br d, J=8.07 Hz, 1H) 9.51 (s, 1H) 9.17 (s, 1H) 9.09 (s, 1H) 8.92 (s, 1H) 8.52 (br d, J=8.80 Hz, 1H) 8.20 (d, J=8.68 Hz, 1H) 7.57 (br d, J=7.70 Hz, 2H) 7.35-7.43 (m, 2H) 7.26-7.33 (m, 1H) 6.01-6.15 (m, 1H) 2.85 (s, 3H) 1.89 (br d, J=6.60 Hz, 3H). MS (M+H)$^+$=405.1

Example 21: Synthesis of 6-(5-hydroxy-3-pyridyl)-4-(1-phenylethylamino) quinoline-3-carbonitrile (Compound 61)

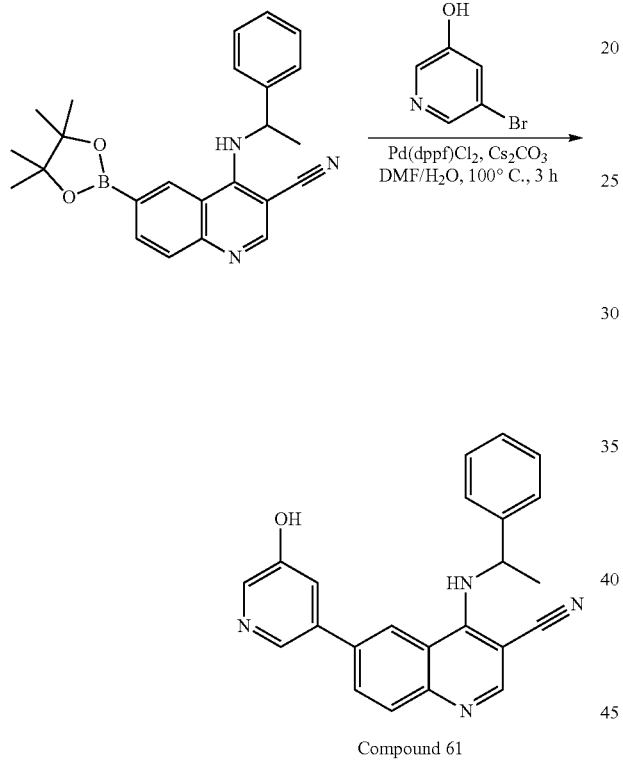

Compound 61

To a stirred solution of 4-(1-phenylethylamino)-6-(4,4,5,5-tetramethyl-1,3,2-dioxaborolan-2-yl)quinoline-3-carbonitrile (100 mg, 250.44 µmol, 1 eq) in DMF (0.5 mL) and H$_2$O (0.1 mL) was added Cs$_2$CO$_3$ (244.80 mg, 751.33 µmol, 3 eq), Pd(dppf)Cl$_2$ (18.33 mg, 25.04 µmol, 0.1 eq) and 5-bromopyridin-3-ol (43.58 mg, 250.44 µmol, 1 eq), the mixture was bubbled with N$_2$, and stirred at 100° C. for 3 h. LCMS showed starting material was consumed completely and the MS of desired product was detected. The reaction was filtered, the filter cake was washed by DMSO then the filtrate was concentrated in vacuum. The crude product was purified by prep-HPLC (column: Phenomenex Luna C18 150*30 mm*5 um; mobile phase: [water (0.1% TFA)-ACN]; B %: 1%-35%, 8 min). Compound 61, 6-(5-hydroxy-3-pyridyl)-4-(1-phenylethylamino)quinoline-3-carbonitrile (30.91 mg, 62.70 µmol, 25.03% yield, 97.45% purity, TFA) was obtained as a yellow solid. $^1$H NMR (400 MHz, DMSO-d6) δ ppm 9.24 (br d, J=8.19 Hz, 1H), 9.06 (d, J=1.22 Hz, 1H), 8.92 (s, 1H), 8.68 (d, J=1.59 Hz, 1H), 8.26-8.35 (m, 2H), 8.01 (d, J=8.68 Hz, 1H), 7.86 (s, 1H), 7.43-7.49 (m, 2H), 7.38 (t, J=7.64 Hz, 2H), 7.25-7.33 (m, 1H), 5.94-6.06 (m, 1H), 1.79 (d, J=6.72 Hz, 3H). MS (M+H)$^+$=367.1

Example 22: Synthesis of 6-(5-cyano-3-pyridyl)-4-(1-phenylethylamino) quinoline-3-carbonitrile (Compound 64)

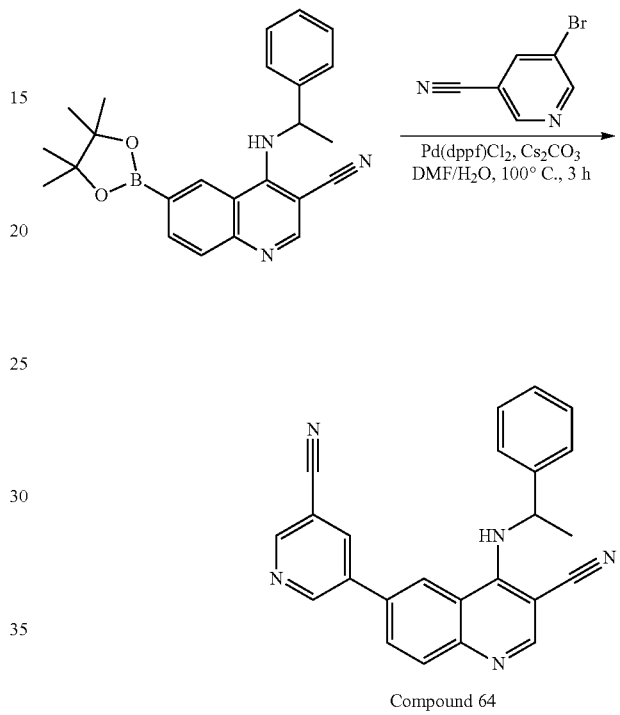

Compound 64

To a solution of 4-(1-phenylethylamino)-6-(4,4,5,5-tetramethyl-1,3,2-dioxaborolan-2-yl)quinoline-3-carbonitrile (100 mg, 250.44 µmol, 1 eq) in DMF (2 mL) and H$_2$O (0.4 mL) was added Cs$_2$CO$_3$ (244.80 mg, 751.33 µmol, 3 eq), Pd(dppf)Cl$_2$ (18.33 mg, 25.04 µmol, 0.1 eq) and 5-bromopyridine-3-carbonitrile (45.83 mg, 250.44 µmol, 1 eq), the mixture was bubbled with N$_2$, and the reaction was stirred at 100° C. for 3 h. LCMS showed starting material was consumed completely and the MS of desired product was detected. The reaction was filtered, the filtrate was purified by prep-HPLC (column: Phenomenex Luna 80*30 mm*3 um; mobile phase: [water (HCl)-ACN]; B %: 15%-45%, 8 min). Compound 64, 6-(5-cyano-3-pyridyl)-4-(1-phenylethylamino)quinoline-3-carbonitrile (12.41 mg, 28.52 µmol, 11.39% yield, 94.65% purity, HCl) was obtained as a yellow solid. $^1$H NMR (400 MHz, DMSO-d6) δ ppm 10.04 (br d, J=7.82 Hz, 1H), 9.51 (d, J=2.20 Hz, 1H), 9.41 (s, 1H), 9.14 (s, 2H), 9.01 (t, J=1.96 Hz, 1H), 8.52 (dd, J=8.74, 1.41 Hz, 1H), 8.20 (d, J=8.68 Hz, 1H), 7.54 (d, J=7.46 Hz, 2H), 7.40 (t, J=7.52 Hz, 2H), 7.27-7.35 (m, 1H), 6.10 (quin, J=7.06 Hz, 1H), 1.87 (d, J=6.60 Hz, 3H). MS (M+H)$^+$=376.2

Example 23: Synthesis of 6-(6-amino-5-cyano-3-pyridyl)-4-(1-phenylethylamino) quinoline-3-carbonitrile (Compound 65)

Example 24: Synthesis of 6-[5-(1-hydroxy-1-methyl-ethyl)-3-pyridyl]-4-(1-phenylethylamino) quinoline-3-carbonitrile (Compound 67)

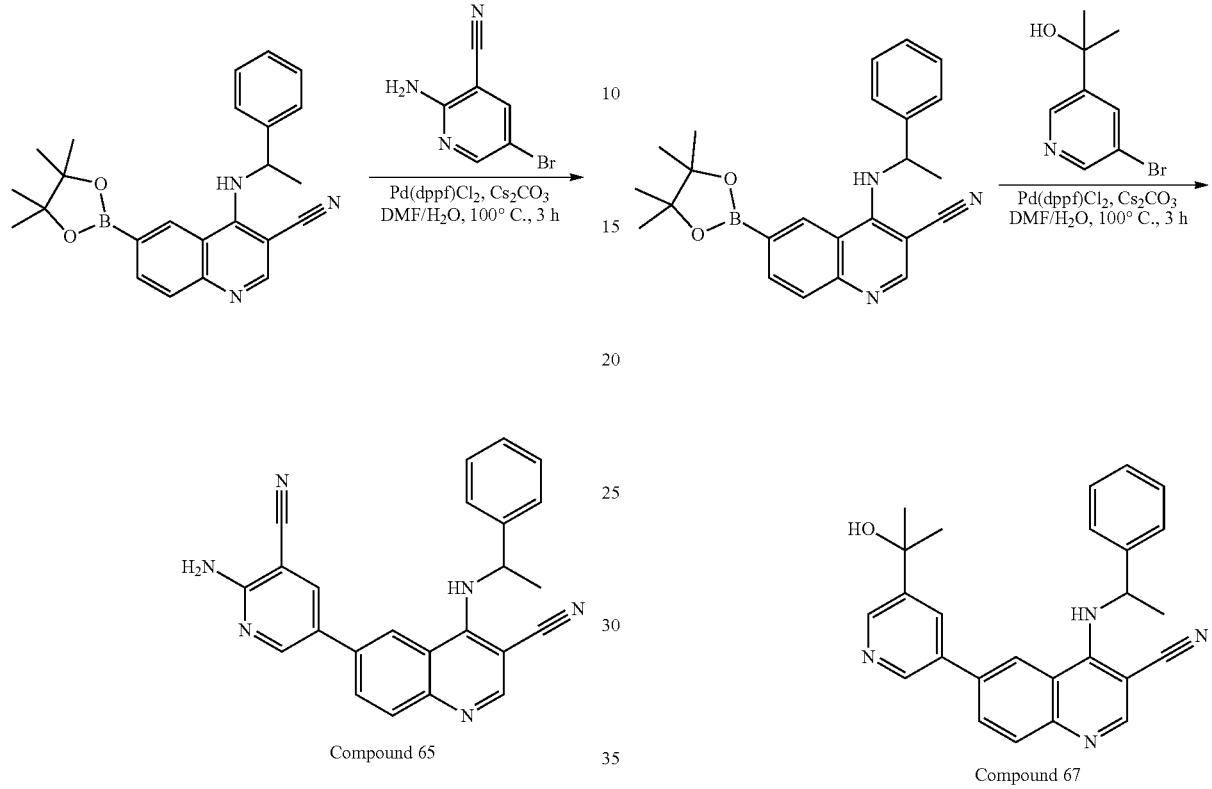

Compound 65

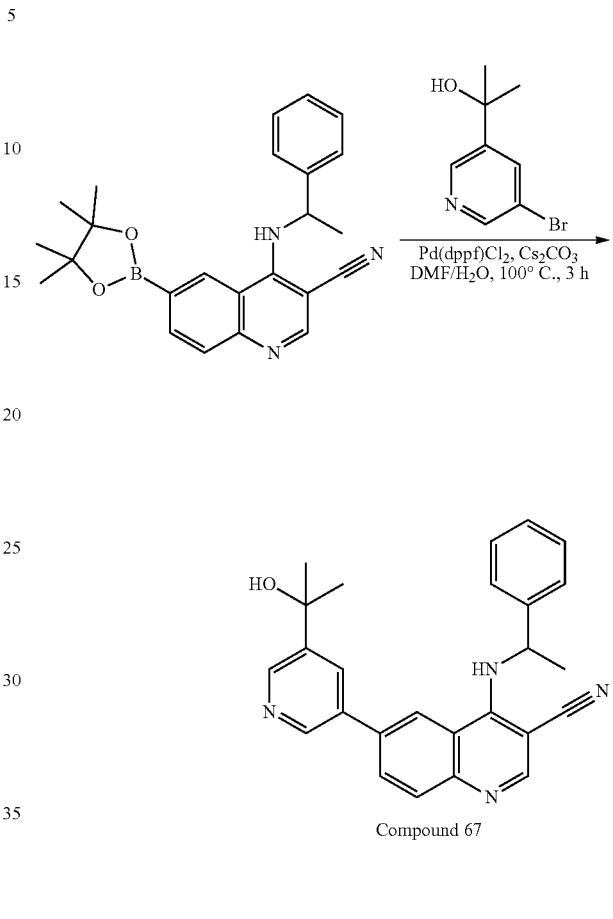

Compound 67

To a solution of 4-(1-phenylethylamino)-6-(4, 4, 5, 5-tetramethyl-1, 3, 2-dioxaborolan-2-yl)quinoline-3-carbonitrile (100 mg, 250.44 µmol, 1 eq) in DMF (2.5 mL) and H$_2$O (0.4 mL) was added Cs$_2$CO$_3$ (244.80 mg, 751.33 µmol, 3 eq), Pd(dppf)Cl$_2$ (18.33 mg, 25.04 µmol, 0.1 eq) and 2-amino-5-bromo-pyridine-3-carbonitrile (49.59 mg, 250.44 µmol, 1 eq), the mixture was bubbled with N$_2$, and the reaction was stirred at 100° C. for 3 h. LCMS showed starting material was consumed completely and the MS of desired product was detected. The reaction was filtered, the filtrate was purified by prep-HPLC (column: Phenomenex luna C18 80*40 mm*3 um; mobile phase: [water (HCl)-ACN]; B %: 17%-43%, 7 min). Compound 65, 6-(6-amino-5-cyano-3-pyridyl)-4-(1-phenylethylamino) quinoline-3-carbonitrile (26.28 mg, 59.16 µmol, 23.62% yield, 96.10% purity, HCl) was obtained as a yellow solid. $^1$H NMR (400 MHz, DMSO-d6) δ ppm 9.86 (br d, J=7.46 Hz, 1H) 9.05-9.19 (m, 2H) 8.83-8.96 (m, 1H) 8.60 (d, J=2.20 Hz, 1H) 8.35-8.43 (m, 1H) 8.01-8.15 (m, 1H) 7.52 (d, J=7.46 Hz, 2H) 7.38-7.42 (m, 2H) 7.30-7.34 (m, 1H) 5.85-6.27 (m, 1H) 1.86 (d, J=6.72 Hz, 3H). MS (M+H)$^+$=391.1

To a stirred solution of 4-(1-phenylethylamino)-6-(4, 4, 5, 5-tetramethyl-1,3,2-dioxaborolan-2-yl)quinoline-3-carbonitrile (120 mg, 300.53 µmol, 1 eq) in DMF (0.5 mL) and H$_2$O (0.1 mL) was added Cs$_2$CO$_3$ (293.76 mg, 901.60 µmol, 3 eq), Pd(dppf)Cl$_2$ (21.99 mg, 30.05 µmol, 0.1 eq) and 2-(5-bromo-3-pyridyl)propan-2-ol (84.42 mg, 390.69 µmol, 1.3 eq), the mixture was bubbled with N$_2$, and stirred at 100° C. for 3 h. LCMS showed starting material was consumed completely and the MS of desired product was detected. The reaction mixture was filtered, filter cake washed by MeOH, the filter liquor was concentrated in vacuum. The crude product was purified by prep-HPLC (column: Phenomenex Luna 80*30 mm*3 um; mobile phase: [water (0.04% HCl)-ACN]; B %: 5%-25%, 8 min). Compound 67, 6-[5-(1-hydroxy-1-methyl-ethyl)-3-pyridyl]-4-(1-phenylethylamino) quinoline-3-carbonitrile (36.18 mg, 77.82 µmol, 25.89% yield, 95.70% purity, HCl) was obtained as a brown solid. $^1$H NMR (400 MHz, DMSO-d6) δ ppm 10.72 (br d, J=8.07 Hz, 1H) 9.91 (s, 1H) 9.62 (s, 1H) 9.39 (s, 1H) 9.11 (s, 1H) 8.94 (s, 1H) 8.60 (br d, J=8.68 Hz, 1H) 8.25 (d, J=8.80 Hz, 1H) 7.62 (d, J=7.58 Hz, 2H) 7.37 (t, J=7.52 Hz, 2H) 7.24-7.33 (m, 1H) 6.02-6.15 (m, 1H) 1.93 (d, J=6.60 Hz, 3H) 1.64 (s, 6H). MS (M+H)$^+$=409.1

Example 25: Synthesis of 6-(5,6-dimethoxy-3-pyridyl)-4-(1-phenylethylamino)quinoline-3-carbonitrile (Compound 68)

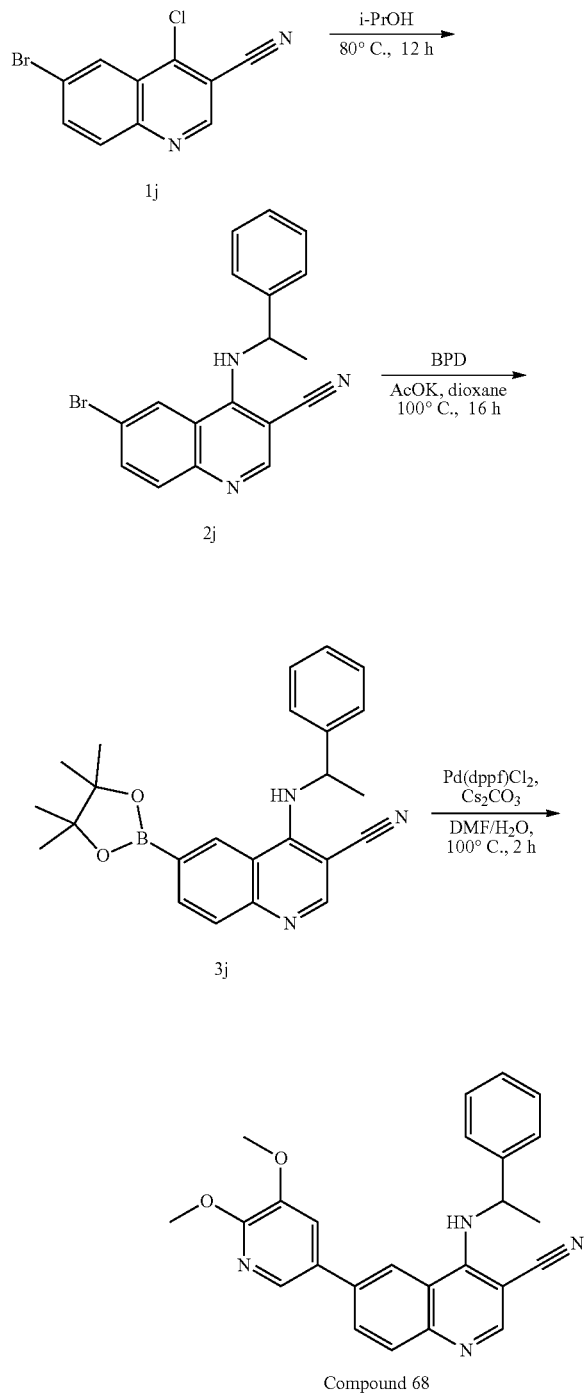

Step 1: Synthesis of 6-bromo-4-(1-phenylethylamino) quinoline-3-carbonitrile (2j)

To a solution of 6-bromo-4-chloro-quinoline-3-carbonitrile (8 g, 29.91 mmol, 1 eq) i-PrOH (30 mL) was added 1-phenylethanamine (3.99 g, 32.90 mmol, 4.20 mL, 1.1 eq) and TEA (4.84 g, 47.85 mmol, 6.66 mL, 1.6 eq), the reaction was stirred at 80° C. for 12 h. LCMS showed starting material was consumed completely and the MS of desired product was detected. The reaction mixture was concentrated in vacuum. Compound 2j, 6-bromo-4-(1-phenylethylamino) quinoline-3-carbonitrile (9 g, 25.55 mmol, 85.44% yield) was obtained as a gray solid. MS (M+H)+=352.1

Step 2: Synthesis of 4-(1-phenylethylamino)-6-(4, 4, 5, 5-tetramethyl-1, 3, 2-dioxaborolan-2-yl) quinoline-3-carbonitrile (3j)

To a solution of 6-bromo-4-(1-phenylethylamino)quinoline-3-carbonitrile, 2j, (7 g, 19.87 mmol, 1 eq) in dioxane (80 mL) was added AcOK (5.85 g, 59.61 mmol, 3 eq), Pd(dppf)Cl$_2$.CH$_2$Cl$_2$ (1.62 g, 1.99 mmol, 0.1 eq), BPD (6.06 g, 23.84 mmol, 1.2 eq), the mixture was purged with Ar then the reaction was stirred at 110° C. for 8 h. LCMS showed starting material was consumed completely and the MS of desired product was detected. TLC (PE:EtOAc=3:1, R$_f$=0.24) showed the starting material was consumed completely and new spot was formed. The reaction mixture was cooled to room temperature and quenched by water (50 mL), extracted with ethyl acetate (40 mL*2). The combined organics were washed with brine (30 mL), dried over Na$_2$SO$_4$, filtered and concentrated under reduced pressure to give a residue. The residue was purified by flash column (ISCO 40 g silica, 50-70% ethyl acetate in petroleum ether, gradient over 40 min). Compound 2j, 4-(1-phenylethylamino)-6-(4,4,5,5-tetramethyl-1,3,2-dioxaborolan-2-yl)quinoline-3-carbonitrile (5.5 g, 13.77 mmol, 69.32% yield) was obtained as brown oil. MS (M+H)+=400.3

Step 3: Synthesis of 6-(5,6-dimethoxy-3-pyridyl)-4-(1-phenylethylamino) quinoline-3-carbonitrile (Compound 68)

To a solution of 4-(1-phenylethylamino)-6-(4, 4, 5,5-tetramethyl-1,3,2-dioxaborolan-2-yl)quinoline-3-carbonitrile, 3j, (230 mg, 576.02 μmol, 1 eq) in DMF (0.5 mL) and H$_2$O (0.1 mL) was added Cs$_2$CO$_3$ (563.04 mg, 1.73 mmol, 3 eq), Pd(dppf)Cl$_2$ (42.15 mg, 57.60 μmol, 0.1 eq) and 5-bromo-2,3-dimethoxy-pyridine (163.28 mg, 748.83 μmol, 1.3 eq), the mixture was bubbled with N$_2$, and the reaction was stirred at 100° C. for 3 h. LCMS showed starting material was consumed completely and the MS of desired product was detected. The reaction mixture was concentrated in vacuum. The crude product was purified by prep-HPLC (column: Phenomenex Luna 80*30 mm*3 um; mobile phase: [water (0.04% HCl)-ACN]; B %: 10%-30%, 8 min). Compound 68, 6-(5,6-dimethoxy-3-pyridyl)-4-(1-phenylethylamino)quinoline-3-carbonitrile (39.53 mg, 88.45 μmol, 15.36% yield, 100% purity, HCl) was obtained as a yellow solid. $^1$H NMR (400 MHz, DMSO-d6) δ ppm 9.05 (br s, 1H) 8.89 (br s, 1H) 8.25-8.39 (m, 2H) 8.00 (br d, J=8.68 Hz, 1H) 7.70-7.82 (m, 1H) 7.45-7.52 (m, 2H) 7.39 (t, J=7.58 Hz, 2H) 7.23-7.34 (m, 1H) 6.00 (br d, J=5.99 Hz, 1H) 3.83-4.05 (m, 6H) 1.80 (br d, J=6.60 Hz, 3H). MS (M+H)+=411.1

Example 26: Synthesis of 4-(1-phenylethylamino)-6-(3H-triazolo [4, 5-b]pyridin-6-yl) quinoline-3-carbonitrile (Compound 70)

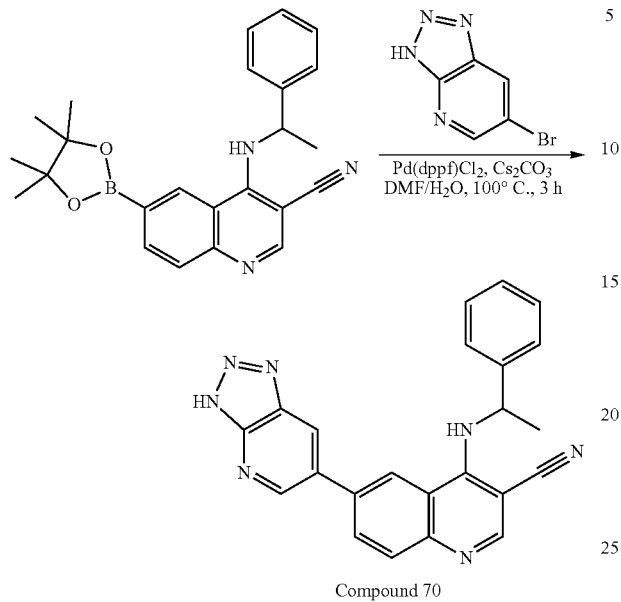

Compound 70

To a solution of 4-(1-phenylethylamino)-6-(4, 4, 5, 5-tetramethyl-1, 3, 2-dioxaborolan-2-yl)quinoline-3-carbonitrile (150 mg, 375.66 μmol, 1 eq) in DMF (2 mL) and H$_2$O (0.4 mL) was added Cs$_2$CO$_3$ (367.20 mg, 1.13 mmol, 3 eq), Pd(dppf)Cl$_2$ (27.49 mg, 37.57 μmol, 0.1 eq) and 6-bromo-3H-triazolo[4,5-b]pyridine (97.19 mg, 488.36 μmol, 1.3 eq), the mixture was bubbled with N$_2$, and stirred at 100° C. for 3 h. LCMS showed starting material was consumed completely and the MS of desired product was detected. The reaction mixture was concentrated in vacuum. The crude product was purified by prep-HPLC (column: Phenomenex Luna C18 75*30 mm*3 um; mobile phase: [water (0.04% HCl)-ACN]; B %: 5%-35%, 8 min). Compound 70, 4-(1-phenylethylamino)-6-(3H-triazolo[4, 5-b]pyridin-6-yl)quinoline-3-carbonitrile (21.49 mg, 49.03 mol, 13.05% yield, 97.63% purity, HCl) was obtained as off-white solid. $^1$H NMR (400 MHz, DMSO-d$_6$) δ=9.36-9.29 (m, 1H), 9.23-9.15 (m, 1H), 9.07-8.82 (m, 2H), 8.56-8.41 (m, 1H), 8.14-7.97 (m, 1H), 7.49 (br d, J=6.9 Hz, 2H), 7.43-7.35 (m, 2H), 7.33-7.25 (m, 2H), 6.10-5.90 (m, 1H), 1.80 (br d, J=6.4 Hz, 3H). MS (M+H)$^+$=392.1

Example 27: Synthesis of 6-(1-methyl pyrazolo [4, 3-b] pyridin-6-yl)-4-(1-phenylethylamino) quinoline-3-carbonitrile (Compound 73)

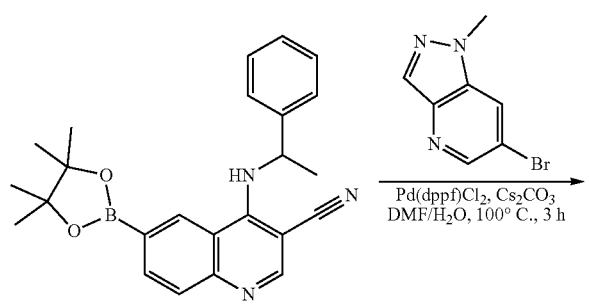

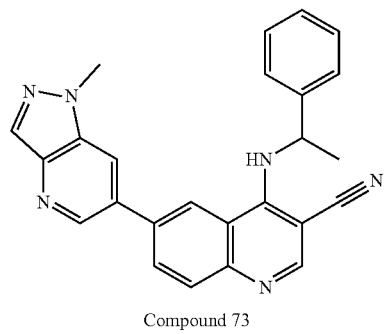

Compound 73

To a stirred solution of 4-(1-phenylethylamino)-6-(4, 4, 5, 5-tetramethyl-1,3,2-dioxaborolan-2-yl)quinoline-3-carbonitrile (200 mg, 500.89 μmol, 1 eq) in DMF (2 mL) and H$_2$O (0.4 mL) was added Cs$_2$CO$_3$ (489.59 mg, 1.50 mmol, 3 eq), Pd(dppf)Cl$_2$ (36.65 mg, 50.09 μmol, 0.1 eq) and 6-bromo-1-methyl-pyrazolo[4,3-b]pyridine (138.07 mg, 651.15 μmol, 1.3 eq), the mixture was bubbled with N$_2$, and stirred at 100° C. for 3 h. LCMS showed starting material was consumed completely and the MS of desired product was detected. The reaction mixture was concentrated in vacuum. The crude product was purified by prp-HPLC (column: Phenomenex Luna 80*30 mm*3 um; mobile phase: [water (0.04% HCl)-ACN]; B %: 10%-30%, 8 min). Compound 73, 6-(1-methylpyrazolo[4, 3-b]pyridin-6-yl)-4-(1-phenylethylamino) quinoline-3-carbonitrile (70.96 mg, 175.44 μmol, 35.03% yield, 100% purity) was obtained as a yellow solid. $^1$H NMR (400 MHz, DMSO-d6) δ ppm 9.94 (br s, 1H), 9.42 (br s, 1H), 9.17 (s, 1H), 9.10 (s, 1H), 8.88 (br s, 1H), 8.55 (br d, J=8.75 Hz, 1H), 8.38 (s, 1H), 8.15 (br d, J=8.75 Hz, 1H), 7.54 (br d, J=7.75 Hz, 2H), 7.40 (t, J=7.63 Hz, 2H), 7.27-7.34 (m, 1H), 6.10 (br t, J=7.07 Hz, 1H), 4.20 (s, 3H), 1.86 (br d, J=6.38 Hz, 3H). MS (M+H)$^+$=405.1

Example 28: Synthesis of 6-(2-amino-1, 3-benzoxazol-5-yl)-4-(1-phenylethylamino) quinoline-3-carbonitrile (Compound 87)

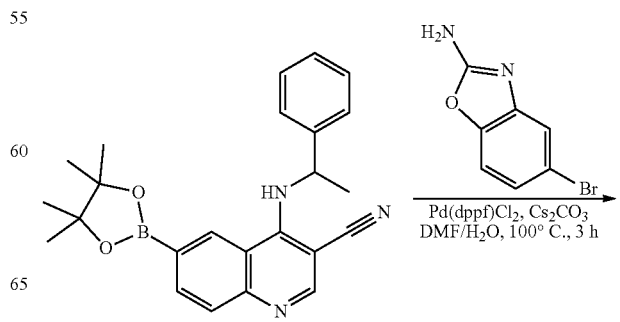

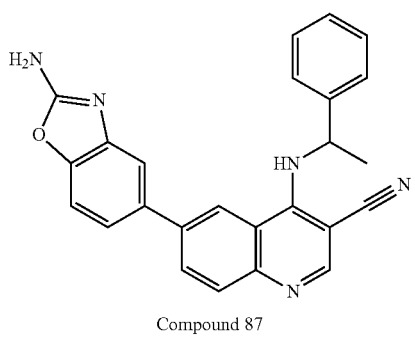

Compound 87

To a solution of 4-(1-phenylethylamino)-6-(4, 4, 5, 5-tetramethyl-1, 3, 2-dioxaborolan-2-yl) quinoline-3-carbonitrile (120 mg, 300.53 μmol, 1 eq) in DMF (2.5 mL) and H$_2$O (0.5 mL) was added Cs$_2$CO$_3$ (293.76 mg, 901.60 μmol, 3 eq), Pd(dppf)Cl$_2$ (21.99 mg, 30.05 μmol, 0.1 eq) and 5-bromo-1,3-benzoxazol-2-amine (83.23 mg, 390.69 μmol, 1.3 eq), the mixture was bubbled with N$_2$, and stirred at 100° C. for 3 h. LCMS showed starting material was consumed completely and the MS of desired product was detected. The reaction mixture was concentrated in vacuum. The crude product was purified by prep-HPLC (column: Phenomenex Luna 80*30 mm*3 um; mobile phase: [water (0.04% HCl)-ACN]; B %: 5%-25%, 8 min). Compound 87, 6-(2-amino-1,3-benzoxazol-5-yl)-4-(1-phenylethylamino)quinoline-3-carbonitrile (15.31 mg, 34.64 mol, 11.53% yield, 100% purity, HCl) was obtained as a yellow solid. $^1$H NMR (400 MHz, DMSO-d6) δ ppm 9.83 (br s, 1H), 9.11 (s, 2H), 8.40 (dd, J=8.82, 1.31 Hz, 1H), 8.11 (br d, J=8.75 Hz, 1H), 8.02 (br s, 1H), 7.82 (s, 1H), 7.57 (s, 2H), 7.51 (d, J=7.50 Hz, 2H), 7.41 (t, J=7.57 Hz, 2H), 7.27-7.35 (m, 1H), 5.95-6.20 (m, 1H), 1.84 (d, J=6.63 Hz, 3H). MS (M+H)$^+$=406.1

Example 29: Synthesis of N-[2-chloro-5-[3-cyano-4-[[(1R)-1-(4-fluorophenyl)ethyl]amino]-6-quinolyl]-3-pyridyl]methanesulfonamide (Compound 97R)

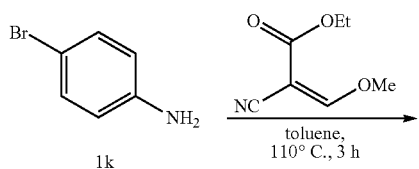

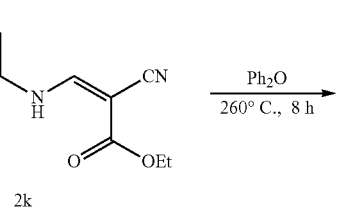

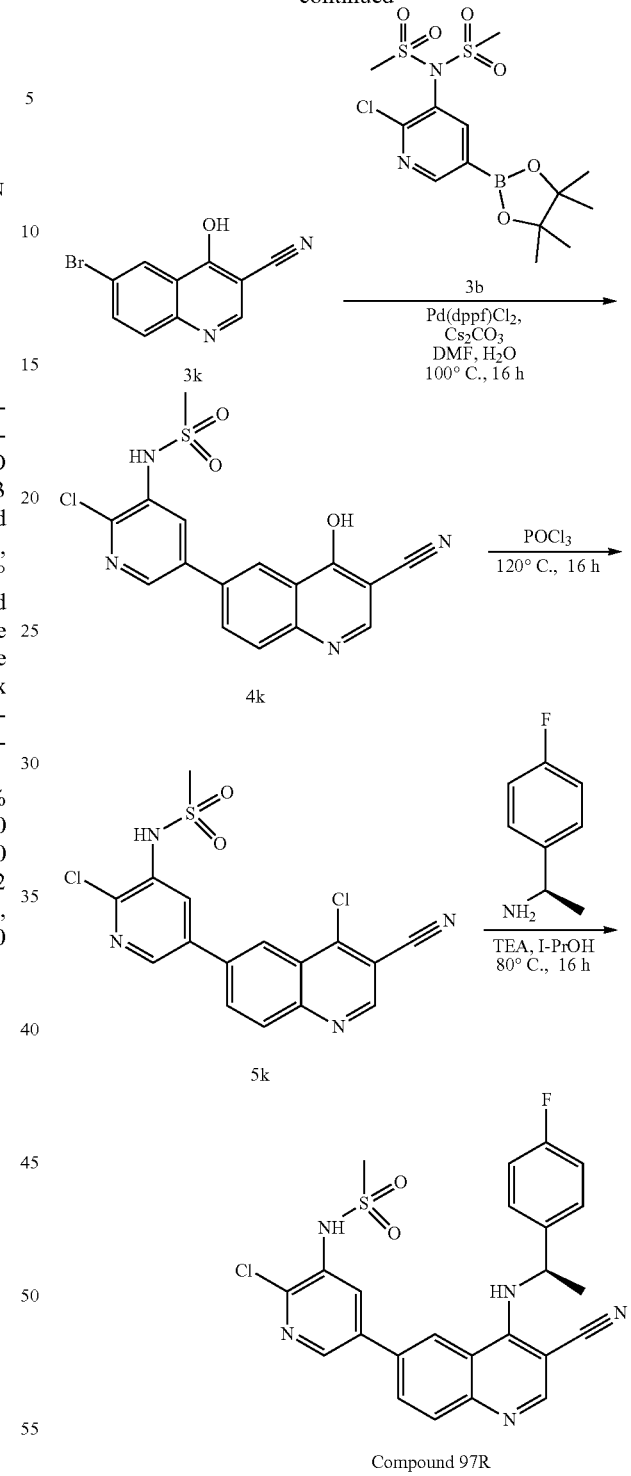

Step 1: Synthesis of ethyl (Z)-3-(4-bromoanilino)-2-cyano-prop-2-enoate (2k)

A solution of 4-bromoaniline (184.88 g, 1.07 mol, 1 eq) in toluene (1.5 L) was added ethyl (E)-2-cyano-3-ethoxy-prop-2-enoate (200 g, 1.18 mol, 1.1 eq), the mixture was stirred at 110° C. for 6 h. TLC (Petroleum ether/Ethyl acetate=3:1, R$_f$=0.88) showed starting material was consumed completely and new spot was formed. The reaction mixture was filtered, and filter caked was concentrate in vacuum. Compound 2k, ethyl (Z)-3-(4-bromoanilino)-2-cyano-prop-2-enoate (150 g, 508.25 mmol, 47.29% yield) was obtained as a white solid. $^1$H NMR (400 MHz, CHLOROFORM-d) δ=10.75 (br d, J=13.0 Hz, 1H), 8.42-7.78 (m, 1H), 7.52 (br d, J=8.6 Hz, 2H), 7.07-6.94 (m, 2H), 4.36-4.24 (m, 2H), 1.43-1.30 (m, 3H).

Step 2: Synthesis of
6-bromo-4-hydroxy-quinoline-3-carbonitrile (3k)

A solution of ethyl (Z)-3-(4-bromoanilino)-2-cyano-prop-2-enoate, 2k, (40 g, 135.53 mmol, 1 eq) in Ph$_2$O (400 mL) was stirred at 270° C. for 8 h. TLC (Petroleum ether/Ethyl acetate=3:1, R$_f$=0.43) showed a little starting material was remained and new spot was formed. The reaction mixture was poured into MTBE (200 mL). The reaction mixture was filtered, and filter cake was concentrated in vacuum. Compound 3k, 6-bromo-4-hydroxy-quinoline-3-carbonitrile (2 g, 8.03 mmol, 5.92% yield) was obtained as a yellow solid.

Step 3: Synthesis of N-[2-chloro-5-(3-cyano-4-hydroxy-6-quinolyl)-3-pyridyl]methanesulfonamide (4k)

To a stirred solution of N-[2-chloro-5-(4,4,5,5-tetramethyl-1,3,2-dioxaborolan-2-yl)-3-pyridyl]-N-methylsulfonylmethanesulfonamide, 3b, (1.7 g, 4.14 mmol, 1 eq) in dioxane (30 mL), H$_2$O (5 mL) was added 6-bromo-4-hydroxy-quinoline-3-carbonitrile, 3k, (1.55 g, 6.21 mmol, 1.5 eq), Pd(dppf)Cl$_2$ (302.87 mg, 413.93 μmol, 0.1 eq), Cs$_2$CO$_3$ (4.05 g, 12.42 mmol, 3 eq) the mixture was bubbled with N$_2$ for 1 minute, and the mixture was stirred at 100° C. for 16 h. LCMS showed the starting material was consumed completely and desired MS was detected. The reaction mixture was concentrate in vacuum. The crude residue was purified by prep-HPLC (Agela DuraShell C18 250*80 mm*10 um column; 1-30% acetonitrile in a 10 mM ammonium bicarbonate solution in water, 20 min gradient). Compound 4k, N-[2-chloro-5-(3-cyano-4-hydroxy-6-quinolyl)-3-pyridyl]methanesulfonamide (1 g, 2.67 mmol, 64.46% yield) was obtained as a white solid. MS (M+H)$^+$=375.0.

Step 4: Synthesis of N-[2-chloro-5-(4-chloro-3-cyano-6-quinolyl)-3-pyridyl]methanesulfonamide (5k)

A solution of N-[2-chloro-5-(3-cyano-4-hydroxy-6-quinolyl)-3-pyridyl]methanesulfonamide, 4k, (1 g, 2.67 mmol, 1 eq) in POCl$_3$ (16.50 g, 107.61 mmol, 10 mL, 40.33 eq) was stirred at 120° C. for 16 h. LCMS showed the starting material was consumed completely and desired MS was detected. The reaction mixture was concentrate in vacuum. The reaction mixture was dissolved with DCM (10 mL), and poured into water (30 mL). The aqueous phase was extracted with ethyl acetate (30 mL*2). The combined organic phase was dried with anhydrous Na$_2$SO$_4$, filtered and concentrated in vacuum. Compound 5k, N-[2-chloro-5-(4-chloro-3-cyano-6-quinolyl)-3-pyridyl]methanesulfonamide (600 mg, 1.53 mmol, 57.19% yield) was obtained as a yellow solid. MS (M+H)$^+$=393.0.

Step 5: Synthesis of N-[2-chloro-5-[3-cyano-4-[[(1R)-1-(4-fluorophenyl) ethyl]amino]-6-quinolyl]-3-pyridyl]methanesulfonamide (Compound 97R)

To a stirred solution of N-[2-chloro-5-(4-chloro-3-cyano-6-quinolyl)-3-pyridyl]methanesulfonamide, 5k, (100 mg, 254.29 μmol, 1 eq) in i-PrOH (3 mL) was added (1R)-1-(4-fluorophenyl)ethanamine (35.39 mg, 254.29 μmol, 1 eq), TEA (41.17 mg, 406.87 μmol, 56.63 L, 1.6 eq), the mixture was stirred at 80° C. for 16 h. LCMS showed the starting material was consumed completely and desired MS was detected. The reaction mixture was concentrated, and the crude residue was purified by prep-HPLC (Phenomenex Gemini-NX 150*30 mm*5 um column; 20-50% acetonitrile in a 0.1% trifluoroacetic acid solution in water, 9 min gradient). Compound 97R, N-[2-chloro-5-[3-cyano-4-[[(1R)-1-(4-fluorophenyl)ethyl]amino]-6-quinolyl]-3-pyridyl]methanesulfonamide (14.70 mg, 23.93 μmol, 9.41% yield, 99.31% purity, TFA) was obtained as a yellow solid. $^1$H NMR (400 MHz, DMSO-d6) δ=9.98 (br s, 1H), 9.01 (s, 1H), 8.90-8.81 (m, 2H), 8.78 (br s, 1H), 8.32-8.22 (m, 2H), 8.01 (d, J=8.8 Hz, 1H), 7.50 (dd, J=5.4, 8.4 Hz, 2H), 7.20 (t, J=8.8 Hz, 2H), 5.94 (br t, J=7.1 Hz, 1H), 3.20 (s, 3H), 1.76 (d, J=6.6 Hz, 3H). MS (M+H)$^+$=496.0.

Compound 97S was synthesized using the same procedure as Compound 97R in Example 29, but substituting (1S)-1-(4-fluorophenyl)ethanamine for (1R)-1-(4-fluorophenyl) ethanamine.

Compound 97S: $^1$H NMR (400 MHz, DMSO-d6) δ=9.98 (br s, 1H), 9.00 (s, 1H), 8.90-8.75 (m, 3H), 8.31-8.23 (m, 2H), 8.01 (d, J=8.6 Hz, 1H), 7.50 (dd, J=5.4, 8.4 Hz, 2H), 7.20 (t, J=8.8 Hz, 2H), 5.94 (br t, J=6.9 Hz, 1H), 3.20 (s, 3H), 1.76 (d, J=6.6 Hz, 3H). MS (M+H)+=496.0.

Example 30: Synthesis of N-[2-chloro-5-[3-cyano-4-(indan-1-ylamino)-6-quinolyl]-3-pyridyl]methanesulfonamide (Compound 101)

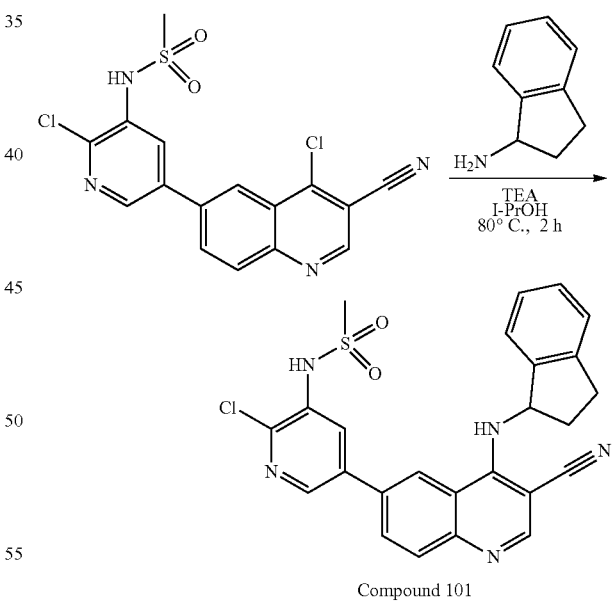

Compound 101

To a solution of N-[2-chloro-5-(4-chloro-3-cyano-6-quinolyl)-3-pyridyl]methanesulfonamide (70 mg, 178.01 μmol, 1 eq) in i-PrOH (1 mL) was added TEA (54.04 mg, 534.02 μmol, 74.33 μL, 3 eq) and indan-1-amine (23.71 mg, 178.01 μmol, 22.80 μL, 1 eq). The mixture was stirred at 80° C. for 2 h. LCMS showed the starting material was consumed completely, and desired MS was detected. The reaction mixture was concentrated in vacuum. The crude product was purified by prep-HPLC (column: Phenomenex luna C18

80*40 mm*3 um; mobile phase: [water (0.04% HCl)-ACN]; B %: 25%-45%, 7 min). Compound 101, N-[2-chloro-5-[3-cyano-4-(indan-1-ylamino)-6-quinolyl]-3-pyridyl] methanesulfonamide (20.04 mg, 38.07 μmol, 21.39% yield, 100% purity, HCl) was obtained as a pale yellow solid. $^1$H NMR (400 MHz, DMSO-d6) δ=9.99 (s, 1H), 9.86 (br d, J=8.4 Hz, 1H), 9.19 (s, 1H), 9.03 (d, J=1.3 Hz, 1H), 8.79 (d, J=2.4 Hz, 1H), 8.39 (dd, J=1.6, 8.8 Hz, 1H), 8.27 (d, J=2.4 Hz, 1H), 8.20 (d, J=8.8 Hz, 1H), 7.43 (d, J=7.4 Hz, 1H), 7.41-7.32 (m, 2H), 7.31-7.25 (m, 1H), 6.30 (q, J=8.0 Hz, 1H), 3.17 (s, 3H), 3.16-3.09 (m, 1H), 3.06-2.95 (m, 1H), 2.76 (dtd, J=2.8, 7.9, 12.8 Hz, 1H), 2.46-2.38 (m, 1H). MS (M+H)$^+$=490.0.

Example 31: Synthesis of N-[2-chloro-5-[3-cyano-4-[(2-hydroxyindan-1-yl)amino]-6-quinolyl]-3-pyridyl]methanesulfonamide (Compound 103)

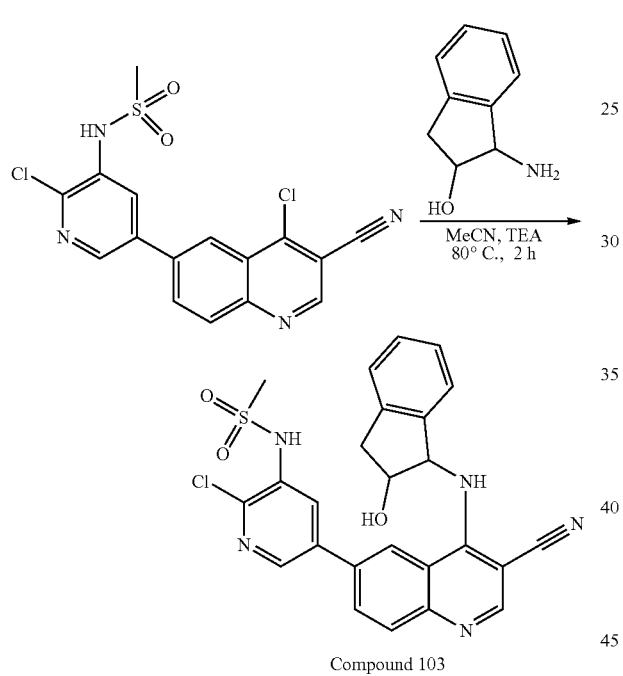

Compound 103

To a solution of N-[2-chloro-5-(4-chloro-3-cyano-6-quinolyl)-3-pyridyl]methane sulfonamide (60 mg, 152.58 μmol, 1 eq) in MeCN (1 mL) was added 1-aminoindan-2-ol (22.76 mg, 152.58 μmol, 1 eq) and TEA (46.32 mg, 457.73 μmol, 63.71 μL, 3 eq). The mixture was stirred at 80° C. for 2 h. LCMS showed the starting material was consumed completely, and desired MS was detected. The reaction mixture was concentrated in vacuum, and the crude product was purified by prep-HPLC (column: Waters Xbridge BEH C18 100*30 mm*10 um; mobile phase: [water (10 mM NH$_4$HCO$_3$)-ACN]; B %: 18%-48%, 8 min). Compound 103, N-[2-chloro-5-[3-cyano-4-[(2-hydroxyindan-1-yl)amino]-6-quinolyl]-3-pyridyl]methanesulfonamide (10.94 mg, 21.62 μmol, 14.17% yield, 100% purity) was obtained as a pale yellow solid. $^1$H NMR (400 MHz, DMSO-d6) δ=9.90 (br s, 1H), 8.86 (d, J=1.6 Hz, 1H), 8.79 (d, J=2.3 Hz, 1H), 8.62 (s, 1H), 8.26 (d, J=2.3 Hz, 1H), 8.20 (br d, J=9.1 Hz, 1H), 8.14 (dd, J=1.7, 8.7 Hz, 1H), 7.99 (d, J=8.6 Hz, 1H), 7.38 (d, J=7.0 Hz, 1H), 7.35-7.24 (m, 3H), 5.92 (dd, J=4.9, 9.0 Hz, 1H), 5.48 (d, J=4.6 Hz, 1H), 4.79-4.73 (m, 1H), 3.23-3.16 (m, 1H), 3.15 (s, 3H), 2.98 (br d, J=15.4 Hz, 1H). MS (M+H)$^+$=506.2.

Example 32: Synthesis of N-[2-chloro-5-[3-cyano-4-[[(1S)-2-hydroxy-1-phenyl-ethyl]amino]-6-quinolyl]-3-pyridyl]methanesulfonamide (Compound 104S)

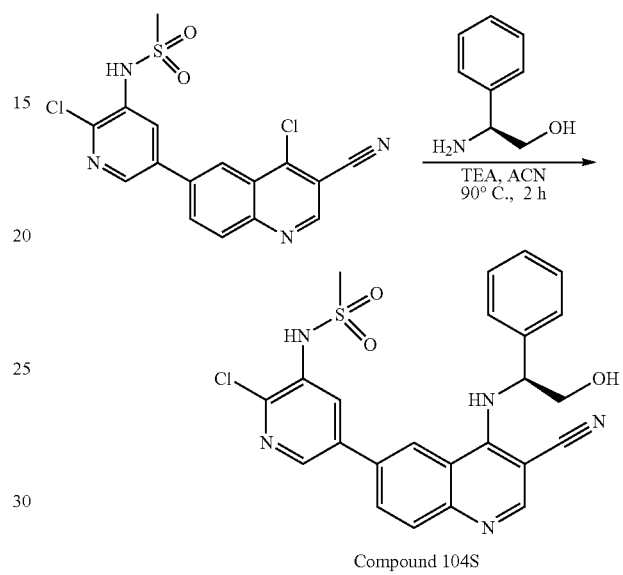

Compound 104S

To a stirred solution of N-[2-chloro-5-(4-chloro-3-cyano-6-quinolyl)-3-pyridyl]methanesulfonamide (80 mg, 203.43 μmol, 1 eq) in MeCN (3 mL) was added (2S)-2-amino-2-phenyl-ethanol (33.49 mg, 244.12 μmol, 1.2 eq), TEA (32.94 mg, 325.50 μmol, 45.30 μL, 1.6 eq), and the mixture was stirred at 90° C. for 2 h. LCMS showed the starting material was consumed completely, and desired MS was detected. The reaction mixture was concentrated in vacuum. The crude product was purified by prep-HPLC (column: Waters Xbridge BEH C18 100*30 mm*10 um; mobile phase: [water (10 mM NH$_4$HCO$_3$)-ACN]; B %: 5%-30%, 8 min).

Compound 104S, N-[2-chloro-5-[3-cyano-4-[[(1S)-2-hydroxy-1-phenyl-ethyl]amino]-6-quinolyl]-3-pyridyl]methane sulfonamide (28 mg, 56.68 μmol, 27.86% yield, 100% purity) was obtained as a white solid. $^1$H NMR (400 MHz, DMSO-d6) δ=9.96 (br s, 1H), 8.98 (s, 1H), 8.85 (d, J=2.0 Hz, 1H), 8.46 (s, 1H), 8.27 (d, J=2.1 Hz, 1H), 8.21-8.12 (m, 2H), 7.97 (d, J=8.6 Hz, 1H), 7.46 (d, J=7.5 Hz, 2H), 7.36 (t, J=7.6 Hz, 2H), 7.30-7.24 (m, 1H), 5.79-5.71 (m, 1H), 5.33 (t, J=5.9 Hz, 1H), 3.97-3.88 (m, 1H), 3.86-3.78 (m, 1H), 3.19 (s, 3H). MS (M+H)$^+$=494.2.

Compound 104R was synthesized using the same procedure as Compound 104S in Example 32, but substituting (2R)-2-amino-2-phenyl-ethanol for (2S)-2-amino-2-phenyl-ethanol.

Compound 104R: $^1$H NMR (400 MHz, DMSO-d6) δ=9.97 (br s, 1H), 8.99 (s, 1H), 8.86 (d, J=2.0 Hz, 1H), 8.47 (s, 1H), 8.28 (d, J=2.3 Hz, 1H), 8.22-8.12 (m, 2H), 7.98 (d, J=8.6 Hz, 1H), 7.47 (d, J=7.4 Hz, 2H), 7.37 (t, J=7.5 Hz, 2H), 7.32-7.25 (m, 1H), 5.80-5.72 (m, 1H), 5.34 (t, J=5.9 Hz, 1H), 3.98-3.89 (m, 1H), 3.83 (td, J=5.2, 10.9 Hz, 1H), 3.20 (s, 3H). MS (M+H)$^+$=494.2

Example 33: Synthesis of N-[2-chloro-5-[3-cyano-4-[(1-phenylcyclopropyl)amino]-6-quinolyl]-3-pyridyl]methanesulfonamide (Compound 106)

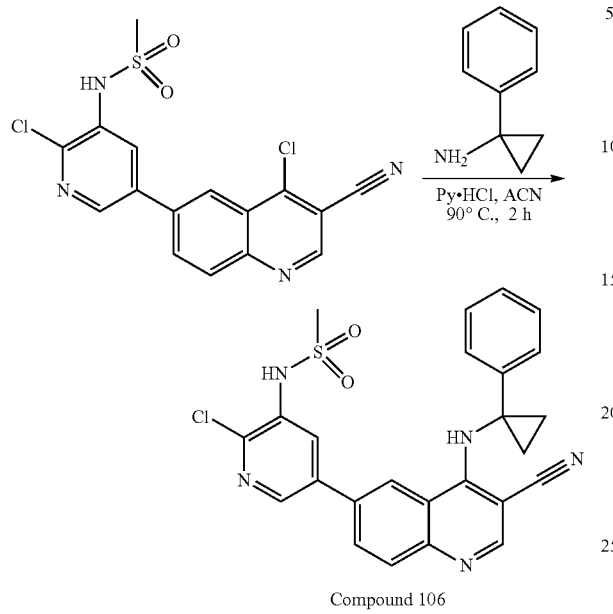

Compound 106

To a stirred solution of N-[2-chloro-5-(4-chloro-3-cyano-6-quinolyl)-3-pyridyl]methane sulfonamide (100 mg, 254.29 μmol, 1 eq) in MeCN (2 mL) was added 1-phenyl-cyclopropanamine hydrochloride (43.14 mg, 254.29 μmol, 1 eq), pyridine hydrochloride (47.02 mg, 406.87 μmol, 1.6 eq), and the mixture was stirred at 90° C. for 2 h. LCMS showed the starting material was consumed completely, and desired MS was detected. The reaction mixture filtered to give a filtrate, and the filtrate was purified by prep-HPLC (column: Phenomenex Gemini-NX 80*40 mm*3 um; mobile phase: [water (10 mM NH$_4$HCO$_3$)-ACN]; B %: 10%-40%, 8 min). Compound 106, N-[2-chloro-5-[3-cyano-4-[(1-phenylcyclopropyl)amino]-6-quinolyl]-3-pyridyl] methane sulfonamide (19.4 mg, 39.21 μmol, 15.42% yield, 99.04% purity) was obtained as a off-white solid. $^1$H NMR (400 MHz, DMSO-d6) δ=9.93 (br s, 1H), 9.15 (s, 1H), 8.92 (d, J=1.6 Hz, 1H), 8.83 (d, J=2.3 Hz, 1H), 8.48 (s, 1H), 8.30 (d, J=2.4 Hz, 1H), 8.18 (dd, J=1.8, 8.7 Hz, 1H), 7.99 (d, J=8.6 Hz, 1H), 7.34-7.28 (m, 2H), 7.21-7.15 (m, 3H), 3.17 (s, 3H), 1.78-1.69 (m, 2H), 1.59 (br s, 2H). MS (M+H)$^+$=490.2.

Example 34: Synthesis of N-[2-chloro-5-[4-[[(1S)-1-(4-fluorophenyl)ethyl]amino]quinazolin-6-yl]-3-pyridyl]methanesulfonamide (Compound 111S)

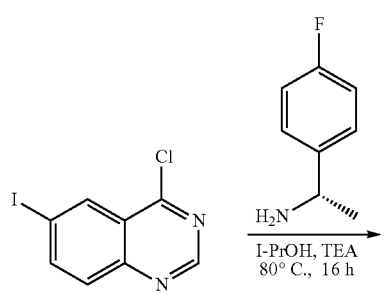

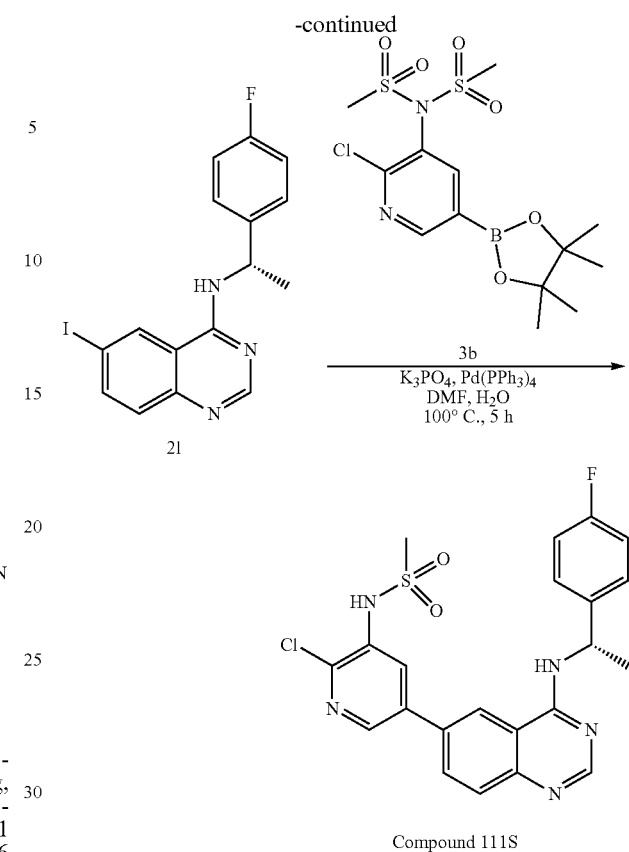

Compound 111S

Step 1: Synthesis of N-[(1S)-1-(4-fluorophenyl)ethyl]-6-iodo-quinazolin-4-amine (2l)

A solution of 4-chloro-6-iodo-quinazoline (2 g, 6.88 mmol, 1 eq) in i-PrOH (20 mL) was added (1S)-1-(4-fluorophenyl)ethanamine (1.05 g, 7.57 mmol, 1.1 eq), TEA (1.11 g, 11.02 mmol, 1.53 mL, 1.6 eq), the mixture was stirred at 80° C. for 16 h. LCMS showed the starting material was consumed completely and desired MS was detected. The reaction mixture was concentrate in vacuum. Compound 2l, N-[(1S)-1-(4-fluorophenyl)ethyl]-6-iodo-quinazolin-4-amine (2.5 g, 6.36 mmol, 92.35% yield) was obtained as a yellow oil. MS (M+H)$^+$=394.1.

Step 2: Synthesis of N-[2-chloro-5-[4-[[(1S)-1-(4-fluorophenyl)ethyl]amino]quinazolin-6-yl]-3-pyridyl]methanesulfonamide (Compound 111S)

To a stirred solution of N-[2-chloro-5-(4,4,5,5-tetramethyl-1,3,2-dioxaborolan-2-yl)-3-pyridyl]-N-methylsulfonylmethanesulfonamide, 3b, (2.09 g, 5.09 mmol, 1 eq) in DMF (15 mL)/H$_2$O (3 mL) was added N-[(1S)-1-(4-fluorophenyl)ethyl]-6-iodo-quinazolin-4-amine, 2l, (2 g, 5.09 mmol, 1 eq), Pd(PPh$_3$)$_4$ (587.78 mg, 508.65 μmol, 0.1 eq), K$_3$PO$_4$ (3.24 g, 15.26 mmol, 3 eq) the mixture was purged with N$_2$ for three times, and the mixture was stirred at 100° C. for 5 h. LCMS showed the starting material was consumed completely and desired MS was detected. The reaction mixture was filtered, and the filtrate was purified by prep-HIPLC (Agela DuraShell C18 250*80 mm*10 um column; 15-45% acetonitrile in a 10 mM ammonium bicarbonate solution in water, 20 min gradient). Compound 111S, N-[2-chloro-5-[4-[[(1S)-1-(4-fluorophenyl)ethyl]amino] quinazolin-6-yl]-3-pyridyl]methanesulfonamide (993.30 mg, 2.10 mmol, 41.38% yield, 100% purity) was obtained as a yellow solid. $^1$H NMR (400 MHz, DMSO-d6+D2O) δ=8.78 (d, J=2.0 Hz, 1H), 8.74 (d, J=2.2 Hz, 1H), 8.51 (s, 1H), 8.21 (d, J=2.2 Hz, 1H), 8.13 (dd, J=2.0, 8.6 Hz, 1H), 7.83 (d, J=8.8 Hz, 1H), 7.50 (dd, J=5.5, 8.6 Hz, 2H), 7.15-7.08 (m, 2H), 5.68 (d, J=6.8 Hz, 1H), 3.18 (s, 3H), 1.64 (d, J=7.1 Hz, 3H). MS (M+H)$^+$=472.1.

Compound 111R was synthesized using the same procedure as Compound 111S in Example 34, but substituting (1R)-1-(4-fluorophenyl)ethanamine for (1S)-1-(4-fluorophenyl)ethanamine.

Compound 111R: $^1$H NMR (400 MHz, DMSO-d6, T=273+80K) δ=8.73 (d, J=2.0 Hz, 1H), 8.71 (d, J=2.2 Hz, 1H), 8.43 (s, 1H), 8.19 (d, J=2.2 Hz, 1H), 8.08 (dd, J=2.0, 8.6 Hz, 1H), 7.81 (d, J=8.6 Hz, 1H), 7.48 (dd, J=5.7, 8.4 Hz, 2H), 7.10 (t, J=8.8 Hz, 2H), 5.63 (q, J=7.0 Hz, 1H), 3.16 (s, 3H), 1.62 (d, J=6.8 Hz, 3H)). MS (M+H)$^+$=472.1.

Example 35: Synthesis of 6-(2-aminopyrimidin-5-yl)-N-[(1R)-1-(4-fluorophenyl)ethyl]quinazolin-4-amine (Compound 121R)

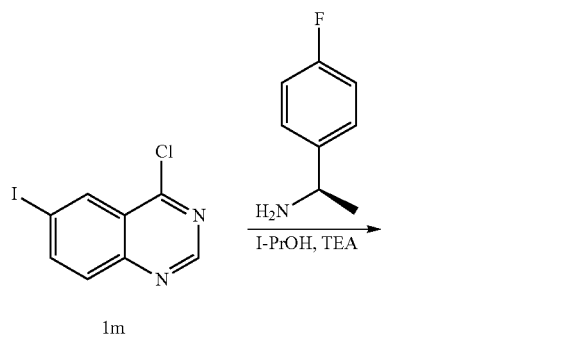

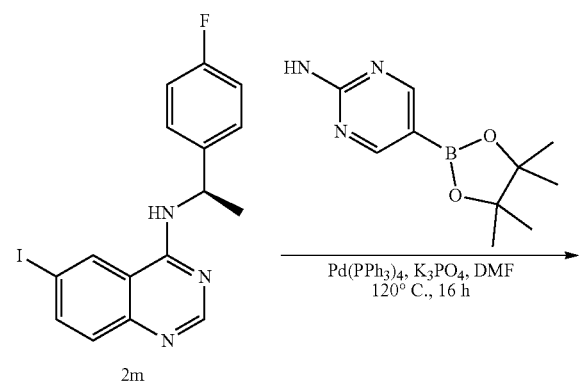

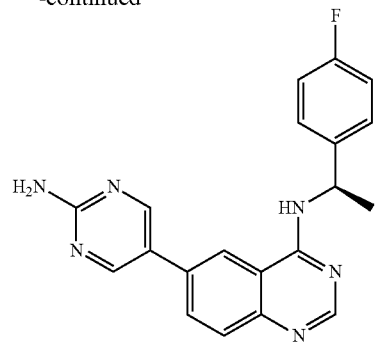

Compound 121R

Step 1: Synthesis of N-(3-ethynylphenyl)-6-iodo-quinazolin-4-amine (2m)

To a stirred solution of 4-chloro-6-iodo-quinazoline, 1m, (300 mg, 1.03 mmol, 1 eq) in i-PrOH (5 mL) was added (1R)-1-(4-fluorophenyl)ethanamine (143.73 mg, 1.03 mmol, 1 eq), TEA (167.20 mg, 1.65 mmol, 229.99 μL, 1.6 eq), and the mixture was stirred at 80° C. for 15 h. LCMS showed the starting material was consumed completely and desired MS was detected. The reaction mixture was concentrate in vacuum. Compound 2m, N-[(1R)-1-(4-fluorophenyl)ethyl]-6-iodo-quinazolin-4-amine (300 mg, 762.98 μmol, 73.88% yield) was obtained as yellow solid. MS (M+H)$^+$=394.1.

Step 2: Synthesis of 6-(2-aminopyrimidin-5-yl)-N-[(1R)-1-(4-fluorophenyl) ethyl]quinazolin-4-amine (Compound 121R)

To a stirred solution of N-[(1R)-1-(4-fluorophenyl)ethyl]-6-iodo-quinazolin-4-amine, 2m, (300 mg, 762.98 μmol, 1 eq) in DMF (5 mL), H$_2$O (1 mL) was added 5-(4,4,5,5-tetramethyl-1,3,2-dioxaborolan-2-yl)pyrimidin-2-amine (168.67 mg, 762.98 μmol, 1 eq), K$_3$PO$_4$ (485.86 mg, 2.29 mmol, 3 eq), Pd(PPh$_3$)$_4$ (88.17 mg, 76.30 μmol, 0.1 eq), the mixture was bubbled with N$_2$ for 1 minute, and the mixture was stirred at 120° C. for 16 h. LCMS showed the starting material was consumed completely and desired MS was detected. The reaction mixture was filtered, and filtrate was purified directly. The crude residue was purified by prep-HPLC (Phenomenex luna C18 250*50 mm*10 um; 10-40% acetonitrile in a 0.05% hydrochloric acid solution in water, 10 min gradient). Compound 121R, 6-(2-aminopyrimidin-5-yl)-N-[(1R)-1-(4-fluorophenyl)ethyl]quinazolin-4-amine (283.62 mg, 707.18 μmol, 92.69% yield, 98.95% purity, HCl) was obtained as pale yellow solid. $^1$H NMR (400 MHz, DMSO-d6, T=273+80K) δ=10.78 (br s, 1H), 9.30 (br s, 1H), 9.00 (s, 2H), 8.83 (s, 1H), 8.37 (dd, J=1.8, 8.8 Hz, 1H), 7.99 (d, J=8.8 Hz, 1H), 7.64 (dd, J=5.5, 8.6 Hz, 2H), 7.17 (t, J=8.8 Hz, 2H), 5.88 (t, J=7.2 Hz, 1H), 1.78 (d, J=7.0 Hz, 3H). MS (M+H)$^+$=361.2.

Example 36: Synthesis of 4-(1-phenylethylamino)-6-(3-quinolyl)quinoline-3-carbonitrile (Compound 122)

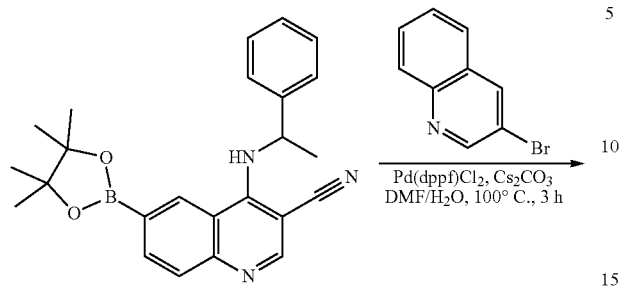

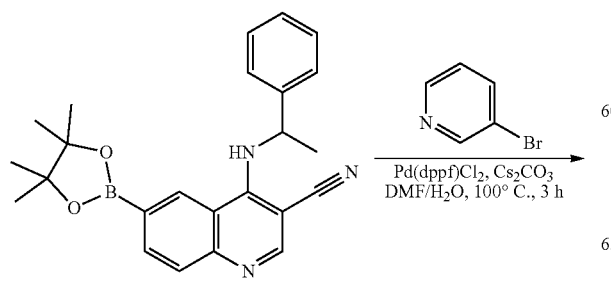

Compound 122

To a stirred solution of 4-(1-phenylethylamino)-6-(4,4,5,5-tetramethyl-1,3,2-dioxaborolan-2-yl)quinoline-3-carbonitrile (100 mg, 250.44 µmol, 1 eq) in DMF (2.5 mL) and H₂O (0.5 mL) was added Cs₂CO₃ (244.80 mg, 751.33 µmol, 3 eq), Pd(dppf)Cl₂ (18.33 mg, 25.04 µmol, 0.1 eq) and 3-bromoquinoline (52.11 mg, 250.44 µmol, 33.62 µL, 1 eq), the mixture was bubbled with N₂, and stirred at 100° C. for 3 h. LCMS showed starting material was consumed completely and the MS of desired product was detected. The reaction mixture was concentrated in vacuum. The crude product was purified by prep-HPLC (column: Waters Xbridge Prep OBD C18 150*40 mm*10 um; mobile phase: [water (10 mM NH₄HCO₃)-ACN]; B %: 35%-65%, 8 min). Compound 122, 4-(1-phenylethylamino)-6-(3-quinolyl)quinoline-3-carbonitrile (19.89 mg, 49.67 mol, 19.83% yield, 100% purity) was obtained as a pale yellow solid. ¹H NMR (400 MHz, DMSO-d6) δ ppm 9.53 (s, 1H), 9.12 (s, 1H), 8.83 (s, 1H), 8.47 (s, 1H), 8.31 (br dd, J=14.43, 8.56 Hz, 2H), 8.08-8.16 (m, 2H), 8.01 (d, J=8.44 Hz, 1H), 7.82 (br t, J=7.58 Hz, 1H), 7.64-7.74 (m, 1H), 7.46 (br d, J=7.58 Hz, 2H), 7.35 (br t, J=7.46 Hz, 2H), 7.20-7.29 (m, 1H), 5.89 (br t, J=7.15 Hz, 1H), 1.75 (br d, J=6.60 Hz, 3H). MS (M+H)⁺=401.1

Example 37: Synthesis of 4-(1-phenylethylamino)-6-(3-pyridyl) quinoline-3-carbonitrile (Compound 123)

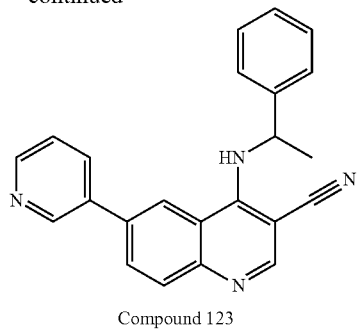

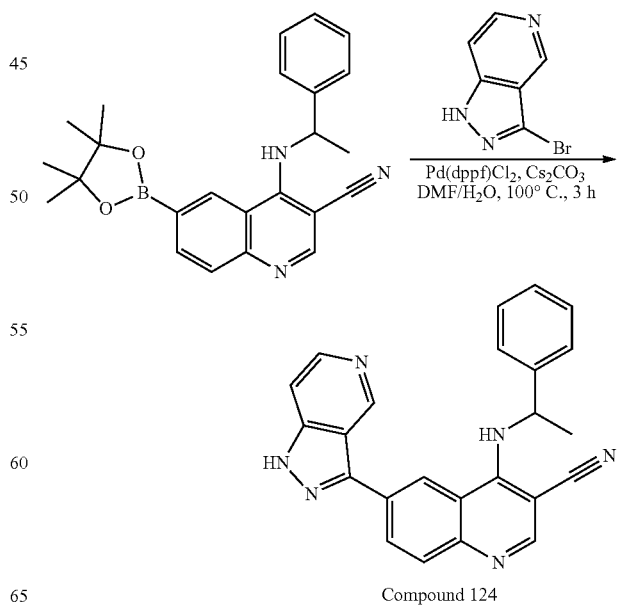

Compound 123

To a stirred solution of 4-(1-phenylethylamino)-6-(4,4,5,5-tetramethyl-1,3,2-dioxaborolan-2-yl)quinoline-3-carbonitrile (100 mg, 250.44 µmol, 1 eq) in DMF (0.5 mL) and H₂O (0.1 mL) was added Cs₂CO₃ (244.80 mg, 751.33 µmol, 3 eq), Pd(dppf)Cl₂ (18.33 mg, 25.04 µmol, 0.1 eq) and 3-bromopyridine (39.57 mg, 250.44 µmol, 24.13 µL, 1 eq), the mixture was bubbled with N₂, and stirred at 100° C. for 3 h. LCMS showed starting material was consumed completely and the MS of desired product was detected. The reaction mixture was concentrated in vacuum. The crude product was purified by prep-HPLC (column: Phenomenex luna C18 100*40 mm*5 um; mobile phase: [water (0.1% TFA)-ACN]; B %: 1%-35%, 8 min). Compound 123, 4-(1-phenylethylamino)-6-(3-pyridyl) quinoline-3-carbonitrile (28.25 mg, 60.83 µmol, 24.29% yield, 100% purity, TFA) was obtained as a yellow solid. ¹H NMR (400 MHz, DMSO-d6) δ=9.30 (br s, 1H), 9.22 (d, J=1.3 Hz, 1H), 9.11 (s, 1H), 8.95 (s, 1H), 8.76 (d, J=4.6 Hz, 1H), 8.47 (br d, J=7.7 Hz, 1H), 8.39 (dd, J=1.4, 8.7 Hz, 1H), 8.04 (d, J=8.7 Hz, 1H), 7.75 (dd, J=5.2, 7.8 Hz, 1H), 7.51-7.45 (m, 2H), 7.39 (t, J=7.6 Hz, 2H), 7.33-7.25 (m, 1H), 6.03 (quin, J=6.9 Hz, 1H), 1.80 (d, J=6.7 Hz, 3H). MS (M+H)⁺=351.1.

Example 38: Synthesis of 4-(1-phenylethylamino)-6-(1H-pyrazolo [4, 3-c]pyridin-3-yl) quinoline-3-carbonitrile (Compound 124)

Compound 124

To a stirred solution of 4-(1-phenylethylamino)-6-(4,4,5,5-tetramethyl-1,3,2-dioxaborolan-2-yl)quinoline-3-carbonitrile (100 mg, 250.44 µmol, 1 eq) in DMF (2.5 mL) and H$_2$O (0.5 mL) was added Cs$_2$CO$_3$ (244.80 mg, 751.33 µmol, 3 eq), Pd(dppf)Cl$_2$ (18.33 mg, 25.04 µmol, 0.1 eq) and 3-bromo-1H-pyrazolo[4,3-c]pyridine (49.59 mg, 250.44 µmol, 49.59 µL, 1 eq), the mixture was bubbled with N$_2$, and stirred at 100° C. for 3 h. LCMS showed starting material was consumed completely and the Ms of desired product was detected. The reaction mixture was concentrated in vacuum. The crude product was purified by prep-HPLC (column: Phenomenex luna C18 100*40 mm*5 um; mobile phase: [water (0.1% TFA)-ACN]; B %: 1%-35%, 8 min) Compound 124, 4-(1-phenylethylamino)-6-(1H-pyrazolo[4,3-c]pyridin-3-yl)quinoline-3-carbonitrile (7.96 mg, 15.17 µmol, 6.06% yield, 96.13% purity, TFA) was obtained as a gray solid. $^1$H NMR (400 MHz, DMSO-d$_6$) δ=15.06-14.65 (m, 1H), 9.92 (s, 1H), 9.30 (d, J=1.3 Hz, 1H), 8.84 (br d, J=6.8 Hz, 1H), 8.71 (s, 1H), 8.62 (d, J=6.7 Hz, 1H), 8.53 (dd, J=1.6, 8.7 Hz, 1H), 8.15 (d, J=6.7 Hz, 1H), 8.06 (d, J=8.6 Hz, 1H), 7.46 (d, J=7.5 Hz, 2H), 7.35 (t, J=7.6 Hz, 2H), 7.30-7.20 (m, 1H), 5.98-5.83 (m, 1H), 1.76 (d, J=6.6 Hz, 3H). MS (M+H)$^+$=391.1

Example 39: Synthesis of 4-(1-phenylethylamino)-6-(1H-pyrazolo [3,4-c]pyridin-3-yl)quinoline-3-carbonitrile (Compound 125)

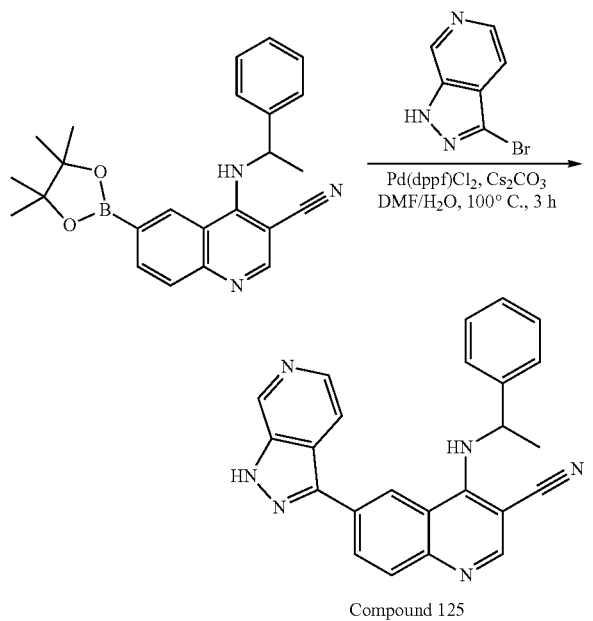

Compound 125

To a stirred solution of 4-(1-phenylethylamino)-6-(4,4,5,5-tetramethyl-1,3,2-dioxaborolan-2-yl)quinoline-3-carbonitrile (100 mg, 250.44 µmol, 1 eq) in DMF (2.5 mL) and H$_2$O (0.5 mL) was added Cs$_2$CO$_3$ (244.80 mg, 751.33 µmol, 3 eq), Pd(dppf)Cl$_2$ (18.33 mg, 25.04 µmol, 0.1 eq) and 3-bromo-1H-pyrazolo[3,4-c]pyridine (59.51 mg, 300.53 µmol, 59.51 µL, 1.2 eq), the mixture was bubbled with N$_2$ for 1 minute, and stirred at 100° C. for 3 h. LCMS showed starting material was consumed completely and the MS of desired product was detected. The reaction was filtered, the filter cake was washed by DMSO then the filtrate was concentrated in vacuum. The crude product was purified by prep-HPLC (column: Waters Xbridge BEH C18 100*30 mm*10 um; mobile phase: [water (NH$_4$HCO$_3$)-ACN]; B %: 35%-60%, 8 min). Compound 125, 4-(1-phenylethylamino)-6-(1H-pyrazolo[3,4-c]pyridin-3-yl)quinoline-3-carbonitrile (7.28 mg, 18.65 mol, 7.45% yield, 100% purity) was obtained as a yellow solid. $^1$H NMR (400 MHz, DMSO-d6) δ ppm 14.02 (br s, 1H), 9.15 (br d, J=9.41 Hz, 2H), 8.46 (s, 1H), 8.40 (br d, J=7.21 Hz, 2H), 8.13 (br d, J=5.13 Hz, 1H), 7.99 (br d, J=8.31 Hz, 1H), 7.46 (br d, J=7.70 Hz, 2H), 7.35 (br t, J=7.15 Hz, 2H), 7.26 (br d, J=7.34 Hz, 1H), 5.84 (br s, 1H), 1.75 (br d, J=5.99 Hz, 3H). MS (M+H)=391.0

Example 40: Synthesis of 6-(5-cyano-6-methoxy-3-pyridyl)-4-(1-phenylethylamino) quinoline-3-carbonitrile (Compound 126)

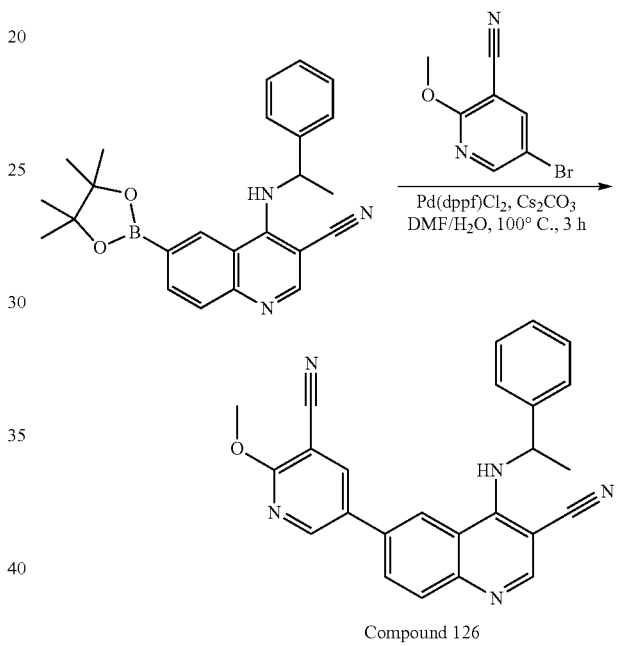

Compound 126

To a solution of 4-(1-phenylethylamino)-6-(4,4,5,5-tetramethyl-1,3,2-dioxaborolan-2-yl)quinoline-3-carbonitrile (100 mg, 250.44 µmol, 1 eq) in DMF (2.5 mL) and H$_2$O (0.4 mL) was added Cs$_2$CO$_3$ (244.80 mg, 751.33 µmol, 3 eq), Pd(dppf)Cl$_2$ (18.33 mg, 25.04 µmol, 0.1 eq) and 5-bromo-2-methoxy-pyridine-3-carbonitrile (53.35 mg, 250.44 µmol, 1 eq), the mixture was bubbled with N$_2$, the reaction was stirred at 100° C. for 3 h. LCMS showed starting material was consumed completely and the MS of desired product was detected. The crude product was purified by prep-HPLC (column: Phenomenex Luna 80*30 mm*3 um; mobile phase: [water (0.04% HCl)-ACN]; B %: 20%-40%, 8 min). Compound 126, 6-(5-cyano-6-methoxy-3-pyridyl)-4-(1-phenylethylamino) quinoline-3-carbonitrile (22.91 mg, 50.74 µmol, 20.26% yield, 97.87% purity, HCl) was obtained as a white solid. $^1$H NMR (400 MHz, DMSO-d6) δ ppm 9.50 (br s, 1H), 9.15 (br s, 1H), 9.10 (d, J=2.20 Hz, 1H), 9.00 (s, 1H), 8.90 (d, J=2.32 Hz, 1H), 8.40 (d, J=8.56 Hz, 1H), 8.02-8.10 (m, 1H), 7.50 (d, J=7.46 Hz, 2H), 7.39 (t, J=7.58 Hz, 2H), 7.27-7.34 (m, 1H), 6.05 (br t, J=7.34 Hz, 1H) 4.09 (s, 3H) 1.83 (d, J=6.72 Hz, 3H). MS (M+H)$^+$=406.1

Example 41: Synthesis of 6-[3-(2-oxo-3H-1, 3, 4-oxadiazol-5-yl) phenyl]-4-(1-phenylethylamino) quinoline-3-carbonitrile (Compound 127)

Example 42: Synthesis of 4-(1-phenylethylamino)-6-[3-(4H-1, 2, 4-triazol-3-yl) phenyl]quinoline-3-carbonitrile (Compound 128)

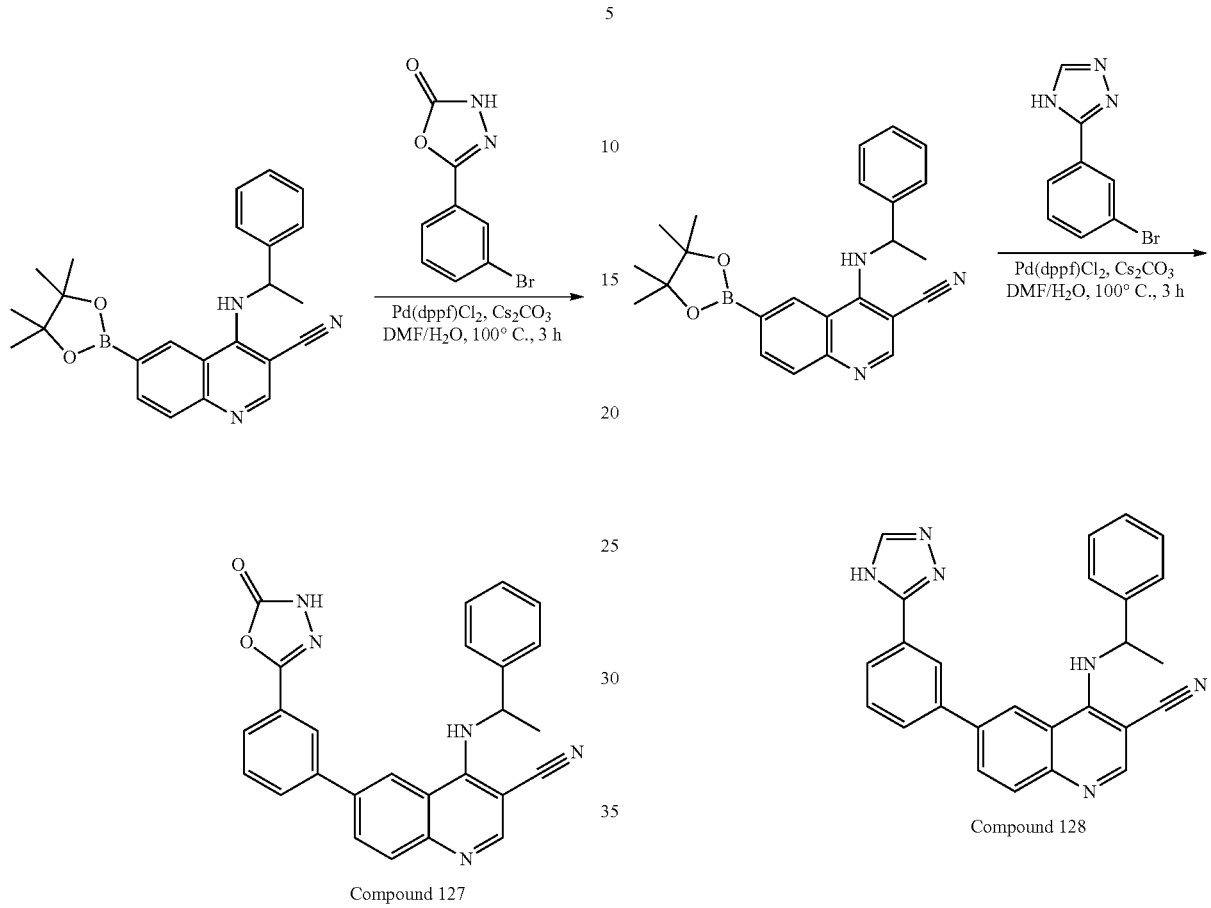

Compound 127

Compound 128

To a solution of 5-(3-bromophenyl)-3H-1, 3, 4-oxadiazol-2-one (50 mg, 207.43 mol, 1 eq) in DMF (1 mL) and $H_2O$ (0.2 mL) was added $Cs_2CO_3$ (202.76 mg, 622.30 µmol, 3 eq), Pd(dppf)Cl$_2$ (15.18 mg, 20.74 µmol, 0.1 eq) and 4-(1-phenylethylamino)-6-(4,4,5,5-tetramethyl-1,3,2-dioxaborolan-2-yl)quinoline-3-carbonitrile (82.83 mg, 207.43 µmol, 1 eq), the mixture was bubbled with $N_2$, the reaction was stirred at 100° C. for 3 h. LCMS showed starting material was consumed completely and the MS of desired product was detected. The crude product was purified by prep-HPLC (column: Phenomenex Luna 80*30 mm*3 um; mobile phase: [water (0.04% HCl)-ACN]; B %: 15%-40%, 8 min). Compound 127, 6-[3-(2-oxo-3H-1, 3, 4-oxadiazol-5-yl)phenyl]-4-(1-phenylethylamino)quinoline-3-carbonitrile (10.32 mg, 21.96 µmol, 10.59% yield, 100% purity, HCl) was obtained as a pale yellow solid. $^1$H NMR (400 MHz, DMSO-d6) δ ppm 12.73 (s, 1H), 9.45 (br s, 1H), 9.06 (s, 1H), 8.96 (s, 1H), 8.34 (d, J=8.80 Hz, 1H), 8.17 (s, 1H), 7.99-8.09 (m, 2H), 7.88 (d, J=7.82 Hz, 1H), 7.69-7.77 (m, 1H), 7.41-7.48 (m, 2H), 7.35 (t, J=7.64 Hz, 2H), 7.22-7.30 (m, 1H), 6.00 (br t, J=7.34 Hz, 1H), 1.78 (d, J=6.72 Hz, 3H). MS (M+H)$^+$=434.0

To a solution of 4-(1-phenylethylamino)-6-(4, 4, 5, 5-tetramethyl-1, 3, 2-dioxaborolan-2-yl) quinoline-3-carbonitrile (100 mg, 250.44 µmol, 1 eq) in DMF (2.5 mL) and $H_2O$ (0.4 mL) was added $Cs_2CO_3$ (244.80 mg, 751.33 µmol, 3 eq), Pd(dppf)Cl$_2$ (18.33 mg, 25.04 µmol, 0.1 eq) and 3-(3-bromophenyl)-1H-1,2,4-triazole (56.11 mg, 250.44 µmol, 1 eq), the mixture was bubbled with $N_2$, the reaction was stirred at 100° C. for 3 h. LCMS showed starting material was consumed completely and the MS of desired product was detected. The reaction was filtered and filtrate was purified by prep-HPLC (column: Phenomenex Luna 80*30 mm*3 um; mobile phase: [water (HCl)-ACN]; B %: 10%-35%, 8 min). Compound 128, 4-(1-phenylethylamino)-6-[3-(4H-1, 2, 4-triazol-3-yl) phenyl] quinoline-3-carbonitrile (12.89 mg, 28.46 µmol, 11.36% yield, 100% purity, HCl) was obtained as a white solid. $^1$H NMR (400 MHz, DMSO-d6) δ ppm 9.82 (br s, 1H), 9.15-9.23 (m, 1H), 9.12 (s, 1H), 8.53 (br s, 2H), 8.43 (d, J=8.31 Hz, 1H), 8.05-8.19 (m, 2H), 7.97 (br d, J=7.82 Hz, 1H), 7.71 (t, J=7.76 Hz, 1H), 7.50 (d, J=7.58 Hz, 2H), 7.40 (t, J=7.58 Hz, 2H), 7.27-7.34 (m, 1H), 6.09 (br t, J=7.40 Hz, 1H), 1.84 (d, J=6.60 Hz, 3H). MS (M+H)$^+$=417.1

Example 43: Synthesis of 6-[5-(2-oxo-3H-1, 3, 4-oxadiazol-5-yl)-3-pyridyl]-4-(1-phenylethylamino) quinoline-3-carbonitrile (Compound 129)

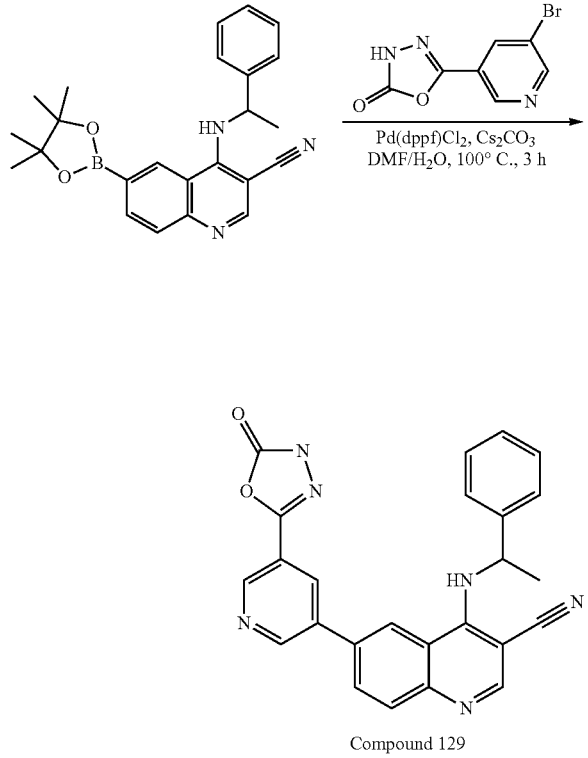

Compound 129

To a solution of 5-(5-bromo-3-pyridyl)-3H-1, 3, 4-oxadiazol-2-one (181.84 mg, 751.33 μmol, 1 eq) in DMF (1 mL) and H₂O (0.2 mL) was added Cs₂CO₃ (734.39 mg, 2.25 mmol, 3 eq), Pd(dppf)Cl₂ (54.98 mg, 75.13 μmol, 0.1 eq) and 4-(1-phenylethylamino)-6-(4,4,5,5-tetramethyl-1,3,2-dioxaborolan-2-yl)quinoline-3-carbonitrile (300 mg, 751.33 μmol, 1 eq), the mixture was bubbled with N₂, the reaction was stirred at 100° C. for 3 h. LCMS showed starting material was consumed completely and the MS of desired product was detected. The reaction was filtered, then the filtrate was concentrated in vacuum. The crude product was purified by prep-HPLC (column: Phenomenex luna C18 80*40 mm*3 um; mobile phase: [water (HCl)-ACN]; B %: 22%-45%, 7 min). Compound 129, 6-[5-(2-oxo-3H-1,3,4-oxadiazol-5-yl)-3-pyridyl]-4-(1-phenylethylamino)quinoline-3-carbonitrile (46.87 mg, 99.53 μmol, 13.25% yield, 100% purity, HCl) was obtained as a yellow solid. ¹H NMR (400 MHz, DMSO-d6) δ ppm 12.97 (s, 1H), 9.82 (br d, J=7.63 Hz, 1H), 9.35 (d, J=2.13 Hz, 1H), 9.27 (s, 1H), 9.13 (s, 1H), 9.08 (d, J=2.00 Hz, 1H), 8.62 (t, J=2.06 Hz, 1H), 8.53 (dd, J=8.76, 1.50 Hz, 1H) 8.16 (d, J=8.75 Hz, 1H) 7.51 (d, J=7.38 Hz, 2H) 7.41 (t, J=7.57 Hz, 2H) 7.29-7.35 (m, 1H) 6.09 (quin, J=7.07 Hz, 1H) 1.85 (d, J=6.63 Hz, 3H). MS (M+H)⁺=435.0

Example 44: Synthesis of 6-(3, 5-difluoro-4-hydroxy-phenyl)-4-(1-phenylethylamino) quinoline-3-carbonitrile (Compound 130)

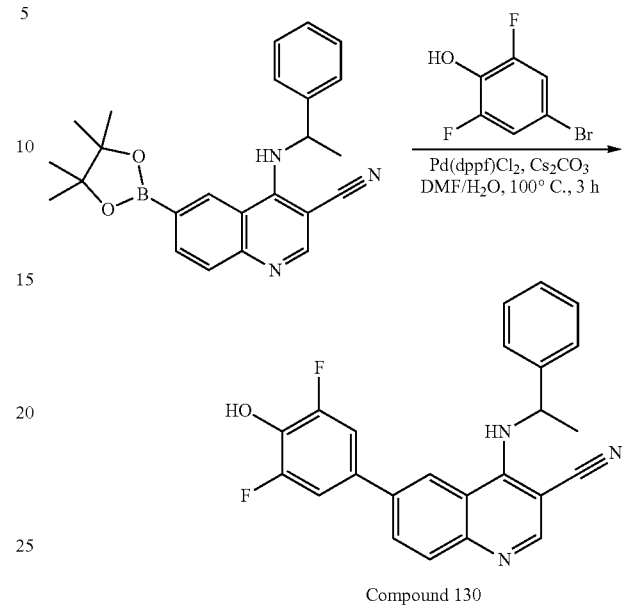

Compound 130

To a solution of 4-(1-phenylethylamino)-6-(4,4,5,5-tetramethyl-1,3,2-dioxaborolan-2-yl)quinoline-3-carbonitrile (80 mg, 200.35 μmol, 1 eq) in DMF (2 mL) and H₂O (0.4 mL) was added Cs₂CO₃ (195.84 mg, 601.06 μmol, 3 eq), Pd(dppf)Cl₂ (14.66 mg, 20.04 μmol, 0.1 eq) and 4-bromo-2,6-difluoro-phenol (41.87 mg, 200.35 μmol, 1 eq), the mixture was bubbled with N₂, the reaction was stirred at 100° C. for 3 h. LCMS showed starting material was consumed completely and the MS of desired product was detected. The reaction was filtered, then the filtrate was purified by prep-HPLC (column: Phenomenex Luna C18 150*30 mm*5 um; mobile phase: [water (0.04% TFA)-ACN]; B %: 1%-40%, 8 min). Compound 130, 6-(3, 5-difluoro-4-hydroxy-phenyl)-4-(1-phenylethylamino) quinoline-3-carbonitrile (11.49 mg, 22.29 μmol, 11.13% yield, 100% purity, TFA) was obtained as off-white solid. ¹H NMR (400 MHz, DMSO-d6) δ ppm 10.60 (br s, 1H), 8.86 (s, 2H) 8.75 (br s, 1H), 8.25 (br d, J=8.88 Hz, 1H), 7.88-7.95 (m, 1H) 7.66-7.74 (m, 2H), 7.43-7.48 (m, 2H), 7.38 (t, J=7.63 Hz, 2H), 7.25-7.32 (m, 1H), 5.97 (br t, J=6.82 Hz, 1H), 1.79 (d, J=6.63 Hz, 3H). MS (M+H)⁺=402.1

Example 45: Synthesis of 6-(3, 5-dichloro-4-hydroxy-phenyl)-4-(1-phenylethylamino) quinoline-3-carbonitrile (Compound 131)

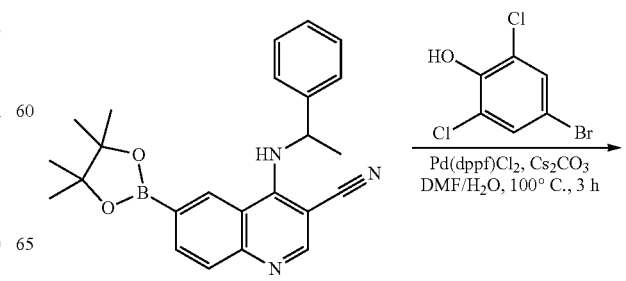

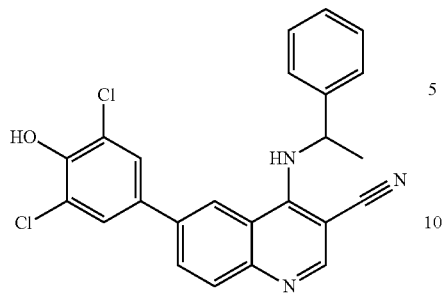

Compound 131

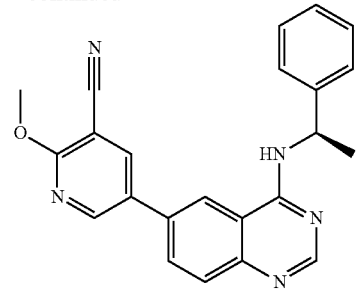

Compound 132

To a solution of 4-(1-phenylethylamino)-6-(4, 4, 5, 5-tetramethyl-1, 3, 2-dioxaborolan-2-yl) quinoline-3-carbonitrile (80 mg, 200.35 μmol, 1 eq) in DMF (2 mL) and H$_2$O (0.4 mL) was added Cs$_2$CO$_3$ (195.84 mg, 601.06 μmol, 3 eq), Pd(dppf)Cl$_2$ (14.66 mg, 20.04 μmol, 0.1 eq) and 4-bromo-2,6-dichloro-phenol (48.47 mg, 200.35 μmol, 1 eq), the mixture was bubbled with N$_2$, the reaction was stirred at 100° C. for 3 h. LCMS showed starting material was consumed completely and the MS of desired product was detected. The reaction was filtered, then the filtrate was concentrated in vacuum. The crude product was purified by prep-HPLC (column: Phenomenex Luna 80*30 mm*3 um; mobile phase: [water (0.04% HCl)-ACN]; B %: 20%-40%, 8 min). Compound 131, 6-(3, 5-dichloro-4-hydroxy-phenyl)-4-(1-phenylethylamino) quinoline-3-carbonitrile (15.23 mg, 32.35 μmol, 16.15% yield, 100% purity, HCl) was obtained as a pale yellow solid. $^1$H NMR (400 MHz, DMSO-d6) δ ppm 10.59 (br s, 1H), 9.53 (br s, 1H), 8.99 (br s, 2H), 8.34 (d, J=8.68 Hz, 1H), 8.02 (br d, J=8.80 Hz, 1H), 7.98 (s, 2H), 7.48 (d, J=7.58 Hz, 2H), 7.39 (t, J=7.58 Hz, 2H), 7.26-7.33 (m, 1H), 6.04 (br t, J=7.15 Hz, 1H), 1.83 (d, J=6.60 Hz, 3H). MS (M+H)=434.0

Example 46: Synthesis of 2-methoxy-5-[4-[[(1R)-1-phenylethyl]amino]quinazolin-6-yl]pyridine-3-carbonitrile (Compound 132)

To a stirred solution of 5-bromo-2-methoxy-pyridine-3-carbonitrile (45.41 mg, 213.18 μmol, 1 eq) in H$_2$O (0.2 mL) and DMF (1 mL) was added N-[(1R)-1-phenylethyl]-6-(4,4,5,5-tetramethyl-1,3,2-dioxaborolan-2-yl)quinazolin-4-amine (80 mg, 213.18 μmol, 1 eq), Cs$_2$CO$_3$ (208.37 mg, 639.54 μmol, 3 eq) and Pd(dppf)Cl$_2$ (15.60 mg, 21.32 μmol, 0.1 eq), the reaction was stirred at 100° C. for 3 h under N$_2$. LCMS showed starting material was consumed completely and the MS of desired product was detected. The reaction was filtered, then the filtrate was concentrated in vacuum. The crude product was purified by prep-HPLC (column: Phenomenex Luna 80*30 mm*3 um; mobile phase: [water (0.04% HCl)-ACN]; B %: 10%-35%, 8 min). Compound 132, 2-methoxy-5-[4-[[(1R)-1-phenylethyl] amino] quinazolin-6-yl] pyridine-3-carbonitrile (3.4 mg, 8.91 μmol, 4.18% yield, 100% purity) was obtained as a pale solid. $^1$H NMR (400 MHz, DMSO-d$_6$) δ ppm 9.75-9.94 (m, 1H), 8.99 (d, J=2.57 Hz, 1H), 8.93 (d, J=0.98 Hz, 1H), 8.75-8.83 (m, 2H), 8.34-8.43 (m, 1H), 7.85 (d, J=8.80 Hz, 1H), 7.49 (d, J=7.58 Hz, 2H), 7.37 (t, J=7.52 Hz, 2H), 7.23-7.33 (m, 1H), 5.72-5.87 (m, 1H), 4.08 (s, 3H), 1.69 (d, J=6.97 Hz, 3H). MS (M+H)$^+$=382.0

Example 47: Synthesis of methyl 5-[4-[[(1R)-1-phenylethyl]amino]quinazolin-6-yl]pyridine-3-carboxylate (Compound 135)

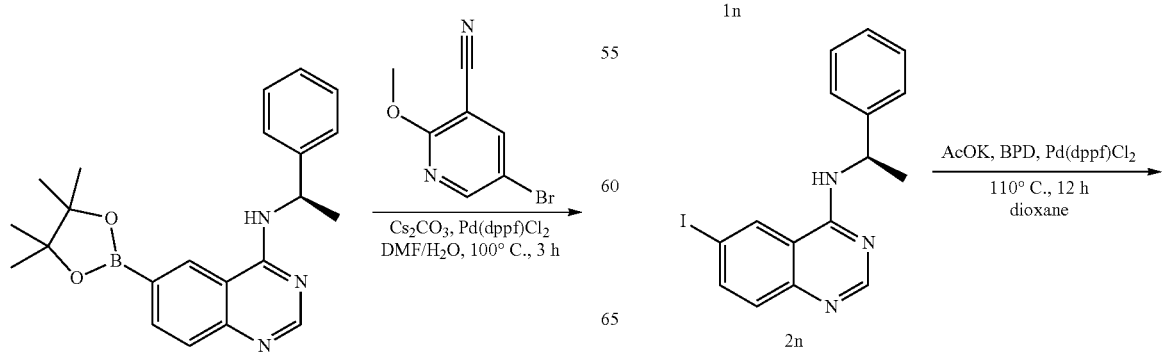

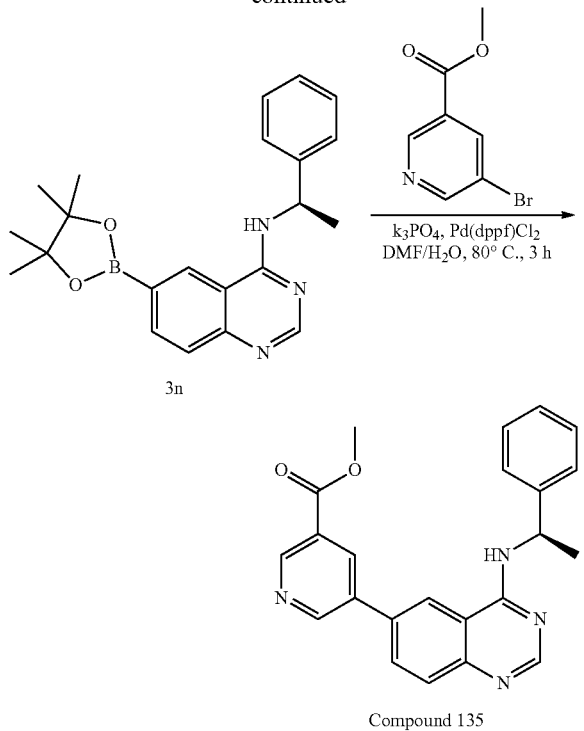

Compound 135

Step 1: Synthesis of 6-bromo-N-[(1R)-1-phenyl-ethyl]quinazolin-4-amine (2n)

To a stirred solution of 6-bromo-4-chloro-quinazoline, 1n, (4 g, 16.43 mmol, 1 eq) in i-PrOH (40 mL) was added (1R)-1-phenylethanamine (1.99 g, 16.43 mmol, 2.12 mL, 1 eq) and TEA (2.66 g, 26.28 mmol, 3.66 mL, 1.6 eq), the reaction was stirred at 80° C. for 3 h under $N_2$. LCMS showed starting material was consumed completely and the MS of desired product was detected. The reaction was cooled to ambient temperature, quenched with water (50 mL) and extracted with ethyl acetate (50 mL). The organic layer was washed with water, brine, dried over anhydrous sodium sulfate, filtered and concentrated in vacuum. Compound 2n, 6-bromo-N-[(1R)-1-phenylethyl] quinazolin-4-amine (5.6 g, crude) was obtained as yellow solid.

Step 2: Synthesis of N-[(1R)-1-phenylethyl]-6-(4,4,5,5-tetramethyl-1,3,2-dioxaborolan-2-yl)quinazolin-4-amine (3n)

To a stirred solution of 6-bromo-N-[(1R)-1-phenylethyl] quinazolin-4-amine, 2n, (5.6 g, 17.06 mmol, 1 eq) in dioxane (60 mL) was added BPD (5.20 g, 20.47 mmol, 1.2 eq), Pd(dppf)$Cl_2$·$CH_2Cl_2$ (1.39 g, 1.71 mmol, 0.1 eq) and AcOK (5.02 g, 51.19 mmol, 3 eq), the reaction was stirred at 110° C. for 12 h under $N_2$. LCMS showed starting material was consumed completely and the MS of desired product was detected. The reaction was cooled to ambient temperature, quenched with water (50 mL) and extracted with ethyl acetate (50 mL). The organic layer was washed with water, brine, dried over anhydrous sodium sulfate, filtered and concentrated in vacuum. The residue was purified by flash column (ISCO 40 g silica, 40-60% ethyl acetate in petroleum ether, gradient over 20 min). Based on TLC (PE:EtOAc=2:1, $R_f$=0.30). Compound 3n, N-[(1R)-1-phe- nylethyl]-6-(4, 4, 5, 5-tetramethyl-1,3,2-dioxaborolan-2-yl) quinazolin-4-amine (1.8 g, 4.80 mmol, 28.11% yield) was obtained as yellow oil.

Step 3: Synthesis of methyl 5-[4-[[(1R)-1-phenyl-ethyl]amino]quinazolin-6-yl]pyridine-3-carboxylate (Compound 135)

To a stirred solution of methyl 5-bromopyridine-3-carboxylate, 3n, (41.45 mg, 191.86 μmol, 1.2 eq) in DMF (1.5 mL) and $H_2O$ (0.3 mL) was added N-[(1R)-1-phenylethyl]-6-(4,4,5,5-tetramethyl-1,3,2-dioxaborolan-2-yl)quinazolin-4-amine (60 mg, 159.88 μmol, 1 eq), $K_3PO_4$ (101.81 mg, 479.65 μmol, 3 eq) and Pd(dppf)$Cl_2$ (11.70 mg, 15.99 μmol, 0.1 eq), the reaction was stirred at 80° C. for 3 h under $N_2$. LCMS showed starting material was consumed completely and the MS of desired product was detected. The reaction was filtered, and filtrate was used for purified directly. The crude product was purified by prep-HPLC (column: Phenomenex Luna 80*30 mm*3 um; mobile phase: [water (TFA)-ACN]; B %: 20%-45%, 8 min). Compound 135, methyl 5-[4-[[(1R)-1-phenylethyl] amino] quinazolin-6-yl] pyridine-3-carboxylate (9.16 mg, 23.19 mol, 14.50% yield, 97.326% purity) was obtained as a brown solid. $^1$H NMR (400 MHz, DMSO-$d_6$) δ ppm 10.22-10.35 (m, 1H), 9.34 (d, J=2.20 Hz, 1H), 9.19 (d, J=1.71 Hz, 1H), 9.08 (s, 1H), 8.92 (s, 1H), 8.67-8.72 (m, 1H), 8.51 (d, J=9.05 Hz, 1H), 7.91 (d, J=8.80 Hz, 1H), 7.50 (d, J=7.34 Hz, 2H), 7.38 (t, J=7.52 Hz, 2H), 7.25-7.34 (m, 1H), 5.75-5.96 (m, 1H), 3.96 (s, 3H), 1.72 (d, J=6.97 Hz, 3H). MS (M+H)$^+$=385.0

Example 48: Synthesis of 6-[4-[[(1R)-1-phenyl-ethyl]amino]quinazolin-6-yl]-3H-isobenzofuran-1-one (Compound 136)

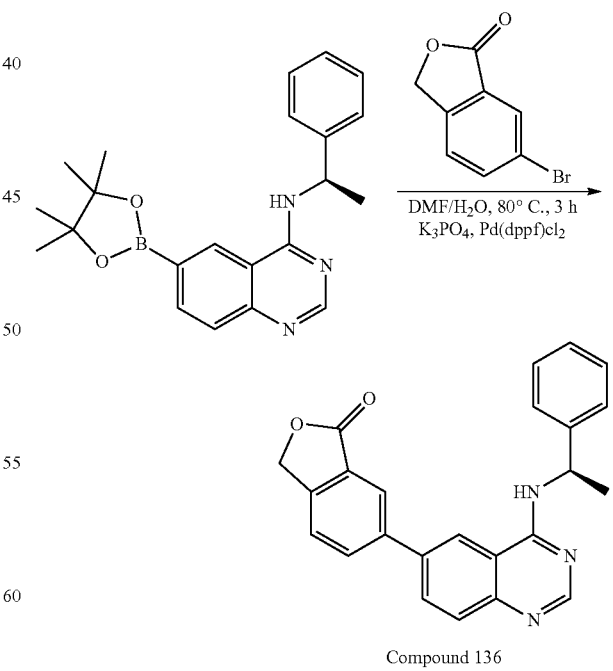

Compound 136

To a stirred solution of 6-bromo-3H-isobenzofuran-1-one (40.87 mg, 191.86 μmol, 1.2 eq) in DMF (1.5 mL) and $H_2O$ (0.3 mL) was added N-[(1R)-1-phenylethyl]-6-(4,4,5,5-tetramethyl-1,3,2-dioxaborolan-2-yl)quinazolin-4-amine (60 mg, 159.88 μmol, 1 eq), K₃PO₄ (101.81 mg, 479.65 μmol, 3 eq) and Pd(dppf)Cl₂ (11.70 mg, 15.99 μmol, 0.1 eq), the reaction was stirred at 80° C. for 3 h under N₂. LCMS showed starting material was consumed completely and the MS of desired product was detected. The reaction was filtered, the filtrate was concentrated, and the crude product was purified by prep-HPLC (column: Phenomenex Luna 80*30 mm*3 um; mobile phase: [water (TFA)-ACN]; B %: 20%-50%, 8 min). Compound 136, 6-[4-[[(1R)-1-phenyl-ethyl]amino]quinazolin-6-yl]-3H-isobenzofuran-1-one (23.53 mg, 60.08 μmol, 37.57% yield, 97.385% purity) was obtained as a pale yellow solid. $^1$H NMR (400 MHz, DMSO-d₆) δ ppm 10.33 (br d, J=7.70 Hz, 1H), 9.07 (d, J=1.47 Hz, 1H), 8.91 (s, 1H), 8.49 (dd, J=8.80, 1.59 Hz, 1H), 8.37 (s, 1H), 8.28 (dd, J=8.01, 1.53 Hz, 1H), 7.83-7.96 (m, 2H), 7.50 (d, J=7.46 Hz, 2H), 7.39 (t, J=7.52 Hz, 2H), 7.25-7.33 (m, 1H), 5.77-5.94 (m, 1H), 5.53 (s, 2H), 1.72 (d, J=6.97 Hz, 3H). MS (M+H)⁺=382.0

Example 49: Synthesis of N-[(1R)-1-phenylethyl]-6-[3-(4H-1,2,4-triazol-3-yl)phenyl]quinazolin-4-amine (Compound 137)

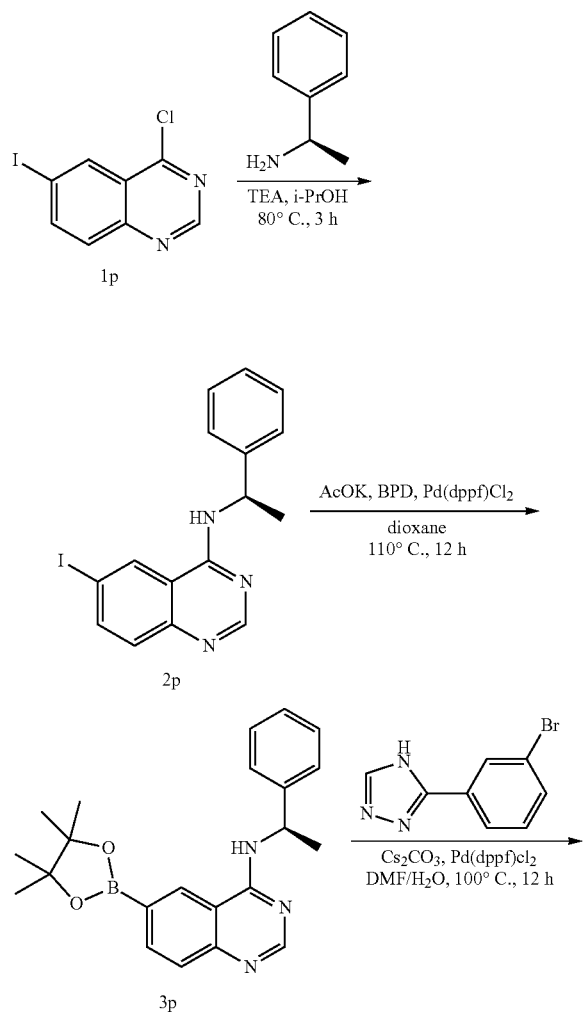

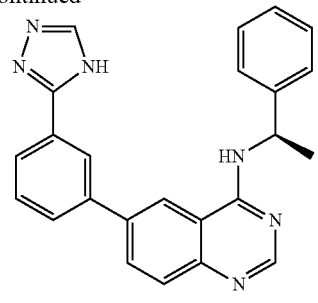

Compound 137

Step 1: Synthesis of 6-iodo-N-[(1R)-1-phenylethyl]quinazolin-4-amine (2p)

To a stirred solution of 4-chloro-6-iodo-quinazoline, 1p, (3 g, 10.33 mmol, 1 eq) in i-PrOH (30 mL) was added (1R)-1-phenylethanamine (1.25 g, 10.33 mmol, 1.33 mL, 1 eq) and TEA (1.67 g, 16.52 mmol, 2.30 mL, 1.6 eq), the reaction was stirred at 80° C. for 3 h under N₂. LCMS showed starting material was consumed completely and the MS of desired product was detected. The reaction was cooled to ambient temperature, quenched with water (50 mL) and extracted with ethyl acetate (50 mL). The organic layer was washed with water, brine, dried over anhydrous sodium sulfate, filtered and concentrated in vacuum. Compound 2p, 6-iodo-N-[(1R)-1-phenylethyl]quinazolin-4-amine (3.2 g, 8.53 mmol, 82.58% yield) was obtained as yellow oil Step 2: Synthesis of N-[(1R)-1-phenylethyl]-6-(4,4,5,5-tetramethyl-1,3,2-dioxaborolan-2-yl)quinazolin-4-amine (3p)

To a stirred solution of 6-iodo-N-[(1R)-1-phenylethyl]quinazolin-4-amine, 2p, (3.20 g, 8.53 mmol, 1 eq) in dioxane (30 mL) was added BPD (2.17 g, 8.53 mmol, 1 eq) Pd(dppf)Cl₂ (624.05 mg, 853.00 μmol, 0.1 eq) and AcOK (2.51 g, 25.59 mmol, 3 eq), the reaction was stirred at 110° C. for 12 h under Ar. LCMS showed starting material was consumed completely and the MS of desired product was detected. The reaction was cooled to ambient temperature, quenched with water (50 mL) and extracted with ethyl acetate (50 mL). The organic layer was washed with water, brine, dried over anhydrous sodium sulfate, filtered and concentrated in vacuum. The residue was purified by flash column (ISCO 80 g silica, 40-60% ethyl acetate in petroleum ether, gradient over 20 min). Based on TLC (PE:EtOAc=1:1, R$_f$=0.30). Compound 3p, N-[(1R)-1-phenyl-ethyl]-6-(4, 4, 5,5-tetramethyl-1,3,2-dioxaborolan-2-yl)quinazolin-4-amine (2.4 g, 6.40 mmol, 74.98% yield) was obtained as a yellow oil.

Step 3: Synthesis of N-[(1R)-1-phenylethyl]-6-[3-(4H-1,2,4-triazol-3-yl)phenyl]quinazolin-4-amine (Compound 137)

To a stirred solution of 3-(3-bromophenyl)-1H-1,2,4-triazole (35.82 mg, 159.88 mol, 1 eq) in DMF (1 mL) and H₂O (0.2 mL) was added N-[(1R)-1-phenylethyl]-6-(4,4,5,5-tetramethyl-1,3,2-dioxaborolan-2-yl)quinazolin-4-amine, ³p, (60 mg, 159.88 μmol, 1 eq), Cs₂CO₃ (156.28 mg, 479.65 μmol, 3 eq) and Pd(dppf)Cl₂ (11.70 mg, 15.99 μmol, 0.1 eq), the reaction was stirred at 100° C. for 12 h under $N_2$. LCMS showed starting material was consumed completely and the MS of desired product was detected. The reaction was filtered, then the filtrate was concentrated in vacuum. The crude product was purified by prep-HPLC (column: Phenomenex Luna 80*30 mm*3 um; mobile phase: [water (0.1% TFA)-ACN]; B %: 10%-30%, 8 min). Compound 137, N-[(1R)-1-phenylethyl]-6-[3-(4H-1, 2, 4-triazol-3-yl) phenyl] quinazolin-4-amine (7.9 mg, 20.13 mol, 12.59% yield, 100% purity) was obtained as a yellow solid. $^1$H NMR (400 MHz, DMSO-$d_6$) δ ppm 10.09-10.48 (m, 1H), 9.02 (s, 1H), 8.89 (s, 1H), 8.45 (s, 1H), 8.41 (d, J=8.92 Hz, 1H), 8.13 (br d, J=8.19 Hz, 1H), 7.90 (d, J=8.68 Hz, 2H), 7.65-7.78 (m, 1H), 7.50 (d, J=7.34 Hz, 2H), 7.38 (t, J=7.46 Hz, 2H), 7.26-7.32 (m, 1H), 5.71-5.98 (m, 1H), 1.72 (d, J=7.09 Hz, 3H). MS (M+H)$^+$=393.1

Example 50: Synthesis of 6-imidazo[1,2-a]pyrazin-3-yl-N-(1-phenylethyl)quinazolin-4-amine (Compound 139)

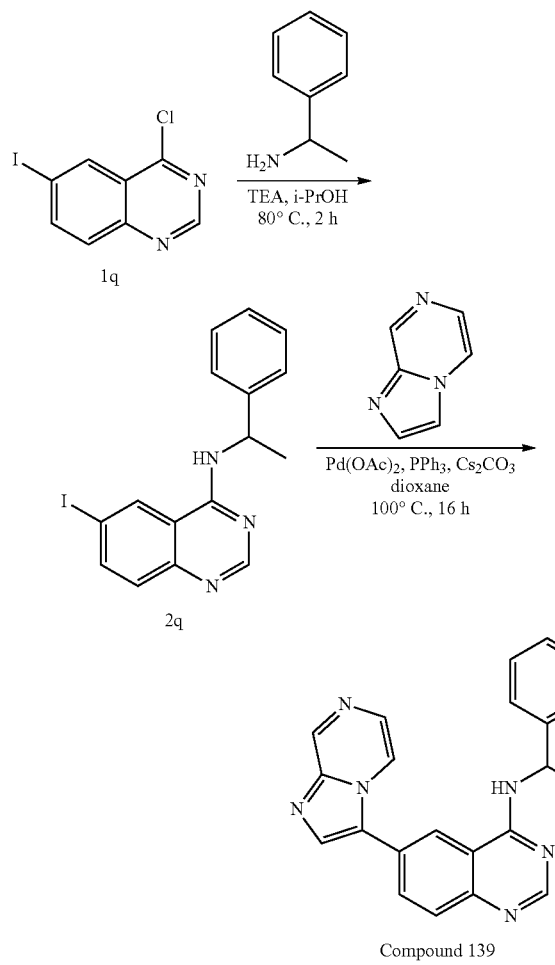

Step 1: Synthesis of 6-iodo-N-(1-phenylethyl)quinazolin-4-amine (2q)

To a solution of 4-chloro-6-iodo-quinazoline, 1 q, (500 mg, 1.72 mmol, 1 eq) in i-PrOH (5 mL) was added 1-phenylethanamine (208.58 mg, 1.72 mmol, 219.56 µL, 1 eq) and TEA (522.51 mg, 5.16 mmol, 718.72 µL, 3 eq), the mixture was stirred at 80° C. for 2 h. LCMS showed the starting material was consumed completely, and desired MS was detected. The reaction mixture was concentrated in vacuum to give a crude product. Compound 2q, 6-iodo-N-(1-phenylethyl)quinazolin-4-amine (800 mg, crude) was obtained as a brown solid. MS (M+H)$^+$=376.1.

Synthesis of 6-imidazo[1,2-a]pyrazin-3-yl-N-(1-phenylethyl)quinazolin-4-amine (Compound 139)

To a stirred solution of 6-iodo-N-(1-phenylethyl)quinazolin-4-amine, 2q, (200 mg, 533.04 µmol, 1 eq) in dioxane (2 mL) was added imidazo[1,2-a]pyrazine (127.00 mg, 1.07 mmol, 2 eq), Pd(OAc)$_2$ (5.98 mg, 26.65 µmol, 0.05 eq), PPh$_3$ (13.98 mg, 53.30 µmol, 0.1 eq), Cs$_2$CO$_3$ (347.35 mg, 1.07 mmol, 2 eq), the mixture was bubbled with $N_2$ for 1 minute, and the mixture was stirred at 100° C. for 16 h. LCMS showed the starting material was consumed completely, and desired MS was detected. The reaction mixture filtered to give a filtrate, and the filtrate was purified by prep-HPLC (column: Phenomenex luna C18 80*40 mm*3 um; mobile phase: [water (0.04% HCl)-ACN]; B %: 18%-42%, 7 min). Compound 139, 6-imidazo[1,2-a]pyrazin-3-yl-N-(1-phenylethyl)quinazolin-4-amine (60.6 mg, 150.42 µmol, 28.22% yield, 100% purity, HCl) was obtained as a yellow solid. $^1$H NMR (400 MHz, DMSO-d6) δ=10.77 (br d, J=7.6 Hz, 1H), 9.28 (dd, J=1.4, 8.5 Hz, 2H), 8.96 (s, 1H), 8.83 (dd, J=1.4, 4.8 Hz, 1H), 8.44 (dd, J=1.7, 8.7 Hz, 1H), 8.37 (s, 1H), 8.13-8.04 (m, 2H), 7.54 (d, J=7.4 Hz, 2H), 7.37 (t, J=7.4 Hz, 2H), 7.32-7.25 (m, 1H), 5.86 (quin, J=7.1 Hz, 1H), 1.73 (d, J=7.0 Hz, 3H). MS (M+H)$^+$=367.1.

Example 51: Synthesis of 2-[(6-imidazo[1,2-a]pyrazin-3-ylquinazolin-4-yl)amino]-2-phenyl-ethanol (Compound 140)

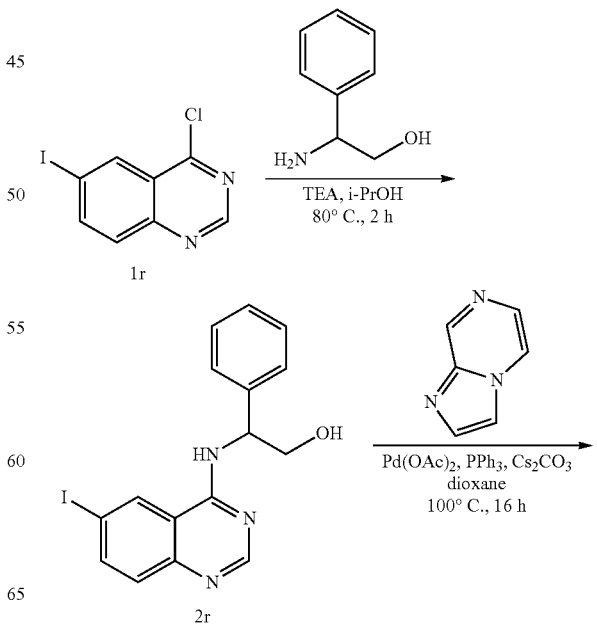

-continued

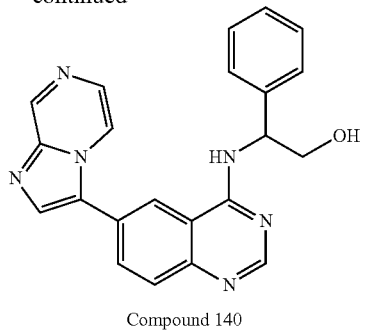

Compound 140

Step 1: Synthesis of 2-[(6-iodoquinazolin-4-yl)amino]-2-phenyl-ethanol (2r)

To a solution of 4-chloro-6-iodo-quinazoline, 1r, (200 mg, 688.50 μmol, 1 eq) in i-PrOH (2 mL) was added TEA (209.00 mg, 2.07 mmol, 287.49 μL, 3 eq) and 2-amino-2-phenyl-ethanol (94.45 mg, 688.50 μmol, 1 eq), the mixture was stirred at 80° C. for 2 h. LCMS showed the starting material was consumed completely, and desired MS was detected. The reaction mixture was concentrated in vacuum to give a crude product. Compound 2r, 2-[(6-iodoquinazolin-4-yl) amino]-2-phenyl-ethanol (300 mg, crude) was obtained as a yellow solid. MS $(M+H)^+=392.0$.

Step 2: Synthesis of 2-[(6-imidazo[1,2-a]pyrazin-3-yl)quinazolin-4-yl)amino]-2-phenyl-ethanol (Compound 140)

To a solution of 2-[(6-iodoquinazolin-4-yl)amino]-2-phenyl-ethanol, 2r, (200 mg, 511.24 μmol, 1 eq) in dioxane (2 mL) was added imidazo[1,2-a]pyrazine (121.80 mg, 1.02 mmol, 2 eq), PPh$_3$ (13.41 mg, 51.12 μmol, 0.1 eq), Cs$_2$CO$_3$ (333.14 mg, 1.02 mmol, 2 eq) and Pd(OAc)$_2$ (5.74 mg, 25.56 μmol, 0.05 eq). The mixture was purged with N$_2$ for 1 minute, and then the mixture was stirred at 100° C. for 16 h under N$_2$ atmosphere. LCMS showed the starting material was consumed completely, and desired MS was detected. The reaction mixture filtered to give a filtrate, and the filtrate was purified by prep-HPLC (column: Phenomenex luna C18 250*50 mm*10 um; mobile phase: [water (0.04% HCl)-ACN]; B %: 10%-40%, 10 min). Compound 140, 2-[(6-imidazo[1,2-a]pyrazin-3-ylquinazolin-4-yl)amino]-2-phenyl-ethanol (36.29 mg, 82.84 μmol, 16.20% yield, 95.62% purity, HCl) was obtained as a yellow solid. $^1$H NMR (400 MHz, DMSO-d6) δ=10.96 (br d, J=7.5 Hz, 1H), 9.58-9.47 (m, 1H), 9.36 (d, J=1.3 Hz, 1H), 9.00-8.91 (m, 2H), 8.51 (s, 1H), 8.46 (dd, J=1.7, 8.7 Hz, 1H), 8.19-8.07 (m, 2H), 7.55 (d, J=7.3 Hz, 2H), 7.40-7.32 (m, 2H), 7.31-7.25 (m, 1H), 5.78-5.67 (m, 1H), 4.08 (dd, J=8.8, 11.4 Hz, 1H), 3.86 (dd, J=4.6, 11.4 Hz, 1H). MS $(M+H)^{+*}=383.1$.

Example 52: Synthesis of N-[5-[4-(benzylamino)quinazolin-6-yl]-2-chloro-3-pyridyl]methanesulfonamide (Comparative Compound 1)

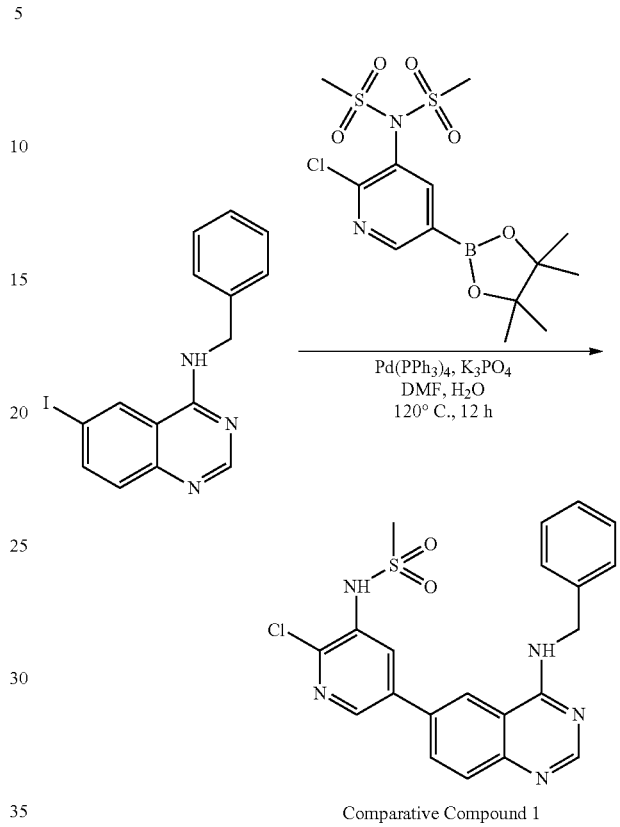

Comparative Compound 1

To a stirred solution of N-benzyl-6-iodo-quinazolin-4-amine (1.8 g, 4.98 mmol, 1 eq) in DMF (25 mL) and H$_2$O (5 mL) was added N-[2-chloro-5-(4,4,5,5-tetramethyl-1,3,2-dioxaborolan-2-yl)-3-pyridyl]-N-methylsulfonyl-methanesulfonamide (2.05 g, 4.98 mmol, 1 eq), K$_3$PO$_4$ (3.17 g, 14.95 mmol, 3 eq), Pd(PPh$_3$)$_4$ (575.89 mg, 498.37 μmol, 0.1 eq), the mixture was bubbled with N$_2$ for 1 minute, and the mixture was stirred at 100° C. for 4 h. LCMS showed the starting material was consumed completely and desired MS was detected. The reaction mixture was filtered and filtrate was concentrated and purified by prep-HPLC (Phenomenex luna c18 250 mm*100 mm*15 um column; 15-45% acetonitrile in a 0.1% trifluoroacetic acid solution in water, 42 min gradient). Comparative Compound 1, N-[5-[4-(benzylamino)quinazolin-6-yl]-2-chloro-3-pyridyl]methanesulfonamide (738.80 mg, 1.30 mmol, 26.09% yield, 97.46% purity, TFA) was obtained as a white solid. $^1$H NMR (400 MHz, DMSO-d6) δ=10.63-10.61 (m, 1H), 10.05 (s, 1H), 8.92 (s, 2H), 8.77 (s, 1H), 8.43-8.40 (m, 1H), 8.26 (s, 1H), 7.98-7.94 (m, 1H), 7.45-7.43 (m, 2H), 7.39-7.35 (m, 2H), 7.32-7.30 (m, 1H), 5.01 (d, J=5.2 Hz, 2H), 3.19 (s, 3H). MS $(M+H)^+=440.1$.

Assay Examples

In the following assay examples, the activity of the compounds of the disclosure can be compared to the following three compounds:

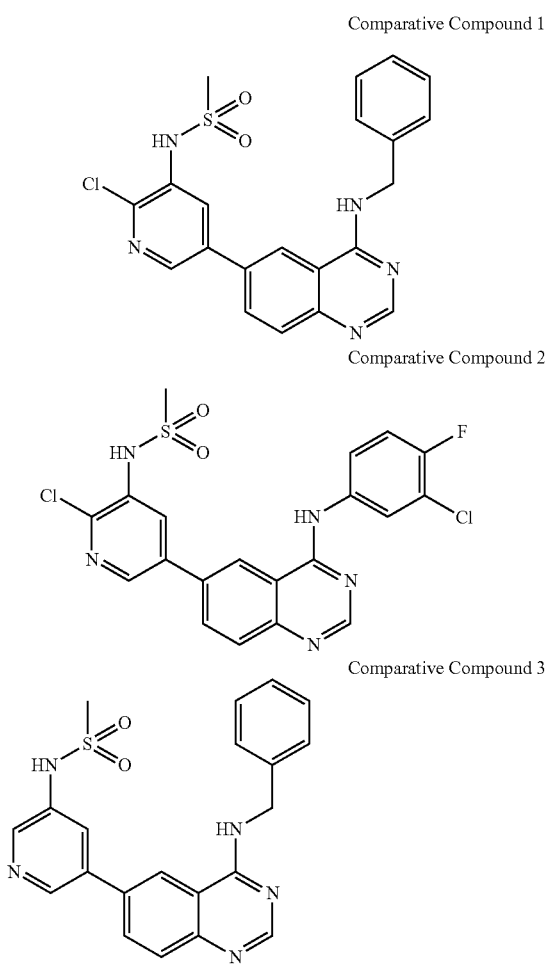

Comparative Compound 1

Comparative Compound 2

Comparative Compound 3

Comparative compound 2 is a dual enzyme inhibitor against EGFR and PI3K. The description and synthesis of Comparative Compound 2 and Comparative Compound 3 can be found in International Application No. PCT/US2015/065827 filed on Dec. 15, 2015 and is referenced as Mol 211 and Mol 167 respectively, the disclosure of which is incorporated herein by reference in its entirety.

Example 53: Affinity of Selected Compounds of the Disclosure for PI3Kα, EGFR, and DNA-PK Enzymes The Z'-LYTE® biochemical assay employs a fluorescence-based, coupled-enzyme format and is based on the differential sensitivity of phosphorylated and non-phosphorylated peptides to proteolytic cleavage (FIG. 6). The peptide substrate is labeled with two fluorophores one at each end—that make up a FRET pair. In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress.

A significant benefit of this ratiometric method for quantitating reaction progress is the elimination of well-to-well variations in FRET-peptide concentration and signal intensities. As a result, the assay yields very high Z'-factor values (>0.7) at a low percent phosphorylation.

Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

Enzyme: The ADAPTA universal kinase assay is a homogenous, fluorescent based immunoassay for the detection of ADP. In contrast to ATP depletion assays, the ADAPTA assay is extremely sensitive to ADP formation such that a majority of the signal change occurs in the first 10-20% conversion of ATP to ADP. This makes the ADAPTA universal kinase assay ideally suited for use with low activity kinases.

The principle of the ADAPTA universal kinase assay is outlined below. The assay itself can be divided into two phases: a kinase reaction phase, and an ADP detection phase. In the kinase reaction phase, all components required for the kinase reaction are added to the well, and the reaction is allowed to incubate for 60 minutes. After the reaction, a detection solution consisting of a europium labeled anti-ADP antibody, an Alexa Fluor® 647 labeled ADP tracer, and EDTA (to stop the kinase reaction) is added to the assay well. ADP formed by the kinase reaction (in the absence of an inhibitor) will displace the Alexa Fluor® 647 labeled ADP tracer from the antibody, resulting in a decrease in the TR-FRET signal. In the presence of an inhibitor, the amount of ADP formed by the kinase reaction is reduced, and the resulting intact antibody-tracer interaction results in a high TR-FRET signal.

Z'-LYTE® Assay Conditions:

Test Compounds: The Test Compounds are screened in 1% DMSO (final) in the well. For 10 point titrations, 3-fold serial dilutions are conducted from the starting concentration.

Peptide/Kinase Mixtures: All Peptide/Kinase Mixtures are diluted to a 2× working concentration in the appropriate Kinase Buffer.

ATP Solution: All ATP Solutions are diluted to a 4× working concentration in Kinase Buffer (50 mM HEPES pH 7.5, 0.01% BRIJ-35, 10 mM $MgCl_2$, 1 mM EGTA). ATP Km apparent is previously determined using a Z'-LYTE® assay.

Development Reagent Solution: The Development Reagent is diluted in Development Buffer.

10× Novel PKC Lipid Mix: 2 mg/mL Phosphatidyl Serine, 0.2 mg/mL DAG in 20 mM HEPES, pH 7.4, 0.3% CHAPS. For 5 mL 10× Novel PKC Lipid Mix: 1. Add 10 mgs Phosphatidyl Serine (Avanti Polar Lipids Part #8400032C or 840039C) and 1 mg DAG (Avanti Polar Lipids Part #800811C) to a glass tube. 2. Remove the chloroform from lipid mixture by evaporating to a clear, thin film under a stream of nitrogen. Continuous rotation of the tube, at an angle to ensure maximum surface area of the lipid solution, will promote the thinnest film. 3. Add 5 mLs resuspension buffer, 20 mM HEPES, 0.3% CHAPS, pH 7.4, to the dried lipid mix 4. Heat gently to 50-60° C. for 1-2 minutes and vortex in short intervals until the lipids are dissolved to a clear or slightly hazy solution. The lipids are typically in solution after 2-3 heat/vortex cycles. 5. Cool to room temperature, aliquot into single use volumes and store at −20° C.

Assay Protocol: Bar-coded Corning, low volume NBS, black 384-well plate (Corning Cat. #4514) 1. 2.5 μL—4× Test Compound or 100 nL 100× plus 2.4 μL kinase buffer. 2. 5 μL—2× Peptide/Kinase Mixture. 3. 2.5 μL—4× ATP Solution. 4. 30-second plate shake. 5. 60-minute Kinase Reaction incubation at room temperature. 6. 5 μL—Development Reagent Solution. 7. 30-second plate shake. 8. 60-minute Development Reaction incubation at room temperature. 9. Read on fluorescence plate reader and analyze the data.

In a typical experiment, each data point uses 100 nL—100× test compound in 100% DMSO. Commonly, 100 nL of a 10 μM solution of test compound is used for each experiment, which is equivalent to 1 picomole of test compound. Accordingly, a 10 μM single-point assay uses 100 picomoles of test compound, and a 10-point titration uses about 200 picomoles of test compound—100 picomoles for the initial test and another 100 picomoles for the serial dilution.

ADP formation is determined by calculating the emission ratio from the assay well. The emission ratio is calculated by dividing the intensity of the tracer (acceptor) emission by the intensity of the Eu (donor) emission at 615 nm as shown in the equation below.

Since the ADAPTA technology measures ADP formation (i.e. conversion of ATP to ADP) it can be used to measure any type of ATP hydrolysis, including intrinsic ATPase activity of kinases. In this case, the substrate is water, not a lipid or peptide. The SelectScreen® service screens CHUK in this way, so a substrate is not included in the kinase reaction. A reference for using intrinsic ATPase activity to screen for kinase inhibitors is provided below.

Adapta® Assay Conditions

Test Compounds: The Test Compounds are screened in 1% DMSO (final) in the well. For 10 point titrations, 3-fold serial dilutions are conducted from the starting concentration.

Substrate/Kinase Mixtures: All Substrate/Kinase Mixtures are diluted to a 2× working concentration in the appropriate Kinase Buffer (see section Kinase Specific Assay Conditions for a complete description).

ATP Solution: All ATP Solutions are diluted to a 4× working concentration in water. ATP Km apparent is previously determined using a radiometric assay except when no substrate is available in which case an Adapta® assay is conducted.

Detection Mix: The Detection Mix is prepared in TR-FRET Dilution Buffer. The Detection mix consists of EDTA (30 mM), Eu-anti-ADP antibody (6 nM) and ADP tracer. The detection mix contains the EC60 concentration of tracer for 5-150 μM ATP.

Assay Protocol: Bar-coded Corning, low volume, white 384-well plate (Corning Cat. #4512) 1. 2.5 μL—4× Test Compound in 30 mM HEPES or 100 nL 100× in 100% DMSO plus 2.4 μL 30 mM HEPES. 2. 2.5 μL—4× ATP Solution. 3. 5 μL—2× Substrate/Kinase Mixture. 4. 30-second plate shake. 5. 1-minute centrifuge at 1000×g. 6. 60-minute Kinase Reaction incubation at room temperature. 7. 5 μL—Detection Mix. 8. 30-second plate shake. 9. 1-minute centrifuge at 1000×g. 10. 60-minute Detection Mix equilibration at room temperature. 11. Read on fluorescence plate reader and analyze the data.

In a typical experiment, each data point uses 100 nL—100× test compound in 100 DMSO. Commonly, 100 nL of a 10 μM solution of test compound is used for each experiment, which is equivalent to 1 picomole of test compound. Accordingly, a 10+M single-point assay uses 100 picomoles of test compound, and a 10-point titration uses about 200 picomoles of test compound—100 picomoles for the initial test and another 100 picomoles for the serial dilution.

The affinity for PI3Ka, EGFR, and DNA-PK enzymes of selected compounds of the disclosure vs. Comparative Compound 1 and Comparative Compound 2 is presented as the 50% inhibitory concentration ($IC_{50}$) in Table 3 below. The $IC_{50}$ data in Table 3 is presented as "++++" (value is 2 nM or less), "+++" (value is greater than 2 nM and less than or equal to 20 nM), "++" (value is greater than 20 nM and less than or equal to 200 nM) and "+" (value is greater than 200 nM). NT is "not tested."

TABLE 3

$IC_{50}$ values for selected compounds of the disclosure.

| Compound | PI3Ka $IC_{50}$ (nM) | EGFR $IC_{50}$ (nM) | DNA-PK $IC_{50}$ (nM) |
| --- | --- | --- | --- |
| Comparative Compound 1 | ++++ | ++ | ++++ |
| Comparative Compound 2 | ++++ | +++ | ++++ |
| Comparative Compound 3 | ++ | ++ | NT |
| Compound 2R | +++ | +++ | +++ |
| Compound 2S | ++++ | + | ++++ |
| Compound 22 | ++ | +++ | + |
| Compound 48R | +++ | +++ | NT |
| Compound 48S | ++++ | + | ++++ |
| Compound 53 | + | +++ | ++ |
| Compound 53R | + | +++ | ++ |
| Compound 54 | + | +++ | +++ |
| Compound 97 S | ++++ | + | ++++ |
| Compound 111R | +++ | ++ | NT |
| Compound 111S | ++++ | + | ++++ |
| Compound 121 | + | +++ | + |
| Compound 129 | ++ | +++ | +++ |

The affinity for PI3Ka, EGFR, and DNA-PK enzymes of selected compounds of the disclosure vs. Comparative Compound 1 and Comparative Compound 2 is presented as the percent inhibition at 100 nM, in Table 4 below. The 00 inhibition at 100 nM data in Table 4 is presented as "*" (value is 100 or less), "" (value is greater than 10% and less than or equal to 80%), "*" (value is greater than 80% and less than or equal to 90%) and "****" (value is greater than 90%).

TABLE 4

Percent inhibition values for selected compounds of the disclosure.

| Compound | PI3Ka % Inh. @ 100 nM | EGFR % Inh. @ 100 nM | DNA-PK % Inh. @ 100 nM |
| --- | --- | --- | --- |
| Comparative Compound 1 | **** | ** | **** |
| Comparative Compound 2 | **** | **** | **** |
| Comparative Compound 3 | *** | **** | **** |
| Compound 2R | **** | *** | **** |
| Compound 2S | **** | * | **** |
| Compound 7 | ** | *** | ** |
| Compound 8 | ** | *** | ** |
| Compound 10 | ** | *** | ** |
| Compound 21 | ** | *** | ** |
| Compound 22 | ** | **** | ** |
| Compound 24 | ** | **** | ** |
| Compound 27 | * | ** | ** |
| Compound 31 | *** | **** | **** |
| Compound 34 | **** | **** | *** |
| Compound 36 | ** | ** | ** |

TABLE 4-continued

Percent inhibition values for selected compounds of the disclosure.

| Compound | PI3Ka % Inh. @ 100 nM | EGFR % Inh. @ 100 nM | DNA-PK % Inh. @ 100 nM |
|---|---|---|---|
| Compound 41 | ** | **** | * |
| Compound 48 | **** | *** | **** |
| Compound 48 | **** | *** | **** |
| Compound 48R | **** | **** | **** |
| Compound 48S | **** | * | **** |
| Compound 53 | ** | *** | ** |
| Compound 53R | ** | **** | ** |
| Comparative Compound 1 | **** | ** | **** |
| Comparative Compound 2 | **** | **** | **** |
| Comparative Compound 3 | *** | **** | **** |
| Compound 54 | ** | **** | *** |
| Compound 54R | ** | *** | ** |
| Compound 55 | * | ** | ** |
| Compound 56 | ** | ** | ** |
| Compound 61 | * | *** | ** |
| Compound 62 | * | ** | ** |
| Compound 64 | ** | ** | ** |
| Compound 65 | ** | *** | ** |
| Compound 67 | ** | ** | ** |
| Compound 68 | ** | *** | ** |
| Compound 70 | ** | *** | ** |
| Compound 73 | ** | ** | * |
| Compound 87 | ** | *** | * |
| Compound 97R | *** | ** | **** |
| Compound 97S | **** | * | **** |
| Compound 101 | **** | ** | **** |
| Compound 103 | **** | * | **** |
| Compound 106 | **** | ** | **** |
| Compound 111R | **** | ** | *** |
| Compound 111S | **** | * | **** |
| Compound 121 | ** | *** | ** |
| Compound 122 | * | ** | * |
| Compound 123 | * | **** | ** |
| Compound 124 | * | **** | * |
| Compound 125 | * | **** | ** |
| Compound 126 | ** | ** | * |
| Comparative Compound 1 | **** | ** | **** |
| Comparative Compound 2 | **** | **** | **** |
| Comparative Compound 3 | *** | **** | **** |
| Compound 127 | * | *** | ** |
| Compound 128 | * | *** | * |
| Compound 129 | ** | *** | *** |
| Compound 130 | * | ** | * |
| Compound 131 | * | ** | * |
| Compound 132 | * | ** | * |
| Compound 133 | * | * | * |
| Compound 134 | * | **** | * |
| Compound 135 | * | **** | * |
| Compound 136 | * | **** | * |
| Compound 137 | ** | **** | * |
| Compound 138 | * | **** | ** |
| Compound 139 | ** | ** | * |
| Compound 140 | * | ** | * |

Example 54: Effect of Compound 2 on Tumor Volumes in Xenograft Mice

Xenograft Studies. Female NCR nude mice (CrTac:NCr-Foxn1nu from Taconic), 6-7 weeks old, were implanted subcutaneously with 5×10$^6$ cells in a 1:1 serum-free media/Matrigel® mixture into the region of the right axilla. Mice were randomized into treatment groups and treatments initiated when tumors reached 100 to 200 mg. Compound 2R was administered daily by oral gavage as a fine suspension in 1:2 propylene (glycol in 1% Tween80/Na$_3$PO$_4$ based upon individual animal body weight (0.2 mL/20 g). Subcutaneous tumor volume and body weights were measured two to three times a week. Tumor volumes were calculated by measuring two perpendicular diameters with calipers and using the formula: tumor volume=(length×width2)/2. Individual mice were dosed daily until their tumor burden reached 500 mg for the CAL-27 and HCC-70 models or 1000 mg for the CAL-33 model, to allow for calculation of increase in progression-free survival. Percent increase in survival was calculated by comparing the median time to reach either 500 mg or 1000 mg in the treated group versus the vehicle control group. A complete response (CR) is defined as a tumor below the limits of palpation (<40 mg).

Figure 2:
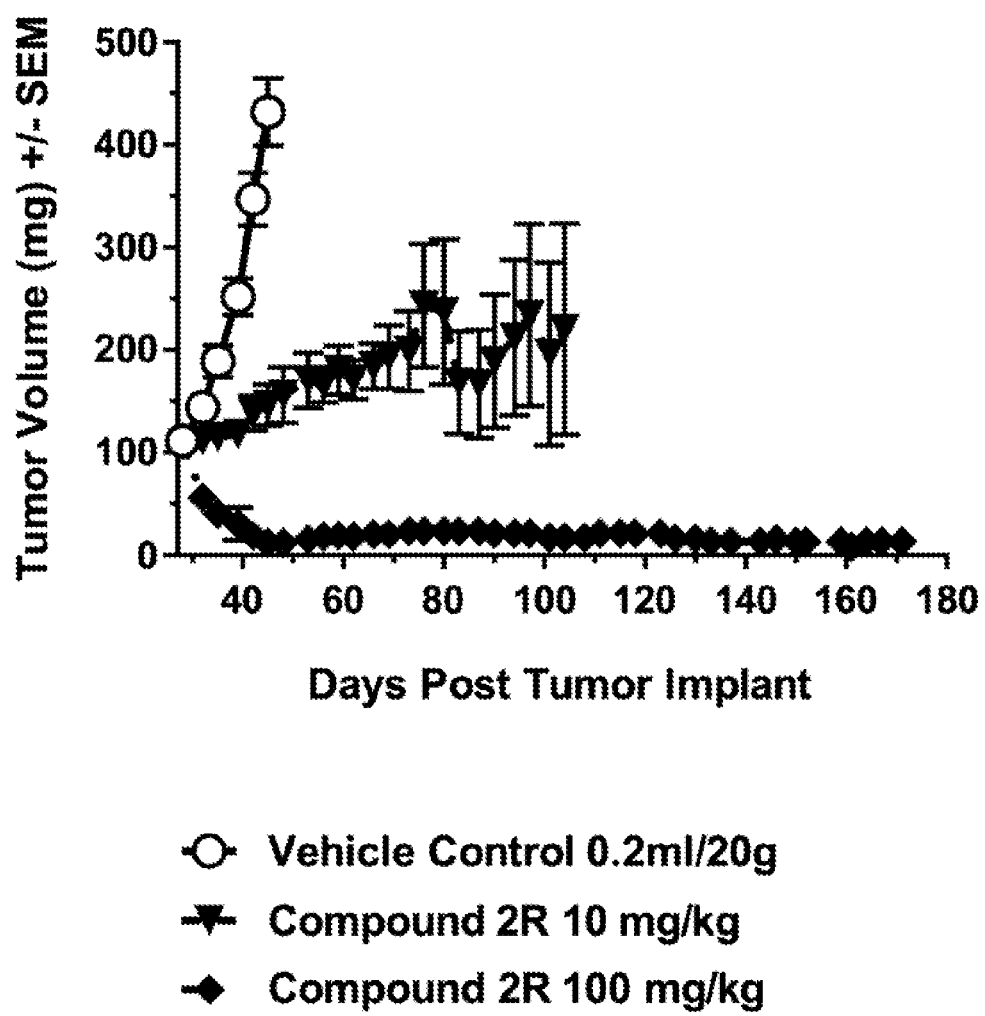
FIG. 2 is a line graph showing a Therapeutic Index Study of Compound 2R against the human squamous head and neck cancer model CAL-27 at 10 mg/Kg and 100 mg/Kg vs. control on the mean tumor burden of a test group.
Figure 3:
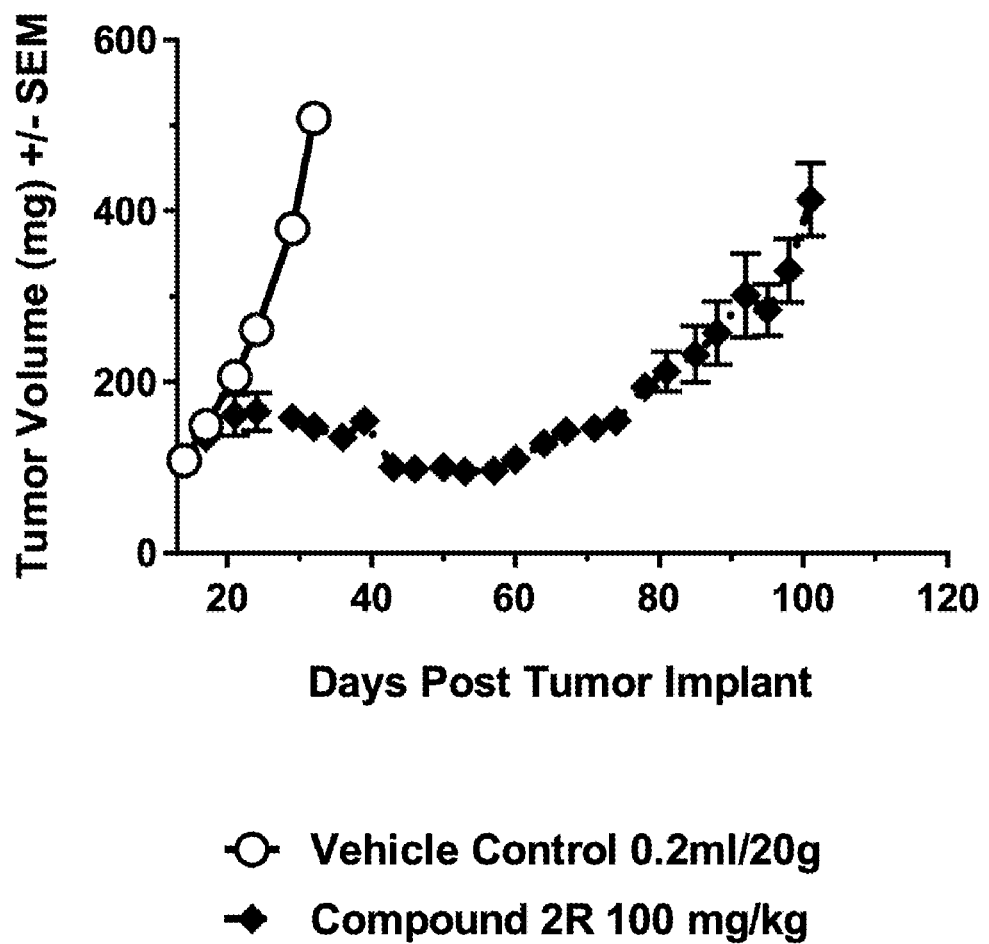
FIG. 3 is a line graph showing an Efficacy Study of Compound 2R against the human triple negative breast cancer model HCC-70 at 100 mg/Kg vs. control on the mean tumor burden of a test group.

FIGS. 1-3 show the performance of Compound 2R in controlling tumor size. Single agent activity of Compound 2R was demonstrated in models of squamous head and neck cancer (PIK3CA mutant human CAL-33, PI3K gamma mutant human CAL-27) as well as a model of triple negative breast cancer (human HCC-70). Tumor growth curves as well as survival and objective response data are summarized in the accompanying FIGS. 1-3 and the table below. In all of these studies, Compound 2R was well tolerated at the highest dose tested (100 mg/kg) with no signs of body weight loss or other clinical signs despite daily dosing over >50 days.

| Model | Dose (mg/kg) | Median Increase In Survival | Incidence of Complete Responders |
|---|---|---|---|
| CAL-33 | 25 | >700 | 4 of 5 (80%) |
|  | 50 | >700 | 4 of 5 (80%) |
|  | 100 | >700 | 5 of 5 (100%) |
| CAL-27 | 10 | 328 | 2 of 6 (33%) |
|  | 100 | >700 | 5 of 6 (83%) |
| HCC-70 | 100 | 363% | — |

Example 55: Assessment of Metabolic Stability in Liver Microsomes

Working solution: 5 µL of compound and control stock solution (10 mM in dimethyl sulfoxide (DMSO)) were diluted with 495 µL of acetonitrile (ACN) (intermediate solution concentration: 100 µM, 99% ACN)

NADPH Cofactor Preparation: NADPH powder: β-Nicotinamide adenine dinucleotide phosphate reduced form, tetrasodium salt; NADPH·4Na. The appropriate amount of NADPH powder was weighed and diluted into a 10 mM MgCl2 solution (working solution concentration: 10 unit/mL; final concentration in reaction system: 1 unit/mL)

Liver Microsomes Preparation: The appropriate concentrations of microsome working solutions were prepared in 100 mM potassium phosphate buffer. Cold (4° C.) acetonitrile (ACN) containing 200 ng/mL tolbutamide and 200 ng/mL labetalol as internal standards (1S) was used as the stop solution Assay Procedure: Pre-warm empty 'Incubation' plates T60 and NCF60 for 10 minutes. Dilute liver microsomes to 0.56 mg/mL in 100 mM phosphate buffer. Transfer 445 µL microsome working solutions (0.56 mg/mL) into pre-warmed 'Incubation' plates T60 and NCF60, Then pre-incubate 'Incubation' plates T60 and NCF60 for 10 min at 37° C. with constant shaking. Transfer 54 µL liver microsomes to blank plate, then add 6 µL NAPDH cofactor to blank plate, and then add 180 µL quenching solution to blank plate. Add 5 µL compound working solution (100 µM) into 'incubation' plates (T60 and NCF60) containing microsomes and mix 3 times thoroughly.

For the NCF60 plate, add 50 µL of buffer and mix 3 times thoroughly. Start timing; plate will be incubated at 37° C. for 60 min while shaking. In 'Quenching' plate T0, add 180 µL quenching solution and 6 µL NAPDH cofactor. Ensure the plate is chilled to prevent evaporation. For the T60 plate, mix 3 times thoroughly, and immediately remove 54 µL mixture for the 0-min time point to 'Quenching' plate. Then add 44 µL NAPDH cofactor to incubation plate (T60). Start timing; plate will be incubated at 37° C. for 60 min while shaking. At 5, 10, 20, 30, and 60 min, add 180 µL quenching solution to 'Quenching' plates, mix once, and serially transfer 60 µL sample from T60 plate per time point to 'Quenching' plates. For NCF60: mix once, and transfer 60 µL sample from the NCF60 incubation to 'Quenching' plate containing quenching solution at the 60-min time point. All sampling plates are shaken for 10 min, then centrifuged at 4000 rpm for 20 minutes at 4° C. Transfer 80 µL supernatant into 240 µL HPLC water, and mix by plate shaker for 10 min. Each bioanalysis plate was sealed and shaken for 10 minutes prior to LC-MS/MS analysis.

The equation of first order kinetics was used to calculate T½ and CLint(mic) (µL/min/mg). Equation of first order kinetics:

$$C_t = C_0 \cdot e^{-k_e \cdot t}$$

when $C_t = \frac{1}{2}C_0$, $$T_{1/2} = \frac{Ln2}{k_e} = \frac{0.693}{k_e}$$

$$CL_{int(mic)} = \frac{0.693}{\text{In vitro } T_{1/2}} \cdot \frac{1}{\text{mg/mL microsomal protein in reaction system}}$$

$$CL_{int(liver)t} = CL_{int(mic)} \cdot \frac{\text{mg microsomes}}{\text{g liver}} \cdot \frac{\text{g liver}}{\text{kg body weight}}$$

The biological stability of the compounds of the disclosure can be measured by determining its ½ life in the presence microsomes. Presented in Table 5, is the ½ life of selected compounds of the disclosure in the presence of human liver microsomes (HLM) or mouse liver microsomes (MLM) as described above. In Table 5, ½ life is presented as "++++" (value is greater than 60 minutes), "+++" (value is greater than 30 minutes and less than or equal to 60 minutes), "++" (value is greater than 15 minutes and less than or equal to 30 minutes) and "+" (value is 15 minutes or less).

TABLE 5

½ life of selected compounds of the disclosure in HLM or MLM.

| Compound | ½ life minutes (HLM) | ½ life minutes (MLM) |
|---|---|---|
| Comparative Compound 1 | ++++ | ++++ |
| Comparative Compound 2 | ++++ | ++++ |
| Comparative Compound 3 | ++++ | + |
| Compound 2R | ++++ | ++++ |
| Compound 2S | ++++ | ++++ |
| Compound 48 | ++++ | ++++ |
| Compound 48 | ++++ | ++++ |
| Compound 48R | +++ | ++++ |
| Compound 48S | ++++ | ++++ |
| Compound 53 | ++++ | +++ |
| Compound 54 | +++ | + |
| Compound 53R | +++ | +++ |
| Compound 97R | ++++ | ++++ |
| Compound 97S | ++++ | ++++ |
| Compound 106 | ++++ | +++ |
| Compound 111R | ++++ | ++++ |

TABLE 5-continued

½ life of selected compounds of the disclosure in HLM or MLM.

| Compound | ½ life minutes (HLM) | ½ life minutes (MLM) |
|---|---|---|
| Compound 111S | ++++ | ++++ |
| Compound 121 | ++++ | ++++ |

The results in Table 5 suggest that the compounds of the present disclosure would possess robust biological stability in vivo, as most of the compounds tested have a half-life greater than 60 minutes in the presence of both human liver microsomes and mouse liver microsomes.

Example 56: Assessment of the Solubility of the Compounds of the Disclosure

Preparation of stock solutions: The stock solutions of test compounds and control compound diclofenac were prepared in DMSO at the concentrations of 10 mM.

Simulated Gastric Fluid (SGF): An aqueous mixture including hydrochloric acid, sodium chloride, and pepsin (pH=1.2).

Simulated Intestinal Fluid (SIF): Prepared by dissolving 6.8 g of $KH_2PO_4$ into about 500 mL ultrapure water and adjust the solution to a pH 6.8 with 0.1 M NaOH. 10 g trypsin is then dissolved into ultrapure water. The two solutions are mixed well and diluted with ultrapure water to a final volume of 1000 mL.

Procedure for solubility determination: 15 µL of stock solution (10 mM) of each sample was placed in order into their proper 96-well rack. 485 µL of (SIF, SGF, PBS 7.4, FESSIF, or FESSGF) was added into each vial of the cap-less Solubility Sample plate. The assay was performed in duplicate. Add one stir stick to each vial and seal using a molded PTFE/Silicone plug. Then the solubility sample plate was transferred to the Eppendorf Thermomixer Comfort plate shaker and shaken at 25° C. at 1100 rpm for 2 hours. After completion of the 2 hours, plugs were removed and the stir sticks were removed using a big magnet, the samples from the Solubility Sample plate were transferred into the filter plate. Using the Vacuum Manifold, all the samples were filtered. Aliquot of 5 µL and 5 µL DMSO were taken from the filtrate followed by addition of 490 µL of a mixture of $H_2O$ and acetonitrile containing internal standard (1:1). A certain proportion of ultrapure water was used to dilute the diluent according to the peak shape. The dilution factor was changed according to the solubility values and the LC-MS signal response.

Preparation of 300 µM standards (STD): From the 10 mM DMSO STD plate, 6 µL was transferred into the remaining empty plate, and then 194 µL of DMSO was added to that plate to have a STD concentration of 300 µM. From the 300 µM DMSO STD plate, 5 µL DMSO STD and 5 µL SIF was transferred into the remaining empty plate, and then 490 µL of a mixture of $H_2O$ and acetonitrile containing internal standard (1:1) was added to that plate to have a final STD concentration of 3 µM. A certain proportion of ultrapure water was used to dilute the diluent according to the peak shape. The concentrations of the standard samples were changed according to the LC-MS signal response.

Procedure for sample analysis: The plate was placed into the well plate autosampler. The samples were evaluated by LC-MS/MS analysis.

Data analysis: All calculations were carried out using Microsoft Excel. The filtrate was analyzed and quantified against a standard of known concentration using LC coupled with mass spectral peak identification and quantitation. Solubility values of the test compound and control compound were calculated as follows:

$$[Sample] = \frac{\text{Area ratio}_{Sample} \times INJ\ VOL\ STD \times DF_{Sample} \times [STD]}{\text{Area ratio } STD \times INJ\ VOL_{Sample}}$$

Any value of the compounds that was not within the specified limits was rejected and the experiment was repeated.

The solubility data for selected compounds of the disclosure is provided in Table 6. The solubility data in Table 6 is presented as "***" (value is greater than 200 μM), "*" (value is greater than 100 μM and less than or equal to 200 μM), "**" (value is greater than 20 μM and less than or equal to 100 μM) and "*" (value is 20 μM or less). NT is "not tested."

TABLE 6

Solubility data for selected compounds of the disclosure.

| Compound | Solubility pH 7.4 PBS buffer | Solubility SIF | Solubility SGF |
|---|---|---|---|
| Comparative Compound 1 | * | * | **** |
| Comparative Compound 2 | * | * | **** |
| Comparative Compound 3 | NT | * | NT |
| Compound 2R | *** | *** | **** |
| Compound 2S | NT | *** | NT |
| Compound 7 | NT | ** | NT |
| Compound 22 | NT | ** | NT |
| Compound 48R | * | * | **** |
| Compound 53 | NT | ** | NT |
| Compound 53R | NT | ** | NT |
| Compound 54 | NT | * | NT |
| Compound 111R | ** | ** | **** |
| Compound 129 | NT | * | NT |

The results in Table 6 show that the solubility of the compounds of the present disclosure are significantly improved compared to Comparative Compounds 1-3. Seven out of ten compounds tested show an improvement in solubility in simulated intestinal fluid, with Compounds 2R and 2S being at least 5 times as soluble. Compound 2R also shows the same improvement in solubility in PBS buffer. As in known to those skilled in the art, increased solubility in an active pharmaceutical ingredient (API) can suggest an increase in bioavailability in, for example, an orally administered composition.

Example 57: Assessment of the Pharmacokinetics of Compound 2R

The pharmacokinetics of Compound 2R (HCl salt) and Comparative Compound 2 were studied following a single intravenous and/or oral administration to mice, dogs, and monkeys (n=3 for all species). The IV and PO solution formulations for Comparative Compound 2 contained 20% (w/v) propylene glycol, 75% (w/v) 50 mM trisodium phosphate (pH 12), and 5% (w/v) Kolliphor EL. The formulation for Compound 2R contained 1:2 propylene glycol: 1% Tween 80/$Na_3PO_4$ (50 mM). Subsequent pharmacokinetic data analysis was performed using non-compartmental analysis modules in Phoenix/WINNONLIN 6.3 (Pharsight, St. Louis, Mo., USA), and the linear trapezoidal rule was used for AUC calculation. Terminal elimination half-life (t½) was calculated based on data points (≥3) in the terminal phase; Tmax=Time of maximum observed concentration; AUClast/D=Area under the concentration-time curve from time zero to the last observed concentration/divided by dose; Cl_obs=Total body clearance; Cmax=maximum observed concentration; F=bioavailability of oral dose form. Blood samples were assayed for compounds using protein precipitation with acetonitrile followed by HPLC/MS/MS analysis. Blood concentration-time data were analyzed by non-compartmental methods.

IV PK Parameters for Comparative Compound 2 and Compound 2R

| | | Mouse | | Dog | | Monkey | |
|---|---|---|---|---|---|---|---|
| PK parameters | Unit | Comparative Compound 2 10 mpk | Compound 2R 5 mpk | Comparative Compound 2 1 mpk | Compound 2R 1 mpk | Comparative Compound 2 1 mpk | Compound 2R 1 mpk |
| Cl_obs | mL/min/kg | 3.3 | 1.2 | 10.50 | 0.52 | 15.71 | 4.81 |
| T1/2 | h | 1.2 | 2.5 | 0.7 | 10.4 | 1.1 | 2.3 |
| C0 | ng/mL | 25567 | 25708 | 5492 | 7148 | 5906 | 4169 |
| AUClast/D | h*mg/mL | 5094 | 14240 | 1975 | 28655 | 1067 | 3783 |

Oral PK Parameters for Comparative Compound 2 and Compound 2R

| | | Mouse | | Dog | | Monkey | |
|---|---|---|---|---|---|---|---|
| PK parameters | Unit | Comparative Compound 2 10 mpk | Compound 2R 25 mpk | Comparative Compound 2 5 mpk | Compound 2R 5 mpk | Comparative Compound 2 10 mpk | Compound 2R 10 mpk |
| T1/2 | h | 1.4 | 4.9 | 0.8 | 12 | 2 | 4 |
| Tmax | h | 1 | 4.17 | 2 | 2 | 1 | 2 |
| Cmax | ng/mL | 8267 | 21679 | 716 | 7090 | 110 | 4713 |
| AUClast/D | h*mg/mL | 3226 | 11819 | 487 | 13808 | 30 | 2222 |
| F | % | 63 | 83 | 25 | 48 | 3 | 59 |

The enhanced solubility of Compound 2R led to improved exposure when compared to Comparative Compound 2 as expressed by the PK parameter AUClast/D. IV pharmacokinetic analysis demonstrated about a 3-fold increase in exposure for mice dosed with Compound 2R (AUClast/D=14,240 vs 5094 h*mg/ml) and monkeys (AUClast/D=3783 vs 1067). Dogs showed approximately a 15-fold increase in exposure when dosed intravenously with Compound 2R compared to Comparative Compound 2 (AUClast/D=28655 vs 1975). Oral PK analysis revealed a similar trend in mice as reflected by 3-fold enhanced exposure with Compound 2R relative to Comparative Compound 2. However, improvement in exposure in response to oral treatment with Compound 2R was especially strong in both dogs (>28-fold) and monkeys (>74-fold) as shown by AUClast/D values of 13,808 vs 487 h*mg/ml (dogs) and 2222 vs 30 h*mg/ml (monkeys).

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present disclosure. One skilled in the art will readily recognize from such discussion and from the accompanying drawings and claims, that various changes, modifications and variations can be made therein without departing from the spirit and scope of the disclosure as defined in the following claims.

We claim:
1. A compound selected from:

| Cmp # | IUPAC Name |
|---|---|
| 2 | N-(2-chloro-5-(4-((1-phenylethyl)amino)quinazolin-6-yl)pyridin-3-yl)methanesulfonamide |
| 2R | N-(2-chloro-5-(4-((1R-phenylethyl)amino)quinazolin-6-yl)pyridin-3-yl)methanesulfonamide |
| 2S | N-(2-chloro-5-(4-((1S-phenylethyl)amino)quinazolin-6-yl)pyridin-3-yl)methanesulfonamide |
| 7 | 6-(2-aminopyrimidin-5-yl)-N-(1-phenylethyl)quinazolin-4-amine |
| 22 | 6-(5,6-dimethoxypyridin-3-yl)-N-(1-phenylethyl)quinazolin-4-amine |
| 48 | N-(2-chloro-5-(3-cyano-4-((1-phenylethyl)amino)quinolin-6-yl)pyridin-3-yl)methanesulfonamide |
| 48R | N-(2-chloro-5-(3-cyano-4-((1R-phenylethyl)amino)quinolin-6-yl)pyridin-3-yl)methanesulfonamide |
| 48S | N-(2-chloro-5-(3-cyano-4-((1S-phenylethyl)amino)quinolin-6-yl)pyridin-3-yl)methanesulfonamide |
| 53 | 6-(2-aminopyrimidin-5-yl)-4-((1-phenylethyl)amino)quinoline-3-carbonitrile |
| 53R | (R)-6-(2-aminopyrimidin-5-yl)-4-((1-phenylethyl)amino)quinoline-3-carbonitrile |
| 97 | N-(2-chloro-5-(3-cyano-4-((1-(4-fluorophenyl)ethyl)amino)quinolin-6-yl)pyridin-3-yl)methanesulfonamide |
| 97R | N-(2-chloro-5-(3-cyano-4-((1R-(4-fluorophenyl)ethyl)amino)quinolin-6-yl)pyridin-3-yl)methanesulfonamide |
| 97S | N-(2-chloro-5-(3-cyano-4-((1S-(4-fluorophenyl)ethyl)amino)quinolin-6-yl)pyridin-3-yl)methanesulfonamide |
| 106 | N-(2-chloro-5-(3-cyano-4-((1-phenylcyclopropyl)amino)quinolin-6-yl)pyridin-3-yl)methanesulfonamide |
| 111 | N-(2-chloro-5-(4-((1-(4-fluorophenyl)ethyl)amino)quinazolin-6-yl)pyridin-3-yl)methanesulfonamide |
| 111R | N-(2-chloro-5-(4-((1R-(4-fluorophenyl)ethyl)amino)quinazolin-6-yl)pyridin-3-yl)methanesulfonamide |
| 111S | N-(2-chloro-5-(4-((1S-(4-fluorophenyl)ethyl)amino)quinazolin-6-yl)pyridin-3-yl)methanesulfonamide |
| 121 | 6-(2-aminopyrimidin-5-yl)-N-(1-(4-fluorophenyl)ethyl)quinazolin-4-amine |
| 121R | 6-(2-aminopyrimidin-5-y))-N-(1R-(4-fluorophenyl)ethyl)quinazolin-4-amine |

| Cmp # | Structure |
|---|---|
| 2 | 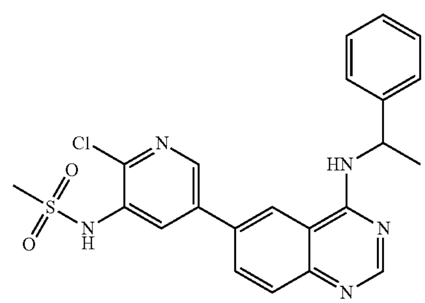 |
| 2R | 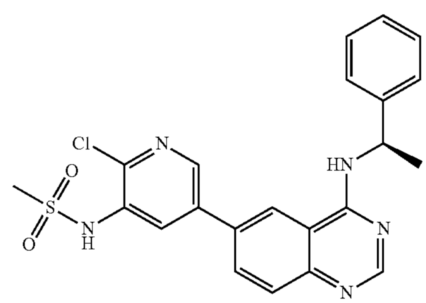 [SMILES: C[C@@H](Nc1ncnc2ccc(-c3cnc(Cl)c(NS(C)(=O)=O)c3)cc12)c1ccccc1] |
| 2S | 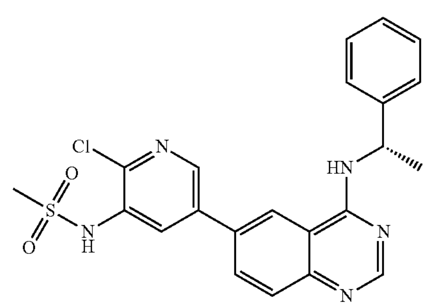 [SMILES: C[C@H](Nc1ncnc2ccc(-c3cnc(Cl)c(NS(C)(=O)=O)c3)cc12)c1ccccc1] |

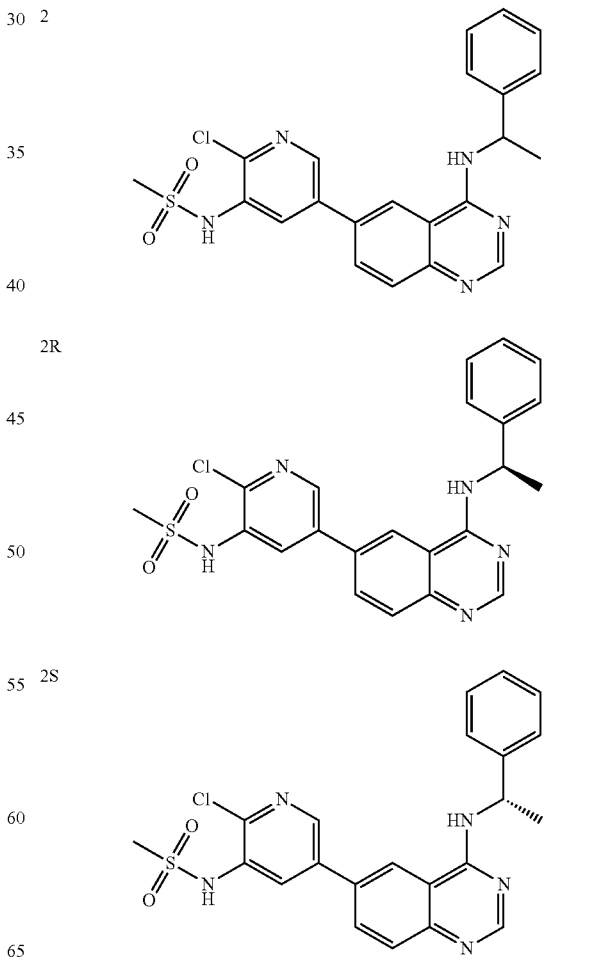

| | |
|---|---|
| 7 | 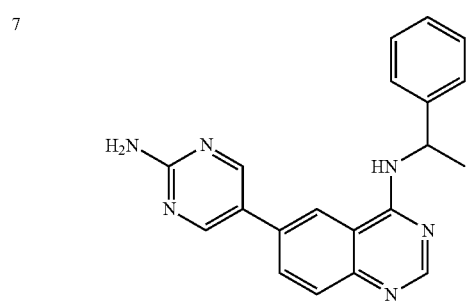 |
| 22 | 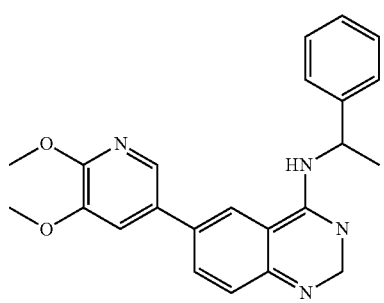 [SMILES: COc1cc(-c2ccc3c(c2)=C(NC(C)c2ccccc2)NCN=3)cnc1OC] |
| 48 | 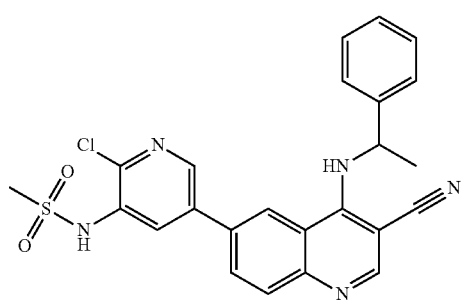 [SMILES: CC(Nc1c(C#N)cnc2ccc(-c3cnc(Cl)c(NS(C)(=O)=O)c3)cc12)c1ccccc1] |
| 48R | 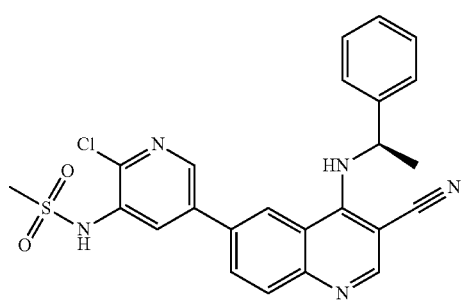 [SMILES: C[C@@H](Nc1c(C#N)cnc2ccc(-c3cnc(Cl)c(NS(C)(=O)=O)c3)cc12)c1ccccc1] |
| 48S | 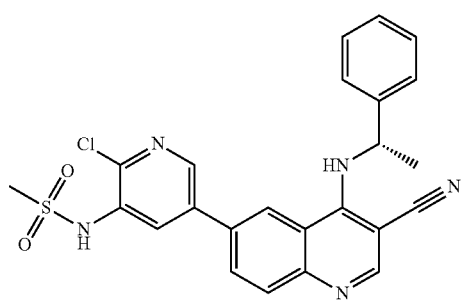 [SMILES: C[C@H](Nc1c(C#N)cnc2ccc(-c3cnc(Cl)c(NS(C)(=O)=O)c3)cc12)c1ccccc1] |
| | |
|---|---|
| 53 | 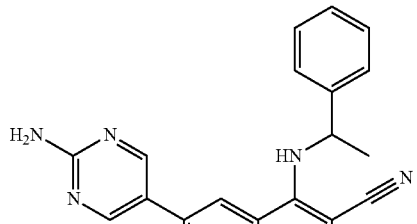 |
| 53R | 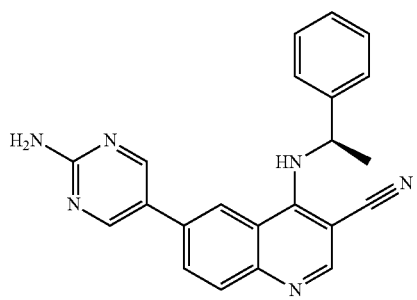 [SMILES: C[C@@H](Nc1c(C#N)cnc2ccc(-c3cnc(N)nc3)cc12)c1ccccc1] |
| 97 | 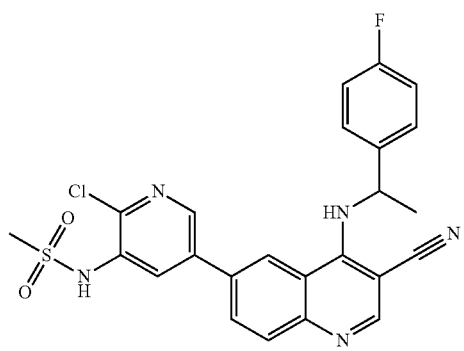 |
| 97R | 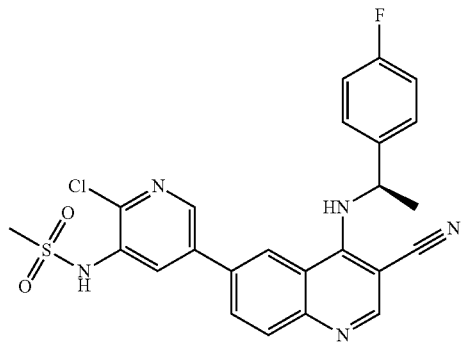 [SMILES: C[C@@H](Nc1c(C#N)cnc2ccc(-c3cnc(Cl)c(NS(C)(=O)=O)c3)cc12)c1ccc(F)cc1] |
| 97S | 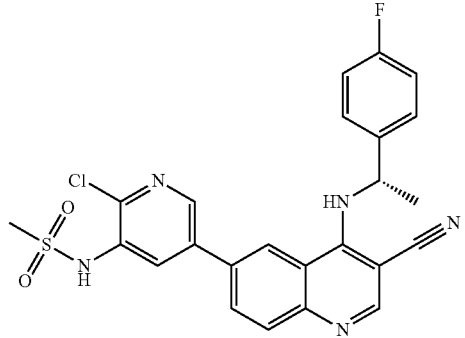 [SMILES: C[C@H](Nc1c(C#N)cnc2ccc(-c3cnc(Cl)c(NS(C)(=O)=O)c3)cc12)c1ccc(F)cc1] |

106 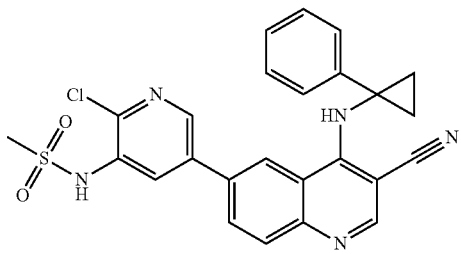 [SMILES: CS(=O)(=O)Nc1cc(-c2ccc3ncc(C#N)c(NC4(c5ccccc5)CC4)c3c2)cnc1Cl]

111 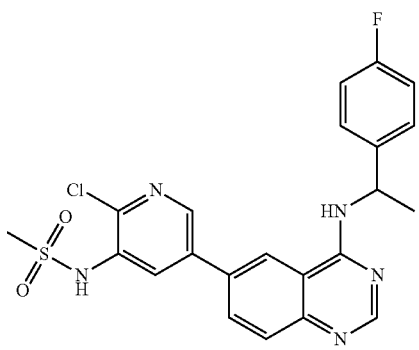 [SMILES: CC(Nc1ncnc2ccc(-c3cnc(Cl)c(NS(C)(=O)=O)c3)cc12)c1ccc(F)cc1]

111R 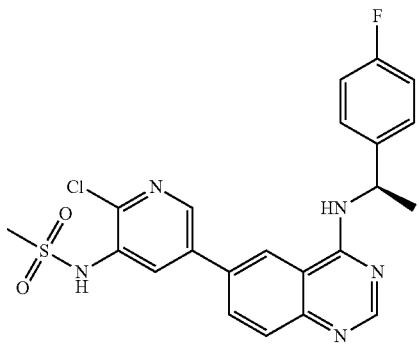 [SMILES: C[C@@H](Nc1ncnc2ccc(-c3cnc(Cl)c(NS(C)(=O)=O)c3)cc12)c1ccc(F)cc1]

111S 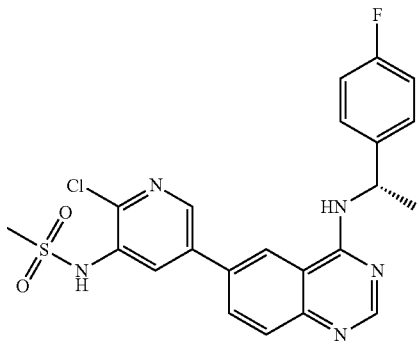 [SMILES: C[C@H](Nc1ncnc2ccc(-c3cnc(Cl)c(NS(C)(=O)=O)c3)cc12)c1ccc(F)cc1]

121 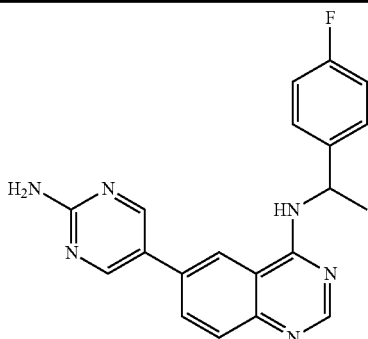

121R 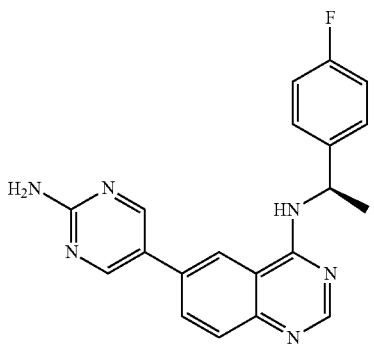 [SMILES: C[C@@H](Nc1ncnc2ccc(-c3cnc(N)nc3)cc12)c1ccc(F)cc1]

or a pharmaceutically acceptable salt thereof.

2. A pharmaceutical composition comprising a compound or a pharmaceutically acceptable salt or solvate thereof, or an enantiomer, a mixture of enantiomers, a mixture of two or more diastereomers, or an isotopic variant thereof, according to claim 1, and a pharmaceutically acceptable excipient.

3. A method of modulating an EGFR and/or PI3K enzyme in a biological sample, said method comprising contacting the biological sample with a compound or salt according to claim 1.

4. A method of ameliorating an EGFR and/or PI3K mediated disease in a subject, said method comprising administering to the subject a compound or salt according to claim 1.

5. The method of claim 4, wherein the EGFR and/or PI3K mediated disease is a cancer.

6. The method of claim 5, wherein the cancer is selected from prostate cancer, liver cancer, renal cancer, lung cancer, breast cancer, colorectal cancer, pancreatic cancer, brain cancer, hepatocellular cancer, lymphoma, leukemia, gastric cancer, cervical cancer, ovarian cancer, thyroid cancer, melanoma, carcinomas of the head and neck, head and neck cancer, skin cancer and soft tissue sarcoma and/or other forms of carcinoma.

7. The method of claim 6, wherein the head and neck cancer is squamous head and neck cancer, and the breast cancer is triple negative breast cancer.

\* \* \* \* \*